(12) United States Patent
Germeroth et al.

(10) Patent No.: US 11,517,627 B2
(45) Date of Patent: Dec. 6, 2022

(54) CELL SURFACE CONJUGATES AND RELATED CELL COMPOSITIONS AND METHODS

(71) Applicant: Juno Therapeutics GmbH, Munich (DE)

(72) Inventors: Lothar Germeroth, Munich (DE); Christian Stemberger, Munich (DE)

(73) Assignee: Juno Therapeutics GmbH, Munich (DE)

( * ) Notice: Subject to any disclaimer, the term of this patent is extended or adjusted under 35 U.S.C. 154(b) by 382 days.

(21) Appl. No.: 16/479,197

(22) PCT Filed: Jan. 19, 2018

(86) PCT No.: PCT/IB2018/000380
§ 371 (c)(1),
(2) Date: Jul. 18, 2019

(87) PCT Pub. No.: WO2018/134691
PCT Pub. Date: Jul. 26, 2018

(65) Prior Publication Data
US 2020/0316218 A1    Oct. 8, 2020

Related U.S. Application Data

(60) Provisional application No. 62/448,936, filed on Jan. 20, 2017.

(51) Int. Cl.
*A61K 47/69* (2017.01)
*C07K 14/705* (2006.01)
*C12N 15/86* (2006.01)

(52) U.S. Cl.
CPC ........ *A61K 47/6901* (2017.08); *C07K 14/705* (2013.01); *C12N 15/86* (2013.01); *C07K 2317/62* (2013.01); *C07K 2318/20* (2013.01); *C07K 2319/03* (2013.01); *C07K 2319/22* (2013.01); *C07K 2319/70* (2013.01)

(58) Field of Classification Search
CPC ................................................ A61K 47/6901
See application file for complete search history.

(56) References Cited

U.S. PATENT DOCUMENTS

| | | |
|---|---|---|
| 4,235,871 A | 11/1980 | Papahadjopoulos |
| 4,452,773 A | 6/1984 | Molday |
| 4,501,728 A | 2/1985 | Geho |
| 4,690,915 A | 9/1987 | Rosenberg |
| 4,795,698 A | 1/1989 | Owen |
| 4,837,028 A | 6/1989 | Allen |
| 4,851,341 A | 7/1989 | Hopp et al. |
| 4,880,935 A | 11/1989 | Thorpe |
| 5,019,369 A | 5/1991 | Presant |
| 5,087,616 A | 2/1992 | Myers |
| 5,168,049 A | 12/1992 | Meade et al. |
| 5,200,084 A | 4/1993 | Liberti |
| 5,219,740 A | 6/1993 | Miller |
| 5,506,121 A | 4/1996 | Skerra |
| 5,821,337 A | 10/1998 | Carter et al. |
| 5,985,658 A | 11/1999 | Colinas et al. |
| 6,022,951 A | 2/2000 | Sano et al. |
| 6,040,177 A | 3/2000 | Riddell et al. |
| 6,060,273 A | 5/2000 | Dirks et al. |
| 6,103,493 A | 8/2000 | Skerra |
| 6,156,493 A | 12/2000 | Stayton |
| 6,165,750 A | 12/2000 | Stayton |
| 6,207,453 B1 | 3/2001 | Maass |
| 6,214,345 B1 | 4/2001 | Firestone et al. |
| 6,368,813 B1 | 4/2002 | Reznik et al. |
| 6,410,319 B1 | 6/2002 | Raubitschek |
| 6,451,995 B1 | 9/2002 | Cheung |
| 6,572,856 B1 | 6/2003 | Taylor et al. |
| 7,070,995 B2 | 7/2006 | Jensen |
| 7,265,209 B2 | 9/2007 | Jensen |
| 7,354,762 B2 | 4/2008 | Jensen |
| 7,446,179 B2 | 11/2008 | Jensen |
| 7,446,190 B2 | 11/2008 | Sadelain |
| 7,446,191 B2 | 11/2008 | Jensen |

(Continued)

FOREIGN PATENT DOCUMENTS

| | | |
|---|---|---|
| AU | 2002356844 | 7/2003 |
| AU | 2006204913 | 7/2006 |

(Continued)

OTHER PUBLICATIONS

US 8,252,592 B2, 08/2012, Sadelain (withdrawn)

(Continued)

*Primary Examiner* — Scott Long
(74) *Attorney, Agent, or Firm* — Morrison & Foerster LLP

(57) ABSTRACT

Provided herein are cell surface conjugates containing a cell surface molecule and at least one agent, such as at least one affinity tag, and engineered cells expressing such cell surface conjugates. In some embodiments, the cell surface molecule does not contain an intracellular signaling domain or is not capable of mediating intracellular signaling. In some embodiments, the cells engineered to contain the cell surface conjugate, such as T cells, further contain a genetically engineered recombinant receptor that specifically binds to antigens, such as a chimeric antigen receptor (CAR). Also provided are methods of detecting, identifying, selecting or targeting cells expressing the cell surface conjugates, such as in connection with methods of manufacturing engineered cells or in connection with administration of such cells to subjects, including methods of adoptive cell therapy.

33 Claims, 2 Drawing Sheets
Specification includes a Sequence Listing.

(56) References Cited

U.S. PATENT DOCUMENTS

| | | | |
|---|---|---|---|
| 7,449,184 | B2 | 11/2008 | Allison et al. |
| 7,476,513 | B2 | 1/2009 | Murphy et al. |
| 7,776,562 | B2 | 8/2010 | Bch et al. |
| 7,981,632 | B2 | 7/2011 | Schmidt |
| 8,298,782 | B2 | 10/2012 | Bch et al. |
| 8,324,353 | B2 | 12/2012 | Jensen |
| 8,339,645 | B2 | 12/2012 | Nakawaki |
| 8,389,282 | B2 | 3/2013 | Sadelain et al. |
| 8,470,330 | B2 | 6/2013 | Maddon et al. |
| 8,479,118 | B2 | 7/2013 | Lyndersay et al. |
| 8,735,540 | B2 | 5/2014 | Schmidt |
| 8,802,374 | B2 | 8/2014 | Jensen |
| 8,911,993 | B2 | 12/2014 | June et al. |
| 8,986,655 | B2 | 3/2015 | Weiss et al. |
| 9,023,604 | B2 | 5/2015 | Schmidt et al. |
| 2002/0049712 | A1 | 4/2002 | Winski et al. |
| 2002/0131960 | A1 | 9/2002 | Sadelain |
| 2002/0147312 | A1 | 10/2002 | O'Keefe et al. |
| 2002/0150914 | A1 | 10/2002 | Anderson et al. |
| 2003/0082187 | A1 | 5/2003 | Thorpe et al. |
| 2003/0170238 | A1 | 9/2003 | Gruenberg |
| 2003/0223994 | A1 | 12/2003 | Hoogenboom et al. |
| 2004/0082012 | A1 | 4/2004 | Busch |
| 2004/0136998 | A1 | 7/2004 | Bander |
| 2004/0191260 | A1 | 9/2004 | Reiter et al. |
| 2005/0202020 | A1 | 9/2005 | Ross et al. |
| 2006/0034850 | A1 | 2/2006 | Weidanz et al. |
| 2006/0088539 | A1 | 4/2006 | Bander |
| 2007/0071759 | A1 | 3/2007 | Shin et al. |
| 2007/0099253 | A1 | 5/2007 | Erkhov et al. |
| 2007/0116690 | A1 | 5/2007 | Yang et al. |
| 2009/0226474 | A1 | 9/2009 | Weidanz et al. |
| 2009/0304679 | A1 | 12/2009 | Weidanz |
| 2010/0297653 | A1 | 11/2010 | Ross |
| 2011/0003380 | A1 | 1/2011 | Miltenyi |
| 2011/0020273 | A1 | 1/2011 | Chang et al. |
| 2012/0301447 | A1 | 11/2012 | Jensen et al. |
| 2013/0149337 | A1 | 6/2013 | Cooper et al. |
| 2013/0225541 | A1 | 8/2013 | Bander |
| 2013/0287748 | A1 | 10/2013 | June |
| 2013/0315830 | A1 | 11/2013 | Bander |
| 2014/0099257 | A1 | 4/2014 | Bander |
| 2014/0186867 | A1 | 7/2014 | Harris et al. |
| 2014/0227180 | A1 | 8/2014 | Govindan et al. |
| 2014/0294841 | A1 | 10/2014 | Scheinberg et al. |
| 2015/0168413 | A1 | 6/2015 | Haber et al. |
| 2015/0184128 | A1 | 7/2015 | Jensen |
| 2016/0303253 | A1 | 10/2016 | Govindan et al. |
| 2017/0051035 | A1 | 2/2017 | Payne et al. |
| 2017/0051074 | A1 | 2/2017 | Kirsher et al. |

FOREIGN PATENT DOCUMENTS

| | | |
|---|---|---|
| AU | 2006235421 | 10/2006 |
| AU | 2006262231 | 1/2007 |
| AU | 2006315500 | 5/2007 |
| AU | 2010325969 | 6/2012 |
| AU | 2013328619 | 4/2015 |
| AU | 2015203742 | 7/2015 |
| AU | 2015205574 | 7/2016 |
| CA | 2353267 | 1/2002 |
| DE | 19641876 | 4/1998 |
| EP | 452342 | 10/1991 |
| EP | 1390069 | 2/2004 |
| EP | 1520588 | 4/2005 |
| EP | 1599228 | 11/2005 |
| EP | 1610818 | 1/2006 |
| EP | 1581794 | 9/2008 |
| EP | 2537416 | 12/2012 |
| EP | 2906250 | 8/2015 |
| EP | 3115066 | 1/2017 |
| WO | WO 1986/002077 | 4/1986 |
| WO | WO 1992/008796 | 5/1992 |
| WO | WO 1994/028143 | 12/1994 |
| WO | WO 1996/013593 | 5/1996 |
| WO | WO 1996/018105 | 6/1996 |
| WO | WO 1996/024606 | 8/1996 |
| WO | WO 1998/040396 | 9/1998 |
| WO | WO 1999/018129 | 4/1999 |
| WO | WO 1999/060120 | 11/1999 |
| WO | WO 2000/014257 | 3/2000 |
| WO | WO 2002/077018 | 10/2002 |
| WO | WO 2003/020763 | 3/2003 |
| WO | WO 2003/068201 | 8/2003 |
| WO | WO 2004/033685 | 4/2004 |
| WO | WO 2005/042029 | 5/2005 |
| WO | WO 2006/000830 | 1/2006 |
| WO | WO 2006/078892 | 7/2006 |
| WO | WO 2009/072003 | 6/2009 |
| WO | WO 2010/033140 | 3/2010 |
| WO | WO 2010/135431 | 11/2010 |
| WO | WO 2011/044186 | 4/2011 |
| WO | WO 2011/056894 | 5/2011 |
| WO | WO 2012/129514 | 9/2012 |
| WO | WO 2013/071154 | 5/2013 |
| WO | WO 2013/123061 | 8/2013 |
| WO | WO 2013/124474 | 8/2013 |
| WO | WO 2013/126726 | 8/2013 |
| WO | WO 2013/166321 | 11/2013 |
| WO | WO 2014/031687 | 2/2014 |
| WO | WO-2014/055668 | 4/2014 |
| WO | WO 2014/076277 | 5/2014 |
| WO | WO 2014/190273 | 11/2014 |
| WO | WO 2014/198223 | 12/2014 |
| WO | WO 2015/067768 | 5/2015 |
| WO | WO 2015/095895 | 6/2015 |
| WO | WO 2015/143029 | 9/2015 |
| WO | WO 2015/157399 | 10/2015 |
| WO | WO 2015/177360 | 11/2015 |
| WO | WO 2016/011210 | 1/2016 |
| WO | WO 2016/033225 | 3/2016 |
| WO | WO 2016/057917 | 4/2016 |
| WO | WO 2016/130819 | 8/2016 |
| WO | WO 2016/192613 | 8/2016 |
| WO | WO 2016/145139 | 9/2016 |
| WO | WO 2016/176651 | 11/2016 |
| WO | WO 2016/201300 | 12/2016 |
| WO | WO 2017/004144 | 1/2017 |
| WO | WO 2017/023761 | 2/2017 |
| WO | WO 2017/060144 | 4/2017 |
| WO | WO 2018/044534 | 3/2018 |
| WO | WO 2018/134691 | 7/2018 |
| WO | WO 2020/033927 | 2/2020 |

OTHER PUBLICATIONS

Abramson et al., "CR rates in relapsed/refractory (R/R) aggressive B-NHL treated with the CD19-directed CAR T-cell product JCAR017 (Transcend NHL 001)," J. Clin. Oncol. (2017) 35 (15): 7513 Abstract.

Abramson et al., "High CR Rates in relapsed/refractory (R/R) aggressive B-NHL treated with CD19-directed CAR T cell product JCAR017 (Transcend NHL 001)," Poster 7513 presented Jun. 2, 2017 at ASCO 2017.

Dai et al., "Chimeric Antigen Receptors Modified T-Cells for Cancer Therapy." J Natl Cancer Inst. (2016) 108(7); djv349.

Davila et al., "Biology and clinical application of CAR T cells for B cell malignancies." Int J Hematol. Jul. 2016;104(1):6-17.

Huss, D., "PET Imaging of Chimeric Antigen Receptor T Cells," Presentation, presented at The World Molecular Imaging Congress (WMIC), Sep. 15, 2017.

McCracken et al., "Noninvasive detection of tumor-infiltrating T cells by PET reporter imaging." J Clin Invest. 2015;125(5):1815-1826.

Minn et al., "Imaging CAR T cell therapy with PSMA-targeted positron emission tomography," Sci Adv. (2019) 5(7): eaaw5096.

Minn et al., "PSMA-Associated PET Imaging of CAR-T Cells," Abstract, Society for Immunotherapy of Cancer 2017; Nov. 8-12, 2017; National Harbor, MD.

Minn et al., "PSMA-Associated PET Imaging of CAR-T Cells," Poster Presentation P300, presented at Society for Immunotherapy of Cancer 2017; Nov. 8-12, 2017; National Harbor, MD.

(56) References Cited

OTHER PUBLICATIONS

Park et al., "CD19-targeted CAR T-cell therapeutics for hematologic malignancies: interpreting clinical outcomes to date." Blood. Jun. 30, 2016;127(26):3312-20.
Rajasekaran et al., "Is prostate-specific membrane antigen a multifunctional protein?" Am J Physiol Cell Physiol. May 2005;288(5):C975-81.
Scott-Browne et al., "Dynamic Changes in Chromatin Accessibility Occur in CD8+ T Cells Responding to Viral Infection." Immunity. (2016) 45(6): 1327-1340.
Silver et al. "Prostate-specific membrane antigen expression in normal and malignant human tissues." Clin Cancer Res.(1997) 3: 81-85.
Yaghoubi et al., "Noninvasive detection of therapeutic cytolytic T cells with 18F-FHBG PET in a patient with glioma." Nat Clin Pract Oncol. (2009) 6(1): 53-58.
U.S. Appl. No. 16/500,352, filed Oct. 2019, by Huss et al. (Copy not provided). (Copy not submitted herewith pursuant to the waiver of 37 C.F. R. § 1.98(a)(2)(iii) issued by the Office on Sep. 21, 2004).
Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2: e93.
Banerjee et al., "Sequential SPECT and optical imaging of experimental models of prostate cancer with a dual modality inhibitor of the prostate-specific membrane antigen," Angew Chem Int Ed Engl. (2011) 50(39):9167-9170.
Barinka et al., "Selection and characterization of Anticalins targeting human prostate-specific membrane antigen (PSMA)," Protein Engineering, Design and Selection. (2016) 29(3):105-115.
Barinka et al., "Amino acids at the N- and C-termini of human glutamate carboxypeptidase II are required for enzymatic activity and proper folding," Eur J Biochem. (2004) 271(13): 2782-2790.
Barrett et al., "Chimeric Antigen Receptor Therapy for Cancer," Annual Review of Medicine (2013) 65:333-347.
Brash et al., "Strontium phosphate transfection of human cells in primary culture: stable expression of the simian virus 40 large-T-antigen gene in primary human bronchial epithelial cells," Mol. Cell Biol. (1987) 7: 2031-2034.
Brentjens et al., "CD19-targeted T cells rapidly induce molecular remissions in adults with chemotherapy-refractory acute lymphoblastic leukemia," Sci Transl Med. (2013) 5(177):177ra38.
Carlens et al., "Ex vivo T lymphocyte expansion for retroviral transduction: influence of serum-free media on variations in cell expansion rates and lymphocyte subset distribution," Exp Hematol (2000) 28(10): 1137-46.
Caromile et al., "PSMA Redirects Cell Survival Signaling From the MAPK to the PI3K-AKT Pathways to Promote the Progression of Prostate Cancer," Sci Signal. (2017) 10(470): eaag3326.
Carrillo et al., "The Multiple Sequence Alignment Problem in Biology," SIAM Journal on Applied Mathematics (1988) 48(5):1073-1082.
Castanares et al.,"Evaluation of prostate-specific membrane antigen as an imaging reporter," The Journal of Nuclear Medicine (2014) 55(5): 805-811.
Cavalieri et al., "Human T lymphocytes transduced by lentiviral vectors in the absence of TCR activation maintain an intact immune competence," Blood (2003) 102(2): 497-505.
Cheadle et al., "Chimeric antigen receptors for T-cell based therapy," Methods Mol Biol (2012) 907:645-666.
Chervin et al., "Engineering higher affinity T cell receptors using a T cell display system," J Immunol Methods. (2008) 339(2): 175-84.
Chicaybam et al., "An efficient low cost method for gene transfer to T lymphocytes," PLoS ONE (2013) 8(3): e60298.
Cho et al., "Human mammalian cell sorting using a highly integrated micro-fabricated fluorescence-activated cell sorter (microFACS)," Lab Chip (2010) 10: 1567-1573.
Chothia et al.,. "The outline structure of the T-cell alpha beta receptor," EMBO J. (1988) 7(12): 3745-55.
Clackson et al., "Making antibody fragments using phage display libraries," Nature (1991) 352(6336):624-628.
Clarke and Davies in: Methods in Molecular Medicine, vol. 58: Metastasis Research Protocols, vol. 2: Cell Behavior In Vitro and In Vivo, Edited by: S. A. Brooks and U. Schumacher© Humana Press Inc., Totowa, NJ (2001) pp. 17-25.
Cohen et al., "Recombinant antibodies with MHC-restricted, peptide-specific, T-cell receptor-like specificity: new tools to study antigen presentation and TCR-peptide-MHC interactions," J Mol Recognit. (2003) 16(5): 324-32.
Conway et al., "Prostate-Specific Membrane Antigen Regulates Angiogenesis by Modulating Integrin Signal Transduction," Mol Cell Biol. (2006) 26(14): 5310-5324.
Cooper et al., "T-cell clones can be rendered specific for CD19: toward the selective augmentation of the graft-versus-B-lineage leukemia effect," Blood. (2003) 101:1637-1644.
Davila et al., "CD19 CAR-targeted T cells induce long-term remission and B Cell Aplasia in an immunocompetent mouse model of B cell acute lymphoblastic leukemia," PLoS ONE (2013) 8(4): e61338.
Davis et al., "Crystal structure of prostate-specific membrane antigen, a tumor marker and peptidase," Proc Natl Acad Sci U S A. (2005) 102(17): 5981-5986.
De Felipe et al., "Targeting of proteins derived from self-processing polyproteins containing multiple signal sequences," Trafic (2004) 5(8):616-626.
De Felipe, "Skipping the co-expression problem: the new 2A "Chysel" technology," Genetics Vaccines and Therapy (2004) 2:13.
Drabkin et al., "Initiation of Protein Synthesis in Mammalian Cells With Codons Other Than AUG and Amino Acids Other Than Methionine," Mol Cell Biol. (1998) 18(9): 5140-5147.
Evan et al., "Isolation of monoclonal antibodies specific for human c-myc proto-oncogene product," Mol Cell Biol. (1985) 5(12): 3610-3616.
Fairhead et al., "Plug-and-play pairing via defined divalent streptavidins," J Mol Biol. (2014) 426(1): 199-214.
Field et al., "Purification of a RAS-responsive adenylyl cyclase complex from *Saccharomyces cerevisiae* by use of an epitope addition method," Mol Cell Biol. (1988) 8(5): 2159-65.
Ghosh et al., "Tumor target prostate specific membrane antigen (PSMA) and its regulation in prostate cancer," Journal of Cellular Biochemistry (2004) 91(3):528-539.
Godin et al., "Microfluidics and photonics for Bio-System-on-a-Chip: a review of advancements in technology towards a microfluidic flow cytometry chip," J Biophoton. (2008) 1(5):355-376.
Hermans et al., "The VITAL assay: a versatile fluorometric technique for assessing CTL- and NKT-mediated cytotoxicity against multiple targets in vitro and in vivo," J. Immunological Methods (2004) 285(1): 25-40.
Holler et al., "In vitro evolution of a T cell receptor with high affinity for peptide/MHC," Proc Natl Acad Sci U S A. (2000) 97(10): 5387-5392.
Holler et al., "TCRs with high affinity for foreign pMHC show self-reactivity," Nat Immunol. Jan. 2003;4(1):55-62.
Howarth et al., "A monovalent streptavidin with a single femtomolar biotin binding site," Nat Methods. (2006) 3(4): 267-273.
Huang et al., "DNA transposons for modification of human primary T lymphocytes," Methods Mol Biol (2009) 506: 115-126.
Hudecek et al., "Receptor affinity and extracellular domain modifications affect tumor recognition by ROR1-specific chimeric antigen receptor T cells," Clin Cancer Res (2013) 19(12):3153-3164.
Hutten et al., "New magnetic nanoparticles for biotechnology," J Biotechnol. (2004) 112(1-2): 47-63.
Janeway et al., Immunobiology: The Immune System in Health and Disease, 3rd ED., Current Biology Publications (1997), p. 4:33.
Jin et al., "PSMA-Specific Ligands in Prostate Cancer Diagnosis and Therapy," EMJ Urol (2016) 4(1): 62-69.
Johnston, et al., "Biolistic transformation: microbes to mice," Nature (1990) 346: 776-777.
Jores et al., "Resolution of hypervariable regions in T-cell receptor beta chains by a modified Wu-Kabat index of amino acid diversity.," PNAS (1990) 87(23):9138-9142.
Kampmeier et al., "Design and preclinical evaluation of a 99mTc-labelled diabody of mAb J591 for SPECT imaging of prostate-specific membrane antigen (PSMA)," EJNMMI Res. (2014) 4(1):13.

(56) References Cited

OTHER PUBLICATIONS

Kindt et al., "Antigens and Antibodies," in Chapter 4 of Kuby Immunology, 6th ed., W.H. Freeman and Co., N.Y, (2007) pp. 91, 14 pages.
Klebanoff et al., "Sorting through subsets: which T-cell populations mediate highly effective adoptive immunotherapy?," J Immunother. (2012) 35(9): 651-660.
Kochenderfer et al., "Construction and preclinical evaluation of an anti-CD19 chimeric antigen receptor," J. Immunotherapy (2009) 32(7): 689-702.
Kochenderfer et al., "Treating B-cell cancer with T cells expressing anti-CD19 chimeric antigen receptors," Nature Reviews Clinical Oncology (2013) 10:267-276.
Koste et al., "T-cell receptor transfer into human T cells with ecotropic retroviral vectors," Gene Therapy (2014) 21: 533-538.
Kotb, "Bacterial pyrogenic exotoxins as superantigens," Clin Microbiol Rev. (1995) 8(3):411-26.
Kurucz et al., "A bacterially expressed single-chain Fv construct from the 2B4 T-cell Yeceptor," Proc Natl Acad Sci U S A. (1993) 90(9): 3830-3834.
Lefranc et al., "IMGT unique numbering for immunoglobulin and T cell receptor variable domains and Ig superfamily V-like domains," Dev Comp Immunol (2003) 27(1):55-77.
Li et al., "Directed evolution of human T-cell receptors with picomolar affinities by phage display," Nat Biotechnol. (2005) 23:349-354.
Lim et al., "Engineered streptavidin monomer and dimer with improved stability and function," Biochemistry. (2011) 50(40):8682-91.
Liu et al., "Inclusion of Strep-tag II in design of antigen receptors for T-cell immunotherapy," Nature Biotechnology (2016) 34(4):430-434.
Liu et al., "Monoclonal antibodies to the extracellular domain of prostate-specific membrane antigen also react with tumor vascular endothelium," Cancer Res. (1997) 57(17): 3629-3634.
Lloyd et al., "Beyond the antigen receptor: editing the genome of T-cells for cancer adoptive cellular therapies," Front Immunol (2013) 4(221):1-7.
Luke et al., 2A to the Fore—Research, Technology and Applications, Biotechnol Genet Eng Rev. (2010) 26:223-260.
Lupton et al., "Dominant positive and negative selection using a hygromycin phosphotransferase-thymidine kinase fusion gene," Mol. and Cell Biol. (1991) 11:6.
Mahalingam et al., "Mipsagargin, a novel thapsigargin-based PSMA activating prodrug:results of a first-in-man phase I clinical trial in patients with refractory, advanced or metastatic solid tumours," British Journal of Cancer (2016) 114(9):986-994.
Manuri et al., "piggyBac transposon/transposase system to generate CD19-specific T cells for the treatment of B-lineage malignancies," Hum Gene Ther (2010) 21(4): 427-437.
Maurer et al., "Current use of PSMA-PET in prostate cancer management," Nat Rev Urol. (2016) 13(4):226-35.
Mease et al., "PET imaging in prostate cancer: focus on prostate-specific membrane antigen," Curr Top Med Chem. (2013) 13(8): 951-962.
Mesters et al., "Structure of glutamate carboxypeptidase II, a drug target in neuronal damage and prostate cancer," EMBO J. (2006) 25(6): 1375-1384.
Mlcochova et al., "Prostate-specific membrane antigen and its truncated form PSM," Prostate (2009)69(5): 471-479.
Mullen et al., "Transfer of the bacterial gene for cytosine deaminase to mammalian cells confers lethal sensitivity to 5-fluorocytosine: a negative selection system," Proc. Natl. Acad. Sci. USA (1992) 89:33.
Noguchi et al., "Preparation and properties of the immunoconjugate composed of anti-human colon cancer monoclonal antibody and mitomycin C-dextran conjugate," Bioconjug Chem. (1992) 3(2): 132-137.
Osborne et al., "Prostate-specific membrane antigen-based imaging," Urol Oncol. (2013) 31(2): 144-54.
Paborsky et al., "Mammalian cell transient expression of tissue factor for the production of antigen," Protein Eng. (1990) 3(6): 547-53.
Park et al., "Treating cancer with genetically engineered T cells," Trends Biotechnol. (2011) 29(11): 550-557.
Portlano et al., "Lack of promiscuity in autoantigen-specific H and L chain combinations as revealed by human H and L chain "roulette"," J Immunol (1993) 150(3):880-887.
Rajasekaran et al., "A novel cytoplasmic tail MXXXL motif mediates the internalization of prostate-specific membrane antigen," Mol Biol Cell. (2003) 14(12): 4835-45.
Rajasekaran et al., "Prostate-specific membrane antigen associates with anaphase-promoting complex and induces chromosomal instability," Mol Cancer Ther. (2008) 7(7) 2142-2151.
Rajasekaran, "Identification and Characterization of Internalization Signal of the Prostate Specific Membrane Antigen," Annual Summary Report, Aug. 1999; Ad No. ADB253500.
Regino et al., "Preclinical evaluation of a monoclonal antibody (3C6) specific for prostate-specific membrane antigen," Curr Radiopharm. (2009) 2(1): 9-17.
Riddell et al., "Phase I study of cellular adoptive immunotherapy using genetically modified CD8+ HIV-specific T cells for HIV seropositive patients undergoing allogeneic bone marrow transplant," Human Gene Therapy (1992) 3:319-338.
Rosenberg, et al., "Cell transfer immunotherapy for metastatic solid cancer—what clinicians need to know," Nat Rev Clin Oncol. (2011) 8(10):577-85).
Rowe et al., "PET imaging of prostate-specific membrane antigen in prostate cancer: current state of the art and future challenges," Prostate Cancer Prostatic Dis. (2016) 19(3): 223-30.
Ruggiero et al., "Targeting the internal epitope of prostate-specific membrane antigen with 89Zr-7E11 immuno-PET," J Nucl Med. (2011) 52(10): 1608-1615.
Sadelain et al., "The basic principles of chimeric antigen receptor design," Cancer Discov. (2013) 3(4): 388-398.
Schlueter et al., "Specificity and binding properties of a single-chain T cell receptor," J Mol Biol. (1996) 256(5): 859-69.
Schmidt et al., "The Strep-tag system for one-step purification and high-affinity detection or capturing of proteins," Nature Protocols (2007) 2(6):1528-1535.
Schuler et al., Schuler et al. SYFPEITHI, Database for Searching and T-Cell Epitope Prediction. in Immunoinformatics Methods in Molecular Biology, (2007) 409(1): 75-93.
Sharma et al., "Efficient sleeping beauty DNA transposition from DNA minicircles," Molec Ther Nucl Acids (2013) 2, e74.
Singh et al., "ProPred: prediction of HLA-DR binding sites," Bioinformatics. (2001) 17(12): 1236-7.
Skerra et al., "Use of the Strep-Tag and streptavidin for detection and purification or recombinant proteins," Methods in Enzymo. (2000) Academioc Press, U.S. 326:271-304.
Soo Hoo et al., "Characterization of a single-chain T-cell receptor expressed in *Escherichia coli*," Proc Natl Acad Sci U S A. (1992) 89(10): 4759-4763.
Speno et al., "Site-directed mutagenesis of predicted active site residues in glutamate carboxypeptidase II," Mol Pharmacol. (1999) 55(1): 179-185.
Stemberger et al., "Novel Serial Positive Enrichment Technology Enables Clinical Multiparameter Cell Sorting," PLoS One (2012) 7(4): e35798.
STREP-TAG "In vivo PPI analysis using Twin-Strep-tag® and Strep-tag," Comprehensive Manual, Oct. 2012, Version PR27-0004. www.strep-tag.com.
Sugimoto et al., "The therapeutic potential of a novel PSMA antibody and its IL-2 conjugate in prostate cancer," Anticancer Research (2014) 34:89-98.
Szoka et al., "Comparative properties and methods of preparation of lipid vesicles (liposomes)," Ann. Rev. Biophys. Bioeng. (1980) 9: 467.
Terakura et al., "Generation of CD19-chimeric antigen receptor modified CD8+ T cells derived from virus-specific central memory T cells," Blood (2012) 1:72-82.

(56) References Cited

OTHER PUBLICATIONS

Themeli et al., "Generation of tumor-targeted human T lymphocytes from induced pluripotent stem cells for cancer therapy," Nat Biotechnol. (2013) 31 (10): 928-933.
Tino et al., "Isolation and characterization of monoclonal antibodies specific for protein conformational epitopes present in prostate-specific membrane antigen (PSMA)," Hybridoma. (2000) 19(3): 249-57. (Abstract only).
Tsukahara et al., "CD19 target-engineered T-cells accumulate at tumor lesions in human B-cell lymphoma xenograft mouse models," Biochem Biophys Res Commun (2013) 438(1): 84-89.
Turtle et al., "Engineered T cells for anti-cancer therapy," Curr. Opin. Immunol. (2012) 24(5): 633-39.
Tykvart et al., "Comparative analysis of monoclonal antibodies against prostate-specific membrane antigen (PSMA)," Prostate. (2014) 74(16): 1674-90.
Van Tendeloo et al., "High-level transgene expression in primary human T Tymphocytes and adult bone marrow CD34+ cells via electroporation-mediated gene delivery," Gene Therapy (2000) 7(16): 1431-1437).
Vedvyas et al., "Longitudinal PET imaging demonastrates biphasic CAR T cell responses in survivors," JCI Insight (2016) 1(19):e90064 (17 pages).
Verhoeyen et al., "Lentiviral vector gene transfer into human T cells," Methods Mol Biol. (2009) 506: 97-114.
Wadhwa et al., "Receptor mediated glycotargeting," J. Drug Targeting (1995) 3: 111.
Wang et al., "A transgene-encoded cell surface polypeptide for selection, in vivo tracking, and ablation of engineered cells," Blood (2011) 118(5):1255-1263.
Wang et al., "Phenotypic and functional attributes of lentivirus-modified CD19-specific human CD8+ central memory T cells manufactured at clinical scale," J Immunother. (2012) 35(9):689-701.
Wigler et al., "Transfer of purified herpes virus thymidine kinase gene to cultured mouse cells," Cell (1997) 11: 223-232.
Wolf, Philipp (2011), Prostate Specific Membrane Antigen as Biomarker and Therapeutic Target for Prostate Cancer, Prostate Cancer—Diagnostic and Therapeutic Advances, Dr. Philippe E. Spiess (Ed.), Intech, pp. 81-100.
Wolf et al., "Three conformational antibodies specific for different PSMA epitopes are promising diagnostic and therapeutic tools for prostate cancer," Prostate. (2010) 70(5): 562-569.
Wu et al., "Adoptive T-cell therapy using autologous tumor-infiltrating lymphocytes for metastatic melanoma: current status and future outlook," Cancer (2012) 18(2): 160-175.
Wu et al., "Engineering soluble monomeric streptavidin with reversible biotin binding capability", J. Biol. Chem. (2005) 280(24): 23225-23231.
Wulfing et al., "Correctly folded T-cell receptor fragments in the periplasm of *Escherichia coli*. Influence of folding catalysts," J Mol Biol. (1994) 242(5): 655-69.
Yu et al., "Targeting Strategies for Multifunctional Nanoparticles in Cancer Imaging and Therapy," Theranostics. (2012); 2(1): 3-44.
Zhang et al., "A novel approach to make homogeneous protease-stable monovalent streptavidin," Biochem Biophys Res Commun. (2015) 463(4): 1059-63.
Zhang et al., "Circulating PD-L1 in NSCLC Patients and the Correlation Between the Level of PD-L1 Expression and the Clinical Characteristics," Thorac Cancer. (2015) 6(4): 534-53.
Zheng et al., "Protein L: a novel reagent for the detection of chimeric antigen receptor (CAR) expression by flow cytometry," J Transl Med. (2012) 10:29, 6 pages.
Bacich et al., "Cloning, Expression, Genomic Localization, and Enzymatic Activities of the Mouse Homolog of Prostate-Specific Membrane antigen/NAALADase/folate Hydrolase," Mamm Genome (2001) 12 (2): 117-23.
Benesova et al., "Preclinical Evaluation of a Tailor-Made DOTA-Conjugated PSMA Inhibitor With Optimized Linker Moiety for Imaging and Endoradiotherapy of Prostate Cancer," J Nucl Med (2015) 56(6): 914-920.
Bhatnagar et al., "Imaging of Genetically Engineered T Cells by PET using Gold Nanoparticle Complexed to Copper-64," Integr Biol (Camb). 2013; 5(1): 231-238.
Chang, "Overview of Prostate-Specific Membrane Antigen," Rev Urol (2004) 6(Suppl 10):S13-S18.
Chen et al., "2-(3-{1-Carboxy-5-[(6-[18F]fluoro-pyridine-3-carbonyl)-amino]-pentyl}-ureido)-pentanedioicAcid, [18F]DCFPyL, a PSMA-based PET Imaging Agent for Prostate Cancer," Clin Cancer Res (2011) 17(24): 7645-7653.
De Goeij et al., "New developments for antibody-drug conjugate-based therapeutic approaches," Curr Opin Immunol (2016) 40: 14-23.
Keu et al. "Reporter Gene Imaging of Targeted T Cell Immunotherapy in Recurrent Glioma," Sci Transl Med (2017) 9 (373), 25 pages.
Kiess et al., "Auger Radiopharmaceutical Therapy Targeting Prostate-Specific Membrane Antigen," J Nucl Med (2015) 56(9): 1401-1407.
Kim et al., "Strategies and Advancement in Antibody-Drug Conjugate Optimization for Targeted Cancer Therapeutics," Biomol Ther (Seoul) (2015) 23(6): 493-509.
Korndorfer et al. "Improved affinity of engineered streptavidin for the Strep-tag li peptide is due to a fixed open conformation of the iid-iike loop at the binding site." Protein science 11.4 (2002): 883-893.
Material Safetydata Sheet Msds Name:Human Her2/ErbB2 Protein, Strep Tag, 2016, p. 1-3.
Najjar et al., "Imaging of Sleeping Beauty-Modified CD19-SpecificT Cells Expressing HSV1-Thymidine Kinase by Positron Emission Tomography," Mol Imaging Biol (2016) 18(6): 838-848.
Pyka et al., "68Ga-PSMA-HBED-CC PET for Differential Diagnosis of Suggestive Lung Lesions in Patients With Prostate Cancer," J Nucl Med (2016) 57(3): 367-371.
Schulke et al., "The Homodimer of Prostate-Specific Membrane Antigen Is a Functional Target for Cancer Therapy," Proc Natl Acad Sci U Sa (2003) 100(22): 12590-12595.
Szabo et al., "Initial Evaluation of [(18)F]DCFPyL for Prostate-Specific Membrane Antigen (PSMA)-Targeted PET Imaging of Prostate Cancer," Mol Imaging Biol (2015) 17(4): 565-574.
Wang et al., "Structure-activity Relationships of 2',5'-oligoadenylate Analogue Modifications of Prostate-Specific Membrane Antigen (PSMA) Antagonists," Nucleosides Nucleotides Nucleic Acids (2012) 31(5): 432-444 (Abstract only).

CELL SURFACE CONJUGATES AND RELATED CELL COMPOSITIONS AND METHODS

CROSS-REFERENCE TO RELATED APPLICATIONS

This application is a national stage application under 35 U.S.C. § 371 of International Application No. PCT/IB2018/000380, filed on Jan. 19, 2018, which claims priority from U.S. provisional application No. 62/448,936, filed Jan. 20, 2017, entitled "CELL SURFACE CONJUGATES AND RELATED CELL COMPOSITIONS AND METHODS," the contents of which are incorporated by reference in their entirety.

INCORPORATION BY REFERENCE OF SEQUENCE LISTING

The present application is being filed along with a Sequence Listing in electronic format. The Sequence Listing is provided as a file entitled 735042002600SeqList.TXT, created Jul. 18, 2019 which is 209,093 bytes in size. The information in the electronic format of the Sequence Listing is incorporated by reference in its entirety.

FIELD

The present disclosure relates in some aspects to cell surface conjugates containing a cell surface molecule and at least one agent, such as at least one affinity tag, and engineered cells expressing such cell surface conjugates. In some embodiments, the cell surface molecule does not contain an intracellular signaling domain or is not capable of mediating intracellular signaling. In some embodiments, the cells engineered to contain the cell surface conjugate, such as T cells, further contain a genetically engineered recombinant receptor, such as a chimeric antigen receptor, that specifically binds to antigen. The present disclosure also provides methods of detecting, identifying, selecting or targeting cells expressing the cell surface conjugtes, such as in connection with methods of manufacturing engineered cells or in connection with administration of such cells to subjects, including methods of adoptive cell therapy.

BACKGROUND

Various strategies are available for treatment of diseases or conditions such as cancers or tumors, including the administration of cell therapies. Further, strategies are available for engineering immune cells to express genetically engineered recombinant receptors, such as chimeric antigen receptors (CARs), and administering compositions containing such cells to subjects. Improved strategies are needed to increase efficacy of the treatments, for example, by improving the engineered compositions and/or improving the ability to monitor or modulate the engineered compositions in connection with such therapies upon administration to subjects. Provided are compositions, cells, and methods that meet such needs.

SUMMARY

Provided herein is a cell surface conjugate containing a cell surface molecule that lacks a functional intracellular signaling domain and/or is not capable of mediating intracellular signaling; and at least one agent linked to the cell surface molecule, the agent being capable of binding streptavidin or a streptavidin mutein. In some embodiments, the agent exhibits a binding affinity for streptavidin or a streptavidin, a streptavidin analog or mutein with an equilibrium dissociation constant ($K_D$) of from or from about $10^{-4}$ M to or to about $10^{-10}$ M.

Also provided is a cell surface conjugate containing a cell surface molecule that lacks a functional intracellular signaling domain and/or is not capable of mediating intracellular signaling; and at least one agent linked to the cell surface molecule and being capable of reversibly binding to a reagent and/or capable of being competed for binding to the reagent in the presence of a competition substance, wherein the agent is a peptide of less than 50 amino acids in length. In some embodiments, the agent exhibits a binding affinity for the reagent with an equilibrium dissociation constant ($K_D$) of from or from about $10^{-4}$ M to or to about $10^{-10}$ M. In some of any such embodiments, the reagent is streptavidin or a streptavidin, a streptavidin analog or mutein.

In some embodiments, the cell surface molecule comprises a transmembrane domain and/or is capable of being expressed on the surface of the cell. In some embodiments, the cell surface molecule is modified compared to a reference cell surface molecule, optionally wherein the reference cell surface molecule is a cell surface receptor comprising an intracellular signaling domain. In some embodiments, the modified cell surface molecule exhibits altered cellular internalization, enzymatic activity and/or ligand binding, compared to the reference cell surface molecule.

Also provided are cell surface conjugates, containing (a) a cell surface molecule that is modified compared to a reference cell surface molecule, wherein the modified cell surface molecule exhibits altered cellular internalization, enzymatic activity and/or ligand binding, compared to the reference cell surface molecule; and (b) at least one agent linked to the cell surface molecule, the agent being capable of binding a streptavidin, a streptavidin analog or a streptavidin mutein.

In some embodiments, the cell surface molecule lacks a functional intracellular signaling domain and/or is not capable of mediating intracellular signaling. Also provided are cell surface conjugates, containing (a) a cell surface molecule comprising a prostate-specific membrane antigen (PSMA) or a modified cell surface molecule thereof; and (b) at least one agent linked to the cell surface molecule, the agent being capable of binding a streptavidin, a streptavidin analog or a streptavidin mutein. In some embodiments, the modified cell surface molecule lacks a functional intracellular signaling domain and/or is not capable of mediating intracellular signaling; and/or the modified cell surface molecule is modified compared to a reference cell surface molecule, wherein the modified cell surface molecule exhibits altered cellular internalization, enzymatic activity and/or ligand binding, compared to the reference cell surface molecule. In some embodiments, the cell surface molecule comprises a transmembrane domain and/or is capable of being expressed on the surface of the cell. In some embodiments, the agent exhibits a binding affinity for a streptavidin, a streptavidin analog or a streptavidin mutein with an equilibrium dissociation constant ($K_D$) of from or from about $10^{-4}$ M to or to about $10^{-10}$ M.

Provided herein is a cell surface conjugate containing a cell surface molecule that lacks a functional intracellular signaling domain and/or is not capable of mediating intracellular signaling; and at least one agent linked to the cell surface molecule, the agent having a binding affinity for a reagent with an equilibrium dissociation constant ($K_D$) of more than $10^{-7}$ M or an equilibrium association constant ($K_A$) of less than $10^7$ M$^{-1}$. In some instances, the reagent is streptavidin or a streptavidin analog or mutein.

In any of the provided embodiments, the cell surface molecule is a cell surface protein.

In some of any such embodiments, the binding of the agent to the reagent is reversible and/or is capable of being competed for binding to the reagent in the presence of a competition substance. In some aspects, the competition substance exhibits a higher binding affinity for the reagent than the binding affinity of the agent for the reagent. In some embodiments, the competition substance exhibits a binding affinity for the reagent with an equilibrium dissociation constant ($K_D$) of between or about between $10^{-10}$ M and $10^{-14}$M; and/or the agent exhibits a binding affinity for the reagent with an equilibrium dissociation constant ($K_D$) of more than $10^{-10}$ M.

In some of any such embodiments, the binding of the agent to the streptavidin or a streptavidin, streptavidin analog or mutein is reversible and/or capable of being competed for binding to the reagent in the presence of biotin, a biotin analog or a biologically active fragment thereof.

In some of any such embodiments, the at least one agent is linked directly to the cell surface molecule. In some of any such embodiments, the at least one agent is linked indirectly to the cell surface molecule via at least one linker.

In some aspects, the cell surface conjugate containing the cell surface molecule and the at least one agent (e.g. a peptide, such as a streptavidin-binding peptide) is a fusion protein.

In some of any such embodiments, the at least one agent includes from or from about 1 to 4 or 1 to 2 agents. In some of any such embodiments, the at least one agent is only one agent. In some of any such embodiments, the agent is linked to an extracellular portion or region of the cell surface molecule, optionally wherein the extracellular portion or region is at the N-terminus or C-terminus of the cell surface molecule. In some of any such embodiments, the agent is linked at the N-terminus of the cell surface molecule. In some of any such embodiments, the agent is linked at the C-terminus of the cell surface molecule.

Also provided is a cell surface conjugate containing a cell surface molecule, such as a cell surface protein, linked at its N-terminus to an agent, the agent being capable of binding a reagent that is or contains streptavidin or a streptavidin mutein.

Also provided is a cell surface conjugate containing a cell surface molecule, such as a cell surface protein, linked at its N-terminus to an agent capable of reversibly binding to a reagent, wherein the agent is a peptide of less than 50 amino acids in length.

In some of any such embodiments, the agent exhibits a binding affinity for a reagent, e.g. a reagent that is or contains a streptavidin or a streptavidin analog or mutein, with an equilibrium dissociation constant ($K_D$) of from or from about $10^{-4}$ to $10^{-10}$ M.

Also provided are cell surface conjugates comprising a cell surface molecule linked, at an extracellular portion or region of the cell surface molecule, to an agent, the agent being capable of binding a reagent that is or comprises streptavidin or a streptavidin mutein, optionally wherein the extracellular portion or region is at the N-terminus or C-terminus of the cell surface molecule.

Also provided are cell surface conjugates comprising a cell surface molecule linked, at an extracellular portion or region of the cell surface molecule, to an agent, the agent being capable of reversibly binding to a reagent, wherein the agent is a peptide of less than 50 amino acids in length optionally wherein the extracellular portion or region is at the N-terminus or C-terminus of the cell surface molecule.

In some embodiments, the agent exhibits a binding affinity with an equilibrium dissociation constant ($K_D$) of from or from about $10^{-4}$ M to or to about $10^{-10}$ M.

Also provided are cell surface conjugates comprising a cell surface molecule linked, at an extracellular portion or region of the cell surface molecule, to an agent, wherein the agent exhibits a binding affinity for a reagent with an equilibrium dissociation constant ($K_D$) of more than $10^{-7}$ M or an equilibrium association constant ($K_A$) of less than $10^7$ M$^{-1}$ optionally wherein the extracellular portion or region is at the N-terminus or C-terminus of the cell surface molecule. In some embodiments, the agent is linked at the N-terminus of the cell surface molecule. In some embodiments, the agent is linked at the C-terminus of the cell surface molecule.

Also provided is a cell surface conjugate containing a cell surface molecule, such as a cell surface protein, linked at its N-terminus to an agent, wherein the agent exhibits a binding affinity for a reagent with an equilibrium dissociation constant ($K_D$) of more than $10^{-7}$ M or an equilibrium association constant ($K_A$) of less than $10^7$ M$^{-1}$. In some of any such embodiments, the reagent is or contains streptavidin or a streptavidin analog or mutein.

In some of any such embodiments, the binding of the agent to the reagent, e.g. a reagent that is or contains a streptavidin or a streptavidin analog or mutein, is reversible and/or capable of being competed for binding to the reagent in the presence of a competition substance. In some cases, the competition substance exhibits a higher binding affinity for the reagent than the binding affinity of the agent for the reagent. In some examples, the competition substance exhibits a binding affinity for the reagent of between or about between $10^{-10}$ and $10^{-14}$; and/or the agent exhibits a binding affinity for the reagent of less than $10^{-10}$. In some of any such embodiments, the reagent is a streptavidin or a streptavidin analog or mutein and the binding of the agent to the streptavidin or a streptavidin analog or mutein is reversible and/or capable of being competed for binding to the reagent in the presence of biotin or a biotin analog.

In some of any such embodiments, the agent is linked directly to the cell surface molecule, such as to a cell surface protein, including to a modified cell surface molecule as described. In some of any such embodiments, the agent is linked indirectly to the cell surface molecule via at least one linker. In some of any such embodiments, the cell surface molecule, such as a cell surface protein, is linked to only one agent.

In some of any such embodiments, the cell surface molecule is not a chimeric antigen receptor (CAR).

In some of any such embodiments, the cell surface molecule, such as a cell surface protein, lacks a functional intracellular signaling domain and/or is not capable of mediating intracellular signaling. In some of any such embodiments, the cell surface molecule is modified compared to a reference cell surface molecule. In some of any such embodiments, the reference cell surface molecule is a native mammalian cell surface molecule. In some of any such embodiments, the modified cell surface molecule comprises or retains an epitope of the reference cell surface molecule capable of being recognized by an antibody or antigen-binding fragment thereof. In some embodiments, the modified cell surface molecule lacks a functional intracellular signaling domain and/or is not capable of mediating intracellular signaling; and/or the modified cell surface molecule exhibits altered cellular internalization, enzymatic activity and/or ligand binding, compared to the reference cell surface molecule.

In some of any such embodiments, the cell surface conjugate is a fusion protein.

In some of any such embodiments, the streptavidin analog or mutein contains the amino acid sequence Val$^{44}$-Thr$^{45}$-Ala$^{46}$-Arg$^{47}$ or Ile$^{44}$-Gly$^{45}$-Ala$^{46}$-Arg$^{47}$ at sequence positions corresponding to positions 44 to 47 with reference to positions in streptavidin in the sequence of amino acids set forth in SEQ ID NO:1. In some of any such embodiments, the streptavidin analog or mutein contains a) the sequence of amino acids set forth in any of SEQ ID NOS: 3-6, 27 and 28; b) a sequence of amino acids that exhibits at least at or about 85%, 86%, 87%, 88%, 89%, 89%, 90%, 91%, 92%, 93%, 94%, 95%, 96%, 97%, 98%, 99% or more sequence identity to any of SEQ ID NOS:3-6, 27 and 28 and contains the amino acid sequence corresponding to Val$^{44}$-Thr$^{45}$-Ala$^{46}$-Arg$^{47}$ or Ile$^{44}$-Gly$^{45}$-Ala$^{46}$-Arg$^{47}$ and that reversibly binds to the agent; or c) a functional fragment of a) or b) that reversibly binds to the agent and/or in which binding to the agent is competed in the presence of a competition substance.

In some of any such embodiments, the streptavidin analog or mutein further contains an amino acid replacement or replacements at a position corresponding to 117, 120 and/or 121 with reference to positions in streptavidin in the sequence of amino acids set forth in SEQ ID NO:1. In some aspects, the amino acid replacement or replacements are selected from among Glu$^{117}$, Asp$^{117}$, Arg$^{117}$, Ser$^{120}$, Ala$^{120}$, Gly$^{120}$, Trp$^{121}$, Tyr$^{121}$ or Phe$^{121}$, or the amino acid replacement or replacements are selected from one or more of Glu$^{117}$, Gly$^{120}$ or Tyr$^{121}$; or the amino acid replacements are selected from Glu$^{117}$, Gly$^{120}$ or Tyr$^{121}$.

In some of any such embodiments, the streptavidin analog or mutein contains a) the sequence of amino acids set forth in SEQ ID NO: 27 or 28; b) a sequence of amino acids that exhibits at least at or about 85%, 86%, 87%, 88%, 89%, 89%, 90%, 91%, 92%, 93%, 94%, 95%, 96%, 97%, 98%, 99% or more sequence identity to SEQ ID NOS: 27 or 28 and contains the amino acid sequence corresponding to Val$^{44}$, Thr$^{45}$, Ala$^{46}$, Arg$^{47}$, Glu$^{120}$, and Tyr$^{121}$ and reversibly binds to the agent and/or in which binding to the agent is competed in the presence of a competition substance; or c) a functional fragment of a) or b) that reversibly binds to the agent and/or in which binding to the agent is competed in the presence of a competition substance.

In some of any such embodiments, the agent is an affinity tag. In some of any such embodiments, the agent is or contains a Strep tag, His tag, Flag tag, Xpress tag, Avi tag, Calmodulin tag, Polyglutamate tag, HA tag, Myc tag, Nus tag, S tag, X tag, SBP tag, Softag, V5 tag, CBP, GST, MBP, GFP, Thioredoxin tag, or any combination thereof. In some of any such embodiments, the agent is or comprises one or more streptavidin binding peptide, which optionally is a Strep tag.

In some of any such embodiments, the streptavidin-binding peptide contains the sequence Trp-Ser-His-Pro-Gln-Phe-Glu-Lys (SEQ ID NO: 8) or Trp-Arg-His-Pro-Gln-Phe-Gly-Gly (SEQ ID NO:7).

In some of any such embodiments, the agent contains the sequence Trp-Ser-His-Pro-Gln-Phe-Glu-Lys-(GlyGlyGlySer)$_3$-Trp-Ser-His-Pro-Gln-Phe-Glu-Lys (SEQ ID NO: 17), Trp-Ser-His-Pro-Gln-Phe-Glu-Lys-(GlyGlyGlySer)$_2$-Trp-Ser-His-Pro-Gln-Phe-Glu-Lys (SEQ ID NO: 18) and Trp-Ser-His-Pro-Gln-Phe-Glu-Lys-(GlyGlyGlySer)$_2$Gly-Gly-Ser-Ala-Trp-Ser-His-Pro-Gln-Phe-Glu-Lys (SEQ ID NO: 19).

In some of any such embodiments, the competition substance is or contains biotin, a biotin analog or a biologically active fragment thereof. Among such embodiments are those in which the agent is a streptavidin binding peptide and the reagent is a streptavidin or a streptavidin mutein or analog, including any as described.

In some of any such embodiments, the reference cell surface molecule is a cell surface protein that is a cell surface receptor, ligand, glycoprotein, cell adhesion molecule, antigen, integrin or cluster of differentiation (CD). In some embodiments, the reference cell surface molecule is a cell surface receptor. In some of any such embodiments, the reference cell surface molecule is selected from EpCAM, VEGFR, integrin (e.g., integrins αvβ3, α4, αIIbβ3, α4β7, α5β1, αvβ3, αv), a member of the TNF receptor superfamily (e.g., TRAIL-R1, TRAIL-R2), a member of the epidermal growth factor receptor family, PDGF Receptor, interferon receptor, folate receptor, GPNMB, ICAM-1, HLA-DR, CEA, CA-125, MUC1, TAG-72, IL-6 receptor, 5T4, GD2, GD3, prostate-specific membrane antigen (PSMA), or clusters of differentiation (e.g., CD2, CD3, CD4, CD5, CD11, CD11a/LFA-1, CD15, CD18/ITGB2, CD19, CD20, CD22, CD23/IgE Receptor, CD25, CD28, CD30, CD33, CD38, CD40, CD41, CD44, CD51, CD52, CD62L, CD74, CD80, CD125, CD147/basigin, CD152/CTLA-4, CD154/CD40L, CD195/CCR5 and CD319/SLAMF7.

In some of any such embodiments, the reference cell surface molecule, such as reference cell surface protein, is a member of the epidermal growth factor receptor family. In some of any such embodiments, the reference cell surface molecule is an epidermal growth factor receptor (EGFR), an erbB-2 receptor tyrosine-protein kinase (errb2, HER2), an erbB-3 receptor tyrosine-protein kinase, an erbB-4 receptor tyrosine-protein kinase, a hepatocyte growth factor receptor (HGFR/c-MET) or an insulin-like growth factor receptor-1 (IGF-1R). In some of any such embodiments, the reference cell surface molecule is a prostate-specific membrane antigen (PSMA).

In some of any such embodiments, the reference cell surface molecule, such as the reference cell surface protein, is human.

In some of any such embodiments, the modified cell surface molecule lacks a functional intracellular signaling domain and/or is not capable of mediating intracellular signaling. In some of any such embodiments, the modified cell surface molecule is truncated compared to the reference cell surface molecule, such as is truncated to remove or delete all or a portion of an intracellular region, i.e. a portion of the molecule contained inside the cell, of the reference cell surface molecule. In some cases, the intracellular region is a region that contains an intracellular signaling domain or trafficking domain. In some of any such embodiments, the modified cell surface molecule is truncated to lack all or a portion of the intracellular signaling domain or trafficking domain compared to the reference cell surface molecule. In some of any such embodiments, the modified cell surface molecule contains one or more extracellular domains of the reference cell surface molecule. In some embodiments, the modified cell surface molecule exhibits altered cellular internalization, enzymatic activity and/or ligand binding, compared to the reference cell surface molecule.

In some of any such embodiments, the modified cell surface molecule is capable of binding to a native ligand or substrate of the reference cell surface molecule. In some of any such embodiments, the modified cell surface molecule is reduced for or does not bind the native ligand or substrate of the reference cell surface molecule. In some of any such embodiments, the modified cell surface molecule contains at least one extracellular domain of the reference cell surface molecule but lacks one or more other extracellular domains recognized by the native ligand or substrate of the reference cell surface molecule. In some aspects, the at least one extracellular domain contains an epitope recognized by an antibody or antigen-binding fragment thereof that specifically binds the reference cell surface molecule. In some of any such embodiments, the antibody or antigen-binding fragment is selected from AMG-102, AMG-479, BIIB022OA-5D5, CP-751,871, IMC-A12, R1507, 3F8, abagovomab, abciximab, adecatumumab, afutuzumab, alemtuzumab, altumomab pentetate, anatumomab mafenatox, apolizumab, arcitumomab, aselizumab, atlizumab (=tocilizumab), basiliximab, bectumomab, benralizumab, besilesomab, bivatuzumab mertansine, blinatumomab, brentuximab vedotin, cantuzumab mertansine, capromab pendetide, catumaxomab, CC49, cedelizumab, celmoleukin, cetuximab, cixutumumab, clenoliximab, clivatuzumab tetraxetan, CNTO-95, conatumumab, dacetuzumab, daclizumab, daratumumab, detumomab, ecromeximab, ertumaxomab, edrecolomab, efalizumab, elotuzumab, enlimomab pegol, epitumomab cituxetan, epratuzumab, erlizumab, etaracizumab, fanolesomab, faralimomab, farletuzumab, figitumumab, galiximab, gavilimomab, gemtuzumab ozogamicin, glembatumumab vedotin, gomiliximab, ibalizumab, ibritumomab tiuxetan, igovomab, intetumumab, iratumumab, inolimomab, inotuzumab ozogamicin, ipilimumab, keliximab, labetuzumab, lintuzumab, lexatumumab, lucatumumab, lumiliximab, mapatumumab, maslimomab, matuzumab, milatuzumab, minretumomab, mitumomab, muromonab-CD3, naptumomab estafenatox, natalizumab, necitumumab, ocrelizumab, odulimomab, ofatumumab, olaratumab, oportuzumab monatox, oregovomab, otelixizumab, panitumumab, pertuzumab, pemtomomab, priliximab, PRO 140, nimotuzumab, robatumumab, rituximab, rovelizumab, ruplizumab, satumomab pendetide, siplizumab, sontuzumab, tadocizumab, taplitumomab paptox, teneliximab, teplizumab, TGN1412, ticilimumab (=tremelimumab), tigatuzumab, tocilizumab (=atlizumab), toralizumab, tositumomab, trastuzumab, tremelimumab, tucotuzumab, vedolizumab, veltuzumab, visilizumab, vitaxin, volociximab, votumumab, zalutumumab, zanolimumab, ziralimumab, zolimomab aritox, Atezolizumab, bevacizumab (Avastin®), denosumab, dinutuximab, nivolumab, obinutuzumab, pembrolizumab, pidilizumab (CT-011), ramucirumab, siltuximab, ado-trastuzumab emtansine, CEA-scan Fab fragment, OC125 monoclonal antibody, ab75705, B72.3, MPDL3280A, MSB001078C, MEDI4736, or an antigen binding fragment thereof.

In some of any such embodiments, the reference cell surface receptor is EGFR and the modified cell surface receptor is a modified EGFR. In some aspects, the modified EGFR contains an epitope specifically recognized by cetuximab or an antigen binding fragment thereof. In some instances, the modified EGFR lacks one or more of an EGFR Domain I, an EGFR Domain II, an EGFR Juxtamembrane Domain, and an EGFR Tyrosine Kinase Domain of the reference EGFR. In some of any such embodiments, the modified EGFR lacks all of the domains EGFR Domain I, an EGFR Domain II, an EGFR Juxtamembrane Domain, and an EGFR Tyrosine Kinase Domain of the reference EGFR of the reference EGFR. In some of any such embodiments, the modified EGFR comprises an extracellular domain that consists of or consists essentially of subdomain III and subdomain IV of the reference EGFR. In some of any such embodiments, the modified EGFR comprises the sequence of amino acids set forth in SEQ ID NOS: 44 or 46 or a sequence of amino acids that exhibits at least at or about 85%, 90%, or 95% sequence identity to SEQ ID NOS: 44 or 46.

In some of any such embodiments, the reference cell surface receptor is HER2 and the modified cell surface receptor is a modified HER2. In some aspects, the modified HER2 contains an epitope specifically recognized by trastuzumab or an antigen binding fragment thereof. In some of any such embodiments, the modified HER2 lacks one or more of an HER2 Domain I, an HER2 Domain II, an HER2 Domain III of the reference HER2. In some of any such embodiments, the modified HER2 lacks all of the domains HER2 Domain I, HER2 Domain II, and HER2 Domain III of the reference EGFR of the reference HER2. In some of any such embodiments, the modified HER2 comprises an extracellular domain that consists of or consists essentially of Domain IV of the reference HER2. In some of any such embodiments, the modified HER2 contains the sequence of amino acids set forth in SEQ ID NO: 92 or a sequence of amino acids that exhibits at least at or about 85%, 90%, or 95% sequence identity to SEQ ID NO: 92.

In some embodiments, the reference cell surface molecule is a reference PSMA and the modified cell surface molecule is a modified PSMA. In some embodiments, the reference PSMA is a wild-type PSMA, optionally wild-type human PSMA. In some embodiments, the reference PSMA is a human PSMA and/or comprises the sequence of amino acids set forth in SEQ ID NO: 94 or a sequence of amino acids encoded by the sequence of nucleotides set forth in SEQ ID NO: 96 or 97. In some embodiments, the modified PSMA comprises an extracellular portion and a transmembrane domain of the reference PSMA.

In some embodiments, the modified PSMA comprises one or more amino acid modifications in the intracellular region compared to the reference PSMA. In some embodiments, the one or more amino acid modification comprises one or more amino acid substitutions, deletions and/or insertions. In some embodiments, the modified PSMA exhibits altered cellular internalization compared to the reference PSMA.

In some embodiments, the modified PSMA comprises an amino acid substitution corresponding to W2G or does not comprise W2 or does not comprise any residue at position 2, with reference to positions in the sequence of amino acids set forth in SEQ ID NO:94. In some embodiments, the modified PSMA comprises a deletion or truncation of 11 N-terminal amino acids, compared to the reference PSMA.

In some embodiments, the modified PSMA comprises an epitope capable of being recognized by an antibody or antigen-binding fragment thereof. In some embodiments, the antibody or antigen-binding fragment thereof is selected from among J591, DFO-J591, CYT-356, J415, 3/A12, 3/F11, 3/E7, D2B, 107-1A4, YPSMA-1, YPSMA-2, 3E6, 2G7, 24.4E6, GCP-02, GCP-04, GCP-05, J533, E99, 1G9, 3C6, 4.40, 026, D7-Fc, D7-CH3, 4D4, A5, and antigen-binding fragments thereof.

In some of any such embodiments, the cell surface conjugate is not immunogenic and/or does not induce an immune response in a subject in which it is administered.

Also provided is a polynucleotide containing a nucleic acid sequence encoding the cell surface conjugate of any of the embodiments described herein. In some embodiments, the nucleic acid sequence further contains a signal sequence.

In some instances, the signal sequence encodes a signal peptide derived from GMCSFR alpha chain.

In some of any such embodiments, the nucleic acid sequence is a first nucleic acid sequence and the polynucleotide further contains a second nucleic acid sequence encoding a recombinant receptor. In some cases, the recombinant receptor is or contains a chimeric antigen receptor (CAR). In some of any such embodiments, the first and second nucleic acid sequences are separated by an internal ribosome entry site (IRES), or a nucleotide sequence encoding a self-cleaving peptide or a peptide that causes ribosome skipping, which optionally is T2A or P2A. In some embodiments, the first nucleic acid sequence is upstream of the second nucleic acid sequence. In some embodiments, the first nucleic acid sequence is downstream of the second nucleic acid sequence.

Provided is a vector containing the polynucleotide of any of the embodiments described herein. In some embodiments, the vector is a viral vector. In some of any such embodiments, the vector is a retroviral vector. In some of any such embodiments, the vector is a lentiviral vector or a gammaretroviral vector.

Also provided is a method of producing an engineered cell including introducing the polynucleotide of any of the embodiments described above or the vector of any of the embodiments described above into a cell. Also provided is an engineered cell produced by the method described herein. In some embodiments, the engineered cell contains the polynucleotide of any of the embodiments described herein or the vector of any of any of the embodiments described herein.

In some of any such embodiments, the engineered cell contains the cell surface conjugate of any of the embodiments described above. In some instances, the engineered cell further contains a recombinant receptor. In some aspects, the recombinant receptor binds to a target antigen that is associated with a disease or disorder. In some cases, the disease or disorder is an infectious disease or disorder, an autoimmune disease, an inflammatory disease, or a tumor or a cancer.

In some of any such embodiments, the target antigen is a tumor antigen. In some embodiments, the target antigen is the target antigen is selected from the group consisting of αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD138, CD171, epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), G Protein Coupled Receptor 5D (GPCR5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22Ra), IL-13 receptor alpha 2 (IL-13Ra2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, mesothelin, c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), vascular endothelial growth factor receptor (VEGFR), vascular endothelial growth factor receptor 2 (VEGFR2), Wilms Tumor 1 (WT-1).

In some of any such embodiments, the target antigen is selected from the group consisting of ROR1, HER2, L1-CAM, CD19, CD20, CD22, mesothelin, CEA, hepatitis B surface antigen, anti-folate receptor, CD23, CD24, CD30, CD33, CD38, CD44, EGFR, EGP-2, EGP-4, EPHa2, ErbB2, ErbB3, ErbB4, FBP, fetal acethycholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, TAG72, VEGF-R2, carcinoembryonic antigen (CEA), prostate specific antigen, PSMA, estrogen receptor, progesterone receptor, ephrinB2, CD123, CS-1, c-Met, GD-2, MAGE A3, CE7, Wilms Tumor 1 (WT-1), and cyclin A1 (CCNA1).

In some of any such embodiments, the recombinant receptor is a functional non-TCR antigen receptor or a transgenic TCR. In some of any such embodiments, the recombinant receptor is a chimeric antigen receptor (CAR). In some of any such embodiments, the recombinant receptor comprises an extracellular portion comprising an antigen-binding domain. In some examples, the antigen-binding domain is or contains an antibody or an antibody fragment.

In some embodiments, the antibody fragment is a single chain fragment. In some embodiments, the fragment contains antibody variable regions joined by a flexible immunoglobulin linker. In some of any such embodiments, the fragment comprises an scFv. In some of any such embodiments, the recombinant receptor comprises an activating intracellular signaling domain.

In some embodiments of the engineered cell, the activating intracellular signaling domain is capable of inducing a primary activation signal in a T cell, is a T cell receptor (TCR) component, and/or contains an immunoreceptor tyrosine-based activation motif (ITAM). In some of any such embodiments, the activating intracellular signaling domain is or contains an intracellular signaling domain of a CD3-zeta (CD3) chain or a signaling portion thereof.

In some of any such embodiments, the engineered cell further contains a transmembrane domain linking the extracellular portion and the activating intracellular signaling domain.

In some of any such embodiments, the recombinant receptor contains a costimulatory signaling domain. In some instances, the costimulatory signaling domain contains an intracellular signaling domain of a T cell costimulatory molecule or a signaling portion thereof. In some of any such embodiments, the costimulatory signaling domain contains an intracellular signaling domain of CD28, 4-1BB or ICOS or a signaling portion thereof. In some of any such embodiments, the costimulatory signaling domain is between the transmembrane domain and the activating intracellular signaling domain.

In some of any such embodiments, the cell is an immune cell. In some cases, the cell is a lymphocyte. In some of any such embodiments, the cell is a T cell or an NK cell. In some examples, the cell is a T cell that is a CD8+ T cell or a CD4+ T cell.

Also provided is a composition containing the engineered cells of any of the embodiments described above. In some cases, the composition further contains a pharmaceutically acceptable excipient.

Also provided is a method of treatment including administering the engineered cells of any of the embodiments described above or the composition of any of the embodiments described above to a subject having a disease or disorder. In some embodiments, the disease or disorder is a cancer, a tumor, an autoimmune disease or disorder, or an infectious disease. In some of any such embodiments, the method further involves administering to the subject a binding molecule capable of recognizing the agent of the cell surface conjugate expressed on the engineered cell and detecting cells that express the cell surface conjugate. In some aspects, detection includes in vivo imaging.

Also provided is a method of identifying a cell expressing a cell surface conjugate, including contacting a composition containing cells that express or are likely to express a cell surface conjugate of any of the embodiments described herein with a binding molecule capable of recognizing the agent of the cell surface conjugate. In some aspects, the method is performed in vitro, ex vivo or in vivo. In some embodiments, n the cell expressing the cell surface molecule is detected via in vivo imaging. In some of any such embodiments, the in vivo imaging method is selected from among magnetic resonance imaging (MRI), single-photon emission computed tomography (SPECT), computed tomography (CT), computed axial tomography (CAT), electron beam computed tomography (EBCT), high resolution computed tomography (HRCT), hypocycloidal tomography, positron emission tomography (PET), scintigraphy, gamma camera, a β+ detector, a γ detector, fluorescence imaging, low-light imaging, X-rays, and bioluminescence imaging.

In some of any such embodiments, the binding molecule is conjugated to a moiety that provides a signal or induces a signal that is detectable in vivo. In some examples, the moiety is a radioisotope, bioluminescent compound, chemiluminescent compound, fluorescent compound, metal chelate or enzyme.

Also provided is a method of identifying cells transduced with a cell surface conjugate, including contacting a composition transduced with a polynucleotide of any of the embodiments described herein or the vector of any of the embodiments described herein encoding the cell surface conjugate with a binding molecule capable of recognizing the agent of the cell surface conjugate; and identifying cells bound to the binding molecule. Also provided is a method of identifying cells transduced with a cell surface conjugate including introducing a polynucleotide of any of the embodiments described herein or the vector of any of the embodiments described herein encoding the cell surface conjugate into a cell; contacting a composition comprising the cell with a binding molecule capable of recognizing the agent of the cell surface conjugate; and identifying cells of the composition bound to the binding molecule.

Also provided is a method of selecting cells transduced with a cell surface conjugate including contacting a composition transduced with a polynucleotide of any of the embodiments described herein or the vector of any of the embodiments described herein encoding the cell surface conjugate with a binding molecule capable of recognizing the agent of the cell surface conjugate; and isolating cells bound to the binding molecule. Further provided is a method of selecting cells transduced with a cell surface conjugate including introducing a polynucleotide of any of the embodiments described herein or the vector of any of the embodiments described herein encoding the cell surface conjugate into a cell; contacting a composition comprising the cell with a binding molecule capable of recognizing the agent of the cell surface conjugate; and isolating cells of the composition bound to the binding molecule.

In some of any such embodiments, the binding molecule is conjugated to a detectable moiety or is capable of producing a detectable signal. In some instances, the detectable moiety contains a fluorescent protein.

In some of any such embodiments, the agent is a streptavidin binding peptide. In some cases, the streptavidin-binding peptide is or comprises the sequence Trp-Ser-His-Pro-Gln-Phe-Glu-Lys (SEQ ID NO: 8) or Trp-Arg-His-Pro-Gln-Phe-Gly-Gly (SEQ ID NO:7). In some aspects, the streptavidin binding peptide is or contains the sequence Trp-Ser-His-Pro-Gln-Phe-Glu-Lys-(GlyGlyGlySer)$_3$-Trp-Ser-His-Pro-Gln-Phe-Glu-Lys (SEQ ID NO: 17), Trp-Ser-His-Pro-Gln-Phe-Glu-Lys-(GlyGlyGlySer)$_2$-Trp-Ser-His-Pro-Gln-Phe-Glu-Lys (SEQ ID NO: 18) and Trp-Ser-His-Pro-Gln-Phe-Glu-Lys-(GlyGlyGlySer)$_2$Gly-Gly-Ser-Ala-Trp-Ser-His-Pro-Gln-Phe-Glu-Lys (SEQ ID NO: 19).

In some embodiments, the binding molecule is a reagent capable of reversibly binding to the agent. In some aspects, the reagent is a streptavidin analog or mutein. In some instances, the streptavidin analog or mutein contains the amino acid sequence Val$^{44}$-Thr$^{45}$-Ala$^{46}$-Arg$^{47}$ or Ile$^{44}$-Gly$^{45}$-Ala$^{46}$-Arg$^{47}$ at sequence positions corresponding to positions 44 to 47 with reference to positions in streptavidin in the sequence of amino acids set forth in SEQ ID NO:1.

In some of any such embodiments, the streptavidin analog or mutein contains a) the sequence of amino acids set forth in any of SEQ ID NOS: 3-6, 27 and 28; b) a sequence of amino acids that exhibits at least at or about 85%, 86%, 87%, 88%, 89%, 89%, 90%, 91%, 92%, 93%, 94%, 95%, 96%, 97%, 98%, 99% or more sequence identity to any of SEQ ID NOS: 3-6, 27 and 28 and contains the amino acid sequence corresponding to Val$^{44}$-Thr$^{45}$-Ala$^{46}$-Arg$^{47}$ or Ile$^{44}$-Gly$^{45}$-Ala$^{46}$-Arg$^{47}$ and that reversibly binds to the agent; or c) a functional fragment of a) or b) that reversibly binds to the agent. In some embodiments, the streptavidin analog or mutein further contains an amino acid replacement or replacements at a position corresponding to 117, 120 and/or 121 with reference to positions in streptavidin in the sequence of amino acids set forth in SEQ ID NO:1.

In some of any such embodiments, the amino acid replacement or replacements are selected from among Glu$^{117}$, Asp$^{117}$, Arg$^{117}$, Ser$^{120}$, Ala$^{120}$, Gly$^{120}$, Trp$^{121}$, Tyr$^{121}$ or Phe$^{121}$, or the amino acid replacement or replacements are selected from one or more of Glu$^{117}$, Gly$^{120}$ or Tyr$^{121}$; or the amino acid replacements are selected from Glu$^{117}$, Gly$^{120}$ or Tyr$^{121}$.

In some of any such embodiments, the streptavidin analog or mutein contains a) the sequence of amino acids set forth in SEQ ID NO: 27 or 28; b) a sequence of amino acids that exhibits at least at or about 85%, 86%, 87%, 88%, 89%, 89%, 90%, 91%, 92%, 93%, 94%, 95%, 96%, 97%, 98%, 99% or more sequence identity to SEQ ID NOS:27 or 28 and contains the amino acid sequence corresponding to Val$^{44}$, Thr$^{45}$, Ala$^{46}$, Arg$^{47}$, Glu$^{117}$, Gly$^{120}$ and Tyr$^{121}$ and reversibly binds to the agent; or c) a functional fragment of a) or b) that reversibly binds to the agent.

In some of any such embodiments, the method further includes disrupting the reversible binding of the binding molecule to the agent. In some aspects, the disruption includes contacting the cells with a composition containing a substance capable of reversing the bond between the binding molecule and agent. In some cases, the substance is a free binding partner and/or is a competition agent. In some embodiments, the substance is or contains biotin, a biotin analog or a biologically active fragment thereof.

In some of any such embodiments, the binding molecule is an antibody or antigen binding fragment that specifically binds the agent. In some examples, the binding molecule is an anti-StrepTag antibody.

Also provided herein is a molecule containing a streptavidin or a streptavidin analog or mutein conjugated to a cytotoxic agent. In some aspects, the molecule contains a streptavidin analog or mutein. In some embodiments, the streptavidin or streptavidin analog binds to a streptavidin binding peptide.

In some examples, the streptavidin-binding peptide is or contains the sequence Trp-Ser-His-Pro-Gln-Phe-Glu-Lys (SEQ ID NO: 8) or Trp-Arg-His-Pro-Gln-Phe-Gly-Gly (SEQ ID NO:7). In some of any such embodiments, the streptavidin binding peptide is or contains the sequence Trp-Ser-His-Pro-Gln-Phe-Glu-Lys-(GlyGlyGlySer)$_3$-Trp-Ser-His-Pro-Gln-Phe-Glu-Lys (SEQ ID NO: 17), Trp-Ser-His-Pro-Gln-Phe-Glu-Lys-(GlyGlyGlySer)$_2$-Trp-Ser-His-Pro-Gln-Phe-Glu-Lys (SEQ ID NO: 18) and Trp-Ser-His-Pro-Gln-Phe-Glu-Lys-(GlyGlyGlySer)$_2$Gly-Gly-Ser-Ala-Trp-Ser-His-Pro-Gln-Phe-Glu-Lys (SEQ ID NO: 19).

In some of any such embodiments, the streptavidin or streptavidin mutein exhibits a binding affinity for the streptavidin binding peptide with an equilibrium dissociation constant ($K_D$) of from or from about $10^{-4}$ to $10^{-10}$ M. In some of any such embodiments, the streptavidin analog or mutein contains the amino acid sequence Val$^{44}$-Thr$^{45}$-Ala$^{46}$-Arg$^{47}$ or Ile$^{44}$-Gly$^{45}$-Ala$^{46}$-Arg$^{47}$ at sequence positions corresponding to positions 44 to 47 with reference to positions in streptavidin in the sequence of amino acids set forth in SEQ ID NO:1.

In some of any such embodiments, the streptavidin analog or mutein contains a) the sequence of amino acids set forth in any of SEQ ID NOS: 3-6, 27 and 28; b) a sequence of amino acids that exhibits at least at or about 85%, 86%, 87%, 88%, 89%, 89%, 90%, 91%, 92%, 93%, 94%, 95%, 96%, 97%, 98%, 99% or more sequence identity to any of SEQ ID NOS: 3-6, 27 and 28 and contains the amino acid sequence corresponding to Val$^{44}$-Thr$^{45}$-Ala$^{46}$-Arg$^{47}$ or Ile$^{44}$-Gly$^{45}$-Ala$^{46}$-Arg$^{47}$ and that reversibly binds to the agent; or c) a functional fragment of a) or b) that binds to the streptavidin binding peptide. In some embodiments, the streptavidin analog or mutein further contains an amino acid replacement or replacements at a position corresponding to 117, 120 and/or 121 with reference to positions in streptavidin in the sequence of amino acids set forth in SEQ ID NO:1.

In some of any such embodiments, the amino acid replacement or replacements are selected from among Glu$^{117}$, Asp$^{117}$, Arg$^{117}$, Ser$^{120}$, Ala$^{120}$, Gly$^{120}$, Trp$^{121}$, Tyr$^{121}$ or Phe$^{121}$; or the amino acid replacement or replacements are selected from one or more of Glu$^{117}$, Gly$^{120}$ or Tyr$^{121}$; or the amino acid replacements are selected from Glu$^{117}$, Gly$^{120}$ or Tyr$^{121}$.

In some of any such embodiments, the streptavidin analog or mutein contains a) the sequence of amino acids set forth in SEQ ID NO: 27 or 28; b) a sequence of amino acids that exhibits at least at or about 85%, 86%, 87%, 88%, 89%, 89%, 90%, 91%, 92%, 93%, 94%, 95%, 96%, 97%, 98%, 99% or more sequence identity to SEQ ID NOS:27 or 28 and contains the amino acid sequence corresponding to Val$^{44}$, Thr$^{45}$, Ala$^{46}$, Arg$^{47}$, Glu$^{117}$, Gly$^{120}$ and Tyr$^{121}$ and reversibly binds to the agent; or c) a functional fragment of a) or b) that reversibly binds to the streptavidin binding peptide.

In some of any such embodiments, the cytotoxic agent is a toxin. In some examples, the toxin is a peptide toxin, ricin A chain toxin, Abrin A chain, Diptheria Toxin (DT) A chain, *Pseudomonas* exotoxin, Shiga Toxin A chain, Gelonin, Momordin, Pokeweed Antiviral Protein, Saporin, Trichosanthin, or Barley Toxin. In some instances, the cell toxin is a phototoxin.

Also provided is a method of killing cells including administering the molecule of any of the embodiments described herein to a subject previously administered the cells of any of the embodiments described herein or the composition of any of the embodiments described above. In some aspects, the molecule is administered at a time at which the subject is exhibiting a toxic outcome associated with the administered cells or at a time at which the subject is exhibiting a detectable and/or cell-mediated immune response to the administered cells. In some instances, the toxic outcome is associated with neurotoxicity or cytokine release syndrome (CRS).

DETAILED DESCRIPTION

Figure 1:
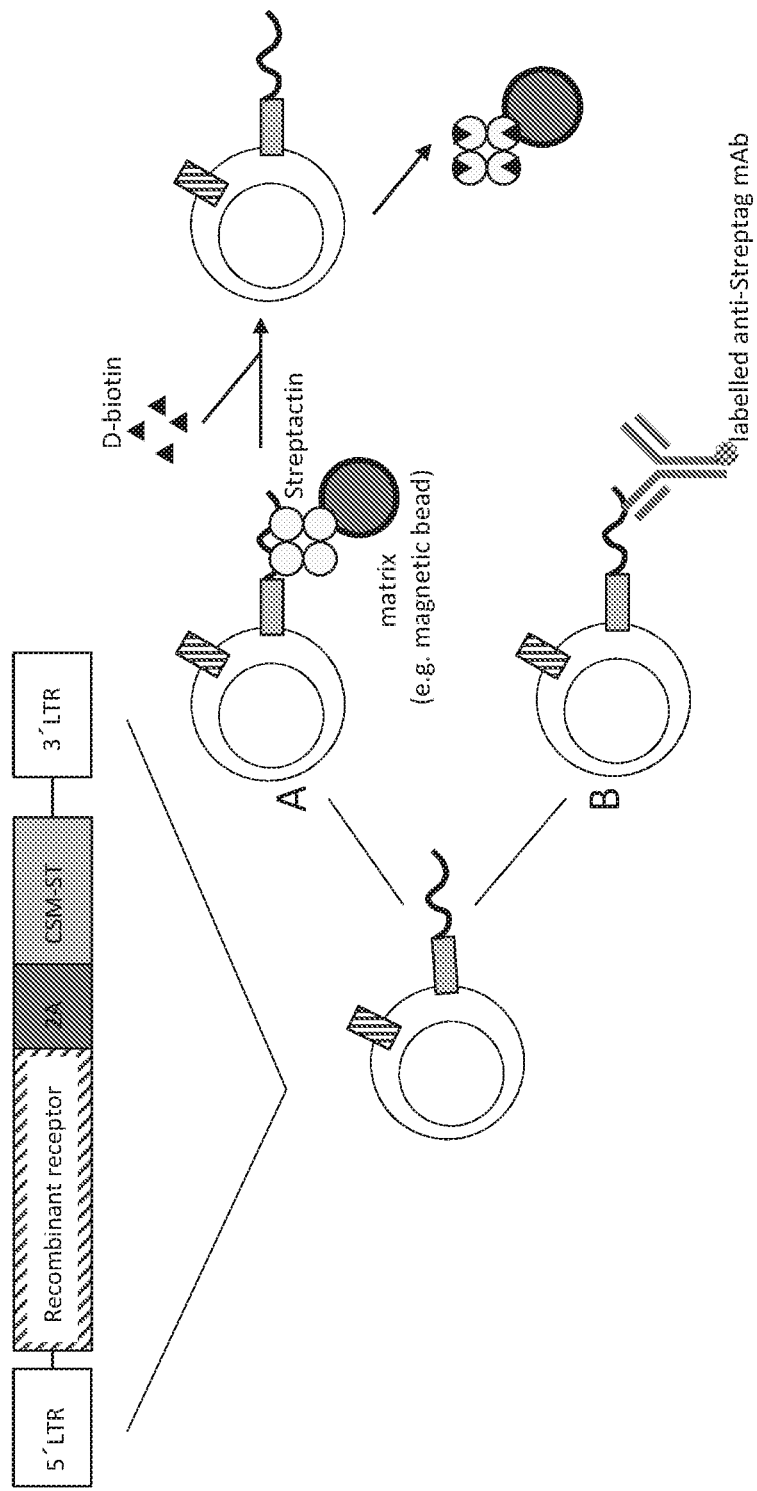
FIG. 1 depicts a schematic of a nucleic acid molecule encoding a recombinant receptor (e.g., CAR) and an exemplary cell surface conjugate as provided (e.g. a cell surface molecule (CSM), linked to a Strep-tag (ST) (CSM-ST) separated by a 2A ribosomal skip element for expressing two proteins in a cell from the same construct. Also shown are exemplary methods of targeting the agent of the expressed cell surface conjugate for selection of gene-modified cells independent of the expressed recombinant receptor by contacting such cell with (A) a non-antibody reagent (e.g. Strep-Tactin) bound to a solid surface or (B) with an anti-Strep-tag antibody specific for the agent of the cell surface conjugate.
Figure 2:
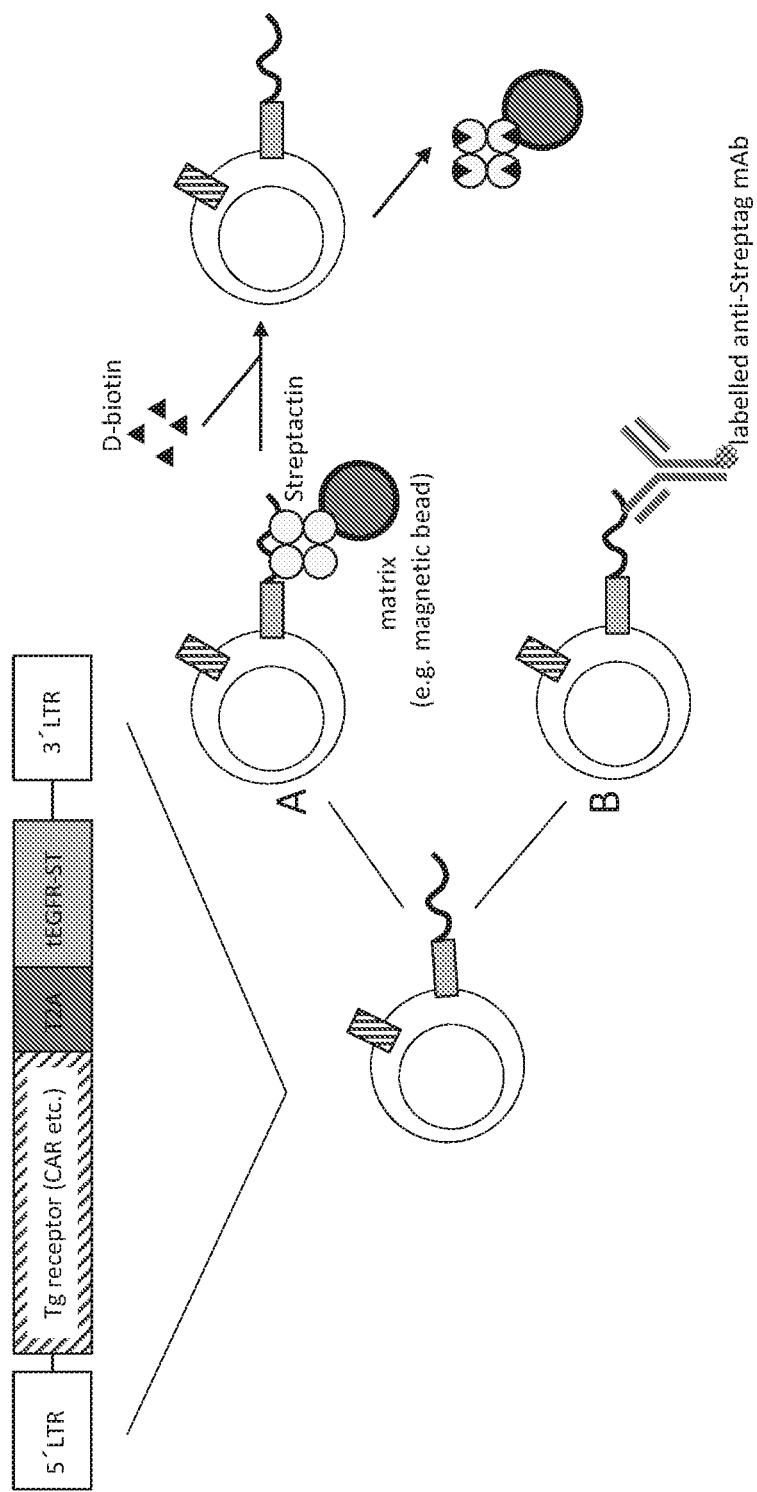
FIG. 2 depicts a schematic of a nucleic acid molecule encoding a recombinant receptor (e.g. Tg receptor) and an exemplary cell surface conjugate as provided (e.g. truncated epidermal growth factor receptor (tEGFR) linked to a Strep-tag (ST) (tEGFR-ST) separated by a T2A ribosome switch for expressing two proteins in a cell from the same construct. Also shown are exemplary methods of targeting the agent of the expressed cell surface conjugate for selection of gene-modified cells independent of the expressed recombinant receptor by contacting such cell with (A) a non-antibody reagent (e.g. Strep-Tactin) bound to a solid surface or (B) with an anti-Strep-tag antibody specific for the agent of the cell surface conjugate.

I. Cell Surface Conjugates for Processing of Gene Modified Cells

Provided herein are cell surface conjugates containing a cell surface molecule, such as a cell surface protein, and at least one agent, such as an affinity tag, e.g. a peptide agent. In some embodiments, the provided cell surface conjugates are engineered or expressed in cells to permit one or more of specific targeting of the cell, isolation or selection of the cell or detection of the cell, such as via a binding molecule specific for the agent of the conjugate, which binding molecule does not bind or recognize the cell surface molecule of the conjugate. In some embodiments, the cell surface molecule is not a recombinant receptor, such as is not an antigen receptor, for example, is not a chimeric antigen receptor (CAR). In some embodiments, the provided cell surface conjugates are co-engineered into cells expressing a recombinant receptor (e.g. a CAR), whereby the cell surface conjugate can be exploited for processing of cells expressing the recombinant receptor, such as in connection with methods for detection, selection, isolation or suicide-based deletion of engineered cells.

Various strategies are available for producing and administering engineered cells for adoptive therapy. The cells generally are engineered by introducing one or more genetically engineered nucleic acid or product thereof. Among such products are genetically engineered antigen receptors, including engineered T cell receptors (TCRs) and functional non-TCR antigen receptors, such as chimeric antigen receptors (CARs), including activating, stimulatory, and costimulatory CARs, and combinations thereof. For example, strategies are available for engineering cells, such as T cells, expressing chimeric receptors, such as CARs, and administering compositions containing such engineered cells to subjects. Throughout the process of producing engineered cells, it is beneficial to be able to identify, detect, locate, and/or select transduced cells. After administration of the engineered cells for adoptive therapy, there is also a need to monitor the transduced cells and to provide a mechanism to deplete or reduce the number of transduced cells in a subject.

Known methods for selecting and isolating cells include use of CAR-specific antibodies to bind cells of interest. For example, the use of a biotinylated goat anti-mouse IgG (Fab')2 (Jackson ImmunoReseach) for detection of CAR-modified T cells is known in the art (Brentjens et al., Sci. Transl. Med. 2013 March; 5(177): 177ra38). As the sensitivity of this polyclonal antibody is low, in the setting of low lymphocyte numbers in patient samples, detection of CAR-modified T cells was accomplished only after non-specific expansion of T cells using Dynabeads. This prevents a direct assessment of circulating CAR-modified T cell in vivo after infusion. The use of Protein L for detection of CAR-modified T cells by flow cytometry has also been described (Zheng et al., J. Transl. Med. 2012 February; 10:29). This reagent has restricted use in terms of detection and sensitivity in a multi-parameter flow cytometry assay. Its use in other assay formats has not been shown. Another approach utilizes Strep-tag II sequences introduced directly into specific sites in the CAR, whereby binding reagents for Strep-Tag are used to directly assess the CAR (Liu et al. (2016) Nature Biotechnology, 34:430; international patent application Pub. No. WO2015095895). Furthermore, monoclonal antibodies that specifically bind to a CAR polypeptide are also known (see international patent application Pub. No. WO2014190273). While useful in some situations, reagents that bind the CAR directly or indirectly may risk activating the CAR to induce cell signaling and activation of the engineered cells, which is not always desired in connection with isolating or selecting cells during ex vivo production and manufacturing.

In some aspects, extrinsic marker genes are utilized in connection with engineered cell therapies to permit detection or selection of cells and, in some cases, also to promote cell suicide by ADCC. Exemplary of such a marker gene is truncated epidermal growth factor receptor (EGFRt), which can be co-expressed with a transgene of interest (a CAR or TCR) in transduced cells (see e.g. U.S. Pat. No. 8,802,374). EGFRt contains the epitope recognized by the antibody cetuximab (Erbitux®). For this reason, Erbitux® can be used to identify or select cells that have been engineered with the EGFRt construct, including in cells also co-engineered with another recombinant receptor, such as a chimeric antigen receptor (CAR). Additionally, EGFRt is commonly used as a suicide mechanism in connection with cell therapies. In some aspects, when EGFRt is co-expressed in cells with a transgene of interest (e.g. CAR or TCR), it can be targeted by the cetuximab monoclonal antibody to reduce or deplete the transferred gene-modified cells via ADCC (see U.S. Pat. No. 8,802,374 and Liu et al., Nature Biotech. 2016 April; 34(4): 430-434). Importantly, the suicide killing approach using tEGFR requires availability of the antibody epitope.

The above approaches known in the art can have potential problems that interfere with the processing, production, and/or function of the cells. There is a need for cell surface markers that aid the production, monitoring, and post-administration stages involving transduced cell products. For example, methods for efficient selection and isolation of cells positive for the transgene and for monitoring transgene-expressing cells in vivo and ex vivo, are desired. The provided cell surface conjugates and methods address such needs and/or address one or more problems associated with existing methods and reagents. In some embodiments, the provided conjugates provide one or more advantages compared to existing markers or selections strategies used in connection with engineered cells.

In some embodiments, the provided conjugates are conjugates containing a cell surface molecule that lacks an intracellular signaling domain and/or is not capable of mediating intracellular signaling having linked or conjugated thereto an agent, such as an affinity tag (e.g. a peptide). In some embodiments, the agent is one that is recognized by a binding molecule. In some embodiments, the agent of the provided cell surface conjugate is a streptavidin binding peptide (e.g. Strep-tag®) for which well-known binding molecules are available. In some aspects, the cell surface conjugate is a fusion protein comprising a cell surface molecule or a modified form thereof and an agent e.g., an affinity tag.

In some embodiments, the cell surface molecule is a modified cell surface molecule that is altered compared to a reference cell surface molecule. In some embodiments, the reference cell surface molecule is a native mammalian cell surface molecule. In some cases, the cell surface molecule is modified, e.g. truncated or contains one or more amino acid substitutions, deletions and/or insertions, compared to a reference cell surface molecule. In some embodiments, the cell surface molecule contains a truncation, e.g., a truncation to remove all or a portion of an intracellular signaling domain and/or other intracellular domains or one or more extracellular domains. In some embodiments, the cell surface molecule contains or retains at least one epitope recognized by an antibody or antigen-binding fragment, which, in some cases, additionally permits targeting of the cell surface molecule of the conjugate independent of the agent, for example, to mediate antibody dependent cell cytotoxicity (ADCC) for selective deletion or suicide of engineered cells as a safety switch mechanism. In some embodiments, the cell surface molecule of the conjugate contains a modified epidermal growth factor receptor (EGFR), such as a truncated EGFR (see e.g. U.S. Pat. No. 8,802,374). In some embodiments, the cell surface molecule of the conjugate contains a modified prostate-specific membrane antigen (PSMA), such as a modified PSMA, e.g., a truncated PSMA (tPSMA).

In some embodiments, the agent is one that is recognized by a binding molecule in which binding thereto is reversible and/or in which binding to a binding molecule is able to be competed or disrupted in the presence of a competition substance. In some embodiments, the binding molecule is or comprises a reagent that exhibits a higher binding affinity for the competition substance than for the agent. In some embodiments, the binding molecule is a reagent that is or comprises a streptavidin or a streptavidin analog or mutein and the agent is a streptavidin binding peptide, e.g. Strep-tag®.

In some embodiments, certain streptavidin mutein molecules (e.g. Strep-Tactin) are able to reversibly bind to certain streptavidin binding peptides (e.g. Strep-tag®) in the presence of a biotin or a biotin analog or mimic that exhibits a higher binding affinity for the streptavidin mutein than the streptavidin mutein exhibits for the streptavidin binding peptide. Thus, in certain aspects, binding between the agent (e.g. streptavidin binding peptide, such as Strep-tag®) of the cell surface conjugate and the binding molecule (e.g. streptavidin mutein, such as Strep-Tactin) can be disrupted by the addition of the competition substance (e.g. biotin or biotin mimic). In some embodiments, such binding reagents, for example streptavidin mutein binding reagents, do not induce suicide-based killing by ADCC. Furthermore, the streptavidin muteins can be formatted as a soluble reagent or associated in a solid phase, such as in a stationary phase, such as is present in a column, e.g. column chromatography or planar chromatography, to facilitate cell selection or isolation.

In some embodiments, the cell surface conjugate contains (1) a modified cell surface molecule, such as a modified cell surface receptor that lacks an intracellular signaling domain and/or one or more extracellular domain for binding to a cognate ligand and (2) at least one streptavidin binding peptide agent (Strep-tag®). Exemplary cell surface molecules are described and include, for example, a modified epidermal growth factor receptor. In some embodiments, the cell surface conjugate can be detected via a binding molecule reagent that is or comprises a streptavidin mutein. In alternative examples, specific detection of a streptavidin or binding peptide (e.g. Strep-tag®) can be achieved by a high affinity monoclonal anti-Streptag antibody.

In some embodiments, the agent is fused to the extracellular (N-terminal or C-terminal) part of the cell surface molecule, such as the modified cell surface molecule. In some embodiments, linkage of the agent only at the exposed N-terminus or C-terminus of the cell surface molecule exposes the agent so that it is easily detectable and/or its detection is not sterically blocked. In some embodiments, the cell surface molecule contains an epitope that is able to be recognized or bound by a binding molecule, such as an antibody or antigen binding fragment or a ligand, for example, to induce or carry our suicide deletion in connection with safety switch methods. Thus, the linkage of the agent at the N-terminal sequence or the C-terminal sequences of the cell surface molecule can retain access of the epitope of the cell surface molecule for recognition by a specific antibody or antigen binding fragment. In some embodiments, the cell surface conjugates retain the safety switch function of the cell surface molecule, e.g. mediated via cetuximab binding to EGFRt on engineered cells.

In some embodiments, the provided cell surface conjugates include those in which selection or identification of cells can be uncoupled from activation or suicide of cells. In some cases, selection processes that use antibodies against specific antigen receptors, e.g. CARs, may lead to accidental activation of the receptor, e.g. CAR, and inadvertent signaling through the receptor, e.g. CAR. This problem is avoided by the provided cell surface conjugates, which are expressed on the cell surface independently from the antigen receptor. In some embodiments, the provided cell surface conjugates allow the function of the recombinant receptor (e.g. CAR) to remain separate and unaffected by activity involving the cell surface conjugate. In some cases, the detecting of the conjugate as confirmation of transduction will not lead to accidental activation of the CAR and inadvertent signaling through the CAR. Therefore, in some embodiments, the likelihood of off target effects can be reduced.

Likewise, since the cell surface molecule of the conjugate is not an antigen receptor, e.g. CAR, and is co-expressed on engineered cells independently from the antigen receptor, recognition of engineered cells can be based on expression of the cell surface conjugate and not on a signaling molecule. In some aspects, the provided cell surface conjugates have the advantage that detection or selection of engineered cells via the agent of the provided conjugates is independent of expression of the antigen receptor, e.g. CAR, and/or how much antigen receptor, e.g. CAR, is expressed.

The provided cell surface conjugates also provide a generic or universal marker for engineered cells, which does not need to be reconfigured or developed for each cell therapy. Thus, unlike certain prior art methods, the provided conjugates and methods avoid the need to develop individual marker reagents for each transgene and/or avoid development of individual selection reagents specifically targeting certain domains of the receptor (e.g. CAR or TCR). Thus, the provided methods are less time consuming than prior art methods and conserve reagent resources.

In available prior art approaches, the selection process can, in some cases, result in the loss or damage of cells. In some aspects, methods of selecting cells and selectively targeting cells for suicide using the same binding molecule (e.g. cetuximab in the case of EGFRt) is not ideal. In some cases, methods of selecting or isolating transduced cells via a protein marker (e.g. EGFRt) using a specific antibody (e.g. cetuximab) can result in a loss of cells due to the ADCC suicide-based mechanisms. During ex vivo production and further processing of engineered cells, however, suicide and loss of cells is not desired. Since the provided cell surface conjugates can be recognized by non-antibody reagents (e.g. streptavidin mutein reagents) such problems associated with loss of cells during selection processes in connection with cell manufacturing can be avoided. Further, unlike reagents that bind the recombinant receptor, e.g. CAR, directly or indirectly, that may risk stimulating the CAR to induce cell signaling and stimulation in the engineered cells, the provided embodiments allow the cells to be engineered, selected, isolated, produced, processed or manufactured without stimulating signals through the CAR.

Further, in some cases, prior art methods employing antibody molecules for cell selection are carried out in a manner in which the binding of the antibody to specific targets is not reversible or is not efficiently or rapidly reversible. In some cases, high affinity antibodies, and in particular antibodies with a $K_D$ of $10^{-9}$M or lower, recognizing a cell surface marker or directly recognizing an antigen receptor (e.g. a CAR) result in a slower detachment of the antibody from the cell. In some cases, when such antibodies are used to select antigen receptor (e.g. CAR) engineered cells in connection with production and manufacturing of cells, there is a risk that residual antibody may be retained in a final formulation or manufacturing product if the antibodies remain attached to cells. Administration of such products to subjects may lead to undesirable effects in the subject. Thus, in some aspects, the cell surface conjugates provided herein contain an agent (e.g. streptavidin binding peptide, such as StrepTag) that exhibits a lower affinity interaction for certain binding molecule reagents (e.g. streptavidin mutein, such as Strep-Tactin) in order to avoid this problem and to decrease the risk that the binding molecule reagent is retained in the drug product. In addition, methods to completely dissociate or disrupt binding of an agent from its binding molecule are desired in connection with manufacturing cell therapies.

In some embodiments, the provided cell surface conjugates retain the safety switch functionality of the cell surface molecule (e.g. EGFRt or PSMA) of the conjugate by virtue of retaining or preserving an epitope recognized by a specific antibody. For example, the provided cell surface conjugates can be specifically bound, such as non-competitively bound, by a binding molecule (e.g. antibody or an antigen-binding fragment thereof) specific to the cell surface molecule of the conjugate and a binding molecule specific to the agent of the conjugate. In some aspects, targeting the cell surface molecule through ADCC, which depends on the availability of the antibody epitope of the cell surface molecule, provides for increased functionality of the cell surface conjugate in a variety of applications.

As an alternative to ADCC mediated activity, depletion or reduction of transduced cell products in a subject can be facilitated by targeting the agent of the cell surface conjugate. In some embodiments, the provided agents can be further modified to exhibit safety switch properties, such as by linkage or conjugation of a binding molecule specific to the agent to a toxin or other cytotoxic agent (hereinafter also called "suicide agent"). In some aspects, the provided suicide agents do not depend on ADCC mechanisms of cell suicide, which in some cases can be slow due to the pharmacokinetics of antibodies. In some embodiment, the binding molecule is not an antibody or antigen-binding fragment. In some embodiments, the binding molecule of the suicide agent is a streptavidin or streptavidin mutein, such as any as described, which, in some cases, bind to an agent that is a streptavidin binding agent. In some embodiments, suicide by delivering a toxin conjugated to the reagent (Strep-Tactin®) to the agent (Strep-tag®) can be used. In some aspects, killing mediated by a toxin-conjugated reagent allows faster delivery compared to using an antibody to activate ADCC. Such suicide agents, e.g. streptavidin mutein-toxins, can exhibit a more rapid or quicker specific cell killing effect on the engineered cells compared to antibody-based suicide mechanisms. In some embodiments, the cell killing is initiated about more than or more than or about 1.5-fold, 2-fold, 3-fold, 4-fold, 5-fold, 6-fold, 7-fold, 8-fold, 9-fold, 10-fold or more quickly than cell killing initiated with antibody-based mechanisms.

Also provided are methods and uses of the cell surface conjugate expressed by cells, such as in connection with processing, manufacture or post-administrative monitoring in connection with adoptive therapy. In some embodiments, provided are methods for in vivo or ex vivo detection of transduced cells expressing the cell surface conjugate. In some embodiments, methods to select, such as isolate or recover, cells that have been successfully transduced to express the cell surface conjugate are provided. In some embodiments, also provided are methods for suicide killing of cells expressing the cell surface conjugate.

In some embodiments, the provided methods involve co-engineering cell with the cell surface conjugate and a desired recombinant receptor transgene (e.g. CAR or TCR). Also provided are vectors for co-engineering cells with the cell surface conjugate and the recombinant receptor. In some embodiments, provided is a backbone vector construct containing the coding sequence for the cell surface conjugate. In some cases, improved efficiency is achieved by using such a backbone construct in approaches to genetically engineering cells to independently express the cell surface conjugate and the recombinant receptor. In some embodiments, the backbone expression vector containing the cell surface conjugate can be used to insert transgene sequences for unique recombinant receptors (CAR, TCR, etc.) specifically targeting an antigen. In some embodiments, the resulting vector construct includes nucleic acid sequences encoding the recombinant receptor, a sequence encoding a 2A element, e.g., a T2A ribosomal skip element and the sequence encoding the cell surface conjugate, e.g., downstream of the sequence encoding the CAR. Thus, in some aspects, the construct encoding the recombinant receptor (e.g. CAR) and conjugate are separated by a 2A element, e.g., a T2A ribosome switch for expressing two proteins from the same construct. In some embodiments, such provided constructs can be modified to easily encode any recombinant receptor (e.g. CAR).

Also provided are methods for using cells expressing the cell surface conjugate. Provided are methods for cell isolation and genetic engineering. Provided are nucleic acids, such as constructs, e.g., viral vectors encoding the cell surface conjugate and/or encoding nucleic acids and/or proteins of the cell surface conjugate, and methods for introducing such nucleic acids into the cells, such as by transduction. Also provided are compositions containing the engineered cells, and methods, kits, and devices for administering and monitoring the cells and compositions to subjects, such as for adoptive cell therapy.

II. Cell Surface Conjugate

Provided herein is a cell surface conjugate containing a cell surface molecule and at least one agent (e.g. peptide), such as an affinity tag, which agent is able to be specifically recognized by a binding molecule. In some embodiments, the provided conjugates are or include fusion proteins. In some embodiments, the cell surface molecule of the conjugate lacks a functional intracellular signaling domain and/or is not capable of mediating intracellular signaling. In some aspects, the cell surface molecule is a modified cell surface molecule that is altered compared to a reference cell surface molecule, for example, is a truncated cell surface receptor that lacks all or a portion of the intracellular signaling domain of the reference cell surface molecule, and/or contains one or more amino acid substitutions, deletions and/or insertions. In some embodiments, the cell surface molecule of the conjugate exhibits altered cellular internalization, enzymatic activity and/or ligand binding. In some embodiments, the agent (e.g. peptide), such as an affinity tag, is linked to the N-terminal or C-terminal part of the cell surface molecule. In some embodiments, the agent is a streptavidin binding peptide (e.g. Strep-tag®) and the cell surface molecule is a modified EGFR, such as a truncated EGFR. In some embodiments, the agent is a streptavidin binding peptide (e.g. Strep-tag®) and the cell surface molecule is a modified PSMA, such as a truncated PSMA.

In some embodiments, the provided conjugates contain the following components: cell surface molecule (CSM), linker (L) and agent (A), which are represented by the formula: CSM-(L)$_q$-(A)$_m$, where q is 0 or more and m is at least 1 or is 1. In some embodiments, the variables q and m are selected such that the resulting cell surface conjugate is expressed on cells and can be detected by a binding molecule via the agent, and optionally, recognized by an antibody or antigen-binding fragment specific to an epitope of the cell surface molecule. In some embodiments, m is 1 to 5, such as 1 to 4 or 1 to 3, for example, at least or at least about or about or 1, 2, 3, 4 or 5. In some embodiments, q is 0 to 5, and can depend on the number of linked agents. In some embodiments, several linkers can be joined in order.

In some aspects, the at least one agent is linked directly to the cell surface molecule. In some aspects, the at least one agent is linked or joined indirectly to the cell surface molecule via at least one linker. In some embodiments, the agent (e.g. a peptide), such as an affinity tag, is linked via its N-terminus or its C-terminus to the cell surface molecule. In some embodiments, the agent is linked at the membrane distal extracellular portion of the cell surface molecule. In some embodiments, the agent is linked at the N-terminus of the cell surface molecule. In some embodiments, the agent is linked at the C-terminus of the cell surface molecule. In some embodiments, the agent is a peptide tag of less than 50 amino acids in length fused, directly or indirectly via a linker, to the extracellular (N-terminal) or (C-terminal) part of the cell surface molecule. In some embodiments, the agent is linked to an extracellular portion or domain of the cell surface molecule. In some embodiments, q is 0 and m is 1 and the agent is linked directly to the N-terminus of the cell surface molecule. In some embodiments, the provided conjugates are or include fusion proteins, such as a fusion protein containing components including one or more of cell surface molecule(s), linker(s) or agent(s).

In some aspects, the linker can be a peptide, a polypeptide or a chemical linker, which can be cleavable or non-cleavable. In some aspects, the linker is a peptide, such as a peptide containing a short sequence of amino acids to join to polypeptide sequences (or nucleic acid encoding such an amino acid sequence). In some embodiments, the linker is one that relieves or decreases steric hindrance that may be caused by proximity of the agent to the cell surface molecule and/or to increase or alter one or more properties of the conjugate, such as expression, specificity or immunogenicity. In some embodiments, the linkage or conjugation can be facilitated by recombinant methods. In some embodiments, the linker is a peptide or a polypeptide and the provided conjugates are fusion proteins.

A fusion protein can include a cell surface molecule that is a cell surface protein, such as any as described, that is linked directly or indirectly to a peptide or polypeptide agent, e.g. affinity tag, such as a streptavidin-binding peptide. A nucleic acid sequence encoding a fusion protein can contain a coding sequence for the cell surface protein and the at least one peptide or polypeptide agent such that the nucleic acid sequence contains a coding sequence for two or more proteins, in some cases 2, 3, 4, 5 or more proteins. In some embodiments, each of the coding sequences are in the same reading frame such that when the fusion protein is transcribed and translated in a host cell, the protein is produced containing the cell surface protein and the at least one peptide or polypeptide agent, e.g. streptavidin-binding peptide. In some aspects, each of the two or more proteins can be adjacent to another protein in the construct or separated by a linker polypeptide, such as a peptide linker, that contains 1, 2, 3 or more, but typically fewer than 20, 15, 10, 9, 8, 7 or 6 amino acids.

Exemplary peptide linkers include (Gly-Ser)$_n$ amino acid sequence, which, in some cases, can include some Glu or Lys residues dispersed throughout to increase solubility. The linker length may be tailored to be longer or shorter to ensure access of a binding molecule for the agent and to ensure access of an antibody or antigen-binding fragment (or other binding molecule) for the cell surface molecule of the conjugate. In some embodiments, the linker is any set forth as GGGSGGGS (SEQ ID NO:59); GGGGS (SEQ ID NO:60); GGGS (SEQ ID NO:61); GGGGSGGGGSGGGGS (SEQ ID NO:62); GSTSGSGKPGSGEGSTKG (SEQ ID NO:55); GGGGSGGGGS (SEQ ID NO:56). In some embodiments, the linker is a cleavable linker. In some embodiments, the cleavable linker comprises a Phe-Leu linker, a Gly-Phe-Leu-Gly linker (SEQ ID NO:99), a Pro-Leu-Gly-Leu-Trp-Ala linker (set forth in SEQ ID NO:98), a Val-Cit linker or a Phe-Lys linker (see, e.g., U.S. Pat. No. 6,214,345).

In some embodiments, the cell surface conjugate is non-immunogenic. In some embodiments, the cell surface conjugate does not comprise an immunogenic epitope and/or is not recognized by the immune response or is not able to induce, elicit or initiate a detectable immune response in an animal, e.g. humoral or cell-mediated immune. Cell-mediated immune responses include, for example, T cell responses, such as T cell proliferation, lymphokine secretion, cytotoxic responses, local inflammatory reactions and/or recruitment of additional immune cells. Humoral responses include, for example, activation of B cells leading to production of antibodies against an immunogenic epitope. The ability of cells expressing a cell surface conjugate to induce or elicit an immune response, such as a humoral or cell-mediated immune response, can be assessed following administration of such cells to a subject. In some embodiments, the presence of antibodies that specifically bind to and/or neutralize binding epitopes of the cell surface conjugate can be identified by methods such as ELISpot, intracellular cytokine staining, ELISAs (e.g. for cytokines), or cell-based antibody detection methods, for example, by flow cytometry, on serum from the subject. In some embodiments, a cell-mediated immune response to the cell surface conjugate can be assessed using a cytotoxic T-lymphocyte (CTL) assay for detection of CD8+ T cells that specifically bind to and induce cytotoxicity and/or a mixed lymphocyte reaction, using cells, e.g., irradiated cells, expressing the cell surface conjugate, as stimulator cells.

In some embodiments, the polynucleotide encoding the cell surface conjugate also contains a signal sequence encoding a signal peptide, such as for targeting the expressed protein to the secretory pathway for insertion of the conjugate into the cell membrane. In some aspects, the signal peptide is about 5-30 amino acids in length and is present at the N-terminus of the encoded conjugate. In some embodiments, the polynucleotide encodes a conjugate containing in order N- to C-terminus: signal peptide, agent (e.g. affinity tag, such as a streptavidin binding peptide) and cell surface molecule (e.g. modified cell surface molecule, such as EGFRt). In some embodiments, the signal peptide is the native signal peptide of the reference cell surface molecule (e.g. native signal peptide contained in a sequence set forth in any of SEQ ID NOS: 64-69). In some embodiments, the signal peptide is a heterologous or non-native signal peptide, such as the GMCSFR alpha chain signal peptide set forth in SEQ ID NO: 48 which, in some cases, is encoded by nucleotides set forth in SEQ ID NO:47. In some embodiments, the polynucleotide encodes a conjugate containing in order N- to C-terminus: cell surface molecule (e.g. PSMA)

or a modified cell surface molecule (e.g., tPSMA) and an agent (e.g. affinity tag, such as a streptavidin binding peptide).

A. Cell Surface Molecule, e.g. Modified Cell Surface Molecule

In some embodiments, the cell surface molecule of the conjugate contains at least one extracellular domain and a transmembrane domain. In some embodiments, the cell surface molecule is capable of being expressed on the surface of the cell. In some embodiments, the cell surface molecule is a cell surface receptor, ligand, glycoprotein, cell adhesion molecule, antigen, integrin, or cluster of differentiation (CD) or is a modified form thereof. In some embodiments, the cell surface molecule is not a chimeric antigen receptor. In some embodiments, the cell surface molecule is a modified cell surface molecule that is altered compared to a reference cell surface molecule. In some cases, the modified cell surface molecule lacks a functional intracellular signaling domain and/or is not capable of mediating intracellular signaling.

In some embodiments, the cell surface molecule of the cell surface conjugate contains a modified cell surface molecule that is altered compared to a reference cell surface molecule. In some embodiments, the reference cell surface molecule is a cell surface receptor, ligand, glycoprotein, cell adhesion molecule, antigen, integrin, or cluster of differentiation (CD). In some embodiments, the reference cell surface molecule is a cell surface receptor. In some embodiments, the reference cell surface molecule is a native mammalian cell surface molecule, such as a native mammalian cell surface receptor. In some cases, the cell surface molecule is a native human membrane protein.

In some embodiments, the reference cell surface molecule can be one that contains an extracellular domain or regions containing one or more epitope(s) recognized by an antibody or an antigen-binding fragment thereof. The antibody or antigen-binding fragment can include polyclonal and monoclonal antibodies, including intact antibodies and functional (antigen-binding) antibody fragments, including fragment antigen binding (Fab) fragments, F(ab')₂ fragments, Fab' fragments, Fv fragments, recombinant IgG (rIgG) fragments, variable heavy chain ($V_H$) regions capable of specifically binding the antigen, single chain antibody fragments, including single chain variable fragments (scFv), and single domain antibodies (e.g., sdAb, sdFv, nanobody) fragments. Antibodies or antigen-binding fragment thereof can include intact or full-length antibodies, including antibodies of any class or sub-class, including IgG and sub-classes thereof, IgM, IgE, IgA, and IgD, or portion or fragments of a full length antibody. In some aspects, the antibody is an antibody or antigen-binding fragment thereof that is clinically approved. In some aspects, the one or more epitopes can contain contiguous or non-contiguous sequences of a molecule or protein. In some aspects, the one or more epitope(s) is present in the extracellular portion or region of the reference cell surface molecule, such that the reference cell surface molecule can be recognized, identified or detected by the antibody or antigen-binding fragment.

In some embodiments, the extracellular domain of the reference cell surface molecule, in some cases, also contains a binding domain capable of specifically binding to a binding partner, an antigen, a substrate or a ligand. In such embodiments, among the provided cell surface molecules are modified cell surface molecules in which such a binding domain is modified or altered, e.g. is mutated or deleted, such that the ability of the modified cell surface molecule to bind to its normal cognate binding partner, antigen, substrate or ligand is reduced compared to the binding of the reference cell surface molecule to the binding partner, antigen, substrate or ligand. In some cases, the altered binding is reduced by greater than or greater than about 40%, greater than or greater than about 50%, greater than or greater than about 60%, greater than or greater than about 70%, greater than or greater than about 80%, greater than or greater than about 90% or more.

In some embodiments, the cell surface molecule is a membrane protein or a membrane-integrated protein. In some embodiments, the cell surface molecule contains a transmembrane domain. In some aspects, the cell surface molecule is a type I, type II, type III or type IV membrane protein. In some aspects, type I proteins have a single transmembrane stretch of hydrophobic residues, with the portion of the polypeptide on the amino (N)-terminal side of the transmembrane domain exposed on the exterior side of the membrane and the carboxy (C)-terminal portion exposed on the cytoplasmic side. In some aspects, type I membrane proteins are subdivided into types Ia (with cleavable signal sequences) and Ib (without cleavable signal sequence). In some aspects, type II membrane proteins span the membrane only once, but they have their amino terminus on the cytoplasmic side of the cell and the carboxy terminus on the exterior. In some aspects, type III membrane proteins have multiple transmembrane domains in a single polypeptide chain and can be sub-divided into type Ma proteins (with cleavable signal sequences) and type IIIb (with amino termini exposed on the exterior surface of the membrane, but without cleavable signal sequences). In some aspects, type IV proteins have multiple homologous domains which make up an assembly that spans the membrane multiple times, with the domains present on a single polypeptide chain or one or more different polypeptide chains.

In some embodiments, the reference cell surface molecule further contains an intracellular (or cytoplasmic) region or domain, i.e., a region of one or more contiguous amino acids present inside the cell and/or in the cytoplasmic side of the cell. In some cases, the intracellular region of a reference cell surface molecule contains an intracellular signaling domain and/or is capable of mediating intracellular signaling by directly or indirectly modulating cellular signal transduction pathways, and/or downstream responses, functions or activities, such as gene and protein expression, changes in subcellular localization of molecules, intracellular trafficking, changes in protein-protein interaction, receptor internalization, cellular differentiation, proliferation and/or survival.

In some embodiments, the intracellular signaling region or domain, e.g. present in or containing a cytoplasmic tail of the reference cell surface molecule, contains one or more motifs or residues that are capable of being phosphorylated and/or interacting with one or more adaptor proteins in a signal transduction pathway or downstream process in the cell upon a molecular or cellular signal, e.g., when activated or exposed to its cognate antigen or ligand. In some embodiments, the motif is or contains a tyrosine-based motif (e.g. YXXO, where Y is tyrosine, X is any amino acid and O is an amino acid with a bulky hydrophobic group), or a dileucine-based motif (e.g. LL). In some aspects, the intracellular signaling domain of a reference cell surface molecule can be present at or near the C-terminus of type I membrane proteins or at or near the N-terminus of type II membrane proteins. In such embodiments, among the provided cell surface molecules are modified cell surface molecules in which amino acid residues of such an intracellular region or domain is modified or altered, such as mutated, e.g., by one or more substitution, deletion, truncation and/or insertion, such that the ability of the modified cell surface molecule to modulate cellular signal transduction pathways, and/or downstream responses, functions or activities is reduced or prevented. In some cases, the altered signaling and/or downstream responses, functions or activities is reduced by greater than or greater than about 40%, greater than or greater than about 50%, greater than or greater than about 60%, greater than or greater than about 70%, greater than or greater than about 80%, greater than or greater than about 90% or more compared to such signaling and/or downstream responses, functions or activities of a reference cell surface molecule.

In some embodiments, the reference cell surface molecule is different from and/or not identical to the antigen, e.g., a cell surface-expressed antigen, targeted by the recombinant receptor, e.g., chimeric antigen receptor (CAR). In some embodiments, the reference cell surface molecule or modified form thereof, is not specifically bound and/or recognized by the ligand- or antigen-binding domain of the recombinant receptor, e.g., chimeric antigen receptor (CAR).

In some embodiments, the reference cell surface molecule is or includes a cell surface protein and/or a receptor. In some embodiments, the reference cell surface molecule is EpCAM, VEGFR, integrins (e.g., integrins αvβ3, α4, αIIbβ3, α4β7, α5β1, αvβ3, αv), TNF receptor superfamily (e.g., TRAIL-R1, TRAIL-R2), PDGF Receptor, interferon receptor, folate receptor, GPNMB, ICAM-1, HLA-DR, CEA, CA-125, MUC1, TAG-72, IL-6 receptor, 5T4, GD2, GD3, prostate-specific membrane antigen (PSMA), or clusters of differentiation (e.g., CD2, CD3, CD4, CD5, CD11, CD11a/LFA-1, CD15, CD18/ITGB2, CD19, CD20, CD22, CD23/IgE Receptor, CD25, CD28, CD30, CD33, CD38, CD40, CD41, CD44, CD51, CD52, CD62L, CD74, CD80, CD125, CD147/basigin, CD152/CTLA-4, CD154/CD40L, CD195/CCR5, CD319/SLAMF7).

Suitable reference cell surface molecule, e.g., cell surface molecules for modification, include those described in U.S. Pat. No. 8,802,374, which is hereby incorporated by reference. In some embodiments, the reference cell surface molecule is an epidermal growth factor receptor (EGFR), an erbB-2 receptor tyrosine-protein kinase, an erbB-3 receptor tyrosine-protein kinase, an erbB-4 receptor tyrosine-protein kinase, a hepatocyte growth factor receptor (HGFR/c-MET) or an insulin-like growth factor receptor-1 (IGFR-1). In some embodiments, the reference cell surface molecule contains the sequence of amino acids set forth in any of SEQ ID NOs: 49-54 or a sequence of amino acids that exhibits at least at or about 85%, 86%, 87%, 88%, 89%, 90%, 91%, 92%, 93%, 94%, 95%, 96%, 97%, 98%, 99% or more sequence identity to any of SEQ ID NOs: 49-54.

In some embodiments, the reference cell surface molecule can be one that comprises an epitope recognized by an antibody including, but not limited to, 3F8, abagovomab, abciximab, adecatumumab, afutuzumab, alemtuzumab, altumomab pentetate, anatumomab mafenatox, apolizumab, arcitumomab, aselizumab, atlizumab (=tocilizumab), basiliximab, bectumomab, benralizumab, besilesomab, bivatuzumab mertansine, blinatumomab, brentuximab vedotin, cantuzumab mertansine, capromab pendetide, catumaxomab, CC49, cedelizumab, celmoleukin, citatuzumab bogatox, clenoliximab, clivatuzumab tetraxetan, CNTO-95, conatumumab, dacetuzumab, daclizumab, daratumumab, detumomab, ecromeximab, edrecolomab, efalizumab, elotuzumab, enlimomab pegol, epitumomab cituxetan, epratuzumab, erlizumab, etaracizumab, fanolesomab, farali- momab, farletuzumab, galiximab, gavilimomab, gemtuzumab ozogamicin, glembatumumab vedotin, gomiliximab, ibalizumab, ibritumomab tiuxetan, igovomab, inetumumab, iratumumab, inolimomab, inotuzumab ozogamicin, ipilimumab, keliximab, labetuzumab, lintuzumab, lexatumumab, lucatumumab, lumiliximab, mapatumumab, maslimomab, milatuzumab, minretumomab, mitumomab, muromonab-CD3, naptumomab estafenatox, natalizumab, ocrelizumab, odulimomab, ofatumumab, olaratumab, oportuzumab monatox, oregovomab, otelixizumab, pemtumomab, priliximab, PRO 140, rituximab, rovelizumab, ruplizumab, satumomab pendetide, siplizumab, sontuzumab, tadocizumab, taplitumomab paptox, teneliximab, teplizumab, TGN1412, ticilimumab (=tremelimumab), tigatuzumab, tocilizumab (=atlizumab), toralizumab, tositumomab, tremelimumab, tucotuzumab, vedolizumab, veltuzumab, visilizumab, vitaxin, volociximab, votumumab, zanolimumab, ziralimumab, zolimomab aritox. Atezolizumab, bevacizumab (Avastin®), denosumab, dinutuximab, nivolumab, obinutuzumab, pembrolizumab, pidilizumab (CT-011), ramucirumab, siltuximab, ado-trastuzumab emtansine, CEA-scan Fab fragment, 0C125 monoclonal antibody, ab75705, B72.3, MPDL3280A, MSB001078C, MEDI4736, or an antigen-binding fragment thereof, analogs or derivatives thereof, or an antigen-binding antibody fragment selected from a Fab fragment, Fab' fragment F(ab)'2 fragment, single chain Fv (scFv) or a disulfide stabilized Fv (dsFv). In some embodiments, the modified cell surface molecule comprises an epitope recognized by any of the above antibodies or an antigen-binding fragment thereof.

In some embodiments, the reference cell surface molecule is a prostate-specific membrane antigen (PSMA). PSMA is a type II transmembrane protein, which contains a short cytoplasmic amino terminus, a single membrane-spanning domain, and a large extracellular domain. PSMA contains a sequence of amino acids that exhibit similarity to the peptidase family M28 proteins that include co-catalytic metallopeptidases. Wild-type, full-length human PSMA, is a 750-amino acid protein that includes an intracellular portion of 19 amino acid residues, a transmembrane portion of 24 amino acid residues, and an extracellular portion of 707 amino acid residue. In humans, PSMA is encoded by the FOLH1 gene, e.g., described in GenBank Accession No. DD461260 (set forth in SEQ ID NO:96), and isoforms and variants thereof. Exemplary human PSMA amino acid sequence is set forth in, e.g., UniProt Accession No. Q04609 (set forth in SEQ ID NO:94).

In some cases, the extracellular portion of PSMA folds into three distinct structural and functional domains: a protease domain (residues 56-116 and 352-590), an apical domain (residues 117-351) and a C-terminal helical domain (residues 592-750), with reference to positions a wild-type human PSMA sequence, e.g., the amino acid sequence set forth in SEQ ID NO:94 (see, e.g., Davis et al., (2005) Proc. Natl. Acad. Sci. 102(17): 5981-5986; Mesters et al., (2006) EMBO Journal 25:1375-1384).

In some cases, PSMA has enzymatic or catalytic activity. In some aspects, particular domains and/or residues in PSMA are involved in the enzymatic or catalytic activity. PSMA generally contains a binuclear zinc site and can act as glutamate carboxypeptidase or folate hydrolase, catalyzing the hydrolytic cleavage of glutamate from poly-γ-glutamated folates. PSMA also has N-acetylated-alpha-linked-acidic dipeptidase (NAALADase) activity and dipeptidyl-peptidase IV type activity. The enzymatic site contains two zinc ions, and is composed of two pockets, the glutamate-sensing pocket (S1' pocket) and the non-pharmacophore pocket (S1 pocket). Amino acid residues from the three domains generally are involved in substrate recognition, binding, and/or catalytic activity. In some cases, active site residues and/or residues involved in substrate binding and/or catalytic activity in PSMA include amino acid residues at positions 210, 257, 269, 272, 377, 387, 387, 424, 424, 425, 433, 436, 453, 517, 518, 519, 552, 553, 534, 535, 536, 552, 553, 628, 666, 689, 699 and/or 700, with reference to positions a wild-type human PSMA sequence, e.g., the amino acid sequence set forth in SEQ ID NO:94. In some cases, active site residues include one more residues to coordinate the active zinc ions, such as one or more residues corresponding to His377, Asp387, Glu425, Asp453, and/or His553, with reference to position of an exemplary human PSMA sequence, e.g. the amino acid sequence set forth in SEQ ID NO:94. In some embodiments, the N-acetylated-alpha-linked-acidic dipeptidase (NAALADase) domain of PSMA can also be defined as including amino acid residues 274-587, with reference to positions a exemplary human PSMA sequence, e.g., the amino acid sequence set forth in SEQ ID NO:94 (Speno et al., (1999) Molecular Pharmacology 55:179-185).

In some aspects, the intracellular (N-terminal) portion of PSMA contains amino acid residues involved in cellular internalization, e.g., clathrin-dependent endocytic internalization of the molecule. In some aspects, the cellular internalization is mediated by N-terminal amino acids, such as amino acid residues at positions 1-5 of the exemplary human PSMA amino acid sequence set forth in SEQ ID NO:94 (e.g., MWNLL; see, e.g., Rajasekaran et al. (2003) Mol. Biol. Cell. 14:4835-4845). In some aspects, the intracellular portion of the PSMA contains motifs or residues that are capable of being phosphorylated and/or interacting with one or more adaptor proteins in a signal transduction pathway or downstream process in the cell upon a molecular or cellular signal, such as for internalization of the molecule. In some embodiments, exemplary motifs include a dileucine-based motif (e.g., LL).

In some embodiments, the reference cell surface molecule is a PSMA, such as a mammalian PSMA, e.g., human PSMA. In some embodiments, the reference surface molecule is wild-type PSMA, optionally wild-type human PSMA, or an allelic variant or other variant thereof, e.g. alternative isoform or fragment thereof. In some embodiments, the PSMA is a full-length PSMA. In some embodiments, the reference cell surface molecule contains the sequence of amino acids set forth in SEQ ID NO:94 or a sequence of amino acids that exhibits at least at or about 85%, 86%, 87%, 88%, 89%, 90%, 91%, 92%, 93%, 94%, 95%, 96%, 97%, 98%, 99% or more sequence identity to SEQ ID NO:94. In some embodiments, the PSMA comprises or consists essentially of the sequence set forth in SEQ ID NO:94.

In some embodiments, the PSMA is encoded by a nucleic acid sequence set forth in SEQ ID NO:96, or a sequence of nucleic acids that exhibits at least at or about 85%, 86%, 87%, 88%, 89%, 89%, 90%, 91%, 92%, 93%, 94%, 95%, 96%, 97%, 98%, 99% or more sequence identity to SEQ ID NO: 96. In some embodiments, the PSMA is encoded by a modified nucleic acid sequence, e.g., a nucleic acid sequence that is modified to be CpG-free and/or is codon optimized. In some embodiments, the modified nucleic acid sequence is codon optimized for expression in human cells. In some aspects, codon optimization involves balancing the percentages of codons selected with the published abundance of human transfer RNAs so that none is overloaded or limiting. In some embodiments, a CpG-free nucleic acid sequence encoding PSMA is or includes modified cDNA sequence that contains no CpG sequences. In some aspects, the CpG-free nucleic acid and/or codon optimized sequence does not does not change the protein sequence, compared to the wild-type or unmodified PSMA. In some embodiments, the reference PSMA is encoded by a nucleic acid sequence set forth in SEQ ID NO:97. In some aspects, the PSMA encoded by the CpG-free PSMA has substantial percent identity to the protein sequence set forth in SEQ ID NO:94.

In some embodiments, the reference cell surface molecule is a PSMA that comprises an epitope recognized by antibodies or antigen-binding fragment thereof, including, but not limited to, J591, DFO-J591, CYT-356, J415, 3/A12, 3/F11, 3/E7, D2B, 107-1A4, YPSMA-1, YPSMA-2, 3E6, 2G7, 24.4E6, GCP-02, GCP-04, GCP-05, J533, E99, 1G9, 3C6, 4.40, 026, D7-Fc, D7-CH3, 4D4, A5, or an antigen-binding fragment thereof, analogs or derivatives thereof, or an antigen-binding antibody fragment selected from a Fab fragment, Fab' fragment F(ab)'2 fragment, single chain Fv (scFv) or a disulfide stabilized Fv (dsFv). In some embodiments, exemplary antibody or antigen-binding fragment thereof include those described in, e.g., US 2002/0049712; US 2002/0147312; US 2003/0082187; US 2004/0136998; US 2005/0202020; US 2006/0088539; US 2007/0071759; US 2010/0297653; US 2011/0020273; US 2013/0225541; US 2013/0315830; US 2014/0099257; US 2014/0227180; US 2015/0168413; US 2016/0303253; US 2017/0051074; U.S. Pat. Nos. 6,572,856; 7,476,513; 8,470,330; 8,986,655; WO 2006/078892; WO 2010/135431; WO 2014/198223; WO 2015/177360; WO 2016/057917; WO 2016/130819; WO 2016/145139; WO 2016/201300; WO 2017/004144; WO 2017/023761; AU 2002/356844; AU 2006/204913; AU 2006/235421; AU 2006/262231; AU 2006/315500; AU 2010/325969; AU 2013/328619; AU 2015/205574; CA 2353267; EP 1390069; EP 1520588; EP 1581794; EP 1599228; EP 1610818; EP 2906250; Banerjee et al. (2011) Angew Chem Int Ed Engl. 50(39): 9167-9170; Maurer et al. (2016) Nature Reviews Urology 13:226-235; Rowe et al. (2016) Prostate Cancer Prostatic Dis. 19(3):223-230; Mease et al., (2013) Curr Top Med Chem. 13(8):951-962; Osborne et al., (2013) Urol Oncol. 31(2): 144-154; Philipp Wolf (2011), Prostate Specific Membrane Antigen as Biomarker and Therapeutic Target for Prostate Cancer, Prostate Cancer—Diagnostic and Therapeutic Advances, Dr. Philippe E. Spiess (Ed.), Intech, pp. 81-100; Ruggiero et al., (2011) J Nucl Med. 52(10): 1608-1615; Liu et al., (1997) Cancer Research 57:3629-3634; Regino et al., (2009) Curr Radiopharm. January; 2(1): 9-17; Kampmeier et al. (2014) EJNMMI Research 4:13; Wolf et al., (2010) The Prostate 70:562-569; Tykvart et al. (2014) The Prostate 74:1674-1690; Jin et al., (2016) EMJ Urol. 4(1):62-69 and Tino et al. (2000) Hybridoma 19(3):24957, or a fragment thereof, a conjugate thereof or a derivative thereof.

1. Exemplary Modified Cell Surface Molecules

In some embodiments, the modified cell surface molecule contains one or more amino acid modifications, such as one or more amino acid substitutions, deletions and/or insertions, compared to the reference cell surface molecule. In some embodiments, the modified cell surface molecule, such as a modified cell surface receptor is modified to remove any signaling and/or trafficking domains. In some cases, the modified cell surface molecule lacks a functional intracellular signaling domain and/or is not capable of mediating intracellular signaling. In some embodiments, the modified cell surface molecule, e.g., a modified cell surface receptor, exhibits altered cellular internalization, cellular trafficking, enzymatic activity and/or ligand binding, compared to the wild-type or unmodified cell surface molecule. In some embodiments, the modified cell surface molecule contains and/or retains epitopes recognized and/or bound by a binding molecule, e.g., antibody or antigen-binding fragment thereof specific for the cell surface molecule and/or a ligand capable of binding the cell surface molecule.

In some embodiments, the one or more amino acid modifications, such as one or more amino acid substitutions, deletions and/or insertions, including truncations, can be present one or more of the intracellular (e.g., cytoplasmic) and/or extracellular portions of the cell surface molecule. In some embodiments, the modified cell surface molecule is truncated, such by contiguous deletion of a contiguous sequence of C-terminal or N-terminal amino acid residues of a reference cell surface molecule, such as deletion of from or from about 50 to 800 amino acids, such as 50 to 600, for example, at least or about at least 50, 60, 70, 80, 90, 100, 200, 300, 400, 500, 600, or more contiguous amino acids of the reference cell surface molecule. In some aspects, the modified cell surface molecule is truncated, such as by deletion of a contiguous amino acid residues of intracellular (e.g., cytoplasmic) portion of the protein, for example, present in the C-terminus portion of type I membrane proteins or in the N-terminus portion of type II membrane proteins. In some aspects, the modified cell surface molecule is truncated, such as by deletion of a contiguous amino acid residues of an extracellular domain or portion of the protein, for example, present in the N-terminus portion of type I membrane proteins or of the C-terminus portion of type II membrane proteins.

In some embodiments, the cell surface molecule comprises one or more extracellular domains or regions, and the modification is in the extracellular portion of the cell surface molecule. In some aspects, exemplary modifications of the extracellular portion of the cell surface molecule can remove domains or regions involved in epitope binding, enzymatic activity and/or ligand binding and/or signaling or function. In some aspects, exemplary modifications of the extracellular portion of the cell surface molecule contains and/or retains one or more epitope(s) recognized and/or bound by a binding molecule, e.g., antibody or antigen-binding fragment thereof specific for the cell surface molecule and/or a ligand capable of binding the cell surface molecule. In some aspects, exemplary modifications of the extracellular portion of the cell surface molecule generates a modified cell surface molecule that exhibits altered enzymatic activity and/or ligand binding, compared to the reference cell surface molecule.

In some embodiments, the cell surface molecule comprises one or more intracellular and/or cytoplasmic domains or regions, and the modification is in the intracellular (e.g., cytoplasmic) portion of the cell surface molecule. In some aspects, modifications, e.g., substitutions, deletions, truncations and/or insertions, of the intracellular (e.g., cytoplasmic) portion of the cell surface molecule can remove domains or regions involved in eliciting, mediating, activating, inhibiting and/or transmitting cellular signaling and/or downstream activities or functions, e.g., gene and protein expression, changes in subcellular localization of molecules, intracellular trafficking, changes in protein-protein interaction, receptor internalization, cellular differentiation, proliferation and/or survival. In some aspects, modifications of the intracellular (e.g., cytoplasmic) portion of the cell surface molecule generates a modified cell surface molecule that lacks a functional intracellular signaling domain and/or is not capable of mediating intracellular signaling and/or exhibits altered function or activity, e.g., altered cellular internalization and/or cellular trafficking. In some embodiments, ability of the modified cell surface molecule to elicit, mediate, activate, inhibit and/or transmit cellular signaling and/or regulating or modulating activity and/or functions associated with the cell surface molecule of the reference cell surface molecule is reduced by greater than or greater than about 20%, 30%, 40%, 50%, 60%, 70%, 80%, 90%, 95% or more. In some embodiments, the modified cell surface molecule, such as modified cell surface receptor, is inert, such is not able to elicit or mediate an intracellular signal.

In some embodiments, the modified cell surface molecule retains the transmembrane domain of the reference cell surface molecule and at least one extracellular domain of the reference cell surface molecule. In some embodiments, the modified cell surface molecule contains the sequence of amino acids set forth in any of SEQ ID NOS:49-54 or 94, but lacks, such as is truncated or deleted for, the amino acid residues corresponding to the cytoplasmic domain of any of SEQ ID NOS: 49-54 or 94, respectively.

In some embodiments, the ability of the modified cell surface molecule of the provided conjugate to bind the native ligand of the reference cell surface molecule is altered. For example, in some embodiments, the ability of the modified cell surface molecule to bind the native ligand of the reference cell surface molecule is reduced and diminished. In some embodiments, the cell surface molecule is modified to contain at least one extracellular domain of the reference cell surface molecule but lacks one or more other extracellular domains recognized by the native ligand of the reference cell surface molecule. In some embodiments, binding of the modified cell surface molecule to the ligand of the reference cell surface molecule is reduced by greater than or greater than about 20%, 30%, 40%, 50%, 60%, 70%, 80%, 90%, 95% or more.

In some embodiments, the modified cell surface molecule, such as modified cell surface receptor, is modified or truncated compared to a reference cell surface molecule to retain a binding domain that contains an extracellular epitope recognized by a known antibody or functional fragment thereof. Thus, in some embodiments, modification of such cell surface molecule is accomplished by keeping an epitope present in the extracellular domain that is recognized by a known antibody or functional fragment thereof and removing any signaling or trafficking domains and/or any extracellular domains unrecognized by a known antibody. A modified cell surface molecule can include any modified cell surface molecule as described that retains binding, e.g. exhibits the same or similar binding as a reference cel surface molecule, to one or more of the exemplary antibodies and antigen-binding fragments described above.

In some embodiments, the modified cell surface molecule is a modified or truncated tyrosine kinase receptor. Examples of tyrosine kinase receptors that may be modified according to the embodiments described herein include, but are not limited to, members of the endothelial growth factor receptor family (EGRF/ErbB1/HER1; ErbB2/HER2/neu; ErbB3/HER3; ErbB4/HER4), hepatocyte growth factor receptor (HGFR/c-MET) and insulin-like growth factor receptor-1 (IGF-1R). According to some embodiments, the provided cell surface conjugates contain a modified tyrosine kinase receptor that retains an extracellular epitope recognized by a known antibody or functional fragment thereof, and lacks the cytoplasmic domain or a functional protein thereof containing at least a tyrosine kinase domain. A modified tyrosine kinase receptor which lacks at least a- tyrosine kinase domain renders the receptor inert. Commercial antibodies that may be used to recognize a modified tyrosine kinase receptor include, but are not limited to specific to the reference cell surface molecule, such as an epitope of an antibody set forth in Table 1 or described herein, e.g., in Section II.A.

TABLE 1

Exemplary Cell Surface Molecules

| Reference Cell Surface Molecule | SEQ ID NO Precursor | mature | Native Ligand | Antibody |
|---|---|---|---|---|
| HER1/ErbB1/EGFR | 64 | 49 | EGF, betacellulin, TGFα, HB-EGF, amphiregulin, epiregulin, epigen | Cetuximab, panitumumab, matuzumab, necitumumab, nimotuzumab, zalutumumab |
| HER2/neu/ErbB2 | 65 | 50 | No ligand binding activity alone Neuregulin (with HER4) EGF with EGFR | Trastuzumab, 2C4, ertumaxomab, pertuzumab |
| HER3/ErbB3 | 66 | 51 | Hergulin (NRG-1), NRG-2 | Patritumab |
| HER4/ErbB4 | 67 | 52 | NRG-2, NRG-3, heparin-binding EGF-like growth factor, betacellulin | |
| HGFR/c-Met | 68 | 53 | HGF | DN30/OA-5D5/AMG 102/ emibetuzumab |
| IGF-1 R | 69 | 54 | IGF-1, insulin | CP-751,871, figitumumab, cixutumumab, dalotuzumab, Ganitumab, R1507 |
| PSMA WT (full length) | | 94 | Native substrate: N-aceylaspartylglutamate (NAAG), tri-alpha-glutamate peptides, and poly-γ-glutamyl folic acid | J591, DFO-J591, CYT-356, J415, 3/A12, 3/F11, 3/E7, D2B, 107-1A4, YPSMA-1, YPSMA-2, 3E6, 2G7, 24.4E6, GCP-02, GCP-04, GCP-05, J533, E99, 1G9, 3C6, 4.40, 026, D7-Fc, D7-CH3, 4D4, A5 |

AMG-102, AMG-479, BIIB022OA-5D5, CP-751,871, IMC-A12, R1507, cetuximab, cixutumumab, ertumaxomab, figitumumab, matuzumab, necitumumab, panitumumab, pertuzumab, nimotuzumab, robatumumab, trastuzumab, zalutumumab.

In some embodiments, the modified cell surface molecule is a modified prostate-specific membrane antigen (PSMA). Antibodies that may be used to recognize a modified tyrosine kinase receptor include, but are not limited to J591, DFO-J591, CYT-356, J415, 3/A12, 3/F11, 3/E7, D2B, 107-1A4, YPSMA-1, YPSMA-2, 3E6, 2G7, 24.4E6, GCP-02, GCP-04, GCP-05, J533, E99, 1G9, 3C6, 4.40, 026, D7-Fc, D7-CH3, 4D4 and A5.

Non-limiting examples of exemplary cell surface molecules of a cell surface conjugate are set forth in Table 1.

In some embodiments, the modified cell surface molecule is modified compared to a reference cell surface molecule having the sequence of amino acids set forth in any of SEQ ID NOs: 49-54 or 94, in which the modified cell surface molecule at least contains a portion of the extracellular domain and the transmembrane domain of the reference cell surface molecule but lacks, such as is truncated or deleted for, the amino acid residues corresponding to the cytoplasmic domain of such reference cell surface molecule. In some embodiments, such as modified cell surface molecule also lacks one or more extracellular ligand binding domains for binding to a native ligand of the cell surface molecule, such as a native ligand set forth in Table 1. In some embodiments, such a modified cell surface molecule exhibits reduced (e.g. reduced by greater than 20%, 30%, 40%, 50%, 60%, 70%, 80%, 90% or more) binding for a native ligand of the reference cell surface molecule. In some embodiments, the modified cell surface molecule retains at least one extracellular domain containing an epitope for a known antibody a. Modified EGFR, e.g. Truncated EGFR In some embodiments, the cell surface molecule is a modified EGFR that is modified or altered compared to a reference EGFR, such as a reference human EGFR, e.g. a reference EGFR set forth in SEQ ID NO: 64 or the mature sequence thereof set forth in SEQ ID NO: 49. The structure of the reference native EGFR contains four extracellular domains (Domains I-IV, corresponding to residues 35-206, 207-333, 334-499 and 500-645, respectively, of SEQ ID NO:64), a transmembrane domain (corresponding to residues 646-668 of SEQ ID NO:64) and a cytoplasmic domain (corresponding to residues 669-1210 of SEQ ID NO:64) in which is contained therein an EGFR Juxtamembrane Domain (corresponding to residues 669-712 of SEQ ID NO:64), and an EGFR Tyrosine Kinase Domain (corresponding to residues 713-982 of SEQ ID NO:64).

In one embodiment, the modified cell surface molecule is a truncated EGFR (tEGFR) that lacks the membrane distal EGF-binding domain and the cytoplasmic signaling tail containing the tyrosine kinase domain, but retains the transmembrane domain and the extracellular membrane proximal epitope recognized by a known antibody or functional fragment thereof (e.g., cetuximab, matuzumab, necitumumab, nimotuzumab, zalutumumab, or panitumumab). In some embodiments, the absence of the EGF-binding domains and intracellular signaling domains renders EGFR inactive (inert) when expressed by T cells.

In some embodiments, the modified EGFR lacks one or more of Domain I, Domain II, the Juxtamembrane Domain and the Tyrosine Kinase Domain of the reference EGFR. In some cases, the modified EGFR lacks all of the Domain I, Domain II, the Juxtamembrane Domain and the Tyrosine Kinase Domain of the reference EGFR. In some cases, the modified EGFR lacks all of the Domain I, Domain II and cytoplasmic domain. In such embodiments, the modified EGFR contains or contains essentially Domain III and IV of the reference EGFR. In some embodiments, such as modified EGFR retains an epitope recognized by a known antibody or functional fragment thereof.

In some embodiments, the modified EGFR comprises amino acids contained in the sequence of amino acids set forth in SEQ ID NO: 44 or the mature form thereof set forth in SEQ ID NO: 46, or a sequence of amino acids that exhibits at least at or about 85%, 86%, 87%, 88%, 89%, 90%, 91%, 92%, 93%, 94%, 95%, 96%, 97%, 98%, 99% or more sequence identity to SEQ ID NO: 44 or 46, in which the modified EGFR lacks the EGF-binding domains, retains an epitope recognized by a known antibody and lacks all of or a functional portion of the cytoplasmic signaling domain of such reference EGFR. Exemplary of a binding molecules that can recognize the epitope on the modified EGFR include the FDA-approved anti-EGFR monoclonal antibody (mAb) cetuximab or another anti-EGFR antibody.

In some embodiments, the modified EGFR, such as tEGFR, is encoded by the sequence of nucleotides set forth in SEQ ID NO: 57 or a sequence that has at least at or about 85%, 86%, 87%, 88%, 89%, 90%, 91%, 92%, 93%, 94%, 95%, 96%, 97%, 98% or 99% sequence identity to SEQ ID NO:57, such as a sequence thereof containing degenerate codons. The encoded modified EGFR can contain a signal peptide for expression as a surface molecule or surface protein. In some embodiments, the modified EGFR, such as tEGFR, is encoded by nucleotides containing a sequence encoding the native signal peptide of the reference EGFR contained in SEQ ID NO: 64. In some embodiments, the modified EGFR, such as tEGFR, is encoded by nucleotides containing a sequence encoding a non-native or heterologous signal peptide, for example, set forth in SEQ ID NO: 48. In some embodiments, the modified EGFR is encoded by the sequence of nucleotides set forth in SEQ ID NO:45 or a sequence that has at least at or about 85%, 86%, 87%, 88%, 89%, 90%, 91%, 92%, 93%, 94%, 95%, 96%, 97%, 98% or 99% sequence identity to SEQ ID NO:45, such as a sequence thereof containing degenerate codons.

b. Modified Her2, e.g. Truncated Her2

In some embodiments, the cell surface molecule is a modified HER2/neu/ErbB2 that is modified or altered compared to a reference HER2/neu/ErbB2, such as a reference human HER2/neu/ErbB2, e.g. a reference HER2/neu/ErbB2 set forth in SEQ ID NO: 65 or the mature sequence thereof set forth in SEQ ID NO: 50. The structure of the reference native HER2/neu/ErbB2 contains an extracellular domain (corresponding to residues 23-652, of SEQ ID NO: 65), a transmembrane domain (corresponding to residues 653-675 of SEQ ID NO:65), and a cytoplasmic domain (corresponding to residues 676-1255 of SEQ ID NO:65). The structure of the reference native HER2/neu/ErbB2 extracellular domain contains Domains I-IV, corresponding to residues 1-195, 196-319, 320-488, and 489-630 respectively, of SEQ ID NO: 50 (U.S. Patent Application Publication No. US2014/0186867 and U.S. Pat. No. 7,449,184).

In one embodiment, the modified cell surface molecule is a truncated HER2/neu/ErbB2 (HER2t) that lacks the cytoplasmic domain, but retains the transmembrane domain and the extracellular membrane proximal epitope recognized by a known antibody or functional fragment thereof (e.g., trastuzumab, 2C4, ertumaxomab, pertuzumab). In some embodiments, the absence of the ligand-binding domains and intracellular signaling domains renders HER2/neu/ErbB2 inactive (inert) when expressed by T cells.

In some embodiments, the modified HER2/neu/ErbB2 lacks one or more of Domain I, Domain II, and Domain III of the reference HER2/neu/ErbB2. In some cases, the modified HER2/neu/ErbB2 lacks all of extracellular domains of the reference HER2/neu/ErbB2. In some cases, the modified HER2/neu/ErbB2 lacks all of the extracellular and cytoplasmic domain. In such embodiments, the modified HER2/neu/ErbB2 contains or contains essentially Domain IV, which is retained and the transmembrane domain of the reference HER2/neu/ErbB2. In some embodiments, such as modified HER2/neu/ErbB2 retains an epitope recognized by a known antibody or functional fragment thereof.

In some embodiments, the modified HER2/neu/ErbB2 comprises amino acids contained in the sequence of amino acids set forth in SEQ ID NO: 92, or a sequence of amino acids that exhibits at least at or about 85%, 86%, 87%, 88%, 89%, 90%, 91%, 92%, 93%, 94%, 95%, 96%, 97%, 98%, 99% or more sequence identity to SEQ ID NO: 92, in which the modified HER2/neu/ErbB2 lacks the ligand-binding domains, retains an epitope recognized by a known antibody and lacks all of or a functional portion of the cytoplasmic signaling domain of such reference HER2/neu/ErbB2. In some embodiments, the ligand-binding domains can be bind to EGF, transforming growth factor α (TGFα), amphiregulin, heparin-binding EGF-like growth factor, betacellulin, and epiregulin. Exemplary of a binding molecules that can recognize the epitope on the modified HER2/neu/ErbB2 include the FDA-approved anti-HER2 monoclonal antibody (mAb) trastuzumab, 2C4, ertumaxomab, pertuzumab, or another anti-HER2/neu/ErbB2 antibody. In some embodiments, the binding molecule can recognize an epitope in domain IV of the modified HER2/neu/ErbB2 (trastuzumab) or can recognize an epitope in domain II of the modified HER2/neu/ErbB2 (pertuzumab).

In some embodiments, the modified HER2/neu/ErbB2, such as HER2t, is encoded by the sequence of nucleotides set forth in SEQ ID NO: 91 or a sequence that has at least at or about 85%, 86%, 87%, 88%, 89%, 90%, 91%, 92%, 93%, 94%, 95%, 96%, 97%, 98% or 99% sequence identity to SEQ ID NO: 91, such as a sequence thereof containing degenerate codons. The encoded modified HER2/neu/ErbB2 can contain a signal peptide for expression as a surface molecule or surface protein. In some embodiments, the modified HER2/neu/ErbB2, such as HER2t, is encoded by nucleotides containing a sequence encoding the native signal peptide of the reference HER2/neu/ErbB2 contained in SEQ ID NO: 65. In some embodiments, the modified HER2/neu/ErbB2, such as HER2t, is encoded by nucleotides containing a sequence encoding a non-native or heterologous signal peptide, for example, set forth in SEQ ID NO: 48. In some embodiments, the modified HER2/neu/ErbB2 is encoded by the sequence of nucleotides set forth in SEQ ID NO: 93 or a sequence that has at least at or about 85%, 86%, 87%, 88%, 89%, 90%, 91%, 92%, 93%, 94%, 95%, 96%, 97%, 98% or 99% sequence identity to SEQ ID NO: 93, such as a sequence thereof containing degenerate codons.

c. Modified PSMA, e.g. Truncated PSMA

In some embodiments, the modified cell surface molecule is a modified prostate-specific membrane antigen (PSMA). In some embodiments, the modified cell surface molecule is modified compared to a reference cell surface molecule that is a PSMA, such as a wild-type or unmodified PSMA, e.g. a human PSMA, e.g., containing the sequence of amino acids set forth in SEQ ID NO:94. In some embodiments, the modified PSMA contains one or more amino acid modification compared to a reference PSMA, such as one or more amino acid substitutions, deletions, truncations and/or insertions. In some embodiments, the modified PSMA exhibits altered cellular internalization, cellular trafficking, enzymatic activity and/or ligand binding, compared to the reference, wild-type or unmodified PSMA.

In some embodiments, the modified PSMA comprises all or substantially all of the transmembrane domain of the wild-type or unmodified PSMA; or the modified PSMA comprises a transmembrane domain with the same or at least the same number of amino acids as the transmembrane domain of a wild-type or unmodified PSMA. In some embodiments, the PSMA comprises an extracellular domain containing an epitope recognized by any of the antibodies or an antigen-binding fragment thereof described herein that bind to PSMA.

In some embodiments, the reference, wild-type or unmodified PSMA is human PSMA and/or comprises the sequence of amino acids set forth in SEQ ID NO:94. In some embodiments, the modified PSMA contains the extracellular domain and/or transmembrane domain of the sequence of amino acids set forth in SEQ ID NO:94 or portion or fragment thereof.

In some embodiments, the modified PSMA comprises at least one amino acid substitution, e.g., at the second amino acid residue, where the tryptophan is substituted by glycine, corresponding to W2G, with reference to positions in PSMA set forth in SEQ ID NO:94. In some embodiments, the modified PSMA comprises at least one amino acid substitution corresponding to W2G or does not comprise W2 or does not comprise any residue at position 2, with reference to positions in the PSMA sequence set forth in SEQ ID NO:94. For example, in some embodiments, the modified PSMA comprises the sequence of amino acids set forth in SEQ ID NO:95 or a fragment thereof, or a sequence of amino acids that exhibits at least or at least about 85%, 86%, 87%, 88%, 89%, 90%, 91%, 92%, 93%, 94%, 95%, 96%, 97%, 98%, 99% or more sequence identity to SEQ ID NOS:95 or a fragment thereof and comprises the at least one amino acid substitution.

In some embodiments, the modified PSMA comprises an amino acid substitution at one or more of amino acid residues at position 2, 3, 4, 5, 6, 7, 8, 9, 10 or 14 with reference to positions in the PSMA sequence set forth in SEQ ID NO:94, to alanine.

In some embodiments, the PSMA is a modified PSMA that comprises a deletion of one or more N-terminal amino acid residues within the intracellular portion, compared to the wild-type or unmodified PSMA. Wild-type, full-length human PSMA, is a 750-amino acid protein that includes an intracellular portion of 19 amino acid residues, a transmembrane portion of 24 amino acid residues, and an extracellular portion of 707 amino acid residue. For example, in some embodiments, the modified PSMA contains a deletion at the N-terminus (corresponding to the 5' end of the coding sequence in the nucleic acid sequence encoding PSMA or modified form thereof), the deletion being within the intracellular portion of PSMA.

In some aspects, the modified PSMA containing one or more deletions within the intracellular portion is also referred to as a truncated form of PSMA, a truncated PSMA or a tPSMA. In some aspects, the truncated PSMA or tPSMA contains a deletion or truncation of one or more amino acid residues, optionally contiguous amino acid residues, at or near the N-terminal of the wild-type or unmodified PSMA. In some aspects, the modified PSMA contains a deletion or truncation of one or more amino acid residues, e.g., one or more contiguous amino acid residues, within an intracellular portion or domain of the PSMA. In some embodiments, the PSMA protein containing a deletion N-terminal amino acids allows the N-terminally modified PSMA to successfully localize to the cell membrane and centrosome and/or (i) exhibits reduced endogenous signaling; (ii) exhibits increased cell surface expression; and/or (iii) exhibits reduced cellular internalization compared to the wild-type or unmodified PSMA. In some embodiments, the modified PSMA exhibits reduced endogenous signaling or reduced cellular internalization, e.g. reduced by greater than or greater than about 20%, 30%, 40%, 50%, 60%, 70%, 80%, 90% or more. In some embodiments, the modified PSMA exhibits increased cell surface expression or increased localization to the cell membrane and centrosome, e.g. increased by greater than or greater than about 20%, 30%, 40%, 50%, 60%, 70%, 80%, 90% or more. In some aspects, cell surface expression and/or cellular internalization can be assessed using cell imaging techniques, such as confocal microscopy using labeled binding molecules, e.g., antibodies, that specifically bind to PSMA or variant thereof.

In some embodiments, the modified PSMA contains or retains a methionine as a first residue, which, in some cases, is required for translation. In some embodiments, the PSMA is a modified PSMA that comprises a deletion of one or more N-terminal amino acid residues, optionally contiguous amino acid residues, within the intracellular portion, compared to the wild-type or unmodified PSMA, but does not include a deletion of the initial methionine required for translation.

In some embodiments, the PSMA or modified PSMA includes a PSMA described in, e.g., International PCT Pub. No. WO2015143029, Rajasekaran et al. (2003) Mol. Biol. Cell. 14:4835-4845, Rajasekaran et al. (2008) Mol Cancer Ther. (2008) 7(7): 2142-2151, Barinka et al. (2004) Eur. J. Biochem. 271:2782-2790, and Davis et al. (2005) Proc. Natl. Acad. Sci. 102(17)-5981-5986.

In some embodiments, the modified PSMA contains a deletion of or lacks 11 N-terminal amino acids and/or the first 11 amino acids, with reference to positions in a wild-type or unmodified PSMA, e.g., the PSMA sequence set forth in SEQ ID NO:94. In some embodiments, the modified PSMA contains a deletion of or lacks 15 N-terminal amino acids, with reference to positions in a wild-type or unmodified PSMA, e.g., the PSMA sequence set forth in SEQ ID NO:94. In some embodiments, the modified PSMA contains deletion or lacks amino acids N-terminal amino acids 6-14, with reference to positions in a wild-type or unmodified PSMA, e.g., the PSMA sequence set forth in SEQ ID NO:94.

In some embodiments, the modified PSMA comprises a deletion of one or more C-terminal amino acid residues. In some embodiments, the modified PSMA comprises a deletion of amino acid residues 103-750, 626-750, 721-747 or 736-750, with reference to positions in PSMA set forth in SEQ ID NO:94. In some embodiments, the modified PSMA comprises a deletion of 15 C-terminal amino acid residues, with reference to positions in PSMA set forth in SEQ ID NO:94.

In some embodiments, the modified PSMA is encoded by a modified nucleic acid sequence, e.g., a nucleic acid sequence that is modified to be CpG-free and/or is codon optimized.

B. Agent (e.g. Affinity Tag)

In some embodiments of the cell surface conjugate, the cell surface molecule, such as a modified cell surface molecule, is linked to at least one agent. In some embodiments, the agent is a peptide or polypeptide. In some embodiments, the agent is a peptide. In some embodiments, the peptide is artificial, synthetic or is a portion of a longer polypeptide. A peptide is generally greater than or equal to 2 amino acids in length, such as one that is greater than or equal to 2 and less than or equal to 50 or 40 amino acids in length. In some embodiments, the peptide is between 7 and 40 amino acids, 8 and 20 amino acids, 10 and 17 amino acids, 7 and 13 amino acids or 8 and 10 amino acids. In some embodiments, the peptide has a length of between 7 and 20 amino acids. In some embodiments, the peptide has a length of 7, 8, 9, 10, 11, 12, 13, 14, 15, 16, 17, 18, 19, or 20 amino acids.

In some embodiments, the agent is an affinity tag that is known to be recognized by a binding molecule. In some embodiments, the affinity tag has enough residues to provide an epitope recognized by an antibody or by a non-antibody binding molecule, yet, in some aspects, is short enough such that it does not interfere with or sterically block an epitope of the cell surface molecule recognized by a known antibody as described above. Suitable tag polypeptides generally have at least 5 or 6 amino acid residues and usually between about 8-50 amino acid residues, typically between 9-30 residues. Such tags are well-known and can be readily synthesized and designed.

In some embodiments, the agent, such as affinity tag, is a streptavidin binding peptide (e.g. Strep-tag), oligohistidine or polyhistidine (e.g. His tag), MAT tag, a glutathione-S-transferase, immunoglobulin domain, calmodulin or an analog thereof, thioredoxin, chitin binding protein (CBP), calmodulin binding peptide (CBP), a FLAG-peptide, an HA-tag, maltose binding protein (MBP), an HSV epitope (e.g. gd tag), a myc epitope, and/or a biotinylated carrier protein. Exemplary of such agents, such as affinity tags, include, MAT tag (sequence: His-Asn-His-Arg-His-Lys-His-Gly-Gly-Gly-Cys) (SEQ ID NO:63), HA-tag (sequence: Tyr-Pro-Tyr-Asp-Val-Pro-Asp-Tyr-Ala) (SEQ ID NO: 20), the VSV-G-tag (sequence: Tyr-Thr-Asp-Ile-Glu-Met-Asn-Arg-Leu-Gly-Lys) (SEQ ID NO: 21), the HSV-tag (sequence: Gln-Pro-Glu-Leu-Ala-Pro-Glu-Asp-Pro-Glu-Asp) (SEQ ID NO: 22), the T7 epitope (Ala-Ser-Met-Thr-Gly-Gly-Gln-Gln-Met-Gly) (SEQ ID NO: 22), maltose binding protein (MBP), the HSV epitope of the sequence Gln-Pro-Glu-Leu-Ala-Pro-Glu-Asp-Pro-Glu-Asp (SEQ ID NO: 24) of herpes simplex virus glycoprotein D, the "myc" epitope of the transcription factor c-myc of the sequence Glu-Gln-Lys-Leu-Ile-Ser-Glu-Glu-Asp-Leu (SEQ ID NO: 25), the V5-tag (sequence: Gly-Lys-Pro-Ile-Pro-Asn-Pro-Leu-Leu-Gly-Leu-Asp-Ser-Thr) (SEQ ID NO: 26), or glutathione-S-transferase (GST). Exemplary of such agents, e.g. affinity tag, also can include a streptavidin binding peptide (e.g. Strep-tag), such as any comprising a sequence set forth in any of SEQ ID NOS: 7-19. Binding molecules known to recognize such tags are known and include, but are not limited to, antibody 12CA5 for recognition of the influenza hemagglutinin (HA) tag polypeptide (Field et al. (1988) Mol. Cell. Biol. 5:2159-2165); 8F9, 3C7, 6E10, G4, B7 and 9E10 antibodies for recognition of the c-myc tag (see, e.g., Evan et al. (1985) Molecular and Cellular Biology 5:3610-3616); and a known antibody for recognizing the Herpes Simplex virus glycoprotein D (gD) tag and its antibody (Paborsky et al. (1990) Protein Engineering 3:547-553), or any known binding molecule recognizing a streptavidin binding peptide (e.g. Strep-tag), such as antibody molecules or reagents comprising a streptavidin mutein (e.g. Strep-Tactin).

Further examples of an agent include, but are not limited to, dinitrophenol or digoxigenin, a lectin, protein A, protein G, a metal, a metal ion, nitrilo triacetic acid derivatives (NTA), RGD-motifs, a dextrane, polyethyleneimine (PEI), a redox polymer, a glycoproteins, an aptamers, a dye, amylose, maltose, cellulose, chitin, glutathione, calmodulin, gelatine, polymyxin, heparin, NAD, NADP, lysine, arginine, benzamidine, poly U, or oligo-dT. Lectins such as Concavalin A are known to bind to polysaccharides and glycosylated proteins. An illustrative example of a dye is a triazine dye such as Cibacron blue F3G-A (CB) or Red HE-3B, which specifically bind NADH-dependent enzymes. Typically, Green A binds to Co A proteins, human serum albumin, and dehydrogenases. In some cases, the dyes 7-aminoactinomycin D and 4',6-diamidino-2-phenylindole bind to DNA.

In some embodiments, the agent (e.g. a peptide), such as affinity tag, is recognized by a binding molecule with an equilibrium dissociation constant ($K_D$) of from or from about $10^{-4}$ to $10^{-10}$ M or an equilibrium association constant ($K_A$) of from or from about $10^4$ to $10^{10}$ M$^{-1}$. In some embodiments, the agent, such as affinity tag, e.g. a peptide, is recognized by a binding molecule with a low binding affinity, such as with a $K_D$ of greater than or greater than about $10^{-7}$ M, $10^{-6}$ M, $10^{-5}$ M, $10^{-4}$ M or greater or with a $K_A$ or less than or less than about $10^7$ M$^{-1}$, $10^6$ M$^{-1}$, $10^5$ M$^{-1}$, $10^4$ M$^{-1}$ or less.

In some embodiments, the agent, such as affinity tag, is recognized by a binding molecule that is or comprises a binding reagent having at least one binding site Z that binds to the agent. In some embodiments, the binding site Z is a natural biotin binding site of avidin or streptavidin or a mutein or analog thereof for which there can be up to four binding sites in an individual molecule (e.g. a tetramer contains four binding sites Z), whereby a homo-tetramer can contain up to 4 binding sites that are the same, i.e. Z1, whereas a hetero-tetramer can contain up to 4 binding sites that may be different, e.g. containing Z1 and Z2.

In some embodiments, the agent is recognized by a binding molecule that is or comprises a reagent that is an oligomer or polymer. In some embodiments, the oligomer or polymer can be generated by linking directly or indirectly individual molecules of the protein as it exists naturally, either by linking directly or indirectly individual molecules of a monomer or a complex of subunits that make up an individual molecule (e.g. linking directly or indirectly dimers, trimers, tetramers, etc. of a protein as it exists naturally). For example, a tetrameric homodimer or heterodimer of streptavidin or avidin may be referred to as an individual molecule or smallest building block of a respective oligomer or polymer. In some embodiments, the oligomer or polymer can contain linkage of at least 2 individual molecules of the protein (e.g. is a 2-mer), or can be at least a 3-mer, 4-mer, 5-mer, 6-mer, 7-mer, 8-mer, 9-mer, 10-mer, 11-mer, 12-mer, 13-mer, 14-mer, 15-mer, 16-mer, 17-mer, 18-mer, 19-mer, 20-mer, 25-mer, 30-mer, 35-mer, 40-mer, 45-mer or 50-mer of individual molecules of the protein (e.g., monomers, tetramers). In some cases, an oligomer can contain a plurality of binding sites Z1, such as at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50 or more binding sites Z1. In some embodiments, the oligomer is generated or produced from a plurality of individual molecules that can be hetero-tetramers (e.g. of a streptavidin, streptavidin mutein, avidin or avidin mutein) and/or from a plurality of two or more different individual molecules (e.g. different homo-tetramers of streptavidin, streptavidin mutein, avidin or avidin mutein) that differ in their binding sites Z, e.g. Z1 and Z2, in which case a plurality of different binding sites Z, e.g. Z1 and Z2, may be present in the oligomer. For example, in some cases, an oligomer can contain a plurality of binding sites Z1 and a plurality of binding sites Z2, which, in combination, can include at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50 or more combined binding sites Z1 and Z2.

Oligomers can be generated using any methods known in the art, such as any described in published U.S. Patent Application No. US2004/0082012. In some embodiments, the oligomer or polymer contains two or more individual molecules that may be crosslinked, such as by a polysaccharide or a bifunctional linker.

In some embodiments, the oligomer or polymer is obtained by crosslinking individual molecules or a complex of subunits that make up an individual molecule in the presence of a polysaccharide. In some embodiments, oligomers or polymers can be prepared by the introduction of carboxyl residues into a polysaccharide, e.g. dextran. In some aspects, individual molecules of the reagent (e.g., monomers, tetramers) can be coupled via primary amino groups of internal lysine residues and/or the free N-terminus to the carboxyl groups in the dextran backbone using conventional carbodiimide chemistry. In some embodiments, the coupling reaction is performed at a molar ratio of about 60 moles of individual molecules of the reagent (e.g., monomers, tetramers) per mole of dextran.

In some cases, the binding interaction between the agent and the at least one binding site Z is a non-covalent interaction. In some embodiments, the binding interaction, such as non-covalent interaction, between the agent and the at least one binding site Z is reversible. In some embodiments, the binding reagent contains a plurality of binding sites capable of reversibly binding to the agent. Binding molecule reagents that can be used in such reversible systems are described and known in the art, see e.g., U.S. Pat. Nos. 5,168,049; 5,506,121; 6,103,493; 7,776,562; 7,981,632; 8,298,782; 8,735,540; 9,023,604; and International published PCT Appl. Nos. WO2013/124474 and WO2014/076277.

In some embodiments, recognition of the agent by the binding molecule is reversible, such as is competed in the presence of a competition substance. In some embodiments, the agent is one in which reversible association can be mediated in the presence of a competition substance that is or contains a binding site that also is able to be recognized or bound by the reagent. In some aspects, the competition substance can act as a competitor due to a higher binding affinity between it and the binding molecule than the binding affinity between the binding molecule and the agent and/or due to the competition substance being present at higher concentration than the agent, thereby detaching and/or dissociating the interaction between the agent and the binding molecule. In some aspects, reversible binding between the agent and the binding molecule can be carried out by contacting cells expressing the cell surface conjugate and bound by the binding molecule with the competition substance, such by adding the competition substance to such a cell composition.

In some embodiment the agent is or includes a moiety known to the skilled artisan as an affinity tag. In some such embodiments, the binding molecule is or comprises a reagent that is a corresponding binding partner, for example, an antibody or an antibody fragment, known to bind to the affinity tag. In such embodiments, the complex formed between the one or more binding sites Z of the reagent which may be an antibody or antibody fragment, and the antigen can be disrupted competitively by adding the free antigen, i.e. the free peptide (epitope tag) or the free protein (such as MBP or CBP). In some embodiments, the affinity tag might also be an oligonucleotide tag. In some cases, such an oligonucleotide tag may, for instance, be used to hybridize to an oligonucleotide with a complementary sequence, linked to or included in the reagent.

In some cases, the binding molecule is or comprises a reagent that contains at least two chelating groups K that may be capable of binding to a transition metal ion, thereby rendering the reagent capable of binding to an oligohistidine affinity tag, multimeric glutathione-S-transferase, or a biotinylated carrier protein or other agent. Generally, cations of metals such as Ni, Cd, Zn, Co, or Cu, are typically used to bind affinity tags such as an oligohistidine containing sequence, including the hexahistidine or the His-Asn-His-Arg-His-Lys-His-Gly-Gly-Gly-Cys tag (MAT tag; SEQ ID NO:63), and N-methacryloyl-(L)-cysteine methyl ester. In some embodiments the binding between the agent (e.g., peptide), such as an affinity tag, and the one or more binding sites Z of the reagent occurs in the presence of a divalent, a trivalent or a tetravalent cation. In this regard, in some embodiments the reagent includes a divalent, a trivalent or a tetravalent cation, typically held, e.g. complexed, by means of a suitable chelator. In some embodiments, the agent (e.g. peptide), such as an affinity tag, may include a moiety that includes, e.g. complexes, a divalent, a trivalent or a tetravalent cation. In some such embodiments, the binding between the agent and the one or more binding sites Z of the reagent can be disrupted by metal ion chelation. The metal chelation may, for example, be accomplished by addition of EGTA or EDTA. Examples of a respective metal chelator, include, but are not limited to, ethylenediamine, ethylene-diaminetetraacetic acid (EDTA), ethylene glycol tetraacetic acid (EGTA), diethylenetri-aminepentaacetic acid (DTPA), N,N-bis(carboxymethyl)glycine (also called nitrilotriacetic acid, NTA), 1,2-bis(o-aminophenoxy)ethane-N,N,N',N'-tetraacetic acid (BAPTA), 2,3-dimer-capto-1-propanol (dimercaprol), porphine and heme. As an example, EDTA forms a complex with most monovalent, divalent, trivalent and tetravalent metal ions, such as e.g. silver ($Ag^+$), calcium ($Ca^{2+}$), manganese ($Mn^{2+}$), copper ($Cu^{2+}$), iron ($Fe^{2+}$), cobalt ($Co^+$) and zirconium ($Zr^{4+}$), while BAPTA is specific for $Ca^{2+}$. As an illustrative example, a standard method used in the art is the formation of a complex between an oligohistidine tag and copper ($Cu^{2+}$), nickel ($Ni^{2+}$), cobalt ($Co^{2+}$), or zinc ($Zn^{2+}$) ions, which are presented by means of the chelator nitrilotriacetic acid (NTA).

In some embodiments, the agent, such as an affinity tag, includes a calmodulin binding peptide and the binding molecule reagent includes multimeric calmodulin as described in U.S. Pat. No. 5,985,658, for example. In some embodiments, the agent, such as an affinity tag, includes a FLAG peptide and the binding molecule reagent includes an antibody that binds to the FLAG peptide, e.g. the FLAG peptide, which binds to the monoclonal antibody 4E11 as described in U.S. Pat. No. 4,851,341. In one embodiment, the agent, such as an affinity tag, includes an oligohistidine tag and the reagent includes an antibody or a transition metal ion binding the oligohistidine tag. In some cases, the disruption of all these binding complexes may be accomplished by metal ion chelation, e.g. calcium chelation, for instance by adding EDTA or EGTA. In some embodiments, calmodulin, antibodies such as 4E11 or chelated metal ions or free chelators may be multimerized by conventional methods, e.g. by biotinylation and complexation with streptavidin or avidin or oligomers thereof or by the introduction of carboxyl residues into a polysaccharide, e.g. dextran, essentially as described in Noguchi, A, et al. Bioconjugate Chemistry (1992) 3, 132-137 in a first step and linking calmodulin or antibodies or chelated metal ions or free chelators via primary amino groups to the carboxyl groups in the polysaccharide, e.g. dextran, backbone using conventional carbodiimide chemistry in a second step.

In some cases, the binding molecule is or comprises a reagent that is a streptavidin or avidin or any analog or mutein of streptavidin or an analog or mutein of avidin (e.g. neutravidin). In some embodiments, the binding molecule reagent is capable of binding to an agent that is a streptavidin binding peptide. In some embodiments, disrupting or reversing binding can be carried out with biotin or a biotin analog or mimic. Exemplary of such streptavidin binding peptides and binding molecule reagents known to recognize such agents are described below.

1. Exemplary Streptavidin Binding Peptide Agents and Binding Molecules Thereto

In some embodiments, the agent (e.g. peptide), such as an affinity tag, is recognized by a reagent that is or that comprises a streptavidin or a streptavidin mutein. In some embodiments, the agent can be a biotin, a biotin derivative or analog, or a streptavidin-binding peptide or other molecule that is able to specifically bind to streptavidin, a streptavidin mutein or analog, avidin or an avidin mutein or analog. In some embodiments, the agent, such as an affinity tag, is a streptavidin binding peptide.

In some embodiments, the streptavidin binding peptide contains a sequence with the general formula set forth in SEQ ID NO: 9, such as contains the sequence set forth in SEQ ID NO: 10. In some embodiments, the peptide sequence has the general formula set forth in SEQ ID NO: 11, such as set forth in SEQ ID NO: 12. In one example, the peptide sequence is Trp-Arg-His-Pro-Gln-Phe-Gly-Gly (also called Strep-tag®, set forth in SEQ ID NO: 7). In one example, the peptide sequence is Ser-Ala-Trp-Ser-His-Pro-Gln-Phe-Glu-Lys (SEQ ID NO:58) or the minimal sequence Trp-Ser-His-Pro-Gln-Phe-Glu-Lys (also called Strep-tag® II, set forth in SEQ ID NO: 8). In some embodiments, the agent contains a sequential arrangement of at least two streptavidin-binding peptide modules, wherein the distance between the two modules is at least 0 and not greater than 50 amino acids, wherein one binding module has 3 to 8 amino acids and contains at least the sequence His-Pro-Xaa (SEQ ID NO: 9), where Xaa is glutamine, asparagine, or methionine, and wherein the other binding module has the same or different streptavidin peptide ligand, such as set forth in SEQ ID NO: 11 (see e.g. International Published PCT Appl. No. WO02/077018; U.S. Pat. No. 7,981,632). In some embodiments, the streptavidin binding peptide contains a sequence having the formula set forth in any of SEQ ID NO: 13 or 14. In some embodiments, the agent can contain twin-strep-tags such as by the sequential arrangement of two streptavidin binding modules, such as is commercially available as Twin-Strep-tag® from IBA GmbH, Gottingen, Germany, for example, containing the sequence (SAWSHPQFEK(GGGS)$_2$GGSAWSHPQFEK)(SEQ ID NO: 16). In some embodiments, the streptavidin binding peptide has the sequence of amino acids set forth in any of SEQ ID NOS: 15-19. In most cases, all these streptavidin binding peptides bind to the same binding site, namely the biotin binding site of streptavidin.

In some embodiments, the streptavidin binding peptide is recognized by a reagent comprising streptavidin or streptavidin mutein, which exhibits binding affinity for the peptide. In some embodiments, the binding affinity of streptavidin or a streptavidin mutein for a streptavidin binding peptide is with a $K_D$ of less than $1\times10^{-4}$ M, $5\times10^{-4}$ M, $1\times10^{-5}$ M, $5\times10^{-5}$ M, $1\times10^{-6}$ M, $5\times10^{-6}$ M or $1\times10^{-7}$ M, but generally greater than $1\times10^{-13}$ M, $1\times10^{-12}$ M or $1\times10^{-11}$ M. For example, peptide sequences (Strep-tags), such as disclosed in U.S. Pat. No. 5,506,121, can act as biotin mimics and demonstrate a binding affinity for streptavidin, e.g., with a $K_D$ of approximately between $10^{-4}$ M and $10^{-5}$ M. In some cases, the binding affinity can be further improved by making a mutation within the streptavidin molecule, see e.g. U.S. Pat. No. 6,103,493 or International published PCT App. No. WO2014/076277. In some embodiments, binding affinity can be determined by methods known in the art, such as any described below.

In some embodiments, the streptavidin binding peptide is recognized by a reagent that is or comprises a streptavidin, a streptavidin mutein or analog, avidin, an avidin mutein or analog (such as neutravidin) or a mixture thereof, in which such reagent contains one or more binding sites Z for reversible association with the agent comprising a streptavidin binding peptide. In some embodiments, the reagent is or contains an analog or mutein of streptavidin or an analog or mutein of avidin that reversibly binds a streptavidin-binding peptide. In some embodiments, the substance (e.g. competitive reagent) can be a biotin, a biotin derivative or analog or a streptavidin-binding peptide capable of competing for binding with the agent for the one or more binding sites Z. In some embodiments, the agent of the conjugate and the substance (e.g. competitive reagent) are different, and the substance (e.g. competitive reagent) exhibits a higher binding affinity for the one or more binding sites Z compared to the affinity of the agent.

In some embodiments, the binding molecule recognizing the agent, e.g. a streptavidin binding peptide (e.g. a Strep-tag), is or comprises a streptavidin that can be wild-type streptavidin, streptavidin muteins or analogs, such as streptavidin-like polypeptides. In some embodiments, the binding molecule is or comprises an avidin that can be wild-type avidin or muteins or analogs of avidin such as neutravidin, a deglycosylated avidin with modified arginines that typically exhibits a more neutral pi and is available as an alternative to native avidin. Generally, deglycosylated, neutral forms of avidin include those commercially available forms such as "Extravidin", available through Sigma Aldrich, or "NeutrAvidin" available from Thermo Scientific or Invitrogen, for example.

In some embodiments, the agent, such as a streptavidin binding peptide, is recognized by a binding molecule reagent that is or comprises a streptavidin or a streptavidin mutein or analog. In some embodiments, wild-type streptavidin (wt-streptavidin) has the amino acid sequence disclosed by Argarana et al, Nucleic Acids Res. 14 (1986) 1871-1882 (SEQ ID NO: 1). In general, streptavidin naturally occurs as a tetramer of four identical subunits, i.e. it is a homo-tetramer, where each subunit contains a single binding site for biotin, a biotin derivative or analog or a biotin mimic. An exemplary sequence of a streptavidin subunit is the sequence of amino acids set forth in SEQ ID NO: 1, but such a sequence also can include a sequence present in homologs thereof from other Streptomyces species. In particular, each subunit of streptavidin may exhibit a strong binding affinity for biotin with a dissociation constant ($K_d$) on the order of about $10^{-14}$ M. In some cases, streptavidin can exist as a monovalent tetramer in which only one of the four binding sites is functional (Howarth et al. (2006) Nat. Methods, 3:267-73; Zhang et al. (2015) Biochem. Biophys. Res. Commun., 463:1059-63)), a divalent tetramer in which two of the four binding sites are functional (Fairhead et al. (2013) J. Mol. Biol., 426:199-214), or can be present in monomeric or dimeric form (Wu et al. (2005) *J. Biol. Chem.*, 280:23225-31; Lim et al. (2010) *Biochemistry*, 50:8682-91).

In some embodiments, the streptavidin may be in any form, such as wild-type or unmodified streptavidin, such as a streptavidin from a *Streptomyces* species or a functionally active fragment thereof that includes at least one functional subunit containing a binding site for the agent (e.g. streptavidin binding peptide) and/or for biotin, a biotin derivative or analog or a biotin mimic, such as generally contains at least one functional subunit of a wild-type streptavidin from *Streptomyces avidinii* set forth in SEQ ID NO: 1 or a functionally active fragment thereof. For example, in some embodiments, streptavidin can include a fragment of wild-type streptavidin, which is shortened at the N- and/or C-terminus. Such minimal streptavidins include any that begin N-terminally in the region of amino acid positions 10 to 16 of SEQ ID NO: 1 and terminate C-terminally in the region of amino acid positions 133 to 142 of SEQ ID NO: 1. In some embodiments, a functionally active fragment of streptavidin contains the sequence of amino acids set forth in SEQ ID NO: 2. In some embodiments, streptavidin, such as set forth in SEQ ID NO: 2, can further contain an N-terminal methionine at a position corresponding to Ala13 with numbering set forth in SEQ ID NO: 1. Reference to the position of residues in streptavidin or streptavidin muteins is with reference to numbering of residues in SEQ ID NO: 1.

In some aspects, streptavidin muteins include polypeptides that are distinguished from the sequence of an unmodified or wild-type streptavidin by one or more amino acid substitutions, deletions, or additions, but that include at least one functional subunit containing a binding site for the agent (e.g. streptavidin binding peptide) and/or biotin, a biotin derivative or analog or a streptavidin-binding peptide. In some aspects, streptavidin-like polypeptides and streptavidin muteins can be polypeptides which essentially are immunologically equivalent to wild-type streptavidin and are in particular capable of binding biotin, biotin derivatives or biotin analogues with the same or different affinity as wt-streptavidin. In some cases, streptavidin-like polypeptides or streptavidin muteins may contain amino acids which are not part of wild-type streptavidin or they may include only a part of wild-type streptavidin. In some embodiments, streptavidin-like polypeptides are polypeptides which are not identical to wild-type streptavidin, since the host does not have the enzymes which are required in order to transform the host-produced polypeptide into the structure of wild-type streptavidin. In some embodiments, streptavidin also may be present as streptavidin tetramers and streptavidin dimers, in particular streptavidin homotetramers, streptavidin homodimers, streptavidin heterotetramers and streptavidin heterodimers. Generally, each subunit normally has a binding site for biotin or biotin analogues or for streptavidin-binding peptides. Examples of streptavidins or streptavidin muteins are mentioned, for example, in WO 86/02077, DE 19641876 A1, U.S. Pat. No. 6,022,951, WO 98/40396 or WO 96/24606.

In some embodiments, a streptavidin mutein can contain amino acids that are not part of an unmodified or wild-type streptavidin or can include only a part of a wild-type or unmodified streptavidin. In some embodiments, a streptavidin mutein contains at least one subunit that can have one more amino acid substitutions (replacements) compared to a subunit of an unmodified or wild-type streptavidin, such as compared to the wild-type streptavidin subunit set forth in SEQ ID NO: 1 or a functionally active fragment thereof, e.g. set forth in SEQ ID NO: 2. In some embodiments, at least one subunit of a streptavidin mutein can have at least 1, 2, 3, 4, 5, 6, 7, 8, 9, 10, 11, 12, 13, 14, 15, 16, 17, 18, 19 or 20 amino acid differences compared to a wild-type or unmodified streptavidin and/or contains at least one subunit that comprising an amino acid sequence that exhibits at least at or about 85%, 86%, 87%, 88%, 89%, 90%, 91%, 92%, 93%, 94%, 95%, 96%, 97%, 98%, 99% or more sequence identity to the sequence of amino acids set forth in SEQ ID NO: 1 or 2, where such streptavidin mutein exhibits functional activity to bind the agent (e.g. streptavidin binding peptide) and/or biotin, a biotin derivative or analog or biotin mimic. In some embodiments, the amino acid replacements (substitutions) are conservative or non-conservative mutations. Examples of streptavidin muteins are known in the art, see e.g., U.S. Pat. Nos. 5,168,049; 5,506,121; 6,022,951; 6,156, 493; 6,165,750; 6,103,493; or 6,368,813; or International published PCT App. No. WO2014/076277.

In some embodiments, streptavidin or a streptavidin mutein includes proteins containing one or more than one functional subunit containing one or more binding sites Z for biotin, a biotin derivative or analog or a streptavidin-binding peptide, such as two or more, three or more, four or more, and, in some cases, 5, 6, 7, 8, 9, 10, 11, 12 or more functional subunits. In some embodiments, streptavidin or streptavidin mutein can include a monomer; a dimer, including a heterodimer or a homodimer; a tetramer, including a homotetramer, a heterotetramer, a monovalent tetramer or a divalent tetramer; or can include higher ordered multimers or oligomers thereof.

In some embodiments, the binding molecule reagent is or contains a streptavidin mutein. In some embodiments, the streptavidin muteins contain one or more mutations (e.g. amino acid replacements) compared to wild-type streptavidin set forth in SEQ ID NO: 1 or a biologically active portion thereof. For example, biologically active portions of streptavidin can include streptavidin variants that are shortened at the N- and/or the C-terminus, which in some cases is called a minimal streptavidin. In some embodiments, an N-terminally shortened minimal streptavidin, to which any of the mutations can be made, begins N-terminally in the region of the amino acid positions 10 to 16 and terminates C-terminally in the region of the amino acid positions 133 to 142 compared to the sequence set forth in SEQ ID NO: 1. In some embodiments, an N-terminally shortened streptavidin, to which any of the mutations can be made, contains the amino acid sequence set forth in SEQ ID NO: 2. In some embodiments, the minimal streptavidin contains an amino acid sequence from position Ala13 to Ser139 and optionally has an N-terminal methionine residue instead of Ala13. For purposes herein, the numbering of amino acid positions refers throughout to the numbering of wt-streptavidin set forth in SEQ ID NO: 1 (e.g. Argarana et al., Nucleic Acids Res. 14 (1986), 1871-1882, cf. also FIG. 3).

In some embodiments, the streptavidin mutein is a mutant as described in U.S. Pat. No. 6,103,493. In some embodiments, the streptavidin mutein contains at least one mutation within the region of amino acid positions 44 to 53, based on the amino acid sequence of wild-type streptavidin, such as set forth in SEQ ID NO: 1. In some embodiments, the streptavidin mutein contains a mutation at one or more residues 44, 45, 46, and/or 47. In some embodiments, the streptavidin mutein contains a replacement of Glu at position 44 of wild-type streptavidin with a hydrophobic aliphatic amino acid, e.g. Val, Ala, Ile or Leu, any amino acid at position 45, an aliphatic amino acid, such as a hydrophobic aliphatic amino acid at position 46 and/or a replacement of Val at position 47 with a basic amino acid, e.g. Arg or Lys, such as generally Arg. In some embodiments, Ala is at position 46 and/or Arg is at position 47 and/or Val or Ile is at position 44. In some embodiments, the streptavidin mutant contains residues Val$^{44}$-Thr$^{45}$-Ala$^{46}$-Arg$^{47}$, such as set forth in exemplary streptavidin muteins containing the sequence of amino acids set forth in SEQ ID NO: 3 or SEQ ID NO: 4 (also known as streptavidin mutant 1, SAM1). In some embodiments, the streptavidin mutein contains residues Ile$^{44}$-Gly$^{45}$-Ala$^{46}$-Arg$^{47}$, such as set forth in exemplary streptavidin muteins containing the sequence of amino acids set forth in SEQ ID NO: 5 or 6 (also known as SAM2). In some cases, such streptavidin mutein are described, for example, in U.S. Pat. No. 6,103,493, and are commercially available under the trademark Strep-Tactin®.

In some embodiment, the streptavidin mutein is a mutant as described in International Published PCT Appl. Nos. WO 2014/076277. In some embodiments, the streptavidin mutein contains at least two cysteine residues in the region of amino acid positions 44 to 53 with reference to amino acid positions set forth in SEQ ID NO: 1. In some embodiments, the cysteine residues are present at positions 45 and 52 to create a disulfide bridge connecting these amino acids. In such an embodiment, amino acid 44 is typically glycine or alanine and amino acid 46 is typically alanine or glycine and amino acid 47 is typically arginine. In some embodiments, the streptavidin mutein contains at least one mutation or amino acid difference in the region of amino acids residues 115 to 121 with reference to amino acid positions set forth in SEQ ID NO: 1. In some embodiments, the streptavidin mutein contains at least one mutation at amino acid position 117, 120 and 121 and/or a deletion of amino acids 118 and 119 and substitution of at least amino acid position 121.

In some embodiments, the streptavidin mutein contains a mutation at a position corresponding to position 117, which mutation can be to a large hydrophobic residue like Trp, Tyr or Phe or a charged residue like Glu, Asp or Arg or a hydrophilic residue like Asn or Gin, or, in some cases, the hydrophobic residues Leu, Met or Ala, or the polar residues Thr, Ser or His. In some embodiments, the mutation at position 117 is combined with a mutation at a position corresponding to position 120, which mutation can be to a small residue like Ser or Ala or Gly, and a mutation at a position corresponding to position 121, which mutation can be to a hydrophobic residue, such as a bulky hydrophobic residue like Trp, Tyr or Phe. In some embodiments, the mutation at position 117 is combined with a mutation at a position corresponding to position 120 of wildtype streptavidin set forth in SEQ ID NO:1 or a biologically active fragment thereof, which mutation can be a hydrophobic residue such as Leu, Ile, Met, or Val or, generally, Tyr or Phe, and a mutation at a position corresponding to position 121 compared to positions of wildtype streptavidin set forth in SEQ ID NO:1 or a biologically active fragment thereof, which mutation can be to a small residue like Gly, Ala, or Ser, or with Gln, or with a hydrophobic residue like Leu, Val, Ile, Trp, Tyr, Phe, or Met. In some embodiments, such muteins also can contain residues Val44-Thr45-Ala46-Arg47 or residues Ile44-Gly45-Ala46-Arg47. In some embodiments, the streptavidin mutein contains the residues Val44, Thr45, Ala46, Arg47, Glu117, Gly120 and Tyr121. In some embodiments, the mutein streptavidin contains the sequence of amino acids set forth in SEQ ID NO:27 or SEQ ID NO:28, or a sequence of amino acids that exhibits at least at or about 85%, 86%, 87%, 88%, 89%, 90%, 91%, 92%, 93%, 94%, 95%, 96%, 97%, 98%, 99% or more sequence identity to the sequence of amino acids set forth in SEQ ID NO: 27 or SEQ ID NO: 28, contains the residues Val44, Thr45, Ala46, Arg47, Glu117, Gly120 and Tyr121 and exhibits functional activity to bind to biotin, a biotin analog or a streptavidin-binding peptide.

In some embodiments, a streptavidin mutein can contain any of the above mutations in any combination, and the resulting streptavidin mutein may exhibit a binding affinity with a $K_D$ that is less than 2.7×10$^4$ M for the streptavidin binding peptide, such as one comprising amino acids Trp Arg His Pro Gln Phe Gly Gly; also called Strep-tag® (set forth in SEQ ID NO: 7) and/or with a $K_D$ that is less than 1.4×10$^4$ M for the streptavidin binding peptide, such as one comprising amino acids Trp Ser His Pro Gln Phe Glu Lys; also called Strep-tag® II (set forth in SEQ ID NO: 8 or SEQ ID NO:58) and/or with a $K_D$ that is less than 1×10$^4$ M, 5×10$^4$ M, 1×10$^{-5}$ M, 5×10$^{-5}$M, 1×10$^{-6}$ M, 5×10$^{-6}$ M or 1×10$^{-7}$ M, but generally greater than 1×10$^{-13}$ M, 1×10$^{-12}$ M or 1×10$^{-11}$M for any of the streptavidin binding peptides set forth in any of SEQ ID NOS:7-19 or 58.

In some embodiments, the streptavidin mutein exhibits the sequence of amino acids set forth in any of SEQ ID NOs: 3-6, 27 or 28, or a sequence of amino acids that exhibits at least 90%, 91%, 92%, 93%, 94%, 95%, 96%, 97%, 98%, 99% or more sequence identity to the sequence of amino acids set forth in any of SEQ ID NO: 3-6, 27 or 28, and exhibits a binding affinity with a $K_D$ that is less than 2.7×10$^{-4}$ M for the streptavidin binding peptide, such as one comprising amino acids Trp Arg His Pro Gln Phe Gly Gly; also called Strep-tag® (set forth in SEQ ID NO: 7) and/or with a $K_D$ that is less than 1.4×10$^{-4}$ M for the streptavidin binding peptide, such as one comprising amino acids Trp Ser His Pro Gln Phe Glu Lys; also called Strep-tag® II (set forth in SEQ ID NO: 8 or 58) and/or with a $K_D$ that is less than 1×10$^{-4}$ M, 5×10$^{-4}$ M, 1×10$^{-5}$ M, 5×10$^{-5}$M, 1×10$^{-6}$ M, 5×10$^{-6}$ M or 1×10$^{-7}$ M, but generally greater than 1×10$^{-13}$ M, 1×10$^{-12}$ M or 1×10$^{-11}$ M for any of the peptide ligands set forth in any of SEQ ID NOS:7-19 or 58.

In some embodiments, the streptavidin mutein also exhibits binding to other streptavidin ligands, such as but not limited to, biotin, iminobiotin, lipoic acid, desthiobiotin, diaminobiotin, HABA (hydroxyazobenzene-benzoic acid) and/or dimethyl-HABA. In some embodiments, the streptavidin mutein exhibits a binding affinity for another streptavidin ligand, such as biotin or desthiobiotin, that is greater than the binding affinity of the streptavidin mutein for a streptavidin peptide ligand, such as set forth in any of SEQ ID NOS: 7-19 or 58. Thus, in some embodiments, biotin or a biotin analog or derivative (e.g. desthiobiotin) can be employed as a competition reagent in the provided methods. For example, as an example, the interaction of a mutein streptavidin designated Strep-tactin® (e.g. containing the sequence set forth in SEQ ID NO: 4) with the streptaviding peptide designated Strep-tag® II (e.g. containing amino acids set forth in SEQ ID NO: 8 or 58) is characterized by a binding affinity with a $K_D$ of approximately 10$^{-6}$ M compared to approximately 10$^{-13}$ M for the bitoin-streptavidin interaction. In some cases, biotin, which can bind with high affinity to the Strep-tactin® with a $K_D$ of between or between about 10$^{-10}$ and 10$^{-13}$ M, can compete with Strep-tag® II for the binding site.

In some embodiments, the binding molecule is a reagent that is an oligomer or a polymer of one or more streptavidin or avidin or of any analog or mutein of streptavidin or an analog or mutein of avidin (e.g. neutravidin). In some embodiments, the oligomer is generated or produced from a plurality of individual molecules (e.g. a plurality of homotetramers) of the same streptavidin, streptavidin mutein, avidin or avidin mutein, in which case each binding site Z, e.g. Z1, of the oligomer is the same.

In some embodiments the binding molecule reagent is an oligomer or a polymer of one or more streptavidin or avidin or of any analog or mutein of streptavidin or an analog or mutein of avidin (e.g. neutravidin). In some embodiments, the oligomer is generated or produced from a plurality of individual molecules (e.g. a plurality of homo-tetramers) of the same streptavidin, streptavidin mutein, avidin or avidin mutein, in which case each binding site Z, e.g. Z1, of the oligomer is the same. For example, in some cases, an oligomer can contain a plurality of binding sites Z1, such as at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50 or more binding sites Z1. In some embodiments, the oligomer is generated or produced from a plurality of individual molecules that can be hetero-tetramers of a streptavidin, streptavidin mutein, avidin or avidin mutein and/or from a plurality of two or more different individual molecules (e.g. different homo-tetramers) of streptavidin, streptavidin mutein, avidin or avidin mutein that differ in their binding sites Z, e.g. Z1 and Z2, in which case a plurality of different binding sites Z, e.g. Z1 and Z2, may be present in the oligomer. For example, in some cases, an oligomer can contain a plurality of binding sites Z1 and a plurality of binding sites Z, which, in combination, can include at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50 or more combined binding sites Z1 and Z2.

In some cases, the respective oligomer or polymer may be crosslinked by a polysaccharide. In one embodiment, oligomers or polymers of streptavidin or of avidin or of analogs of streptavidin or of avidin (e.g., neutravidin) can be prepared by the introduction of carboxyl residues into a polysaccharide, e. g. dextran, essentially as described in Noguchi, A, et al, Bioconjugate Chemistry (1992) 3, 132-137 in a first step. In some such aspects, streptavidin or avidin or analogs thereof then may be linked via primary amino groups of internal lysine residue and/or the free N-terminus to the carboxyl groups in the dextran backbone using conventional carbodiimide chemistry in a second step. In some cases, cross-linked oligomers or polymers of streptavidin or avidin or of any analog of streptavidin or avidin may also be obtained by crosslinking via bifunctional molecules, serving as a linker, such as glutardialdehyde or by other methods described in the art.

In some embodiments, the oligomer or polymer is obtained by crosslinking individual molecules or a complex of subunits that make up an individual molecule using a bifunctional linker or other chemical linker, such as glutardialdehyde or by other methods known in the art. In some aspects, cross-linked oligomers or polymers of streptavidin or avidin or of any mutein or analog of streptavidin or avidin may be obtained by crosslinking individual streptavidin or avidin molecules via bifunctional molecules, serving as a linker, such as glutardialdehyde or by other methods described in the art. It is, for example, possible to generate oligomers of streptavidin muteins by introducing thiol groups into the streptavidin mutein (this can, for example, be done by reacting the streptavidin mutein with 2-iminothiolan (Trauts reagent) and by activating, for example in a separate reaction, amino groups available in the streptavidin mutein. In some embodiments, this activation of amino groups can be achieved by reaction of the streptavidin mutein with a commercially available heterobifunctional crosslinker such as sulfosuccinimidyl 4-(N-maleimidomethyl)cyclohexane-1-carboxylate (sulfo SMCC) or Succinimidyl-6[(β-maleimidopropionamido)hexanoate (SMPH). In some such embodiments, the two reaction products so obtained are mixed together, typically leading to the reaction of the thiol groups contained in the one batch of modified streptavidin mutein with the activated (such as by maleimide functions) amino acids of the other batch of modified streptavidin mutein. In some cases, by this reaction, multimers/oligomers of the streptavidin mutein are formed. These oligomers can have any suitable number of individual molecules, such as at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50 or more, and the oligomerization degree can be varied according to the reaction condition.

In some embodiments, the oligomeric or polymeric reagent can be isolated via size exclusion chromatography and any desired fraction can be used as the binding molecule reagent. For example, in some embodiments, after reacting the modified streptavidin mutein, in the presence of 2-iminothiolan and a heterobifunctional crosslinker such as sulfo SMCC, the oligomeric or polymeric reagent can be isolated via size exclusion chromatography and any desired fraction can be used as the reagent. In some embodiments, the oligomers do not have (and do not need to have) a single molecular weight but they may observe a statistical weight distribution such as Gaussian distribution. In some cases, any oligomer with more than three streptavidin or mutein tetramers, e.g., homotetramers or heterotetramers, can be used as a soluble reagent, such as generally 3 to 50 tetramers, e.g., homotetramers or heterotetramers, 10 to 40 tetramers, e.g., homotetramers or heterotetramers, or 25 to 35 tetramers, e.g., homotetramers or heterotetramers. The oligomers might have, for example, from 3 to 25 streptavidin mutein tetramers, e.g., homotetramers or heterotetramers. In some aspects, with a molecular weight of about 50 kDa for streptavidin muteins, the soluble oligomers can have a molecular weight from about 150 kDa to about 2000 kDa, about 150 kDa to about 1500 kDa, about 150 kDa to about 1250 kDa, about 150 kDa to 1000 kDa, about 150 kDa to about 500 kDa or about 150 kDa to about 300 kDa, about 300 kDa to about 2000 kDa, about 300 kDa to about 1500 kDa, about 300 kDa to about 1250 kDa, about 300 kDa to 1000 kDa, about 300 kDa to about 500 kDa, about 500 kDa to about 2000 kDa, about 500 kDa to about 1500 kDa, about 500 kDa to about 1250 kDa, about 500 kDa to 1000 kDa, about 1000 kDa to about 2000 kDa, about 1000 kDa to about 1500 kDa, about 1000 kDa to about 1250 kDa, about 1250 kDa to about 2000 kDa or about 1500 kDa to about 2000 kDa. Generally, because each streptavidin molecule/mutein has four biotin binding sites, such a reagent can provide 12 to 160 binding sites Z, such as 12 to 100 binding sites Z.

In some embodiments, the binding molecule reagent, such as any of the described streptavidin or streptavidin mutein (e.g. Strep-Tactin®) reagents, can be labeled with one or more detectable markers. In some embodiments, the reagent is labeled with a fluorescent marker. Exemplary labeled Strep-Tactin® reagents are known or are commercially available including, for example, Strep-Tactin-HRP, Strep-Tactin AP, Strep-Tactin Chromeo 488, Strep-Tactin Chromeo 546, or Strep-Tactin Oyster 645, each available from IBA (Goettingen Germany).

In some embodiments, a streptavidin binding peptide (e.g. Strep-tag, such as Strep-tag® II or twin-Strep-tag) can be recognized by an antibody or antigen-binding fragment. In some embodiments, the antibody contains at least one binding site that can specifically bind an epitope or region of the agent of the cell surface conjugate. Antibodies against such streptavidin binding peptides are known, including antibodies against the peptide sequence SAWSHPQFEK (SEQ ID NO:58) or the minimal sequence WSHPQFEK (SEQ ID NO:8), such as present in Strep-tag® II or twin-strep-tag (Schmidt T. & Skerra A., Nature protocols, 2007; international patent application publication number WO2015067768). In some embodiments, a streptavidin binding peptide (e.g. Strep-tag, such as Strep-tag® II or twin-Strep-tag) can be detected using for example, the commercially available StrepMAB-Classic (IBA, Goettingen Germany), StrepMAB-lmmo (IBA), anti-Streptag II antibody (Genscript), or Strep-tag antibody (Qiagen). In some embodiments, the antibodies or binding partners are labeled with one or more detectable marker, to facilitate purification, selection and/or detection of engineered cells. For example, separation may be based on binding to fluorescently labeled antibodies.

C. Exemplary Conjugates

In some embodiments, the conjugate contains a modified EGFR and at least one agent (e.g. affinity tag) that is capable of binding streptavidin or a streptavidin mutein. In some embodiments, the modified EGFR is any as described above, such as the EGFRt set forth in SEQ ID NO: 46. In some embodiments, the conjugate contains a modified HER2 and at least one agent (e.g. affinity tag) that is capable of binding streptavidin or a streptavidin mutein. In some embodiments, the modified HER2/neu/ErbB2 is any as described above, such as the HER2t set forth in SEQ ID NO: 92. In some such embodiments, the agent is a streptavidin binding peptide, such as a Strep-tag®, Strep-Tag® II or twin-strep-Tag, including any described above and set forth in SEQ ID NO:7, 8, 15-19 or 58.

In some embodiments, the streptavidin binding peptide is fused to the N-terminal part of the cell surface molecule. In some embodiments, the provided cell surface conjugate comprises an amino acid sequence containing amino acid residues in which the N-terminal to C-terminal order comprises: the streptavidin binding peptide (e.g. Strep-tag®, Strep-Tag® II or twin-strep-Tag, such as set forth in any of SEQ ID NOS: 7, 8, 15-19 or 58) and a modified EGFR (e.g. EGFRt, such as set forth in SEQ ID NO: 46). In some instances, the streptavidin-binding peptide is directly fused to the modified EGFR. In some instances, the streptavidin-binding peptide is indirectly fused or joined to the modified EGFR, such as via at least one polypeptide linker as described (e.g. set forth in any one of SEQ ID NO: 55, 56, 59-62, 98 or 99). For example, in some aspects, the streptavidin binding peptide is connected to a first polypeptide linker that is attached to the modified EGFR. In some aspects the cell surface conjugate containing the EGFRt and streptavidin binding peptide is a fusion protein.

In some embodiments, the provided cell surface conjugate comprises an amino acid sequence containing amino acid residues in which the N-terminal to C-terminal order comprises: the streptavidin binding peptide (e.g. Strep-tag®, Strep-Tag® II or twin-strep-Tag, such as set forth in any of SEQ ID NOS: 7, 8, 15-19 or 58) and a modified HER2/neu/ErbB2 (e.g. HEr2t, such as set forth in SEQ ID NO: 92). In some instances, the streptavidin-binding peptide is directly fused to the modified HER2/neu/ErbB2. In some instances, the streptavidin-binding peptide is indirectly fused or joined to the modified EGFR, such as via at least one polypeptide linker as described (e.g. set forth in any one of SEQ ID NO: 55, 56, 59-62, 98 or 99). For example, in some aspects, the streptavidin binding peptide is connected to a first polypeptide linker that is attached to the modified HER2/neu/ErbB2. In some aspects the cell surface conjugate containing the HER2t and streptavidin binding peptide is a fusion protein.

In some embodiments, the conjugate comprises in N-terminal to C-terminal order: (1) at least one an agent (e.g. Strep-tag®) that has the sequence of amino acids set forth in any of SEQ ID NOs: 8, 15-19 or 58 or a sequence that has at least at or about 85%, 86%, 87%, 88%, 89%, 90%, 91%, 92%, 93%, 94%, 95%, 96%, 97%, 98%, 99% sequence identity to any of SEQ ID NOs: 8, 15-19 or 58; (2) optionally, at least one peptide linker, such as a peptide linker set forth in SEQ ID NO: 55, 56, 59-62, 98 or 99; and (3) a modified EGFR that has the sequence of amino acids set forth in SEQ ID NO: 46 or a sequence that has at least at or about 85%, 86%, 87%, 88%, 89%, 90%, 91%, 92%, 93%, 94%, 95%, 96%, 97%, 98%, 99% sequence identity to SEQ ID NOs: 46.

In some embodiments, the conjugate comprises in N-terminal to C-terminal order: (1) at least one an agent (e.g. Strep-tag®) that has the sequence of amino acids set forth in any of SEQ ID NOS: 8, 15-19 or 58 or a sequence that has at least at or about 85%, 86%, 87%, 88%, 89%, 90%, 91%, 92%, 93%, 94%, 95%, 96%, 97%, 98%, 99% sequence identity to any of SEQ ID NOS: 8, 15-19 or 58; (2) optionally, at least one peptide linker, such as a peptide linker set forth in SEQ ID NOS: 55, 56, 59-62, 98 or 99; and (3) a modified HER2/neu/ErbB2 that has the sequence of amino acids set forth in SEQ ID NO: 92 or a sequence that has at least at or about 85%, 86%, 87%, 88%, 89%, 90%, 91%, 92%, 93%, 94%, 95%, 96%, 97%, 98%, 99% sequence identity to SEQ ID NO: 92.

In some embodiments, the conjugate contains a PSMA or a modified form thereof, e.g., a modified PSMA, and at least one agent (e.g. affinity tag) that is capable of binding streptavidin or a streptavidin mutein. In some embodiments, the modified PSMA is any as described above, such as set forth in SEQ ID NO: 95 or an N-terminal truncation of SEQ ID NO:94. In some such embodiments, the agent is a streptavidin binding peptide, such as a Strep-tag®, Strep-Tag® II or twin-strep-Tag, including any described above and set forth in SEQ ID NOS: 7, 8, 15-19, or 58.

In some embodiments, the conjugate comprises in N-terminal to C-terminal order: (1) a PSMA or a modified PSMA that has the sequence of amino acids set forth in any of SEQ ID NOS: 94 or 95 or a sequence that has at least at or about 85%, 86%, 87%, 88%, 89%, 90%, 91%, 92%, 93%, 94%, 95%, 96%, 97%, 98%, 99% sequence identity to any of SEQ ID NOS: 94 or 95; (2) optionally, at least one peptide linker, such as a peptide linker set forth in SEQ ID NOS: 55, 56, 59-62, 98 or 99; and (3) at least one an agent (e.g. Strep-tag®) that has the sequence of amino acids set forth in any of SEQ ID NOS: 8, 15-19 or 58 or a sequence that has at least at or about 85%, 86%, 87%, 88%, 89%, 90%, 91%, 92%, 93%, 94%, 95%, 96%, 97%, 98%, 99% sequence identity to any of SEQ ID NOS: 8, 15-19 or 58.

In some embodiments, the cell surface conjugate protein further contains at its N-terminus a signal peptide for targeting the expressed conjugate to the secretory pathway for insertion into the membrane as a surface or membrane protein. In some embodiments, the signal peptide is the native signal peptide of the cell surface molecule, e.g. EGFR contained in SEQ ID NO:64. In some embodiments, the signal peptide is a non-native or heterologous signal peptide. In some embodiments, the signal peptide is derived from Granulocyte macrophage colony-stimulating factor receptor (GMCSFR) alpha chain that has the sequence of amino acids set forth in SEQ ID NO: 48, such as is encoded by the sequence set forth in SEQ ID NO: 47 or a sequence with degenerate codons thereof.

III. Engineered Cells

Provided herein are engineered cells that express any of the provided cell surface conjugates. In some embodiments, the engineered cells co-express the cell surface conjugate and one or more recombinant antigen receptor. In some embodiments, the cells can include cells genetically engineered with a recombinant receptor, such as a chimeric antigen receptor.

A. Recombinant Antigen Receptors

Provided are engineered cells, such as T cells, that express a recombinant receptor, including chimeric receptors containing ligand-binding domains or binding fragments thereof, such as functional non-TCR antigen receptors, such as chimeric antigen receptors (CARs), and also including T cell receptors (TCRs), such as transgenic TCRs, and components thereof. The chimeric receptor, such as a CAR, generally includes the extracellular antigen (or ligand) binding domain linked to one or more intracellular signaling components, in some aspects via linkers and/or transmembrane domain(s).

1. Chimeric Antigen Receptors

In some embodiments, engineered cells, such as T cells, are provided that express a CAR with specificity for a particular antigen (or marker or ligand), such as an antigen expressed on the surface of a particular cell type. In some embodiments, the antigen is a polypeptide. In some embodiments, it is a carbohydrate or other molecule. In some embodiments, the antigen is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

In particular embodiments, the recombinant receptor, such as chimeric receptor, contains an intracellular signaling domain or region, which includes an activating or stimulating cytoplasmic signaling domain or region (also interchangeably called an activating or stimulating intracellular signaling domain or region), such as an activating or stimulating cytoplasmic (intracellular) domain or region capable of inducing a primary activation signal in a T cell, for example, a cytoplasmic signaling domain or region of a T cell receptor (TCR) component (e.g. a cytoplasmic signaling domain or region of a zeta chain of a CD3-zeta (CD3ζ) chain or a functional variant or signaling portion thereof) and/or that comprises an immunoreceptor tyrosine-based activation motif (ITAM).

In some embodiments, the chimeric receptor further contains an extracellular ligand-binding domain that specifically binds to a ligand (e.g. antigen) antigen. In some embodiments, the chimeric receptor is a CAR that contains an extracellular antigen-recognition domain that specifically binds to an antigen. In some embodiments, the ligand, such as an antigen, is a protein expressed on the surface of cells. In some embodiments, the CAR is a TCR-like CAR and the antigen is a processed peptide antigen, such as a peptide antigen of an intracellular protein, which, like a TCR, is recognized on the cell surface in the context of a major histocompatibility complex (MHC) molecule.

Exemplary antigen receptors, including CARs, and methods for engineering and introducing such receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) PLoS ONE 8(4): e61338; Turtle et al., Curr. Opin. Immunol., 2012 October; 24(5): 633-39; Wu et al., Cancer, 2012 March 18(2): 160-75. In some aspects, the antigen receptors include a CAR as described in U.S. Pat. No. 7,446,190, and those described in International Patent Application Publication No.: WO/2014055668 A1. Examples of the CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, Kochenderfer et al., 2013, Nature Reviews Clinical Oncology, 10, 267-276 (2013); Wang et al. (2012) J. Immunother. 35(9): 689-701; and Brentjens et al., Sci Transl Med. 2013 5(177). See also WO2014031687, U.S. Pat. Nos. 8,339,645, 7,446,179, US 2013/0149337, U.S. Pat. Nos. 7,446,190, and 8,389,282.

In some embodiments, the CAR is constructed with a specificity for a particular antigen (or marker or ligand), such as an antigen expressed in a particular cell type to be targeted by adoptive therapy, e.g., a cancer marker, and/or an antigen intended to induce a dampening response, such as an antigen expressed on a normal or non-diseased cell type. Thus, the CAR typically includes in its extracellular portion one or more antigen binding molecules, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy (VH) and variable light (VL) chains of a monoclonal antibody (mAb).

In some embodiments, the antibody or antigen-binding portion thereof is expressed on cells as part of a recombinant receptor, such as an antigen receptor. Among the antigen receptors are functional non-TCR antigen receptors, such as chimeric antigen receptors (CARs). Generally, a CAR containing an antibody or antigen-binding fragment that exhibits TCR-like specificity directed against peptide-MHC complexes also may be referred to as a TCR-like CAR. In some embodiments, the extracellular antigen binding domain specific for an MHC-peptide complex of a TCR-like CAR is linked to one or more intracellular signaling components, in some aspects via linkers and/or transmembrane domain(s). In some embodiments, such molecules can typically mimic or approximate a signal through a natural antigen receptor, such as a TCR, and, optionally, a signal through such a receptor in combination with a costimulatory receptor.

In some embodiments, the recombinant receptor, such as a chimeric receptor (e.g. CAR), includes a ligand-binding domain that binds, such as specifically binds, to an antigen (or a ligand). Among the antigens targeted by the chimeric receptors are those expressed in the context of a disease, condition, or cell type to be targeted via the adoptive cell therapy. Among the diseases and conditions are proliferative, neoplastic, and malignant diseases and disorders, including cancers and tumors, including hematologic cancers, cancers of the immune system, such as lymphomas, leukemias, and/or myelomas, such as B, T, and myeloid leukemias, lymphomas, and multiple myelomas.

In some embodiments, the antigen (or a ligand) is a polypeptide. In some embodiments, it is a carbohydrate or other molecule. In some embodiments, the antigen (or a ligand) is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

In some embodiments, the CAR contains an antibody or an antigen-binding fragment (e.g. scFv) that specifically recognizes an antigen, such as an intact antigen, expressed on the surface of a cell.

In some embodiments, the antigen (or a ligand) is a tumor antigen or cancer marker. In some embodiments, the antigen (or a ligand) is or includes αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD138, CD171, epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), G Protein Coupled Receptor 5D (GPCR5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22Ra), IL-13 receptor alpha 2 (IL-13Ra2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, mesothelin, c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), vascular endothelial growth factor receptor (VEGFR), vascular endothelial growth factor receptor 2 (VEGFR2), Wilms Tumor 1 (WT-1), a pathogen-specific antigen, or an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen is or includes CD20, CD19, CD22, ROR1, CD45, CD21, CD5, CD33, Igkappa, Iglambda, CD79a, CD79b or CD30.

In some embodiments, the antigen (or a ligand) is a tumor antigen or cancer marker. In some embodiments, the antigen (or a ligand) is or includes orphan tyrosine kinase receptor ROR1, tEGFR, Her2, L1-CAM, CD19, CD20, CD22, BCMA, mesothelin, CEA, and hepatitis B surface antigen, anti-folate receptor, CD23, CD24, CD30, CD33, CD38, CD44, EGFR, EGP-2, EGP-4, EPHa2, ErbB2, 3, or 4, FBP, fetal acethycholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, TAG72, VEGF-R2, carcinoembryonic antigen (CEA), prostate specific antigen, PSMA, Her2/neu, estrogen receptor, progesterone receptor, ephrinB2, CD123, CS-1, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen targeted by the receptor is CD20, CD19, CD22, ROR1, CD45, CD21, CD5, CD33, Igkappa, Iglambda, CD79a, CD79b or CD30.

In some embodiments, the antigen is a pathogen-specific or pathogen-expressed antigen. In some embodiments, the antigen is a viral antigen (such as a viral antigen from HIV, HCV, HBV, etc.), bacterial antigens, and/or parasitic antigens.

In some embodiments, the CAR contains a TCR-like antibody, such as an antibody or an antigen-binding fragment (e.g. scFv) that specifically recognizes an intracellular antigen, such as a tumor-associated antigen, presented on the cell surface as a MHC-peptide complex. In some embodiments, an antibody or antigen-binding portion thereof that recognizes an MHC-peptide complex can be expressed on cells as part of a recombinant receptor, such as an antigen receptor. Among the antigen receptors are functional non-TCR antigen receptors, such as chimeric antigen receptors (CARs). Generally, a CAR containing an antibody or antigen-binding fragment that exhibits TCR-like specificity directed against peptide-MHC complexes also may be referred to as a TCR-like CAR.

Reference to "Major histocompatibility complex" (MHC) refers to a protein, generally a glycoprotein, that contains a polymorphic peptide binding site or binding groove that can, in some cases, complex with peptide antigens of polypeptides, including peptide antigens processed by the cell machinery. In some cases, MHC molecules can be displayed or expressed on the cell surface, including as a complex with peptide, i.e. MHC-peptide complex, for presentation of an antigen in a conformation recognizable by an antigen receptor on T cells, such as a TCRs or TCR-like antibody. Generally, MHC class I molecules are heterodimers having a membrane spanning a chain, in some cases with three a domains, and a non-covalently associated (32 microglobulin. Generally, MHC class II molecules are composed of two transmembrane glycoproteins, a and (3, both of which typically span the membrane. An MHC molecule can include an effective portion of an MHC that contains an antigen binding site or sites for binding a peptide and the sequences necessary for recognition by the appropriate antigen receptor. In some embodiments, MHC class I molecules deliver peptides originating in the cytosol to the cell surface, where a MHC-peptide complex is recognized by T cells, such as generally $CD8^+$ T cells, but in some cases CD4+ T cells. In some embodiments, MHC class II molecules deliver peptides originating in the vesicular system to the cell surface, where they are typically recognized by CD4⁺ T cells. Generally, MHC molecules are encoded by a group of linked loci, which are collectively termed H-2 in the mouse and human leukocyte antigen (HLA) in humans. Hence, typically human MHC can also be referred to as human leukocyte antigen (HLA).

The term "MHC-peptide complex" or "peptide-MHC complex" or variations thereof, refers to a complex or association of a peptide antigen and an MHC molecule, such as, generally, by non-covalent interactions of the peptide in the binding groove or cleft of the MHC molecule. In some embodiments, the MHC-peptide complex is present or displayed on the surface of cells. In some embodiments, the MHC-peptide complex can be specifically recognized by an antigen receptor, such as a TCR, TCR-like CAR or antigen-binding portions thereof.

In some embodiments, a peptide, such as a peptide antigen or epitope, of a polypeptide can associate with an MHC molecule, such as for recognition by an antigen receptor. Generally, the peptide is derived from or based on a fragment of a longer biological molecule, such as a polypeptide or protein. In some embodiments, the peptide typically is about 8 to about 24 amino acids in length. In some embodiments, a peptide has a length of from or from about 9 to 22 amino acids for recognition in the MHC Class II complex. In some embodiments, a peptide has a length of from or from about 8 to 13 amino acids for recognition in the MHC Class I complex. In some embodiments, upon recognition of the peptide in the context of an MHC molecule, such as MHC-peptide complex, the antigen receptor, such as TCR or TCR-like CAR, produces or triggers an activation signal to the T cell that induces a T cell response, such as T cell proliferation, cytokine production, a cytotoxic T cell response or other response.

In some embodiments, a TCR-like antibody or antigen-binding portion, are known or can be produced by methods known in the art (see e.g. US Published Application Nos. US 2002/0150914; US 2003/0223994; US 2004/0191260; US 2006/0034850; US 2007/00992530; US20090226474; US20090304679; and International PCT Publication No. WO 03/068201).

In some embodiments, an antibody or antigen-binding portion thereof that specifically binds to a MHC-peptide complex, can be produced by immunizing a host with an effective amount of an immunogen containing a specific MHC-peptide complex. In some cases, the peptide of the MHC-peptide complex is an epitope of antigen capable of binding to the MHC, such as a tumor antigen, for example a universal tumor antigen, myeloma antigen or other antigen as described below. In some embodiments, an effective amount of the immunogen is then administered to a host for eliciting an immune response, wherein the immunogen retains a three-dimensional form thereof for a period of time sufficient to elicit an immune response against the three-dimensional presentation of the peptide in the binding groove of the MHC molecule. Serum collected from the host is then assayed to determine if desired antibodies that recognize a three-dimensional presentation of the peptide in the binding groove of the MHC molecule is being produced. In some embodiments, the produced antibodies can be assessed to confirm that the antibody can differentiate the MHC-peptide complex from the MHC molecule alone, the peptide of interest alone, and a complex of MHC and irrelevant peptide. The desired antibodies can then be isolated.

In some embodiments, an antibody or antigen-binding portion thereof that specifically binds to an MHC-peptide complex can be produced by employing antibody library display methods, such as phage antibody libraries. In some embodiments, phage display libraries of mutant Fab, scFV or other antibody forms can be generated, for example, in which members of the library are mutated at one or more residues of a CDR or CDRs. Exemplary of such methods are known in the art (see e.g. US published application No. US20020150914, US2014/0294841; and Cohen CJ. et al. (2003) *J Mol. Recogn.* 16:324-332).

The term "antibody" herein is used in the broadest sense and includes polyclonal and monoclonal antibodies, including intact antibodies and functional (antigen-binding) antibody fragments, including fragment antigen binding (Fab) fragments, F(ab')₂ fragments, Fab' fragments, Fv fragments, recombinant IgG (rIgG) fragments, variable heavy chain ($V_H$) regions capable of specifically binding the antigen, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and subclasses thereof, IgM, IgE, IgA, and IgD.

In some embodiments, the antigen-binding proteins, antibodies and antigen binding fragments thereof specifically recognize an antigen of a full-length antibody. In some embodiments, the heavy and light chains of an antibody can be full-length or can be an antigen-binding portion (a Fab, F(ab')2, Fv or a single chain Fv fragment (scFv)). In other embodiments, the antibody heavy chain constant region is chosen from, e.g., IgG1, IgG2, IgG3, IgG4, IgM, IgA1, IgA2, IgD, and IgE, particularly chosen from, e.g., IgG1, IgG2, IgG3, and IgG4, more particularly, IgG1 (e.g., human IgG1). In another embodiment, the antibody light chain constant region is chosen from, e.g., kappa or lambda, particularly kappa.

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')₂; diabodies; linear antibodies; variable heavy chain ($V_H$) regions, single-chain antibody molecules such as scFvs and single-domain $V_H$ single antibodies; and multispecific antibodies formed from antibody fragments. In particular embodiments, the antibodies are single-chain antibody fragments comprising a variable heavy chain region and/or a variable light chain region, such as scFvs.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J. Immunol. 150: 880-887 (1993); Clarkson et al., Nature 352:624-628 (1991).

Single-domain antibodies are antibody fragments comprising all or a portion of the heavy chain variable domain or all or a portion of the light chain variable domain of an antibody. In certain embodiments, a single-domain antibody is a human single-domain antibody. In some embodiments, the CAR comprises an antibody heavy chain domain that specifically binds the antigen, such as a cancer marker or cell surface antigen of a cell or disease to be targeted, such as a tumor cell or a cancer cell, such as any of the target antigens described herein or known in the art.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some embodiments, the antibody fragments are scFvs.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

Thus, in some embodiments, the chimeric antigen receptor, including TCR-like CARs, includes an extracellular portion containing an antibody or antibody fragment. In some embodiments, the antibody or fragment includes an scFv. In some aspects, the chimeric antigen receptor includes an extracellular portion containing the antibody or fragment and an intracellular signaling domain.

In some embodiments, the recombinant receptor such as the CAR, such as the antibody portion thereof, further includes a spacer, which may be or include at least a portion of an immunoglobulin constant region or variant or modified version thereof, such as a hinge region, e.g., an IgG4 hinge region, and/or a CH1/CL and/or Fc region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. In some examples, the spacer is at or about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include IgG4 hinge alone, IgG4 hinge linked to CH2 and CH3 domains, or IgG4 hinge linked to the CH3 domain. Exemplary spacers include, but are not limited to, those described in Hudecek et al. (2013) Clin. Cancer Res., 19:3153 or international patent application publication number WO2014031687. In some embodiments, the spacer has the sequence set forth in SEQ ID NO: 70, and is encoded by the sequence set forth in SEQ ID NO: 71. In some embodiments, the spacer has the sequence set forth in SEQ ID NO: 72. In some embodiments, the spacer has the sequence set forth in SEQ ID NO: 73.

In some embodiments, the constant region or portion is of IgD. In some embodiments, the spacer has the sequence set forth in SEQ ID NO: 74. In some embodiments, the spacer has a sequence of amino acids that exhibits at least at or about 85%, 86%, 87%, 88%, 89%, 90%, 91%, 92%, 93%, 94%, 95%, 96%, 97%, 98%, 99% or more sequence identity to any of SEQ ID NOS: 70, 72, 73 and 74.

The antigen recognition domain generally is linked to one or more intracellular signaling components, such as signaling components that mimic activation through an antigen receptor complex, such as a TCR complex, in the case of a CAR, and/or signal via another cell surface receptor. Thus, in some embodiments, the antigen binding component (e.g., antibody) is linked to one or more transmembrane and intracellular signaling domains. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

The receptor, e.g., the CAR, generally includes at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the ROR1-binding antibody is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25, or CD16. For example, in some aspects, the CAR includes a chimeric molecule between CD3-zeta (CD3-ζ) or Fc receptor γ and CD8, CD4, CD25 or CD16.

In some embodiments, upon ligation of the CAR, the cytoplasmic domain or intracellular signaling domain of the CAR activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptor to initiate signal transduction following antigen receptor engagement, and/or any derivative or variant of such molecules, and/or any synthetic sequence that has the same functional capability.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR or CD3 zeta, FcR gamma or FcR beta. In some embodiments, cytoplasmic signaling molecule(s) in the CAR contain(s) a cytoplasmic signaling domain, portion thereof, or sequence derived from CD3 zeta.

In some embodiments, the CAR includes a signaling domain and/or transmembrane portion of a costimulatory receptor, such as CD28, 4-1BB, OX40, DAP10, and ICOS. In some aspects, the same CAR includes both the activating and costimulatory components.

In some embodiments, the activating domain is included within one CAR, whereas the costimulatory component is provided by another CAR recognizing another antigen. In some embodiments, the CARs include activating or stimulatory CARs, and costimulatory CARs, both expressed on the same cell (see WO2014/055668).

In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR in some aspects is one that includes multiple costimulatory domains of different costimulatory receptors.

In some embodiments, the chimeric antigen receptor includes an extracellular portion containing the antibody or fragment described herein. In some aspects, the chimeric antigen receptor includes an extracellular portion containing the antibody or fragment described herein and an intracellular signaling domain. In some embodiments, the antibody or fragment includes an scFv or a single-domain $V_H$ antibody and the intracellular domain contains an ITAM. In some aspects, the intracellular signaling domain includes a signaling domain of a zeta chain of a CD3-zeta (CD3ζ) chain. In some embodiments, the chimeric antigen receptor includes a transmembrane domain linking the extracellular domain and the intracellular signaling domain.

In some aspects, the transmembrane domain contains a transmembrane portion of CD28. The extracellular domain and transmembrane can be linked directly or indirectly. In some embodiments, the extracellular domain and transmembrane are linked by a spacer, such as any described herein. In some embodiments, the chimeric antigen receptor contains an intracellular domain of a T cell costimulatory molecule, such as between the transmembrane domain and intracellular signaling domain. In some aspects, the T cell costimulatory molecule is CD28 or 41BB.

In some embodiments, the CAR contains an antibody, e.g., an antibody fragment, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer.

In some embodiments, the transmembrane domain of the receptor, e.g., the CAR is a transmembrane domain of human CD28 or variant thereof, e.g., a 27-amino acid transmembrane domain of a human CD28 (Accession No.: P10747.1), or is a transmembrane domain that comprises the sequence of amino acids set forth in SEQ ID NO: 77 or a sequence of amino acids that exhibits at least at or about 85%, 86%, 87%, 88%, 89%, 90%, 91%, 92%, 93%, 94%, 95%, 96%, 97%, 98%, 99% or more sequence identity to SEQ ID NO:77; in some embodiments, the transmembrane-domain containing portion of the recombinant receptor comprises the sequence of amino acids set forth in SEQ ID NO: 78 or a sequence of amino acids having at least at or about 85%, 86%, 87%, 88%, 89%, 90%, 91%, 92%, 93%, 94%, 95%, 96%, 97%, 98%, 99% or more sequence identity thereto.

In some embodiments, the chimeric antigen receptor contains an intracellular domain of a T cell costimulatory molecule. In some aspects, the T cell costimulatory molecule is CD28 or 41BB.

In some embodiments, the intracellular signaling domain comprises an intracellular costimulatory signaling domain of human CD28 or functional variant or portion thereof, such as a 41 amino acid domain thereof and/or such a domain with an LL to GG substitution at positions 186-187 of a native CD28 protein. In some embodiments, the intracellular signaling domain can comprise the sequence of amino acids set forth in SEQ ID NO: 79 or 80 or a sequence of amino acids that exhibits at least at or about 85%, 86%, 87%, 88%, 89%, 90%, 91%, 92%, 93%, 94%, 95%, 96%, 97%, 98%, 99% or more sequence identity to SEQ ID NO: 79 or 80. In some embodiments, the intracellular domain comprises an intracellular costimulatory signaling domain of 41BB or functional variant or portion thereof, such as a 42-amino acid cytoplasmic domain of a human 4-1BB (Accession No. Q07011.1) or functional variant or portion thereof, such as the sequence of amino acids set forth in SEQ ID NO: 81 or a sequence of amino acids that exhibits at least at or about 85%, 86%, 87%, 88%, 89%, 90%, 91%, 92%, 93%, 94%, 95%, 96%, 97%, 98%, 99% or more sequence identity to SEQ ID NO: 81.

In some embodiments, the intracellular signaling domain comprises a human CD3 zeta stimulatory signaling domain or functional variant thereof, such as an 112 AA cytoplasmic domain of isoform 3 of human CD3ζ (Accession No.: P20963.2) or a CD3 zeta signaling domain as described in U.S. Pat. No. 7,446,190 or 8,911,993. In some embodiments, the intracellular signaling domain comprises the sequence of amino acids set forth in SEQ ID NO: 82, 83 or 84 or a sequence of amino acids that exhibits at least at or about 85%, 86%, 87%, 88%, 89%, 90%, 91%, 92%, 93%, 94%, 95%, 96%, 97%, 98%, 99% or more sequence identity to SEQ ID NO: 82, 83 or 84.

In some aspects, the spacer contains only a hinge region of an IgG, such as only a hinge of IgG4 or IgG1, such as the hinge only spacer set forth in SEQ ID NO:70. In other embodiments, the spacer is an Ig hinge, e.g., and IgG4 hinge, linked to a CH2 and/or CH3 domains. In some embodiments, the spacer is an Ig hinge, e.g., an IgG4 hinge, linked to CH2 and CH3 domains, such as set forth in SEQ ID NO:73. In some embodiments, the spacer is an Ig hinge, e.g., an IgG4 hinge, linked to a CH3 domain only, such as set forth in SEQ ID NO:72. In some embodiments, the spacer is or comprises a glycine-serine rich sequence or other flexible linker such as known flexible linkers.

2. T cell Receptors

In some embodiments, engineered cells, such as T cells, are provided that express a T cell receptor (TCR) or antigen-binding portion thereof that recognizes an peptide epitope or T cell epitope of a target polypeptide, such as an antigen of a tumor, viral or autoimmune protein.

In some embodiments, a "T cell receptor" or "TCR" is a molecule that contains a variable α and β chains (also known as TCRα and TCRβ, respectively) or a variable γ and δ chains (also known as TCRα and TCRβ, respectively), or antigen-binding portions thereof, and which is capable of specifically binding to a peptide bound to an MHC molecule. In some embodiments, the TCR is in the αβ form. Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules.

Unless otherwise stated, the term "TCR" should be understood to encompass full TCRs as well as antigen-binding portions or antigen-binding fragments thereof. In some embodiments, the TCR is an intact or full-length TCR, including TCRs in the αβ form or γδ form. In some embodiments, the TCR is an antigen-binding portion that is less than a full-length TCR but that binds to a specific peptide bound in an MHC molecule, such as binds to an MHC-peptide complex. In some cases, an antigen-binding portion or fragment of a TCR can contain only a portion of the structural domains of a full-length or intact TCR, but yet is able to bind the peptide epitope, such as MHC-peptide complex, to which the full TCR binds. In some cases, an antigen-binding portion contains the variable domains of a TCR, such as variable α chain and variable β chain of a TCR, sufficient to form a binding site for binding to a specific MHC-peptide complex. Generally, the variable chains of a TCR contain complementarity determining regions involved in recognition of the peptide, MHC and/or MHC-peptide complex.

In some embodiments, the variable domains of the TCR contain hypervariable loops, or complementarity determining regions (CDRs), which generally are the primary contributors to antigen recognition and binding capabilities and specificity. In some embodiments, a CDR of a TCR or combination thereof forms all or substantially all of the antigen-binding site of a given TCR molecule. The various CDRs within a variable region of a TCR chain generally are separated by framework regions (FRs), which generally display less variability among TCR molecules as compared to the CDRs (see, e.g., Jores et al., Proc. Nat'l Acad. Sci. U.S.A. 87:9138, 1990; Chothia et al., EMBO J. 7:3745, 1988; see also Lefranc et al., Dev. Comp. Immunol. 27:55, 2003). In some embodiments, CDR3 is the main CDR responsible for antigen binding or specificity, or is the most important among the three CDRs on a given TCR variable region for antigen recognition, and/or for interaction with the processed peptide portion of the peptide-MHC complex. In some contexts, the CDR1 of the alpha chain can interact with the N-terminal part of certain antigenic peptides. In some contexts, CDR1 of the beta chain can interact with the C-terminal part of the peptide. In some contexts, CDR2 contributes most strongly to or is the primary CDR responsible for the interaction with or recognition of the MHC portion of the MHC-peptide complex. In some embodiments, the variable region of the β-chain can contain a further hypervariable region (CDR4 or HVR4), which generally is involved in superantigen binding and not antigen recognition (Kotb (1995) Clinical Microbiology Reviews, 8:411-426).

In some embodiments, a TCR also can contain a constant domain, a transmembrane domain and/or a short cytoplasmic tail (see, e.g., Janeway et al., Immunobiology: The Immune System in Health and Disease, 3rd Ed., Current Biology Publications, p. 4:33, 1997). In some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction.

In some embodiments, a TCR chain contains one or more constant domain. For example, the extracellular portion of a given TCR chain (e.g., α-chain or β-chain) can contain two immunoglobulin-like domains, such as a variable domain (e.g., Vα or Vβ; typically amino acids 1 to 116 based on Kabat numbering Kabat et al., "Sequences of Proteins of Immunological Interest, US Dept. Health and Human Services, Public Health Service National Institutes of Health, 1991, 5th ed.) and a constant domain (e.g., α-chain constant domain or Cα, typically positions 117 to 259 of the chain based on Kabat numbering or β chain constant domain or Cβ, typically positions 117 to 295 of the chain based on Kabat) adjacent to the cell membrane. For example, in some cases, the extracellular portion of the TCR formed by the two chains contains two membrane-proximal constant domains, and two membrane-distal variable domains, which variable domains each contain CDRs. The constant domain of the TCR may contain short connecting sequences in which a cysteine residue forms a disulfide bond, thereby linking the two chains of the TCR. In some embodiments, a TCR may have an additional cysteine residue in each of the α and β chains, such that the TCR contains two disulfide bonds in the constant domains.

In some embodiments, the TCR chains contain a transmembrane domain. In some embodiments, the transmembrane domain is positively charged. In some cases, the TCR chain contains a cytoplasmic tail. In some cases, the structure allows the TCR to associate with other molecules like CD3 and subunits thereof. For example, a TCR containing constant domains with a transmembrane region may anchor the protein in the cell membrane and associate with invariant subunits of the CD3 signaling apparatus or complex. The intracellular tails of CD3 signaling subunits (e.g. CD3γ, CD3δ, CD3ε and CD3ζ chains) contain one or more immunoreceptor tyrosine-based activation motif or ITAM that are involved in the signaling capacity of the TCR complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds.

In some embodiments, the TCR can be generated from a known TCR sequence(s), such as sequences of Vα,β chains, for which a substantially full-length coding sequence is readily available. Methods for obtaining full-length TCR sequences, including V chain sequences, from cell sources are well known. In some embodiments, nucleic acids encoding the TCR can be obtained from a variety of sources, such as by polymerase chain reaction (PCR) amplification of TCR-encoding nucleic acids within or isolated from a given cell or cells, or synthesis of publicly available TCR DNA sequences.

In some embodiments, the TCR is obtained from a biological source, such as from cells such as from a T cell (e.g. cytotoxic T cell), T-cell hybridomas or other publicly available source. In some embodiments, the T-cells can be obtained from in vivo isolated cells. In some embodiments, the TCR is a thymically selected TCR. In some embodiments, the TCR is a neoepitope-restricted TCR. In some embodiments, the T-cells can be a cultured T-cell hybridoma or clone. In some embodiments, the TCR or antigen-binding portion thereof can be synthetically generated from knowledge of the sequence of the TCR.

In some embodiments, the TCR is generated from a TCR identified or selected from screening a library of candidate TCRs against a target polypeptide antigen, or target T cell epitope thereof. TCR libraries can be generated by amplification of the repertoire of Vα and Vβ from T cells isolated from a subject, including cells present in PBMCs, spleen or other lymphoid organ. In some cases, T cells can be amplified from tumor-infiltrating lymphocytes (TILs). In some embodiments, TCR libraries can be generated from CD4+ or CD8+ cells. In some embodiments, the TCRs can be amplified from a T cell source of a normal of healthy subject, i.e. normal TCR libraries. In some embodiments, the TCRs can be amplified from a T cell source of a diseased subject, i.e. diseased TCR libraries. In some embodiments, degenerate primers are used to amplify the gene repertoire of Vα and Vβ, such as by RT-PCR in samples, such as T cells, obtained from humans. In some embodiments, scTv libraries can be assembled from naïve Vα and Vβ libraries in which the amplified products are cloned or assembled to be separated by a linker. Depending on the source of the subject and cells, the libraries can be HLA allele-specific. Alternatively, in some embodiments, TCR libraries can be generated by mutagenesis or diversification of a parent or scaffold TCR molecule. In some aspects, the TCRs are subjected to directed evolution, such as by mutagenesis, e.g., of the α or β chain. In some aspects, particular residues within CDRs of the TCR are altered. In some embodiments, selected TCRs can be modified by affinity maturation. In some embodiments, antigen-specific T cells may be selected, such as by screening to assess CTL activity against the peptide. In some aspects, TCRs, e.g. present on the antigen-specific T cells, may be selected, such as by binding activity, e.g., particular affinity or avidity for the antigen.

In some embodiments, the TCR or antigen-binding portion thereof is one that has been modified or engineered. In some embodiments, directed evolution methods are used to generate TCRs with altered properties, such as with higher affinity for a specific MHC-peptide complex. In some embodiments, directed evolution is achieved by display methods including, but not limited to, yeast display (Holler et al. (2003) Nat Immunol, 4, 55-62; Holler et al. (2000) Proc Natl Acad Sci USA, 97, 5387-92), phage display (Li et al. (2005) Nat Biotechnol, 23, 349-54), or T cell display (Chervin et al. (2008) J Immunol Methods, 339, 175-84). In some embodiments, display approaches involve engineering, or modifying, a known, parent or reference TCR. For example, in some cases, a wild-type TCR can be used as a template for producing mutagenized TCRs in which in one or more residues of the CDRs are mutated, and mutants with an desired altered property, such as higher affinity for a desired target antigen, are selected.

In some embodiments, peptides of a target polypeptide for use in producing or generating a TCR of interest are known or can be readily identified by a skilled artisan. In some embodiments, peptides suitable for use in generating TCRs or antigen-binding portions can be determined based on the presence of an HLA-restricted motif in a target polypeptide of interest, such as a target polypeptide described below. In some embodiments, peptides are identified using computer prediction models known to those of skill in the art. In some embodiments, for predicting MHC class I binding sites, such models include, but are not limited to, ProPred1 (Singh and Raghava (2001) Bioinformatics 17(12):1236-1237, and SYFPEITHI (see Schuler et al. (2007) Immunoinformatics Methods in Molecular Biology, 409(1): 75-93 2007). In some embodiments, the MHC-restricted epitope is HLA-A0201, which is expressed in approximately 39-46% of all Caucasians and therefore, represents a suitable choice of MHC antigen for use preparing a TCR or other MHC-peptide binding molecule.

HLA-A0201-binding motifs and the cleavage sites for proteasomes and immune-proteasomes using computer prediction models are known to those of skill in the art. For predicting MHC class I binding sites, such models include, but are not limited to, ProPred1 (described in more detail in Singh and Raghava, ProPred: prediction of HLA-DR binding sites. BIOINFORMATICS 17(12):1236-1237 2001), and SYFPEITHI (see Schuler et al. SYFPEITHI, Database for Searching and T-Cell Epitope Prediction. in Immunoinformatics Methods in Molecular Biology, vol 409(1): 75-93 2007)

In some embodiments, the TCR or antigen binding portion thereof may be a recombinantly produced natural protein or mutated form thereof in which one or more property, such as binding characteristic, has been altered. In some embodiments, a TCR may be derived from one of various animal species, such as human, mouse, rat, or other mammal. A TCR may be cell-bound or in soluble form. In some embodiments, for purposes of the provided methods, the TCR is in cell-bound form expressed on the surface of a cell.

In some embodiments, the TCR is a full-length TCR. In some embodiments, the TCR is an antigen-binding portion. In some embodiments, the TCR is a dimeric TCR (dTCR). In some embodiments, the TCR is a single-chain TCR (sc-TCR). In some embodiments, a dTCR or scTCR have the structures as described in WO 03/020763, WO 04/033685, WO2011/044186.

In some embodiments, the TCR contains a sequence corresponding to the transmembrane sequence. In some embodiments, the TCR does contain a sequence corresponding to cytoplasmic sequences. In some embodiments, the TCR is capable of forming a TCR complex with CD3. In some embodiments, any of the TCRs, including a dTCR or scTCR, can be linked to signaling domains that yield an active TCR on the surface of a T cell. In some embodiments, the TCR is expressed on the surface of cells.

In some embodiments a dTCR contains a first polypeptide wherein a sequence corresponding to a TCR α chain variable region sequence is fused to the N terminus of a sequence corresponding to a TCR α chain constant region extracellular sequence, and a second polypeptide wherein a sequence corresponding to a TCR β chain variable region sequence is fused to the N terminus a sequence corresponding to a TCR β chain constant region extracellular sequence, the first and second polypeptides being linked by a disulfide bond. In some embodiments, the bond can correspond to the native inter-chain disulfide bond present in native dimeric αβ TCRs. In some embodiments, the interchain disulfide bonds are not present in a native TCR. For example, in some embodiments, one or more cysteines can be incorporated into the constant region extracellular sequences of dTCR polypeptide pair. In some cases, both a native and a non-native disulfide bond may be desirable. In some embodiments, the TCR contains a transmembrane sequence to anchor the membrane.

In some embodiments, a dTCR contains a TCR α chain containing a variable α domain, a constant α domain and a first dimerization motif attached to the C-terminus of the constant α domain, and a TCR β chain comprising a variable β domain, a constant β domain and a first dimerization motif attached to the C-terminus of the constant β domain, wherein the first and second dimerization motifs easily interact to form a covalent bond between an amino acid in the first dimerization motif and an amino acid in the second dimerization motif linking the TCR α chain and TCR β chain together.

In some embodiments, the TCR is a scTCR. Typically, a scTCR can be generated using methods known to those of skill in the art, See e.g., Soo Hoo, W. F. et al. PNAS (USA) 89, 4759 (1992); Wülfing, C. and Plückthun, A., J. Mol. Biol. 242, 655 (1994); Kurucz, I. et al. PNAS (USA) 90 3830 (1993); International published PCT Nos. WO 96/13593, WO 96/18105, WO99/60120, WO99/18129, WO 03/020763, WO2011/044186; and Schlueter, C. J. et al. J. Mol. Biol. 256, 859 (1996). In some embodiments, a scTCR contains an introduced non-native disulfide interchain bond to facilitate the association of the TCR chains (see e.g. International published PCT No. WO 03/020763). In some embodiments, a scTCR is a non-disulfide linked truncated TCR in which heterologous leucine zippers fused to the C-termini thereof facilitate chain association (see e.g. International published PCT No. WO99/60120). In some embodiments, a scTCR contain a TCRα variable domain covalently linked to a TCRβ variable domain via a peptide linker (see e.g., International published PCT No. WO99/18129).

In some embodiments, a scTCR contains a first segment constituted by an amino acid sequence corresponding to a TCR α chain variable region, a second segment constituted by an amino acid sequence corresponding to a TCR β chain variable region sequence fused to the N terminus of an amino acid sequence corresponding to a TCR β chain constant domain extracellular sequence, and a linker sequence linking the C terminus of the first segment to the N terminus of the second segment.

In some embodiments, a scTCR contains a first segment constituted by an α chain variable region sequence fused to the N terminus of an α chain extracellular constant domain sequence, and a second segment constituted by a β chain variable region sequence fused to the N terminus of a sequence β chain extracellular constant and transmembrane sequence, and, optionally, a linker sequence linking the C terminus of the first segment to the N terminus of the second segment.

In some embodiments, a scTCR contains a first segment constituted by a TCR β chain variable region sequence fused to the N terminus of a β chain extracellular constant domain sequence, and a second segment constituted by an α chain variable region sequence fused to the N terminus of a sequence α chain extracellular constant and transmembrane sequence, and, optionally, a linker sequence linking the C terminus of the first segment to the N terminus of the second segment.

In some embodiments, the linker of a scTCRs that links the first and second TCR segments can be any linker capable of forming a single polypeptide strand, while retaining TCR binding specificity. In some embodiments, the linker sequence may, for example, have the formula -P-AA-P- wherein P is proline and AA represents an amino acid sequence wherein the amino acids are glycine and serine. In some embodiments, the first and second segments are paired so that the variable region sequences thereof are orientated for such binding. Hence, in some cases, the linker has a sufficient length to span the distance between the C terminus of the first segment and the N terminus of the second segment, or vice versa, but is not too long to block or reduces bonding of the scTCR to the target ligand. In some embodiments, the linker can contain from or from about 10 to 45 amino acids, such as 10 to 30 amino acids or 26 to 41 amino acids residues, for example 29, 30, 31 or 32 amino acids. In some embodiments, the linker has the formula -PGGG-(SGGGG)$_5$-P- wherein P is proline, G is glycine and S is serine (SEQ ID NO:89). In some embodiments, the linker has the sequence GSADDAKKDAAKKDGKS (SEQ ID NO:90)

In some embodiments, the scTCR contains a covalent disulfide bond linking a residue of the immunoglobulin region of the constant domain of the α chain to a residue of the immunoglobulin region of the constant domain of the β chain. In some embodiments, the interchain disulfide bond in a native TCR is not present. For example, in some embodiments, one or more cysteines can be incorporated into the constant region extracellular sequences of the first and second segments of the scTCR polypeptide. In some cases, both a native and a non-native disulfide bond may be desirable.

In some embodiments of a dTCR or scTCR containing introduced interchain disulfide bonds, the native disulfide bonds are not present. In some embodiments, the one or more of the native cysteines forming a native interchain disulfide bonds are substituted to another residue, such as to a serine or alanine. In some embodiments, an introduced disulfide bond can be formed by mutating non-cysteine residues on the first and second segments to cysteine. Exemplary non-native disulfide bonds of a TCR are described in published International PCT No. WO2006/000830.

In some embodiments, the TCR or antigen-binding fragment thereof exhibits an affinity with an equilibrium binding constant for a target antigen of between or between about 10-5 and 10-12 M and all individual values and ranges therein. In some embodiments, the target antigen is an MHC-peptide complex or ligand.

In some embodiments, nucleic acid or nucleic acids encoding a TCR, such as α and β chains, can be amplified by PCR, cloning or other suitable means and cloned into a suitable expression vector or vectors. The expression vector can be any suitable recombinant expression vector, and can be used to transform or transfect any suitable host. Suitable vectors include those designed for propagation and expansion or for expression or both, such as plasmids and viruses.

In some embodiments, the vector can a vector of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), or the pEX series (Clontech, Palo Alto, Calif.). In some cases, bacteriophage vectors, such as λG10, λGT11, λZapII (Stratagene), λEMBL4, and λNM1149, also can be used. In some embodiments, plant expression vectors can be used and include pBI01, pBI101.2, pBI101.3, pBI121 and pBIN19 (Clontech). In some embodiments, animal expression vectors include pEUK-Cl, pMAM and pMAM-neo (Clontech). In some embodiments, a viral vector is used, such as a retroviral vector.

In some embodiments, the recombinant expression vectors can be prepared using standard recombinant DNA techniques. In some embodiments, vectors can contain regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based. In some embodiments, the vector can contain a nonnative promoter operably linked to the nucleotide sequence encoding the TCR or antigen-binding portion (or other MHC-peptide binding molecule). In some embodiments, the promoter can be a non-viral promoter or a viral promoter, such as a cytomegalovirus (CMV) promoter, an SV40 promoter, an RSV promoter, and a promoter found in the long-terminal repeat of the murine stem cell virus. Other promoters known to a skilled artisan also are contemplated.

In some embodiments, to generate a vector encoding a TCR, the α and β chains are PCR amplified from total cDNA isolated from a T cell clone expressing the TCR of interest and cloned into an expression vector. In some embodiments, the α and β chains are cloned into the same vector. In some embodiments, the α and β chains are cloned into different vectors. In some embodiments, the generated α and β chains are incorporated into a retroviral, e.g. lentiviral, vector.

3. Chimeric Auto-Antibody Receptors (CAARs)

In some embodiments, the recombinant receptor is a chimeric autoantibody receptor (CAAR). In some embodiments, the CAAR is specific for an autoantibody. In some embodiments, a cell expressing the CAAR, such as a T cell engineered to express a CAAR, can be used to specifically bind to and kill autoantibody-expressing cells, but not normal antibody expressing cells. In some embodiments, CAAR-expressing cells can be used to treat an autoimmune disease associated with expression of self-antigens, such as autoimmune diseases. In some embodiments, CAAR-expressing cells can target B cells that ultimately produce the autoantibodies and display the autoantibodies on their cell surfaces, mark these B cells as disease-specific targets for therapeutic intervention. In some embodiments, CAAR-expressing cells can be used to efficiently targeting and killing the pathogenic B cells in autoimmune diseases by targeting the disease-causing B cells using an antigen-specific chimeric autoantibody receptor. In some embodiments, the recombinant receptor is a CAAR, such as any described in U.S. Patent Application Pub. No. US 2017/0051035.

In some embodiments, the CAAR comprises an autoantibody binding domain, a transmembrane domain, and an intracellular signaling region. In some embodiments, the intracellular signaling region comprises an intracellular signaling domain. In some embodiments, the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM). In some embodiments, the intracellular signaling region comprises a secondary or costimulatory signaling region (secondary intracellular signaling regions).

In some embodiments, the autoantibody binding domain comprises an autoantigen or a fragment thereof. The choice of autoantigen can depend upon the type of autoantibody being targeted. For example, the autoantigen may be chosen because it recognizes an autoantibody on a target cell, such as a B cell, associated with a particular disease state, e.g. an autoimmune disease, such as an autoantibody-mediated autoimmune disease. In some embodiments, the autoimmune disease includes pemphigus vulgaris (PV). Exemplary autoantigens include desmoglein 1 (Dsg1) and Dsg3.

B. Nucleic Acids and Vectors

Provided are polynucleotides (nucleic acid molecules) encoding the cell surface conjugates and recombinant receptors, vectors for genetically engineering cells to express such conjugates and receptors and methods for producing the engineered cells.

In some embodiments, provided are polynucleotides that encode any of the cell surface conjugates provided herein. In some aspects, the polynucleotide contains a single coding sequence, such as only a coding sequence encoding the cell surface conjugate. In other instances, the polynucleotide contains at least two different coding sequences, such as a first nucleic acid sequence encoding the cell surface conjugate and a second nucleic acid sequence encoding a recombinant receptor. In some aspects, the recombinant receptor is or contains a chimeric antigen receptor (CAR). In some aspects, the recombinant receptor is or contains a T cell receptor (TCR), e.g., a transgenic TCR. In some aspects, the recombinant receptor is or contains a chimeric autoantibody receptor (CAAR). In some embodiments, the polynucleotides and vectors are used for co-expression in cells of the cell surface conjugate and the recombinant receptor. In some embodiments, the polynucleotide encodes a cell surface conjugate that is capable of being expressed on the surface of a cell. In some embodiments, the nucleic acid encoding the cell surface conjugates encode a cell surface molecule comprising an extracellular portion and a transmembrane portion.

In some cases, the nucleic acid sequence encoding the conjugate contains a signal sequence that encodes a signal peptide. In some aspects, the signal sequence may encode a signal peptide derived from the native cell surface molecule. In other aspects, the signal sequence may encode a heterologous or non-native signal peptide, such as the exemplary signal peptide of the GMCSFR alpha chain set forth in SEQ ID NO: 48 and encoded by the nucleotide sequence set forth in SEQ ID NO:47.

In some cases, the nucleic acid sequence encoding the chimeric antigen receptor (CAR) contains a signal sequence that encodes a signal peptide. Non-limiting exemplary examples of signal peptides include, for example, the GMCSFR alpha chain signal peptide set forth in SEQ ID NO: 48 or the CD8 alpha signal peptide set forth in SEQ ID NO:75.

In some embodiments, the polynucleotide encoding the cell surface conjugate and/or recombinant receptor contains at least one promoter that is operatively linked to control expression of the cell surface conjugate and/or recombinant receptor. In some examples, the polynucleotide contains two, three, or more promoters operatively linked to control expression of the cell surface conjugate and/or recombinant receptor.

In certain cases where nucleic acid molecules encode two or more different polypeptide chains, each of the polypeptide chains can be encoded by a separate nucleic acid molecule. For example, two separate nucleic acids are provided, and each can be individually transferred or introduced into the cell for expression in the cell.

In some embodiments, such as those where the polynucleotide contains a first and second nucleic acid sequence, the coding sequences encoding each of the different polypeptide chains can be operatively linked to a promoter, which can be the same or different. In some embodiments, the nucleic acid molecule can contain a promoter that drives the expression of two or more different polypeptide chains. In some embodiments, such nucleic acid molecules can be multicistronic (bicistronic or tricistronic, see e.g., U.S. Pat. No. 6,060,273). In some embodiments, transcription units can be engineered as a bicistronic unit containing an IRES (internal ribosome entry site), which allows coexpression of gene products ((e.g. encoding the conjugate and encoding the recombinant receptor) by a message from a single promoter. Alternatively, in some cases, a single promoter may direct expression of an RNA that contains, in a single open reading frame (ORF), two or three genes (e.g. encoding the conjugate and encoding the recombinant receptor) separated from one another by sequences encoding a self-cleavage peptide (e.g., 2A sequences) or a protease recognition site (e.g., furin). The ORF thus encodes a single polypeptide, which, either during (in the case of 2A) or after translation, is processed into the individual proteins. In some cases, the peptide, such as T2A, can cause the ribosome to skip (ribosome skipping) synthesis of a peptide bond at the C-terminus of a 2A element, leading to separation between the end of the 2A sequence and the next peptide downstream (see, for example, de Felipe. *Genetic Vaccines and Ther.* 2:13 (2004) and deFelipe et al. *Traffic* 5:616-626 (2004)). Many 2A elements are known in the art. Examples of 2A sequences that can be used in the methods and system disclosed herein, without limitation, 2A sequences from the foot-and-mouth disease virus (F2A, e.g., SEQ ID NO: 88), equine rhinitis A virus (E2A, e.g., SEQ ID NO: 87), Thosea asigna virus (T2A, e.g., SEQ ID NO: 43 or SEQ ID NO:76), and porcine teschovirus-1 (P2A, e.g., SEQ ID NO: 85 or 86) as described in U.S. Patent Publication No. 20070116690.

In some embodiments, the polynucleotide encoding the cell surface conjugate and/or recombinant receptor is introduced into a composition containing cultured cells, such as by retroviral transduction, transfection, or transformation.

Also provided are sets or combinations of polynucleotides. In some embodiments, the set or combination comprises a first polynucleotide comprising a nucleic acid encoding a cell surface conjugate, such as any described herein, and a second polynucleotide comprising a nucleic acid encoding a recombinant receptor. Also provided are compositions containing such set or combination of polynucleotides. In some embodiments, the set or combination of polynucleotides, are used together for engineering of cells. In some embodiments, the first and the second polynucleotides in the set are introduced simultaneously or sequentially, in any order into a cell for engineering. In some embodiments, there is a set of polynucleotides comprising a first polynucleotide comprising a nucleic acid encoding a cell surface conjugate, such as any described herein, and a second polynucleotide comprising a nucleic acid encoding a chimeric receptor and/or a recombinant antigen receptor.

Also provided are vectors or constructs containing such nucleic acid molecules. In some embodiments, the vectors or constructs contain one or more promoters operatively linked to the nucleotide encoding the polypeptide or receptor to drive expression thereof. In some embodiments, the promoter is operatively linked to one or more than one nucleic acid molecule. Thus, also provided are vectors, such as those that contain any of the polynucleotides provided herein. In some cases, the vector is a viral vector, such as a retroviral vector, e.g., a lentiviral vector or a gammaretroviral vector.

Also provided a set or combination of vectors. In some embodiments, the set or combination of vectors comprises a first vector and a second vector, wherein the first vector comprises the first polynucleotide, e.g., a first polynucleotide encoding a cell surface conjugate, and the second vector comprises the second polynucleotide encoding a recombinant receptor, e.g., CAR. Also provided are compositions containing such set or combination of vectors. In some embodiments, the set or combination of vectors, are used together for engineering of cells. In some embodiments, the first and the second vectors in the set are introduced simultaneously or sequentially, in any order into a cell for engineering.

In some embodiments, the vectors include viral vectors, e.g., retroviral or lentiviral, non-viral vectors or transposons, e.g. Sleeping Beauty transposon system, vectors derived from simian virus 40 (SV40), adenoviruses, adeno-associated virus (AAV), lentiviral vectors or retroviral vectors, such as gamma-retroviral vectors, retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV) or adeno-associated virus (AAV).

Any of the cell surface conjugate and/or recombinant receptors described herein can be encoded by polynucleotides containing one or more nucleic acid sequences encoding cell surface conjugate and/or recombinant receptors, in any combinations or arrangements. For example, one, two, three or more polynucleotides can encode one, two, three or more different polypeptides, e.g., cell surface conjugate and/or recombinant receptors. In some embodiments, one vector or construct contains a nucleic acid sequence encoding cell surface conjugate, and a separate vector or construct contains a nucleic acid sequence encoding a recombinant receptor, e.g., CAR. In some embodiments, the nucleic acid encoding the cell surface conjugate and the nucleic acid encoding the recombinant receptor are operably linked to two different promoters. In some embodiments, the nucleic acid encoding the recombinant receptor is present downstream of the nucleic acid encoding the cell surface conjugate.

C. Cells and Preparation of Cells for Engineering

Also provided are cells, such as cells that contain the cell surface conjugate and/or an engineered recombinant receptor, such as described herein. Also provided are populations of such cells, compositions containing such cells and/or enriched for such cells, such as in which cells expressing the cell surface conjugate and/or recombinant receptor, e.g. chimeric receptor, make up at least 50, 60, 70, 80, 90, 91, 92, 93, 94, 95, 96, 97, 98, 99, or more percent of the total cells in the composition or cells of a certain type such as T cells or CD8+ or CD4+ cells. Among the compositions are pharmaceutical compositions and formulations for administration, such as for adoptive cell therapy. Also provided are therapeutic methods for administering the cells and compositions to subjects, e.g., patients.

Thus, also provided are genetically engineered cells expressing the cell surface conjugates and/or recombinant receptors e.g., CARs. The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells and/or of CD4+ and/or of CD8+ T cells are naïve T (TN) cells, effector T cells (TEFF), memory T cells and sub-types thereof, such as stem cell memory T (TSCM), central memory T (TCM), effector memory T (TEM), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the cells include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

In some embodiments, preparation of the engineered cells includes one or more culture and/or preparation steps. The cells for introduction of the cells surface conjugate and/or recombinant receptor, e.g., CAR, may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, or pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, Ca++/Mg++ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface molecules or surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, surface molecules or surface proteins, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., CD28+, CD62L+, CCR7+, CD27+, CD127+, CD4+, CD8+, CD45RA+, and/or CD45RO+ T cells, are isolated by positive or negative selection techniques.

For example, CD3+, CD28+ T cells can be positively selected using anti-CD3/anti-CD28 conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker+) at a relatively higher level (markerhigh) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations.

In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T (TCM) cells is carried out to increase efficacy, such as to improve long-term survival, expansion, and/or engraftment following administration, which in some aspects is particularly robust in such subpopulations. See Terakura et al. (2012) Blood. 1:72-82; Wang et al. (2012) J Immunother. 35(9):689-701. In some embodiments, combining TCM-enriched CD8+ T cells and CD4+ T cells further enhances efficacy.

In embodiments, memory T cells are present in both CD62L+ and CD62L− subsets of CD8+ peripheral blood lymphocytes. PBMC can be enriched for or depleted of CD62L-CD8+ and/or CD62L+CD8+ fractions, such as using anti-CD8 and anti-CD62L antibodies.

In some embodiments, the enrichment for central memory T (TCM) cells is based on positive or high surface expression of CD45RO, CD62L, CCR7, CD28, CD3, and/or CD127; in some aspects, it is based on negative selection for cells expressing or highly expressing CD45RA and/or granzyme B. In some aspects, isolation of a CD8+ population enriched for TCM cells is carried out by depletion of cells expressing CD4, CD14, CD45RA, and positive selection or enrichment for cells expressing CD62L. In one aspect, enrichment for central memory T (TCM) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or subpopulation, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of CD4+ cells, where both the negative and positive fractions are retained. The negative fraction then is subjected to negative selection based on expression of CD14 and CD45RA or ROR1, and positive selection based on a marker characteristic of central memory T cells, such as CD62L or CCR7, where the positive and negative selections are carried out in either order.

CD4+T helper cells are sorted into naïve, central memory, and effector cells by identifying cell populations that have cell surface antigens. CD4+ lymphocytes can be obtained by standard methods. In some embodiments, naive CD4+T lymphocytes are CD45RO−, CD45RA+, CD62L+, CD4+ T cells. In some embodiments, central memory CD4+ cells are CD62L+ and CD45RO+. In some embodiments, effector CD4+ cells are CD62L− and CD45RO−.

In one example, to enrich for CD4+ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher© Humana Press Inc., Totowa, N.J.).

In some aspects, the sample or composition of cells to be separated is incubated with small, magnetizable or magnetically responsive material, such as magnetically responsive particles or microparticles, such as paramagnetic beads (e.g., such as Dynalbeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In some embodiments, the affinity-based selection is via magnetic-activated cell sorting (MACS) (Miltenyi Biotec, Auburn, Calif.). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotec), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood may be automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) J Immunother. 35(9): 651-660, Terakura et al. (2012) Blood. 1:72-82, and Wang et al. (2012) J Immunother. 35(9):689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) Lab Chip 10, 1567-1573; and Godin et al. (2008) J Biophoton. 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are then frozen to −80° C. at a rate of 1° per minute and stored in the vapor phase of a liquid nitrogen storage tank.

In some embodiments, the provided methods include cultivation, incubation, culture, and/or genetic engineering steps. For example, in some embodiments, provided are methods for incubating and/or engineering the depleted cell populations and culture-initiating compositions.

Thus, in some embodiments, the cell populations are incubated in a culture-initiating composition. The incubation and/or engineering may be carried out in a culture vessel, such as a unit, chamber, well, column, tube, tubing set, valve, vial, culture dish, bag, or other container for culture or cultivating cells.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/mL.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) Blood. 1:72-82, and/or Wang et al. (2012) J Immunother. 35(9):689-701.

In some embodiments, the T cells are expanded by adding to the culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4+ and/or CD8+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

D. Vectors and Methods for Genetic Engineering

Various methods for the introduction of genetically engineered components, e.g., cell surface conjugates and recombinant receptors, e.g., CARs or TCRs, are well known and may be used with the provided methods and compositions. Exemplary methods include those for transfer of nucleic acids encoding the polypeptides or receptors, including via viral vectors, e.g., retroviral or lentiviral, non-viral vectors or transposons, e.g. Sleeping Beauty transposon system. Methods of gene transfer can include transduction, electroporation or other method that results into gene transfer into the cell.

In some embodiments, gene transfer is accomplished by first stimulating the cell, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

In some contexts, it may be desired to safeguard against the potential that overexpression of a stimulatory factor (for example, a lymphokine or a cytokine) could potentially result in an unwanted outcome or lower efficacy in a subject, such as a factor associated with toxicity in a subject. Thus, in some contexts, the engineered cells include gene segments that cause the cells to be susceptible to negative selection in vivo, such as upon administration in adoptive immunotherapy. For example in some aspects, the cells are engineered so that they can be eliminated as a result of a change in the in vivo condition of the patient to which they are administered. The negative selectable phenotype may result from the insertion of a gene that confers sensitivity to an administered agent, for example, a compound. Negative selectable genes include the Herpes simplex virus type I thymidine kinase (HSV-I TK) gene (Wigler et al., Cell 2:223, 1977) which confers ganciclovir sensitivity; the cellular hypoxanthine phosphribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)).

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) *J Immunother.* 35(9): 689-701; Cooper et al. (2003) *Blood.* 101: 1637-1644; Verhoeyen et al. (2009) *Methods Mol Biol.* 506: 97-114; and Cavalieri et al. (2003) Blood. 102(2): 497-505.

In some embodiments, recombinant nucleic acids are transferred into T cells via electroporation (see, e.g., Chicaybam et al, (2013) *PLoS ONE* 8(3): e60298 and Van Tedeloo et al. (2000) *Gene Therapy* 7(16): 1431-1437). In some embodiments, recombinant nucleic acids are transferred into T cells via transposition (see, e.g., Manuri et al. (2010) Hum Gene Ther 21(4): 427-437; Sharma et al. (2013) *Molec Ther Nucl Acids* 2, e74; and Huang et al. (2009) *Methods Mol Biol* 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

Other approaches and vectors for transfer of the nucleic acids encoding the recombinant products are those described, e.g., in international patent application, Publication No.: WO2014055668, and U.S. Pat. No. 7,446,190.

In some embodiments, the cells, e.g., T cells, may be transfected either during or after expansion, e.g. with a cell surface conjugate, a T cell receptor (TCR), or a chimeric antigen receptor (CAR). This transfection for the introduction of the gene of the desired polypeptide or receptor can be carried out with any suitable retroviral vector, for example. The genetically modified cell population can then be liberated from the initial stimulus (the CD3/CD28 stimulus, for example) and subsequently be stimulated with a second type of stimulus e.g. via a de novo introduced receptor). This second type of stimulus may include an antigenic stimulus in form of a peptide/MHC molecule, the cognate (cross-linking) ligand of the genetically introduced receptor (e.g. natural ligand of a CAR) or any ligand (such as an antibody) that directly binds within the framework of the new receptor (e.g. by recognizing constant regions within the receptor). See, for example, Cheadle et al, "Chimeric antigen receptors for T-cell based therapy" Methods Mol Biol. 2012; 907:645-66 or Barrett et al., Chimeric Antigen Receptor Therapy for Cancer Annual Review of Medicine Vol. 65: 333-347 (2014).

Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., *Mol. and Cell Biol.,* 11:6 (1991); and Riddell et al., *Human Gene Therapy* 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

In some embodiments, the cells are incubated and/or cultured prior to or in connection with genetic engineering. The incubation steps can include culture, cultivation, stimulation, activation, and/or propagation. The incubation and/or engineering may be carried out in a culture vessel, such as a unit, chamber, well, column, tube, tubing set, valve, vial, culture dish, bag, or other container for culture or cultivating cells. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR, e.g. anti-CD3. In some embodiments, the stimulating conditions include one or more agent, e.g. ligand, which is capable of stimulating a costimulatory receptor, e.g., anti-CD28. In some embodiments, such agents and/or ligands may be, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2, IL-15 and/or IL-7. In some aspects, the IL-2 concentration is at least about 10 units/mL.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) Blood. 1:72-82, and/or Wang et al. (2012) J Immunother. 35(9):689-701.

In some embodiments, the T cells are expanded by adding to a culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are generally then frozen to −80° C. at a rate of 1° per minute and stored in the vapor phase of a liquid nitrogen storage tank.

IV. Methods of Selecting or Detecting Transduced Cells

Provided are methods of targeting the agent (e.g. affinity tag, such as a strep-tag) of the cell surface conjugate in connection with manufacturing, such as preparing and processing, genetically engineered cells. In some embodiments, the cell surface conjugate containing a cell surface molecule and at least one agent is used for detection of cells transduced with the cell surface conjugate. In further embodiments, the cell detection of cells transduced with the cell surface conjugate is followed by isolation and identification of cells transduced with the cell surface conjugate.

In some aspects, provided are methods of detecting, selecting or isolating gene modified cells before, during or after one or more steps of gene transfer, cell processing, incubation, culture, and/or formulation steps of the methods of engineering cells, such as during any of the process steps as described above. In some aspects, during production and further processing of gene modified cells (e.g. T cells), it is of interest to specifically select and further process only those cells that are positive for the transgene. In the provided methods, detection and selection of gene modified cells is carried out by detection of the agent (e.g. peptide), such as affinity tag, of the cell surface conjugate, such as by detection of the streptavidin binding protein (e.g. Strep-tag). In some aspects, detection of the cell surface conjugate is a surrogate marker for the recombinant receptor co-introduced and/or co-expressed with the cell surface conjugate.

In some aspects, the compositions containing cells for detection include samples resulting from one or more processing steps, such as separation, centrifugation, genetic engineering (e.g. transduction with viral vector), washing, and/or incubation. In some embodiments, cells or a composition of cells obtained before, during or after one or more steps of gene transfer (e.g. transduction with a viral vector), cell processing, incubation, culture, washing and/or formulation steps of the methods of engineering cells, such as any described herein, are contacted with the binding molecule specific for the agent of the conjugate. In certain embodiments, the contacting is under conditions permissive for binding of the binding molecule to the agent of the cell surface conjugate present in cells of the composition. In certain embodiments, the methods further include detecting whether a complex is formed between the binding molecule and the agent of the conjugate in the sample, and/or detecting the presence or absence or level of such binding. In some embodiments, the binding molecule is detectably labeled, such as labeled with a fluorescent moiety.

In some aspects of the provided methods, detection is carried out using an antibody or antigen-binding fragment that is capable of specifically binding the agent (e.g. peptide), such as affinity tag, of the cell surface conjugate. Any of the known antibody or antigen-binding fragments against an affinity tag of the cell surface conjugate can be used, such as any as described above. In some embodiments, the cell surface conjugate contains a streptavidin binding peptide as described, such as a Strep-tag (e.g. Strep-tag® II or a twin-strep tag), and the antibody or antigen-binding fragment specifically binds the streptavidin binding peptide. In some embodiments, the antibody is detectably labeled, such as fluorescently labeled.

In some aspects of the provided methods, detection is carried out using a non-antibody binding molecule reagent. In some embodiments, the cell surface conjugate contains a streptavidin binding peptide as described, such as a Strep-tag (e.g. Strep-tag® II or a twin-strep tag) and the reagent is or comprises a streptavidin or streptavidin mutein or an oligomer of streptavidin or streptavidin mutein. In some embodiments, the binding molecule reagent is or comprises a streptavidin mutein set forth in any of SEQ ID NOS: 3, 4, 5, 6, 27 or 28 or is an oligomer thereof. In some embodiments, the binding molecule reagent is the commercially available reagent known as Strep-Tactin® or Strep-Tacin® XT. In some embodiments, the non-antibody binding molecule reagent is detectably labeled, such as fluorescently labeled.

In some embodiments, the binding molecules can be used to identify, sort, enrich or isolate cells expressing a cell surface conjugate of this disclosure, such as for isolation of gene modified cells that are positive for the cell surface conjugate (e.g. ST-EGFRt or ST-PSMA) and hence, also positive for the recombinant receptor. In some embodiments, the provided methods include contacting cells or a composition of cells obtained before, during or after one or more steps of gene transfer (e.g. transduction with viral vector), washing, cell processing, incubation, culture, and/or formulation steps with a binding molecule specific for the agent of the conjugate and selecting or isolating cells that are positive for binding of the binding molecule. In some embodiments, the binding molecule is an antibody or an antigen binding fragment that specifically binds the agent (e.g., anti-agent antibodies, such as anti-Strep-Tag® antibody). In some embodiments, the binding molecule is a non-antibody protein reagent that specifically binds an agent (e.g., Strep-Tactin® binding to Strep-tag). In some aspects, matrices, such as magnetic beads, agarose particles, cell culture dishes or other solid surface matrix can be employed, in which a binding molecule specific for the agent of the conjugate (e.g. specific for an affinity tag) has been immobilized, conjugated or bound. In some embodiments, the reagent is comprised on a support, such as a solid support or surface, e.g., bead, or a stationary phase (chromatography matrix). In certain embodiments, such cells are sorted, enriched or isolated using magnetic bead or paramagnetic bead-based separations or by using an affinity column.

In some embodiments, the binding molecule specific for the agent, such as any antibody or non-antibody reagent (e.g. streptavidin mutein, such as Strept-tacin), is comprised on a support, such as a solid support or surface, e.g., bead, or a stationary phase (chromatography matrix). In some such embodiments, the reagent is reversibly immobilized on the support. In some cases, the reagent is immobilized to the support via covalent bonds. In some aspects, the reagent is reversibly immobilized to the support non-covalently.

In some embodiments, the support is a solid support. Any solid support (surface) can be used for the immobilization of the binding molecule, including an antibody or a non-antibody reagent. Illustrative examples of solid supports on which the binding molecule can be immobilized include a magnetic bead, a polymeric bead, a cell culture plate, a microtiter plate, a membrane, or a hollow fiber. In some aspects, hollow fibers can be used as a bioreactor in the Quantum® Cell Expansion System, available from TerumoBCT Inc. (Lakewood, Colo., USA). In some embodiments, the binding molecule is covalently attached to the solid support. In other embodiments, non-covalent interactions can also be used for immobilization, for example on plastic substrates.

In some embodiments, the binding molecule can, for example, be a non-antibody reagent comprising streptavidin or avidin mutein that binds a streptavidin binding peptide as described. Such streptavidin muteins can be covalently attached to any surface, for example, resin (beads) used for chromatography purification and are commercially available in such form from IBA GmbH, Gottingen, for example, as Strep-Tactin® Sepharose, Strep-Tactin® Superflow®, Strep-Tactin® Superflow® high capacity or Strep-Tactin® MacroPrep®.

Other illustrative examples that are readily commercially available are immobilized metal affinity chromatography (IMAC) resins such as the TALON® resins (Westburg, Leusden, The Netherlands) that can be used for the immobilization of oligo-histidine tagged (his-tagged) proteins, such as for the binding of an oligohistidine tag such as an penta- or hexa-histidine tag. Other examples include calmodulin sepharose available from GE Life Sciences which can be used for binding a conjugate in which the agent (affinity tag) is a calmodulin binding peptide. Further examples include sepharose to which glutathion is coupled, which can be used for binding a conjugate in which the agent (affinity tag) is glutathion-S-transferase.

In some embodiments, a solid support employed in the present methods may include magnetically attractable matter such as one or more magnetically attractable particles or a ferrofluid. A respective magnetically attractable particle may comprise a reagent with a binding site that is capable of binding a target cell. In some cases, magnetically attractable particles may contain diamagnetic, ferromagnetic, paramagnetic or superparamagnetic material. In general, superparamagnetic material responds to a magnetic field with an induced magnetic field without a resulting permanent magnetization. Magnetic particles based on iron oxide are for example commercially available as Dynabeads® from Dynal Biotech, as magnetic MicroBeads from Miltenyi Biotec, as magnetic porous glass beads from CPG Inc., as well as from various other sources, such as Roche Applied Science, BIOCLON, BioSource International Inc., micromod, AMBION, Merck, Bangs Laboratories, Polysciences, or Novagen Inc., to name only a few. Magnetic nanoparticles based on superparamagnetic Co and FeCo, as well as ferromagnetic Co nanocrystals have been described, for example by Hutten, A. et al. (J. Biotech. (2004), 112, 47-63). In some embodiments, the cells and cell populations are separated or isolated using immunomagnetic (or affinity magnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher© Humana Press Inc., Totowa, N.J.).

In some embodiments, the support contains a stationary phase. Thus, in some embodiments, the binding molecule is comprised on a stationary phase (also called chromatography matrix). In some such embodiments, the binding molecule is reversibly immobilized on the stationary phase. In some cases, the binding molecule is reversibly immobilized to the stationary phase via covalent bonds. In some aspects, the binding molecule is reversibly immobilized to the stationary phase non-covalently.

Any material may be employed as a chromatography matrix. In general, a suitable chromatography material is essentially innocuous, i.e. not detrimental to cell viability, such as when used in a packed chromatography column under desired conditions. In some embodiments, the stationary phase remains in a predefined location, such as a predefined position, whereas the location of the sample is being altered. Thus, in some embodiments the stationary phase is the part of a chromatographic system through which the mobile phase flows (either by flow through or in a batch mode) and where distribution of the components contained in the liquid phase (either dissolved or dispersed) between the phases occurs.

In some embodiments, the chromatography matrix has the form of a solid or semisolid phase, whereas the sample that contains the target cell to be isolated/separated is a fluid phase. The chromatography matrix can be a particulate material (of any suitable size and shape) or a monolithic chromatography material, including a paper substrate or membrane. Thus, in some aspects, the chromatography can be both column chromatography as well as planar chromatography. In some embodiments, in addition to standard chromatography columns, columns allowing a bidirectional flow such as PhyTip® columns available from PhyNexus, Inc. San Jose, Calif., U.S.A. or pipette tips can be used for column based/flow through mode based methods. Thus, in some cases, pipette tips or columns allowing a bidirectional flow are also comprised by chromatography columns useful in the present methods. In some cases, such as where a particulate matrix material is used, the particulate matrix material may, for example, have a mean particle size of about 5 μm to about 200 μm, or from about 5 μm to about 400 μm, or from about 5 μm to about 600 μm. In some aspects, the chromatography matrix may, for example, be or include a polymeric resin or a metal oxide or a metalloid oxide. In some aspects, such as where planar chromatography is used, the matrix material may be any material suitable for planar chromatography, such as conventional cellulose-based or organic polymer based membranes (for example, a paper membrane, a nitrocellulose membrane or a polyvinylidene difluoride (PVDF) membrane) or silica coated glass plates. In one embodiment, the chromatography matrix/stationary phase is a non-magnetic material or non-magnetizable material. In other embodiments, a chromatography matrix employed in the present methods is void of any magnetically attractable matter.

In some embodiments, non-magnetic or non-magnetizable chromatography stationary phases that are suitable in the present methods include derivatized silica or a cross-linked gel. In some aspects, a crosslinked gel may be based on a natural polymer, such as on a polymer class that occurs in nature. For example, a natural polymer on which a chromatography stationary phase may be based is a polysaccharide. In some cases, a respective polysaccharide is generally crosslinked. An example of a polysaccharide matrix includes, but is not limited to, an agarose gel (for example, Superflow™ agarose or a Sepharose® material such as Superflow™ Sepharose® that are commercially available in different bead and pore sizes) or a gel of crosslinked dextran(s). A further illustrative example is a particulate cross-linked agarose matrix, to which dextran is covalently bonded, that is commercially available (in various bead sizes and with various pore sizes) as Sephadex® or Superdex®, both available from GE Healthcare. Another illustrative example of such a chromatography material is Sephacryl® which is also available in different bead and pore sizes from GE Healthcare.

In some embodiments, a crosslinked gel may also be based on a synthetic polymer, such as on a polymer class that does not occur in nature. In some aspects, such a synthetic polymer on which a chromatography stationary phase is based is a polymer that has polar monomer units, and which is therefore in itself polar. Thus, in some cases, such a polar polymer is hydrophilic. Hydrophilic molecules, also termed lipophobic, in some aspects contain moieties that can form dipole-dipole interactions with water molecules. In general, hydrophobic molecules, also termed lipophilic, have a tendency to separate from water.

Illustrative examples of suitable synthetic polymers are polyacrylamide(s), a styrene-divinylbenzene gel and a copolymer of an acrylate and a diol or of an acrylamide and a diol. An illustrative example is a polymethacrylate gel, commercially available as a Fractogel®. A further example is a copolymer of ethylene glycol and methacrylate, commercially available as a Toyopearl®. In some embodiments, a chromatography stationary phase may also include natural and synthetic polymer components, such as a composite matrix or a composite or a copolymer of a polysaccharide and agarose, e.g. a polyacrylamide/agarose composite, or of a polysaccharide and N,N'-methylenebisacrylamide. An illustrative example of a copolymer of a dextran and N,N'-methylenebisacrylamide is the above-mentioned Sephacryl® series of material. In some embodiments, a derivatized silica may include silica particles that are coupled to a synthetic or to a natural polymer. Examples of such embodiments include, but are not limited to, polysaccharide grafted silica, polyvinylpyrrolidone grafted silica, polyethylene oxide grafted silica, poly(-hydroxyethylaspartamide) silica and poly(N-isopropylacrylamide) grafted silica.

In some embodiments, the solid support, such as a bead or chromatography matrix, can be used in enrichment and selection methods as described herein by contacting said solid support (e.g. matrix) with a sample containing cells to be enriched or selected as described. In some embodiments, the selected cells are eluted or released from the solid support (e.g. matrix) by disrupting the interaction of the binding molecule and the agent (e.g. affinity tag).

In some embodiments, binding of the binding molecule to the agent of the cell surface conjugate is reversible. In some embodiments, disrupting the reversible binding of the binding molecule to the agent is achieved by contacting the cells with a composition comprising a substance capable of reversing the bond between the binding molecule and agent. For example, the substance is s free binding partner and/or is a competition agent (e.g. a biotin, a biotin analog, a biologically active fragment thereof). In some embodiments, the methods include after contacting cells in the sample to the solid support containing the binding molecule bound thereto, applying a competition substance to disrupt the bond between the agent (e.g. affinity tag) of the conjugate and binding molecule, thereby recovering the selected cells from the solid surface. Exemplary competition substances for use in the provided methods are described above and the choice of competition substance depends on the particular agent and binding molecule. In some embodiments, the binding molecule is a streptavidin mutein (e.g. Strep-Tactin) for recognition of a streptavidin binding peptide (e.g. Strep-tag) agent and competition substance is biotin or biotin analog.

In provided embodiments, selection of transduced cells during the manufacturing process using reversible binding between the binding molecule (e.g. streptavidin mutein reagent, such as Strep-Tactin) and the agent (e.g. Strep-tag) of the cell surface conjugate is advantageous over using antibodies with higher affinity to the cell surface conjugate, which may remain attached to cells in products that are administered to subjects. In some embodiments, a Strep-Tactin® is used as the reagent. In some embodiments, detection of the agent portion of the cell surface conjugate with the reagent is reversible and addition of biotin to the sample can gently release the transduced cells.

In some aspects, reversibility can be achieved because the bond between the streptavidin binding peptide (e.g. Strep-tag) and streptavidin mutein binding reagent is high, but is less than the binding affinity of the streptavidin binding reagent for biotin or a biotin analog. Hence, in some embodiments, biotin (Vitamin H) or a biotin analog can be added to compete for binding to disrupt the binding interaction between the streptavidin mutein binding reagent on the solid support (e.g. bead or chromatography matrix) and the streptavidin binding peptide (e.g. Strep-tag) of the conjugate. In some embodiments, the interaction can be reversed in the presence of low concentrations of biotin or analog, such as in the presence of 0.1 mM to 10 mM, 0.5 mM to 5 mM or 1 mM to 3 mM, such as generally at least or at least about 1 mM or at least 2 mM, for example at or about 2.5 mM. In some embodiments, incubation in the presence of a competing agent, such as a biotin or biotin analog, releases the selected cell from the solid support, such as chromatography matrix or bead.

In some embodiments, the method further includes separating or removing one or more of the components remaining after the reversible dissociation of components. In some embodiments, any unbound or residual biotin in the target cells (e.g. gene modified, such as transduced, T cells) can be separated or removed. In some embodiments, the binding molecule reagent is removed or separated from the cells in the target cell composition. In some embodiments, due to the dissociation of the reversibly bound binding molecules (e.g. reagents containing a streptavidin mutein, such as Strep-Tactin reagents) from the cell surface conjugate, the provided method has the added advantage that the isolated cells are free of the binding molecule at the end of the contacting or incubation period. In some embodiments, the composition containing target cells is free of any reactants, which in some aspects is an advantageous for use in connection with diagnostic applications (for example, further FACS™ sorting) or for any cell based therapeutic application.

In some embodiments, the separation/removal of the binding molecule can be carried out using a second stationary phase. For this purpose, a mixture comprising the target cells and one or more remaining components are exposed, before or after being applied onto the first stationary phase described above, to chromatography on a suitable second stationary phase. This secondary stationary phase may be a gel filtration matrix and/or affinity chromatography matrix, wherein the gel filtration and/or affinity chromatography matrix comprises an affinity reagent. The affinity reagent comprised on the chromatography resin include a binding partner D that (specifically) binds to the binding site Z of the binding molecule reagent (e.g. a streptavidin mutein, such as Strep-Tactin), thereby immobilizing the binding molecule reagent on the stationary phase. If a streptavidin based binding molecule reagent is used, such as Strep-Tactin) and the agent of the conjugate is or comprises a streptavidin binding peptide (e.g. Strep-tag), the binding partner D that is comprised in the affinity reagent of this second stationary phase can be biotin. Any remaining streptavidin or of a streptavidin mutein in the composition then binds to the biotin that is usually covalently coupled to a chromatography matrix such as biotin-Sepharose™ that is commercially available. In some such embodiments, the target cells (e.g. gene modified, such as transduced, T cells) can be recovered away from the binding molecule reagent.

In some embodiments, the competition substance used to disrupt or reverse binding between the agent and binding molecule can be easily removed from the stimulated cell population via a "removal cartridge" (see e.g. described in International patent application WO 2013/124474). In some cases, for example in which the binding molecule is immobilized on a solid support, such as a bioreactor surface or a magnetic bead, it is being held back. Thus, the use of a removal cartridge for removal of the free agent and the competition reagent, can include loading the elution sample (e.g. sample obtained after disruption of the reversible binding) onto a second chromatography column. In some embodiments, this chromatography column has a suitable stationary phase that is both an affinity chromatography matrix and, at the same time, can act as gel permeation matrix. In some aspects, this affinity chromatography matrix has an affinity reagent immobilized thereon. In some embodiments, the affinity reagent may, for instance, be streptavidin, a streptavidin mutein, avidin, an avidin mutein or a mixture thereof.

In some embodiments, the chromatography matrix is a gel filtration matrix, for example, when used in a removal cartridge as described herein. Generally, a gel filtration can be characterized by the property that it is designed to undergo. Hence, a gel filtration matrix in some aspects allows the separation of cells or other biological entities largely on the basis of their size. In some such aspects, the respective chromatography matrix is typically a particulate porous material as mentioned above. The chromatography matrix may have a certain exclusion limit, which is typically defined in terms of a molecular weight above which molecules are entirely excluded from entering the pores. In some embodiments, the respective molecular weight defining the size exclusion limit may be selected to be below the weight corresponding to the weight of a target cell. In such an embodiment, the target cell is prevented from entering the pores of the size exclusion chromatography matrix. Likewise, a stationary phase may have pores that are of a size that is smaller than the size of a chosen target cell. In illustrative embodiments chromatography matrix has a mean pore size of 0 to about 500 nm.

In some embodiments, components present in a sample such as a competition substance may have a size that is below the exclusion limit of the pores and thus can enter the pores of the chromatography matrix. In some aspects, of such components that are able to partially or fully enter the pore volume, larger molecules, with less access to the pore volume can elute first, whereas the smallest molecules typically elute last. In some embodiments, the exclusion limit of the chromatography matrix is selected to be below the maximal width of the target cell. Hence, in some aspects, components that have access to the pore volume can remain longer in/on the chromatography matrix than target cell. Thus, in some cases, target cells can be collected in the eluate of a chromatography column separately from other matter/components of a sample. Therefore, in some aspects, components such as a competition substance, may elute at a later point of time from a gel filtration matrix than the target cell. In some embodiments, this effect can be further increased, such as if the gel permeation matrix contains an affinity reagent (such as covalently bound thereon) that contains binding sites Z that are able to bind a competition substance present in a sample. In some cases, the competition substance can be bound by the binding sites Z of the reagent and thereby immobilized on the matrix. In some aspects, this method is carried out in a removal cartridge.

In some embodiments, provided is an apparatus that contains at least one arrangement of a first and a second stationary phase, such as chromatography column for selection of target cells (a selection cartridge) and a second chromatography column (a removal cartridge) for removal of reagents. The apparatus may comprise a plurality of arrangements of first and second stationary phases (chromatography columns) being fluidly connected in series. The apparatus may comprise a sample inlet being fluidly connected to the first stationary phase of the first arrangement of the first and second stationary phases. In some embodiments, the apparatus may also comprise a sample outlet for cells, the sample outlet being fluidly connected to the second stationary phase of the last of the at least one arrangement of a first and second stationary phases for chromatography. In some aspects, the apparatus may also comprise a competition reagent container that is fluidly connected to at least one of the first stationary phases of the arrangements of the first and second stationary phases.

In some embodiments, the ability to remove the reagent and other components from the composition has the further advantage of being able to avoid any solid support such as magnetic beads. In some embodiments, this means there is no risk or minimal risk of contamination of the target cells (e.g. gene modified, such as transduced, T cells) by such magnetic beads. In some embodiments, this also means that a process that is compliant with GMP standards can be more easily established compared to other methods, such as the use of Dynabeads® in which additional measures have to be taken to ensure that the final T cell population is free of magnetic beads.

In some embodiments, since no solid phase (e.g. magnetic beads) are present, the present invention also provides for an automated closed system for expansion of the cells that can be integrated into known cell expansion systems such as the Xuri Cell Expansion System W25 and WAVE Bioreactor 2/10 System, available from GE Healthcare (HYPERLINK "http://en.wikipedia.org/wiki/Little_Chalfont" \o "Little Chalfont" Little Chalfont, Buckinghamshire, United Kingdom) or the Quantum® Cell Expansion System, available from TerumoBCT Inc. (Lakewood, Colo., USA).

In some embodiments, the closed system is automated. In some embodiments, components associated with the system can include an integrated microcomputer, peristaltic pump, and various valves, such as pinch valves or stop cocks, to control flow of fluid between the various parts of the system. The integrated computer in some aspects controls all components of the instrument and directs the system to perform repeated procedures in a standardized sequence. In some embodiments, the peristaltic pump controls the flow rate throughout the tubing set and, together with the pinch valves, ensures the controlled flow of buffer through the system.

In some embodiments, the methods is carried out to select, isolate or enrich cells that express the cell surface conjugate based on detection of the agent (e.g. affinity tag), such as a streptavidin binding peptide, of the conjugate. In some aspects, the isolated, enriched or selected cells represent cells that have been genetically engineered, such as by transduction, with a nucleic acid molecule encoding the cell surface conjugate, and, optionally, a co-expressed recombinant receptor, such as a CAR. In some embodiments, the provided methods produce or result in a cell composition containing cells enriched for cells expressing the cell surface conjugate, and hence also cells expressing a recombinant receptor.

In some embodiments, the yield of cells expressing the cell surface conjugate in the enriched composition, i.e. the number of enriched cells in the population compared to the number of the same population of cells in the starting sample, is 10% to 100%, such as 20% to 80%, 20% to 60%, 20% to 40%, 40% to 80%, 40% to 60%, or 60% to 80%.

In some embodiments, the percentage of the cells expressing the cell surface conjugate in the enriched or isolated composition, i.e. the percentage of cells positive for the selected cell surface conjugate versus total cells in the population of enriched or isolated cells, is at least at or about 70%, 75%, 80%, 85%, 86%, 87%, 88%, 89%, 90%, 91%, 92%, 93%, 94%, and is generally at least at or about 95%, 96%, 97%, 98%, 99% or greater.

V. Compositions and Formulations

Provided are compositions including cells, such as engineered cells containing the cell surface conjugate and/or additional recombinant receptors, e.g., CAR, for administration. In some aspects, the pharmaceutical compositions and formulations are provided as unit dose form compositions including the number of cells for administration in a given dose or fraction thereof. The pharmaceutical compositions and formulations generally include one or more optional pharmaceutically acceptable carrier or excipient. In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulation or composition may also contain more than one active ingredients useful for the particular indication, disease, or condition being treated with the cells, preferably those with activities complementary to the cell, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In some embodiments, the cells or antibodies are administered in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

Active ingredients may be entrapped in microcapsules, in colloidal drug delivery systems (for example, liposomes, albumin microspheres, microemulsions, nano-particles and nanocapsules) or in macroemulsions. In certain embodiments, the pharmaceutical composition is formulated as an inclusion complex, such as cyclodextrin inclusion complex, or as a liposome. Liposomes can serve to target the host cells (e.g., T-cells or NK cells) to a particular tissue. Many methods are available for preparing liposomes, such as those described in, for example, Szoka et al., Ann. Rev. Biophys. Bioeng., 9: 467 (1980), and U.S. Pat. Nos. 4,235,871, 4,501,728, 4,837,028, and 5,019,369.

The pharmaceutical composition in some aspects can employ time-released, delayed release, and sustained release delivery systems such that the delivery of the composition occurs prior to, and with sufficient time to cause, sensitization of the site to be treated. Many types of release delivery systems are available and known. Such systems can avoid repeated administrations of the composition, thereby increasing convenience to the subject and the physician.

The pharmaceutical composition in some embodiments contains engineered cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

The pharmaceutical compositions, such as those containing the engineered cells, may be administered using standard administration techniques, formulations, and/or devices. Provided are formulations and devices, such as syringes and vials, for storage and administration of the compositions. Administration of the engineered cells can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cell populations are administered to a subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin.

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

VI. Methods of Administration and Treatment and Related Methods

Also provided are methods of using and uses of the molecules and compositions, such as containing the engineered cells, in the treatment of diseases, conditions, and disorders in which the antigen recognized by the recombinant receptor (e.g. CAR) is expressed. Also provided are methods and uses for identification, detection or selection of the molecules and compositions, such as containing the engineered cells, by recognition of the cell surface conjugate expressed by the engineered cells. In some embodiments, such methods include diagnostic and prognostic methods as well as, in some cases, suicide or deletion methods of the engineered cells. Included among such methods are methods of monitoring the administered engineered cells and methods of modulating the engineered cells, such as in connection with adoptive cell therapy.

In some embodiments, the cell surface conjugate containing a cell surface molecule and at least one agent is used for detection of cells transduced with the cell surface conjugate. In some embodiments, the detection is in vivo or ex vivo. In some embodiments, the cell surface receptor conjugate is used for targeting engineered cells for suicide killing of engineered cells. In some aspects, killing of cells transduced to express the cell surface conjugate uses binding molecules specific for the cell surface molecule of the expressed cell surface conjugate. In other aspects, provided are methods of killing cells by targeting the agent of the cell surface conjugate using a molecule comprising a binding molecule specific for the agent of the conjugate linked to a cytotoxic agent, such as a toxin.

A. Adoptive Cell Therapy Methods

Provided are methods of administering the engineered cells and compositions, and uses of such engineered cells and compositions to treat or prevent diseases, conditions, and disorders, including cancers. In some embodiments, the engineered cells and compositions are administered to a subject or patient having the particular disease or condition to be treated, e.g., via adoptive cell therapy, such as adoptive T cell therapy. In some embodiments, provided cells and compositions are administered to a subject, such as a subject having or at risk for the disease or condition. In some aspects, the methods thereby treat, e.g., ameliorate one or more symptom of, the disease or condition, such as by lessening tumor burden in a cancer expressing an antigen recognized by an engineered T cell.

Methods for administration of engineered cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338.

As used herein, a "subject" is a mammal, such as a human or other animal, and typically is human. In some embodiments, the subject, e.g., patient, to whom the immunomodulatory polypeptides, engineered cells, or compositions are administered, is a mammal, typically a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided cells and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, cells that suppress tumor growth reduce the rate of growth of the tumor compared to the rate of growth of the tumor in the absence of the cells.

An "effective amount" of an agent, e.g., a pharmaceutical formulation, cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation or engineered cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the immunomodulatory polypeptides or engineered cells administered. In some embodiments, the provided methods involve administering the immunomodulatory polypeptides, engineered cells, or compositions at effective amounts, e.g., therapeutically effective amounts.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The disease or condition that is treated can be any in which expression of an antigen is associated with and/or involved in the etiology of a disease condition or disorder, e.g. causes, exacerbates or otherwise is involved in such disease, condition, or disorder. Exemplary diseases and conditions can include diseases or conditions associated with malignancy or transformation of cells (e.g. cancer), autoimmune or inflammatory disease, or an infectious disease, e.g. caused by a bacterial, viral or other pathogen. Exemplary antigens, which include antigens associated with various diseases and conditions that can be treated, are described above. In particular embodiments, the immunomodulatory polypeptide and/or recombinant receptor, e.g., the chimeric antigen receptor or transgenic TCR, specifically binds to an antigen associated with the disease or condition.

In some embodiments, the disease or condition is a tumor, such as a solid tumor, lymphoma, leukemia, blood tumor, metastatic tumor, or other cancer or tumor type.

In some embodiments, the disease or condition is an infectious disease or condition, such as, but not limited to, viral, retroviral, bacterial, and protozoal infections, immunodeficiency, Cytomegalovirus (CMV), Epstein-Barr virus (EBV), adenovirus, BK polyomavirus. In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease, Grave's disease, Crohn's disease, multiple sclerosis, asthma, and/or a disease or condition associated with transplant.

In some embodiments, the antigen associated with the disease or disorder is selected from the group consisting of αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD138, CD171, epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), G Protein Coupled Receptor 5D (GPCR5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22Ra), IL-13 receptor alpha 2 (IL-13Ra2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, mesothelin, c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), vascular endothelial growth factor receptor (VEGFR), vascular endothelial growth factor receptor 2 (VEGFR2), Wilms Tumor 1 (WT-1), a pathogen-specific antigen, or an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen is or includes CD20, CD19, CD22, ROR1, CD45, CD21, CD5, CD33, Igkappa, Iglambda, CD79a, CD79b or CD30.

In some embodiments, the antigen is or includes a pathogen-specific or pathogen-expressed antigen. In some embodiments, the antigen is a viral antigen (such as a viral antigen from HIV, HCV, HBV, etc.), bacterial antigens, and/or parasitic antigens.

In some embodiments, the antigen associated with the disease or disorder is selected from the group consisting of orphan tyrosine kinase receptor ROR1, tEGFR, HER2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, 0EPHa2, ErbB2, 3, or 4, FBP, fetal acethycholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, TAG72, VEGF-R2, carcinoembryonic antigen (CEA), prostate specific antigen, PSMA, HER2/neu, estrogen receptor, progesterone receptor, ephrinB2, CD123, CS-1, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogens.

The provided methods and uses include methods and uses for adoptive cell therapy. In some embodiments, the methods include administration of the engineered cells or a composition containing the cells to a subject, tissue, or cell, such as one having, at risk for, or suspected of having the disease, condition or disorder. In some embodiments, the cells, populations, and compositions are administered to a subject having the particular disease or condition to be treated, e.g., via adoptive cell therapy, such as adoptive T cell therapy. In some embodiments, the cells or compositions are administered to the subject, such as a subject having or at risk for the disease or condition, ameliorate one or more symptom of the disease or condition.

In some embodiments, the cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or super type as the first subject. The cells can be administered by any suitable means. Dosing and administration may depend in part on whether the administration is brief or chronic. Various dosing schedules include but are not limited to single or multiple administrations over various timepoints, bolus administration, and pulse infusion.

In certain embodiments, the cells, or individual populations of sub-types of cells, are administered to the subject at a range of about one million to about 100 billion cells and/or that amount of cells per kilogram of body weight, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight. Dosages may vary depending on attributes particular to the disease or disorder and/or patient and/or other treatments.

In some embodiments, for example, where the subject is a human, the dose includes fewer than about $5\times10^8$ total recombinant receptor (e.g., CAR)-expressing cells, T cells, or peripheral blood mononuclear cells (PBMCs), e.g., in the range of about $1\times10^6$ to $5\times10^8$ such cells, such as $2\times10^6$, $5\times10^6$, $1\times10^7$, $5\times10^7$, $1\times10^8$, or $5\times10^8$ or total such cells, or the range between any two of the foregoing values.

In some embodiments, the cell therapy comprises administration of a dose comprising a number of cell from or from about $1\times10^5$ to $5\times10^8$ total recombinant receptor-expressing cells, total T cells, or total peripheral blood mononuclear cells (PBMCs), from or from about $5\times10^5$ to $1\times10^7$ total recombinant receptor-expressing cells, total T cells, or total peripheral blood mononuclear cells (PBMCs) or from or from about $1\times10^6$ to $1\times10^7$ total recombinant receptor-expressing cells, total T cells, or total peripheral blood mononuclear cells (PBMCs), each inclusive. In some embodiments, the cell therapy comprises administration of a dose of cells comprising a number of cells at least at or about $1\times10^5$ total recombinant receptor-expressing cells, total T cells, or total peripheral blood mononuclear cells (PBMCs), such at least or at least $1\times10^6$, at least at or about $1\times10^7$, at least at or about $1\times10^8$ of such cells. In some embodiments, the number is with reference to the total number of CD3+ or CD8+, in some cases also recombinant receptor-expressing (e.g. CAR+) cells. In some embodiments, the cell therapy comprises administration of a dose comprising a number of cell from or from about $1\times10^5$ to $5\times10^8$ CD3+ or CD8+ total T cells or CD3+ or CD8+ recombinant receptor-expressing cells, from or from about $5\times10^5$ to $1\times10^7$ CD3+ or CD8+ total T cells or CD3+ or CD8+ recombinant receptor-expressing cells, or from or from about $1\times10^6$ to $1\times10^7$ CD3+ or CD8+ total T cells or CD3+ or CD8+ recombinant receptor-expressing cells, each inclusive. In some embodiments, the cell therapy comprises administration of a dose comprising a number of cell from or from about $1\times10^5$ to $5\times10^8$ total CD3+/CAR+ or CD8+/CAR+ cells, from or from about $5\times10^5$ to $1\times10^7$ total CD3+/CAR+ or CD8+/CAR+ cells, or from or from about $1\times10^6$ to $1\times10^7$ total CD3+/CAR+ or CD8+/CAR+ cells, each inclusive.

In some embodiments, the T cells of the dose include CD4+ T cells, CD8+ T cells or CD4+ and CD8+ T cells.

In some embodiments, for example, where the subject is human, the CD8+ T cells of the dose, including in a dose including CD4+ and CD8+ T cells, includes between about $1\times10^6$ and $5\times10^8$ total recombinant receptor (e.g., CAR)-expressing CD8+ cells, e.g., in the range of about $5\times10^6$ to $1\times10^8$ such cells, such cells $1\times10^7$, $2.5\times10^7$, $5\times10^7$, $7.5\times10^7$, $1\times10^8$, or $5\times10^8$ total such cells, or the range between any two of the foregoing values. In some embodiments, the patient is administered multiple doses, and each of the doses or the total dose can be within any of the foregoing values. In some embodiments, the dose of cells comprises the administration of from or from about $1\times10^7$ to $0.75\times10^8$ total recombinant receptor-expressing CD8+ T cells, $1\times10^7$ to $2.5\times10^7$ total recombinant receptor-expressing CD8+ T cells, from or from about $1\times10^7$ to $0.75\times10^8$ total recombinant receptor-expressing CD8+ T cells, each inclusive. In some embodiments, the dose of cells comprises the administration of or about $1\times10^7$, $2.5\times10^7$, $5\times10^7$ $7.5\times10^7$, $1\times10^8$, or $5\times10^8$ total recombinant receptor-expressing CD8+ T cells.

In some embodiments, the dose of cells, e.g., recombinant receptor-expressing T cells, is administered to the subject as a single dose or is administered only one time within a period of two weeks, one month, three months, six months, 1 year or more.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents include a cytokine, such as IL-2, for example, to enhance persistence. In some embodiments, the methods comprise administration of a chemotherapeutic agent.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD107a, IFNγ, IL-2, and TNF. In some aspects the biological activity is measured by assessing clinical outcome, such as reduction in tumor burden or load.

In certain embodiments, the engineered cells are further modified in any number of ways, such that their therapeutic or prophylactic efficacy is increased. For example, the engineered recombinant receptor, such as CAR or TCR, expressed by the population can be conjugated either directly or indirectly through a linker to a targeting moiety. The practice of conjugating compounds, e.g., the CAR or TCR, to targeting moieties is known in the art. See, for instance, Wadwa et al., J. Drug Targeting 3: 111 (1995), and U.S. Pat. No. 5,087,616.

B. Detection and Monitoring

In some embodiments, methods are provided for monitoring, such as detecting or identifying, cells administered to the subject, such as for determining or assessing the presence, number or location of such cells in the subject. In some embodiments, detection is carried out ex vivo from a sample from the subject. In some embodiments, detection is carried out in vivo.

In some embodiments, the method of monitoring is performed ex vivo and includes detecting cells expressing the cell surface conjugate by contacting a composition containing cells that express or are likely to express the cell surface conjugate with a binding molecule capable of recognizing the agent of the cell surface conjugate. In some aspects, a sample is obtained from the subject and contacted with a binding molecule that binds the agent of the conjugate, such as an antibody or non-antibody reagent, including any as described. For example, biological samples include, but are not limited to, body fluids, such as blood, plasma, serum, cerebrospinal fluid, synovial fluid, urine and sweat, tissue and organ samples, including processed samples derived therefrom.

In some embodiments, any of the methods as described above can be employed for detecting or identifying cells expressing the cell surface conjugate obtained from a sample from a subject. In certain embodiments, recombinant cells expressing the conjugate may be detected or tracked ex vivo by using antibodies that bind with specificity to the agent or by using a non-antibody reagent (e.g., Strep-Tactin® binding to the Strep-tag®). In some embodiments, the agent is a streptavidin binding peptide, such as a Strep-tag, including a Strep-tag® II or twin-Strep-tag as described. In some embodiments, the binding molecule that recognizes the agent is a reagent capable of reversibly binding to the agent, such as a streptavidin mutein, including Strep-Tactin or other streptavidin mutein that specifically binds to the agent. In some embodiments, the binding molecule that recognizes the agent is an antibody, such as an anti-Strep-tag antibody.

In some aspects, the detection of cells expressing the cell surface conjugate is followed by a step for isolating or selecting the cells bound to the binding molecule. In some embodiments, the cells can be further analyzed or assessed for one or more properties or activities, such as for cell surface phenotype based on expression of cell surface markers (e.g. activation markers), expression of the recombinant receptor (e.g. CAR), or for one or more antigen-specific activities, including cytotoxic activity, ability to secrete cytokines or ability to proliferate.

In some embodiments, the method of monitoring is performed in vivo by administering to the subject a binding molecule that specifically binds the agent of the conjugate. In some embodiments, the binding molecule administered to the subject is one that recognizes the agent, such as any as described herein. In some embodiments, the agent is a streptavidin binding peptide, such as a Strep-tag, including a Strep-tag® II or twin-Strep-tag as described. In some embodiments, the binding molecule is a non-antibody agent capable of reversibly binding to the agent, such as a streptavidin mutein, including Strep-Tactin or other streptavidin mutein that specifically binds to the agent. In some embodiments, the binding molecule that recognizes the agent is an antibody, such as an anti-Strep-tag antibody. In some embodiments, imaging of cells, such as cells expressing the conjugate and hence, a recombinant receptor, in real time reveals the locations of transduced cells in vivo.

In aspects of such methods, the binding molecule administered to a subject is soluble. In embodiments, the binding molecule is an antibody or is an antigen-binding fragment comprising a portion of an intact antibody that binds the agent (e.g. Strep-tag) to which the intact antibody binds. In other embodiments, the binding molecule is a non-antibody reagent capable of binding to the agent of the conjugate.

In the case of non-antibody reagents, such as a streptavidin mutein, including Strep-Tactin or other streptavidin mutein, the binding molecule is not bound to a solid support, i.e. it is present in soluble form or is soluble. In principle, the same reagent can be used as in the case of a reagent that is immobilized on a support, such as a solid support or stationary phase, such as described above. For example, any of the exemplary of reagents described above can be used without immobilizing or attaching such reagent to a support, e.g. not attaching solid support or stationary phase. In some cases, the reagent is an oligomer or polymer of individual molecules or an oligomer or polymer of a complex of subunits that make up the individual molecule (e.g. oligomers or polymers of a dimeric, trimeric or tetrameric protein). In some embodiments, the reagent can, for example, be a streptavidin mutein oligomer, a calmodulin oligomer, a compound (oligomer) that provides least two chelating groups K, wherein the at least two chelating groups are capable of binding to a transition metal ion, thereby rendering the reagent capable of binding to an oligohistidine affinity tag, multimeric glutathione-S-transferase, or a biotinylated carrier protein.

In some embodiments, the binding molecule, such as a non-antibody reagent (e.g. a streptavidin or mutein, such as tetrameric streptavidin muteins), is characterized by the absence of a solid support (surface) attached to the reagent. For example, in some embodiments, the reagent does not comprise or is not attached (directly or indirectly) to a particle, bead, nanoparticle, microsphere or other solid support. In some embodiments, the reagent is not rigid, inflexible or stiff or does not comprise or is not attached to a rigid, inflexible, or stiff surface. In some embodiments, the reagent is flexible or substantially flexible. In some cases, the reagent is able to adjust or adapt to the form of the surface of the cells. In some embodiments, the reagent does not or does not comprise a shape that is spherical or substantially spherical.

In some embodiments, substantially all, i.e. more than 80%, 85%, 90%, 91%, 92%, 93%, 94%, 95%, 96%, 97%, 98%, 99% or more of the binding molecule, such as a non-antibody reagent (e.g. a streptavidin or mutein, such as tetrameric streptavidin muteins), is composed of or contains organic material. For example, in some embodiments, more than 80%, 85%, 90%, 91%, 92%, 93%, 94%, 95%, 96%, 97%, 98%, 99% or more of the reagent is, is composed of or contains lipids, carbohydrates, proteins, peptides or mixtures thereof. In some embodiments, the binding molecule, such as a non-antibody reagent (e.g. a streptavidin or mutein, such as tetrameric streptavidin muteins), is composed of or contains an essential absence of inorganic material, an inorganic core, e.g. metal, e.g. iron, synthetic or inorganic polymers, such as styrene polymers, e.g. polystyrene, latex, silica or magnetic cores. For example, in some embodiments, the relative percentage of inorganic material of the reagent or that is comprised as part of the reagent is less than 20%, 15%, 10%, 5% or less.

In some embodiments, the majority (i.e. more than 50%), such as more than 60%, 70%, 80%, 90%, 95%, 99% or more of the total volume of the binding molecule, such as anon-antibody reagent (e.g. a streptavidin or mutein, such as tetrameric streptavidin muteins), in aqueous solution consists of the individual protein molecules that comprise the reagent, such as oligomers or polymers of individual molecules or a complex of subunits that make up an individual molecule (e.g. tetrameric molecule). In some embodiments, the total density of the soluble reagent is less than 1.2 g/cm$^3$, 1.1 g/cm$^3$, 1.0 g/cm$^3$ or less.

In some embodiments, the soluble reagent, e.g. not being attached to a support or solid support (e.g. is not attached to a bead), has a relatively small size, such as generally less than or about less than 20 nM in size, such as less than or about less than 15 nM, less than or about less than 10 nM, less than or about less than 5 nM or smaller.

In some embodiments, the soluble reagent, e.g. not being attached to a support or solid support (e.g. is not attached to a bead), is biologically inert, i.e. it is non-toxic to living cells. In some embodiments, the reagent may be biodegradable, for example, it can be degraded by enzymatic activity or cleared by phagocytic cells.

In some embodiments, it is possible to react the binding molecule, such as a non-antibody reagent (e.g. a streptavidin mutein or oligomers thereof) to a carrier, such as an organic carrier. In some aspects, in addition to a reaction with a polysaccharide, it is also possible to use physiologically or pharmaceutically acceptable proteins such as serum albumin (for example human serum albumin (HSA) or bovine serum albumin (BSA)) as carrier protein. In such a case, the reagent, such as streptavidin or a streptavidin mutein (either as individual tetramer or also in the form of oligomers), can be coupled to the carrier protein via non-covalent interaction. In some such embodiments, biotinylated BSA (which is commercially available from various suppliers such as ThermoFisher Scientific, Sigma Aldrich or Vectorlabs, to name only a few) can be reacted with the reagent (e.g. streptavidin mutein). In some aspects, some of the reagent oligomers (e.g. streptavidin oligomers) can non-covalently bind via one or more binding sites Z to the biotinylated carrier protein, leaving the majority of the binding sites Z of the oligomer available for binding the agent (e.g., receptor-binding agent or selection agent) and any further agent as described herein. Thus, by such an approach a soluble reagent with a multitude of binding sites Z can be prepared.

In other embodiments, a reagent, such as a streptavidin mutein (either as an individual tetramer or also in the form of an oligomer), can be covalently coupled to a synthetic carrier such as a polyethylene glycol (PEG) molecule. Any suitable PEG molecule can be used for this purpose, for example, and the PEG molecule and the respective reagent can be soluble. Typically, PEG molecules up to a molecular weight of 1000 Da are soluble in water or culture media that may be used in the present methods. In some cases, such PEG based reagent can be prepared using commercially available activated PEG molecules (for example, PEG-NHS derivatives available from NOF North America Corporation, Irvine, Calif., USA, or activated PEG derivatives available from Creative PEGWorks, Chapel Hills, N.C., USA) with amino groups of the streptavidin mutein.

In some aspects, in vivo detection is carried out using a binding molecule, such antibody or non-antibody reagent (e.g. a streptavidin or mutein, such as tetrameric streptavidin muteins) that is conjugated to a moiety that provides a signal or induces a signal that is detectable in vivo. In some embodiments, the binding molecule is conjugated to an imaging modality. In some aspects, the imaging modality includes but is not limited to a fluorescent compound, radioisotope, bioluminescent compound, chemiluminescent compound, metal chelate, enzyme, iron-oxide nanoparticle, or other imaging agent known in the art for detection by X-ray, CT-scan, MRI-scan, PET-scan, ultrasound, flow-cytometry, near infrared imaging systems, or other imaging modalities (see, e.g., Yu et al., Theranostics 2:3, 2012).

In some embodiments, the reagent is tagged with a detectable marker, such as a bioluminescent compound, chemiluminescent compound, metal chelate, enzyme, iron-oxide nanoparticle, a nanoparticle, a fluorescent compound, a fluorescent marker, and an enzyme. Examples of detectable markers/labels include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase. Examples of suitable prosthetic group complexes include streptavidin/biotin and avidin/biotin. Examples of suitable fluorescent materials include umbelliferone, fluorescein, fluorescein isothiocyanate, rhodamine, dichlorot[pi]azinylamine fluorescein, dansyl chloride or phycoerythrin. Example of a luminescent material includes luminol. Examples of bioluminescent materials include luciferase, luciferin, and aequorin. In certain embodiments of the method of diagnosis described herein, the detectable moiety is a radionuclide. In certain embodiments, the radionuclide is selected from the group consisting of $^{47}$Sc, $^{64}$Cu, $^{67}$Cu, $^{89}$Sr, $^{86}$Y, $^{87}$Y, $^{90}$Y, $^{105}$Rh, $^{108}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, $^{212}$Bi, $^{18}$F, $^{124}$I, $^{125}$I, $^{131}$I, $^{55}$Co, $^{60}$Cu, $^{61}$Cu, $^{62}$Cu, $^{64}$Cu, $^{66}$Ga, $^{67}$Cu, $^{67}$Ga, $^{68}$Ga, $^{82}$Rb, $^{86}$Y, $^{87}$Y, $^{90}$Y, $^{111}$In, $^{99}$Tc, and $^{201}$Tl.

In some embodiments, the in vivo imaging method for detecting cells can be magnetic resonance imaging (MRI), single-photon emission computed tomography (SPECT), computed tomography (CT), computed axial tomography (CAT), electron beam computed tomography (EBCT), high resolution computed tomography (HRCT), hypocycloidal tomography, positron emission tomography (PET), scintigraphy, gamma camera, a β+ detector, a γ detector, fluorescence imaging, low-light imaging, X-rays, bioluminescence imaging, and other imaging modalities.

In some embodiments, the detection and/or monitoring can be performed by detecting and/or monitoring the cell surface molecule portion of the conjugate. For example, in some embodiments, the modified cell surface molecule can be detected and/or monitored by contacting with binding molecules or targeting molecules that can bind or target the cell surface molecule, and that can be detected, e.g., contains a detectable label. In some embodiments, the cell surface conjugate can be detected using corresponding antibodies or antigen-binding fragment thereof or other cell surface molecule-targeting molecules, such as any antibodies or antigen binding fragment therein described in Table 1. In some embodiments, such antibodies or antigen-binding fragments thereof or other targeting molecules can be used in any of the detection or monitoring methods provided herein.

In some embodiments, the targeting molecule to target, detect and/or monitor the cell surface molecule portion of the cell surface conjugate can include, e.g., an antibody including, but not limited to, 3F8, abagovomab, abciximab, adecatumumab, afutuzumab, alemtuzumab, altumomab pentetate, anatumomab mafenatox, apolizumab, arcitumomab, aselizumab, atlizumab (=tocilizumab), basiliximab, bectumomab, benralizumab, besilesomab, bivatuzumab mertansine, blinatumomab, brentuximab vedotin, cantuzumab mertansine, capromab pendetide, catumaxomab, CC49, cedelizumab, celmoleukin, citatuzumab bogatox, clenoliximab, clivatuzumab tetraxetan, CNTO-95, conatumumab, dacetuzumab, daclizumab, daratumumab, detumomab, ecromeximab, edrecolomab, efalizumab, elotuzumab, enlimomab pegol, epitumomab cituxetan, epratuzumab, erlizumab, etaracizumab, fanolesomab, faralimomab, farletuzumab, galiximab, gavilimomab, gemtuzumab ozogamicin, glembatumumab vedotin, gomiliximab, ibalizumab, ibritumomab tiuxetan, igovomab, intetumumab, iratumumab, inolimomab, inotuzumab ozogamicin, ipilimumab, keliximab, labetuzumab, lintuzumab, lexatumumab, lucatumumab, lumiliximab, mapatumumab, maslimomab, milatuzumab, minretumomab, mitumomab, muromonab-CD3, naptumomab estafenatox, natalizumab, ocrelizumab, odulimomab, ofatumumab, olaratumab, oportuzumab monatox, oregovomab, otelixizumab, pemtumomab, priliximab, PRO 140, rituximab, rovelizumab, ruplizumab, satumomab pendetide, siplizumab, sontuzumab, tadocizumab, taplitumomab paptox, teneliximab, teplizumab, TGN1412, ticilimumab (=tremelimumab), tigatuzumab, tocilizumab (=atlizumab), toralizumab, tositumomab, tremelimumab, tucotuzumab, vedolizumab, veltuzumab, visilizumab, vitaxin, volociximab, votumumab, zanolimumab, ziralimumab, zolimomab aritox. Atezolizumab, bevacizumab (Avastin®), denosumab, dinutuximab, nivolumab, obinutuzumab, pembrolizumab, pidilizumab (CT-011), ramucirumab, ado-trastuzumab emtansine, CEA-scan Fab fragment, OC125 monoclonal antibody, ab75705, B72.3, MPDL3280A, MSB001078C, MEDI4736, or an antigen-binding fragment thereof, analogs or derivatives thereof, or an antigen-binding antibody fragment selected from a Fab fragment, Fab' fragment F(ab)'2 fragment, single chain Fv (scFv) or a disulfide stabilized Fv (dsFv). In some embodiments, the modified cell surface molecule comprises an epitope recognized by any of the above antibodies or an antigen-binding fragment thereof.

In some embodiments, the cell surface molecule is a PSMA or a modified form thereof. In some embodiments, the binding molecule or targeting molecule is or comprises an antibody or antigen-binding fragment thereof. In some embodiments, the binding molecule or targeting molecule is or comprises a ligand and/or small molecule. In some embodiments, the binding molecule is or comprises a small molecule that is capable of binding the active site or substrate binding site of PSMA. In some embodiments, the binding molecule is or comprises is an antagonist, a selective antagonist, an inverse agonist, a selective inverse agonist, an agonist, a selective agonist, an inhibitor, and/or a selective inhibitor of a PSMA and/or of the modified form thereof. In some embodiments, the binding molecule is or comprises an inhibitor of PSMA. In some embodiments, the binding molecule is or comprises a small molecule, and/or a low molecular weight molecule and/or a low molecular weight inhibitor. In some embodiments, the binding molecule that is or comprises a portion that is capable of binding PSMA or modified form thereof that is a small molecule and/or detectable moiety. In some embodiments, the detectable moiety or is capable of producing a detectable signal. In some instances, the detectable moiety contains a fluorescent protein and/or a radionucleide. In some embodiments, the binding molecule or targeting molecule is or includes an aptamer, a peptide, or a conjugate thereof.

In some embodiments, the binding molecule or targeting molecule is or includes antibody or antigen-binding fragment thereof is selected from among J591, DFO-J591, CYT-356, J415, 3/A12, 3/F11, 3/E7, D2B, 107-1A4, YPSMA-1, YPSMA-2, 3E6, 2G7, 24.4E6, GCP-02, GCP-04, GCP-05, J533, E99, 1G9, 3C6, 4.40, 026, D7-Fc, D7-CH3, 4D4, A5, or an antigen-binding fragment thereof, analogs or derivatives thereof, or an antigen-binding antibody fragment selected from a Fab fragment, Fab' fragment F(ab)'2 fragment, single chain Fv (scFv) or a disulfide stabilized Fv (dsFv). In some embodiments, the modified cell surface molecule comprises an epitope recognized by any of the above antibodies or an antigen-binding fragment thereof.

In some embodiments, the binding molecule or targeting molecule is or includes those described in, e.g., US 2002/0049712; US 2002/0147312; US 2003/0082187; US 2004/0136998; US 2005/0202020; US 2006/0088539; US 2007/0071759; US 2010/0297653; US 2011/0020273; US 2013/0225541; US 2013/0315830; US 2014/0099257; US 2014/0227180; US 2015/0168413; US 2016/0303253; US 2017/0051074; U.S. Pat. Nos. 6,572,856; 7,476,513; 8,470,330; 8,986,655; WO 2006/078892; WO 2010/135431; WO 2014/198223; WO 2015/177360; WO 2016/057917; WO 2016/130819; WO 2016/145139; WO 2016/201300; WO 2017/004144; WO 2017/023761; AU 2002/356844; AU 2006/204913; AU 2006/235421; AU 2006/262231; AU 2006/315500; AU 2010/325969; AU 2013/328619; AU 2015/205574; CA 2353267; EP 1390069; EP 1520588; EP 1581794; EP 1599228; EP 1610818; EP 2906250; Banerjee et al. (2011) Angew Chem Int Ed Engl. 50(39): 9167-9170; Maurer et al. (2016) Nature Reviews Urology 13:226-235; Rowe et al. (2016) Prostate Cancer Prostatic Dis. 19(3):223-230; Mease et al., (2013) Curr Top Med Chem. 13(8):951-962; Osborne et al., (2013) Urol Oncol. 31(2): 144-154; Philipp Wolf (2011), Prostate Specific Membrane Antigen as Biomarker and Therapeutic Target for Prostate Cancer, Prostate Cancer—Diagnostic and Therapeutic Advances, Dr. Philippe E. Spiess (Ed.), Intech, pp. 81-100; Ruggiero et al., (2011) J Nucl Med. 52(10): 1608-1615; Liu et al., (1997) Cancer Research 57:3629-3634; Regino et al., (2009) Curr Radiopharm. January; 2(1): 9-17; Kampmeier et al. (2014) EJNMMI Research 4:13; Wolf et al., (2010) The Prostate 70:562-569; Tykvart et al. (2014) The Prostate 74:1674-1690; Jin et al., (2016) EMJ Urol. 4(1):62-69 and Tino et al. (2000) Hybridoma 19(3):24957, or a fragment thereof, a conjugate thereof or a derivative thereof.

C. Suicide Killing

In some embodiments, provided are methods can be used for ablation and/or depletion of engineered cells in vivo, for example, mediated via antibody-dependent cell-mediated cytotoxicity (ADCC) or via specific targeting of cells with a cytotoxic agent.

1. ADCC

In some embodiments, the cell surface conjugate may be used to induce cell suicide. For example, the cell surface molecule, e.g., modified cell surface molecules described herein, may be used as a suicide gene via antibody dependent cell mediated cytotoxicity (ADCC) pathways. ADCC refers to a cell-mediated reaction in which nonspecific cytotoxic cells that express Fc receptors, such as natural killer cells, neutrophils, and macrophages, recognize bound antibody on a target cell and cause lysis of the target cell. ADCC activity may be assessed using methods, such as those described in U.S. Pat. No. 5,821,337.

In some embodiments, ADCC may be mediated by a administering to a subject any antibody targeting the cell surface molecule of the conjugate. In some embodiments, exemplary modified cell surface molecules provided in Table 1 may be used as a suicide gene via activation of ADCC mediated by administration to the subject of the corresponding antibodies provided in Table 1. In some aspects, modified EGFR cell surface molecule may be used as a suicide gene via cetuximab mediated activation of ADCC. In some aspects, suicide killing mediated by cetuximab or the ADCC pathway is unaffected by selection process that utilizes the agent (Strep-Tag®) linked to the cell surface molecule. In some aspects, PSMA or modified form thereof, engineered to be expressed on the cell surface, may be used as a suicide gene via administration of a binding molecule or targeting molecule that is an anti-PSMA antibody, such as any described herein, for example, by activation of ADCC. In another embodiment, elimination of engineered T cells expressing the cell surface conjugate provided herein may be accomplished by administering an antibody specific for the agent (e.g. affinity tag) of the conjugate. Exemplary antibody agents specific for affinity tags, including those described herein, are known. In some embodiments, if a streptavidin binding peptide, such as a Strep-Tag®, is used as the agent, then an anti-Strep-Tag® antibody or anti-Strep-Tag® scFv can be used to activate the ADCC pathway. Exemplary anti-Strep-tag antibodies include commercially available StrepMAB-Classic, monoclonal antibodies StrepMAB-Immo (IBA), anti-Streptag II antibody (Genscript), or Strep-tag antibody (Qiagen).

2. Agent Targeted by a Cytotoxic Molecule

In some embodiments, suicide killing is accomplished by administering to the subject a cytotoxic molecule specific for the agent (e.g. affinity tag) of the conjugate. In some embodiments, such cytotoxic molecules include those in which a binding molecule specific for the agent, including an antibody or non-antibody reagent, is conjugated to a cytotoxic agent. In aspects of such methods, a cytotoxic molecule is administered to a subject when the subject is known or suspected of having or likely having or developing an adverse side effect to the administered cells, such as associated with toxicity or immunogencitiy of the engineered cells.

In some embodiments, the binding molecule is a streptavidin mutein, such as any as described including Strept-Tactin or other streptavidin mutein or is an oligomer thereof. Also provided herein are streptavidin or streptavidin muteins or oligomers of streptavidin or a streptavidin mutein, such as any described herein, linked or conjugated to a cytotoxic agent. In some aspects, the binding molecule reagent comprises a streptavidin or streptavidin mutein set forth in any of SEQ ID NOS: 3-6, 27 or 28 or a sequence of amino acids that exhibits at least at or about 85%, 86%, 87%, 88%, 89%, 90%, 91%, 92%, 93%, 94%, 95%, 96%, 97%, 98%, 99% or more sequence identity to any of SEQ ID NOS: 3-6, 27 or 28 and binds the streptavidin binding peptide agent (e.g. Strep-tag). In some embodiments, the binding molecule is an antibody or antigen-binding fragment specific for the agent.

In some cases, the cytotoxic agent can be a toxin or a radiometal. Other cytotoxic agents include, but are not limited to cytotoxic components (e.g., chemotherapeutic drugs such as anti-mitotics (e.g., vindesine), antifolates, alkylating agents (e.g., temozolomide), bacterial toxins, ricin, anti-virals, radioisotopes, radiometals). Such cytotoxic agents, when targeted to specific cells, can be useful for specific killing or disabling an engineered cells, for example, when activity of a recombinant receptor is not desired.

In some embodiments the cell-toxic reagent is a bacterial toxin that belongs to a major class of bacterial toxins, termed AB toxins, which use a transporter protein (B or binding unit) that actively translocates enzymes (A unit) into cells. Examples of AB toxins include botulinum neurotoxin, anthrax toxin, diphtheria toxin, shiga toxin, shiga like toxin, exotoxin A, and cholera toxin. Due to the similar mechanism of action between all of these toxins, all these toxins are contemplated to work in the various aspects of the present invention. The A and B components of these and a variety of other toxins are well known.

Bacterial toxins frequently have two functionally distinct moieties, termed A and B. The "A" component is usually the "active" portion, and the "B" component is usually the "binding" portion. Thus, the A moiety or component contains the catalytic activity, while the B moiety or component possesses determinants needed for the cytoplasmic delivery of the A moieties into target cells. These delivery determinants include receptor binding activity, and often, but not always, membrane penetration activity. Many bacterial toxins, such as diphtheria toxin, contain both moieties within a single polypeptide. Anthrax toxin, by contrast, is a member of the so-called binary toxins, a class in which the A and B functions inhabit separate proteins. Although separate, the proteins having the A and B functions interact during the intoxication of cells. Anthrax toxin uses a single B moiety, protective antigen (PA; 83 kDa), for the delivery of two alternative A moieties, edema factor (EF; 89 kDa) and lethal factor (LF; 89 kDa) into the cytoplasm (see international patent application publication number WO2012096926 for examples of bacterial toxins).

In some aspects, the toxin is a peptide toxin, ricin A chain toxin, Abrin A chain, Diptheria Toxin (DT) A chain, *Pseudomonas* exotoxin, Shiga Toxin A chain, Gelonin, Momordin, Pokeweed Antiviral Protein, Saporin, Trichosanthin, or Barley Toxin. In some aspects, the toxin is a phototoxin. In some embodiments, the peptide toxin comprises a sequence of amino acids set forth in SEQ ID NO:100.

In some embodiments, administration of the cytotoxic agent does not, or does not substantially, induce killing or destruction of healthy tissue or healthy cells, of cells or tissues not containing the engineered cells and/or not expressing the antigen.

3. Dimerization-Mediated Killing

In some embodiments, suicide killing of cells expressing the cell surface conjugate is accomplished by employing a cell surface conjugate having an intracellular signaling domain capable of mediating killing of cells, such as upon dimerization. In some embodiments, the killing is mediated via caspase activity which initiates cellular destruction leading to apoptosis. In some aspects, the cell surface conjugate comprises the signaling domain of caspase-9, which is a part of the apoptotic pathway.

In some embodiments, dimerization is carried out by administering to the subject a binding molecule that specifically binds the agent of the conjugate. In some embodiments, binding of the binding molecule to the agent of the conjugate induces dimerization of caspase subunits and induces, modulates, activates, mediates and/or promotes signaling through the signaling domain. In some embodiments, dimerization can result in caspase-9 dependent cell death of the cell.

In some embodiments, the binding molecule administered to the subject is one that recognizes the agent, such as any as described herein. In some embodiments, the agent is a streptavidin binding peptide, such as a Strep-tag, including a Strep-tag® II or twin-Strep-tag as described. In some embodiments, the binding molecule is a non-antibody agent capable of specifically, and in some cases reversibly, binding to the agent, such as a streptavidin mutein, including Strep-Tactin or other streptavidin mutein and oligomers thereof. In some embodiments, the binding molecule that recognizes the agent is an antibody, such as an anti-Strep-tag antibody.

VII. Definitions

As used herein, recitation that nucleotides or amino acid positions "correspond to" nucleotides or amino acid positions in a disclosed sequence, such as set forth in the Sequence listing, refers to nucleotides or amino acid positions identified upon alignment with the disclosed sequence to maximize identity using a standard alignment algorithm, such as the GAP algorithm. By aligning the sequences, one skilled in the art can identify corresponding residues, for example, using conserved and identical amino acid residues as guides. In general, to identify corresponding positions, the sequences of amino acids are aligned so that the highest order match is obtained (see, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New. Jersey, 1994;

Sequence Analysis in Molecular Biology, von Heinje, G., Academic Press, 1987; and Sequence Analysis Primer, Gribskov, M. and Devereux, J., eds., M Stockton Press, New York, 1991; Carrillo et al. (1988) SIAM J Applied Math 48: 1073).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors." Among the vectors are viral vectors, such as retroviral, e.g., gammaretroviral and lentiviral vectors.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

As used herein, "percent (%) amino acid sequence identity" and "percent identity" when used with respect to an amino acid sequence (reference polypeptide sequence) is defined as the percentage of amino acid residues in a candidate sequence (e.g., the subject antibody or fragment) that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

As used herein, a composition refers to any mixture of two or more products, substances, or compounds, including cells. It may be a solution, a suspension, liquid, powder, a paste, aqueous, non-aqueous or any combination thereof.

As used herein, a "subject" is a mammal, such as a human or other animal, and typically is human.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section heading used herein are for organizational purposes only and are not to be construed as limiting the subject matter described.

VIII. Exemplary Embodiments

Among the provided embodiments are:

1. A cell surface conjugate, comprising:

(a) a cell surface molecule that lacks a functional intracellular signaling domain and/or is not capable of mediating intracellular signaling; and (b) at least one agent linked to the cell surface molecule, the agent being capable of binding a streptavidin, a streptavidin analog or a streptavidin mutein.

2. The cell surface conjugate of embodiment 1, wherein the agent exhibits a binding affinity for streptavidin or a streptavidin mutein with an equilibrium dissociation constant ($K_D$) of from or from about $10^{-4}$ M to or to about $10^{-10}$ M.

3. A cell surface conjugate, comprising:

(a) a cell surface molecule that lacks a functional intracellular signaling domain and/or is not capable of mediating intracellular signaling; and (b) at least one agent linked to the cell surface molecule and being capable of reversibly binding to a reagent and/or capable of being competed in the presence of a competition substance, wherein the agent is a peptide of less than 50 amino acids in length.

4. The cell surface conjugate of embodiment 3, wherein the agent exhibits a binding affinity for the reagent with an equilibrium dissociation constant ($K_D$) of from or from about $10^{-4}$ M to or to about $10^{-10}$ M.

5. The cell surface conjugate of embodiment 3 or embodiment 4, wherein the reagent is a streptavidin, a streptavidin analog or a streptavidin mutein.

6. A cell surface conjugate, comprising:

(a) a cell surface molecule that lacks a functional intracellular signaling domain and/or is not capable of mediating intracellular signaling; and (b) at least one agent linked to the cell surface molecule, the agent having a binding affinity for a reagent with an equilibrium dissociation constant ($K_D$) of more than $10^{-7}$ M or an equilibrium association constant ($K_A$) of less than $10^7$ $M^{-1}$.

7. The cell surface conjugate of embodiment 6, wherein the reagent is a streptavidin, a streptavidin analog or a streptavidin mutein.

8. The cell surface conjugate of any of embodiments 1-7, wherein the cell surface molecule comprises a transmembrane domain and/or is capable of being expressed on the surface of the cell.

9. The cell surface conjugate of any of embodiments 1-8, wherein the cell surface molecule is modified compared to a reference cell surface molecule, optionally wherein the reference cell surface molecule is a cell surface receptor comprising an intracellular signaling domain.

10. The cell surface conjugate of embodiment 9, wherein the modified cell surface molecule exhibits altered cellular internalization, enzymatic activity and/or ligand binding, compared to the reference cell surface molecule.

11. A cell surface conjugate, comprising:

(a) a cell surface molecule that is modified compared to a reference cell surface molecule, wherein the modified cell surface molecule exhibits altered cellular internalization, enzymatic activity and/or ligand binding, compared to the reference cell surface molecule; and (b) at least one agent linked to the cell surface molecule, the agent being capable of binding a streptavidin, a streptavidin analog or a streptavidin mutein.

12. The cell surface conjugate of embodiment 11, wherein the cell surface molecule lacks a functional intracellular signaling domain and/or is not capable of mediating intracellular signaling.

13. A cell surface conjugate, comprising:

(a) a cell surface molecule comprising a prostate-specific membrane antigen (PSMA) or a modified cell surface molecule thereof and (b) at least one agent linked to the cell surface molecule, the agent being capable of binding a streptavidin, a streptavidin analog or a streptavidin mutein.

14. The cell surface conjugate of embodiment 13, wherein:

the modified cell surface molecule lacks a functional intracellular signaling domain and/or is not capable of mediating intracellular signaling; and/or the modified cell surface molecule is modified compared to a reference cell surface molecule, wherein the modified cell surface molecule exhibits altered cellular internalization, enzymatic activity and/or ligand binding, compared to the reference cell surface molecule.

15. The cell surface conjugate of any of embodiments 11-14, wherein the cell surface molecule comprises a transmembrane domain and/or is capable of being expressed on the surface of the cell.

16. The cell surface conjugate of any of embodiments 11-15, wherein the agent exhibits a binding affinity for a streptavidin, a streptavidin analog or a streptavidin mutein with an equilibrium dissociation constant ($K_D$) of from or from about $10^{-4}$ M to or to about $10^{-10}$ M.

17. The cell surface conjugate of any of embodiments 1-16, wherein the binding of the agent to the reagent is reversible and/or capable of being competed in the presence of a competition substance.

18. The cell surface conjugate of embodiment 17, wherein the competition substance exhibits a higher binding affinity for the reagent than the binding affinity of the agent for the reagent.

19. The cell surface conjugate of embodiment 18, wherein:

the competition substance exhibits a binding affinity for the reagent with an equilibrium dissociation constant ($K_D$) of between or about between $10^{-10}$ M and $10^{-14}$ M; and/or the agent exhibits a binding affinity for the reagent with an equilibrium dissociation constant ($K_D$) of more than $10^{-10}$ M.

20. The cell surface conjugate of any of embodiments 1, 2, 5, 7-20, wherein the binding of the agent to the streptavidin, streptavidin analog or streptavidin mutein is reversible and/or capable of being competed in the presence of biotin, a biotin analog or a biologically active fragment thereof.

21. The cell surface conjugate of any of embodiments 1-20, wherein the at least one agent is linked directly to the cell surface molecule.

22. The cell surface conjugate of any of embodiments 1-20, wherein the at least one agent is linked indirectly to the cell surface molecule via at least one linker.

23. The cell surface conjugate of any of embodiments 1-22, wherein the at least one agent comprises from or from about 1 to 4 or 1 to 2 agents.

24. The cell surface conjugate of any of embodiments 1-23, wherein the at least one agent comprises only one agent.

25. The cell surface conjugate of any of embodiments 1-24, wherein the agent is linked to an extracellular portion or region of the cell surface molecule, optionally wherein the extracellular portion or region is at the N-terminus or C-terminus of the cell surface molecule.

26. The cell surface conjugate of any of embodiments 1-25, wherein the agent is linked at the N-terminus of the cell surface molecule.

27. The cell surface conjugate of any of embodiments 1-26, wherein the agent is linked at the C-terminus of the cell surface molecule.

28. A cell surface conjugate, comprising a cell surface molecule linked, at an extracellular portion or region of the cell surface molecule, to an agent, the agent being capable of binding a reagent that is or comprises streptavidin or a streptavidin mutein, optionally wherein the extracellular portion or region is at the N-terminus or C-terminus of the cell surface molecule.

29. A cell surface conjugate, comprising a cell surface molecule linked, at an extracellular portion or region of the cell surface molecule, to an agent, the agent being capable of reversibly binding to a reagent, wherein the agent is a peptide of less than 50 amino acids in length optionally wherein the extracellular portion or region is at the N-terminus or C-terminus of the cell surface molecule.

30. The cell surface conjugate of embodiment 28 or embodiment 29, wherein the agent exhibits a binding affinity with an equilibrium dissociation constant ($K_D$) of from or from about $10^{-4}$ M to or to about $10^{-10}$ M.

31. A cell surface conjugate, comprising a cell surface molecule linked, at an extracellular portion or region of the cell surface molecule, to an agent, wherein the agent exhibits a binding affinity for a reagent with an equilibrium dissociation constant ($K_D$) of more than $10^{-7}$ M or an equilibrium association constant ($K_A$) of less than $10^7$ M$^{-1}$ optionally wherein the extracellular portion or region is at the N-terminus or C-terminus of the cell surface molecule.

32. The cell surface conjugate of any of embodiments 28-31, wherein the agent is linked at the N-terminus of the cell surface molecule.

33. The cell surface conjugate of any of embodiments 28-31, wherein the agent is linked at the C-terminus of the cell surface molecule.

34. The cell surface conjugate of any of embodiments 28-33, wherein the reagent is or comprises a streptavidin, a streptavidin analog or a streptavidin mutein.

35. The cell surface conjugate of any of embodiments 28-34, wherein the binding of the agent to the reagent is reversible and/or capable of being competed in the presence of a competition substance.

36. The cell surface conjugate of embodiment 35, wherein the competition substance exhibits a higher binding affinity for the reagent than the binding affinity of the agent for the reagent.

37. The cell surface conjugate of embodiment 36, wherein:
the competition substance exhibits a binding affinity for the reagent with an equilibrium dissociation constant ($K_D$) of between or about between $10^{-10}$ M and $10^{-14}$ M; and/or
the agent exhibits a binding affinity for the reagent with an equilibrium dissociation constant ($K_D$) of more than $10^{-10}$ M.

38. The cell surface conjugate of any of embodiments 28, 34-37, wherein the binding of the agent to the streptavidin, streptavidin analog or streptavidin mutein is reversible and/or capable of being competed in the presence of biotin or a biotin analog.

39. The cell surface conjugate of any of embodiments 28-38, wherein the agent is linked directly to the cell surface molecule.

40. The cell surface conjugate of any of embodiments 28-38, wherein the agent is linked indirectly to the cell surface molecule via at least one linker.

41. The cell surface conjugate of any of embodiments 28-40, wherein the cell surface molecule is linked to only one agent.

42. The cell surface conjugate of any of embodiments 1-41, wherein the cell surface molecule is not a chimeric antigen receptor (CAR).

43. The cell surface conjugate of any of embodiments 28-30, wherein the cell surface molecule is modified compared to a reference cell surface molecule.

44. The cell surface conjugate of embodiment 43, wherein the modified cell surface molecule lacks a functional intracellular signaling domain and/or is not capable of mediating intracellular signaling; and/or the modified cell surface molecule exhibits altered cellular internalization, enzymatic activity and/or ligand binding, compared to the reference cell surface molecule.

45. The cell surface conjugate of embodiment 43 or embodiment 44, wherein the reference cell surface molecule is a native mammalian cell surface molecule.

46. The cell surface conjugate of any of embodiments 1-45, wherein the cell surface molecule comprises an epitope capable of being recognized by an antibody or antigen-binding fragment thereof.

47. The cell surface conjugate of any of embodiments 1-33 that is a fusion protein.

48. The cell surface conjugate of any of embodiments 1, 2, 5, 7-28 and 34-47, wherein the streptavidin analog or mutein comprises the amino acid sequence Val$^{44}$-Thr$^{45}$-Ala$^{46}$-Arg$^{47}$ or Ile$^{44}$-Gly$^{45}$-Ala$^{46}$-Arg$^{47}$ at sequence positions corresponding to positions 44 to 47 with reference to positions in streptavidin in the sequence of amino acids set forth in SEQ ID NO:1.

49. The cell surface conjugate of any of embodiments 1, 2, 5, 7-28 and 34-48, wherein the streptavidin analog or mutein comprises:
a) the sequence of amino acids set forth in any of SEQ ID NOS: 3-6, 27 and 28;
b) a sequence of amino acids that exhibits at least at or about 85%, 86%, 87%, 88%, 89%, 89%, 90%, 91%, 92%, 93%, 94%, 95%, 96%, 97%, 98%, 99% or more sequence identity to any of SEQ ID NOS:3-6, 27 and 28 and contains the amino acid sequence corresponding to Val$^{44}$-Thr$^{45}$-Ala$^{46}$-Arg$^{47}$ or Ile$^{44}$-Gly$^{45}$-Ala$^{46}$-Arg$^{47}$ and that reversibly binds to the agent; or
c) a functional fragment of a) or b) that reversibly binds to the agent.

50. The cell surface conjugate of embodiment 48 or embodiment 49, wherein the streptavidin analog or mutein further comprises an amino acid replacement or replacements at a position corresponding to 117, 120 and/or 121 with reference to positions in streptavidin in the sequence of amino acids set forth in SEQ ID NO:1.

51. The cell surface conjugate of embodiment 50, wherein:
the amino acid replacement or replacements are selected from among Glu$^{117}$, Asp$^{117}$, Arg$^{117}$, Ser$^{120}$, Ala$^{120}$, Gly$^{120}$, Trp$^{121}$, Tyr$^{121}$ or Phe$^{121}$; or
the amino acid replacement or replacements are selected from one or more of Glu$^{117}$, Gly$^{120}$ or Tyr$^{121}$; or
the amino acid replacements are selected from Glu$^{117}$, Gly$^{120}$ or Tyr$^{121}$.

52. The cell surface conjugate of any of embodiments any of embodiments 1, 2, 5, 7-28 and 34-51, wherein the streptavidin analog or mutein comprises:

a) the sequence of amino acids set forth in SEQ ID NO: 27 or 28;

b) a sequence of amino acids that exhibits at least at or about 85%, 86%, 87%, 88%, 89%, 89%, 90%, 91%, 92%, 93%, 94%, 95%, 96%, 97%, 98%, 99% or more sequence identity to SEQ ID NOS: 27 or 28 and contains the amino acid sequence corresponding to Val$^{44}$, Thr$^{45}$, Ala$^{46}$, Arg$^{47}$, Glu$^{117}$, Gly$^{120}$ and Tyr$^{121}$ and reversibly binds to the agent; or c) a functional fragment of a) or b) that reversibly binds to the agent.

53. The cell surface conjugate of any of embodiments 3-5, 17-19 and 35-37, wherein the competition substance is or comprises biotin, a biotin analog or a biologically active fragment thereof.

54. The cell surface conjugate of any of embodiments 1-53, wherein the agent is an affinity tag.

55. The cell surface conjugate of any of embodiments 3, 4, 6, 8-10, 17-19, 21-27, 29-33, 35-37, 39-47 and 54, wherein the agent is or comprises a Strep tag, His tag, Flag tag, Xpress tag, Avi tag, Calmodulin tag, Polyglutamate tag, HA tag, Myc tag, Nus tag, S tag, X tag, SBP tag, Softag, V5 tag, CBP, GST, MBP, GFP, Thioredoxin tag, or any combination thereof.

56. The cell surface conjugate of any of embodiments 1-55, wherein the agent is or comprises one or more streptavidin binding peptide, which optionally is a Strep tag.

57. The cell surface conjugate of embodiment 56, wherein the streptavidin binding peptide comprises the sequence Trp-Ser-His-Pro-Gln-Phe-Glu-Lys (SEQ ID NO: 8) or Trp-Arg-His-Pro-Gln-Phe-Gly-Gly (SEQ ID NO:7).

58. The cell surface conjugate of embodiment 56 or embodiment 57, wherein the agent comprises the sequence Trp-Ser-His-Pro-Gln-Phe-Glu-Lys-(GlyGlyGlySer)$_3$-Trp-Ser-His-Pro-Gln-Phe-Glu-Lys (SEQ ID NO: 17), Trp-Ser-His-Pro-Gln-Phe-Glu-Lys-(GlyGlyGlySer)$_2$-Trp-Ser-His-Pro-Gln-Phe-Glu-Lys (SEQ ID NO: 18) and Trp-Ser-His-Pro-Gln-Phe-Glu-Lys-(GlyGlyGlySer)$_2$Gly-Gly-Ser-Ala-Trp-Ser-His-Pro-Gln-Phe-Glu-Lys (SEQ ID NO: 19).

59. The cell surface conjugate of any of embodiments 9-58, wherein the reference cell surface molecule is a cell surface receptor, ligand, glycoprotein, cell adhesion molecule, antigen, integrin or cluster of differentiation (CD).

60. The cell surface conjugate of embodiment 59, wherein the reference cell surface molecule is a cell surface receptor.

61. The cell surface conjugate of any of embodiments 9-60, wherein the reference cell surface molecule is selected from EpCAM, VEGFR, integrin, optionally integrins αvβ3, α4, αIIbβ3, α4β7, α5β1, αvβ3 or αv, a member of the TNF receptor superfamily, optionally TRAIL-R1 or TRAIL-R2, a member of the epidermal growth factor receptor family, PDGF Receptor, interferon receptor, folate receptor, GPNMB, ICAM-1, HLA-DR, CEA, CA-125, MUC1, TAG-72, IL-6 receptor, 5T4, GD2, GD3, prostate-specific membrane antigen (PSMA) or a clusters of differentiation cell surface molecule, optionally CD2, CD3, CD4, CD5, CD11, CD11a/LFA-1, CD15, CD18/ITGB2, CD19, CD20, CD22, CD23/IgE Receptor, CD25, CD28, CD30, CD33, CD38, CD40, CD41, CD44, CD51, CD52, CD62L, CD74, CD80, CD125, CD147/basigin, CD152/CTLA-4, CD154/CD40L, CD195/CCR5 and CD319/SLAMF7.

62. The cell surface conjugate of any of embodiments 9-61, wherein the reference cell surface molecule is a member of the epidermal growth factor receptor family.

63. The cell surface conjugate of any of embodiments 9-62, wherein the reference cell surface molecule is an epidermal growth factor receptor (EGFR), an erbB-2 receptor tyrosine-protein kinase (errb2, HER2), an erbB-3 receptor tyrosine-protein kinase, an erbB-4 receptor tyrosine-protein kinase, a hepatocyte growth factor receptor (HGFR/c-MET) or an insulin-like growth factor receptor-1 (IGF-1R).

64. The cell surface conjugate of any of embodiments 9-63, wherein the reference cell surface molecule is human.

65. The cell surface conjugate of any of embodiments 9-64, wherein the modified cell surface molecule lacks a functional intracellular signaling domain and/or is not capable of mediating intracellular signaling.

66. The cell surface conjugate of any of embodiments 9-65, wherein the modified cell surface molecule is truncated to lack all or a portion of the intracellular signaling domain or trafficking domain compared to the reference cell surface molecule.

67. The cell surface conjugate of any of embodiments 9-66, wherein the modified cell surface molecule exhibits altered cellular internalization, enzymatic activity and/or ligand binding, compared to the reference cell surface molecule.

68. The cell surface conjugate of any of embodiments 9-67, wherein the modified cell surface molecule comprises one or more extracellular domains of the reference cell surface molecule.

69. The cell surface conjugate of any of embodiments 9-68, wherein the modified cell surface molecule is capable of binding to a native ligand and/or substrate of the reference cell surface molecule.

70. The cell surface conjugate of any of embodiments 9-68, wherein the modified cell surface molecule is reduced for or does not bind the native ligand and/or substrate of the reference cell surface molecule.

71. The cell surface conjugate of embodiment 70, wherein the modified cell surface molecule comprises at least one extracellular domain of the reference cell surface molecule but lacks one or more other extracellular domains recognized by the native ligand and/or substrate of the reference cell surface molecule.

72. The cell surface conjugate of embodiment 71, wherein the at least one extracellular domain comprises an epitope recognized by an antibody or antigen-binding fragment thereof that specifically binds the reference cell surface molecule.

73. The cell surface conjugate of any of embodiments 46-72, wherein the antibody or antigen-binding fragment is selected from AMG-102, AMG-479, BIIB022OA-5D5, CP-751,871, IMC-Al2, R1507, 3F8, abagovomab, abciximab, adecatumumab, afutuzumab, alemtuzumab, altumomab pentetate, anatumomab mafenatox, apolizumab, arcitumomab, aselizumab, atlizumab (=tocilizumab), basiliximab, bectumomab, benralizumab, besilesomab, bivatuzumab mertansine, blinatumomab, brentuximab vedotin, cantuzumab mertansine, capromab pendetide, catumaxomab, CC49, cedelizumab, celmoleukin, cetuximab, cixutumumab, clenoliximab, clivatuzumab tetraxetan, CNTO-95, conatumumab, dacetuzumab, daclizumab, daratumumab, detumomab, ecromeximab, ertumaxomab, edrecolomab, efalizumab, elotuzumab, enlimomab pegol, epitumomab cituxetan, epratuzumab, erlizumab, etaracizumab, fanolesomab, faralimomab, farletuzumab, figitumumab, galiximab, gavilimomab, gemtuzumab ozogamicin, glembatumumab vedotin, gomiliximab, ibalizumab, ibritumomab tiuxetan, igovomab, intetumumab, iratumumab, inolimomab, inotuzumab ozogamicin, ipilimumab, keliximab, labetuzumab, lintuzumab, lexatumumab, lucatumumab, lumiliximab, mapatumumab, maslimomab, matuzumab, milatuximab, minretumomab, mitumomab, muromonab-CD3, naptumomab estafenatox, natalizumab, necitumumab, ocrelizumab, odulimomab, ofatumumab, olaratumab, oportuzumab monatox, oregovomab, otelixizumab, panitumumab, pertuzumab, pemtumomab, priliximab, PRO 140, nimotuzumab, robatumumab, rituximab, rovelizumab, ruplizumab, satumomab pendetide, siplizumab, sontuzumab, tadocizumab, taplitumomab paptox, teneliximab, teplizumab, TGN1412, ticilimumab (=tremelimumab), tigatuzumab, tocilizumab (=atlizumab), toralizumab, tositumomab, trastuzumab, tremelimumab, tucotuzumab, vedolizumab, veltuzumab, visilizumab, vitaxin, volociximab, votumumab, zalutumumab, zanolimumab, ziralimumab, zolimomab aritox, Atezolizumab, bevacizumab (Avastin®), denosumab, dinutuximab, nivolumab, obinutuzumab, pembrolizumab, pidilizumab (CT-011), ramucirumab, siltuximab, ado-trastuzumab emtansine, CEA-scan Fab fragment, OC125 monoclonal antibody, ab75705, B72.3, MPDL3280A, MSB001078C, MEDI4736, or an antigen binding fragment thereof.

74. The cell surface conjugate of any of embodiments 9-73, wherein the reference cell surface molecule is a reference EGFR and the modified cell surface molecule is a modified EGFR.

75. The cell surface conjugate of embodiment 74 wherein the modified EGFR comprises an epitope specifically recognized by cetuximab or an antigen binding fragment thereof 76. The cell surface conjugate of embodiment 74 or embodiment 75, wherein the modified EGFR lacks one or more of an EGFR Domain I, an EGFR Domain II, an EGFR Juxtamembrane Domain, and an EGFR Tyrosine Kinase Domain of the reference EGFR.

77. The cell surface conjugate of any of embodiments 74-76, wherein the modified EGFR lacks all of the domains EGFR Domain I, an EGFR Domain II, an EGFR Juxtamembrane Domain, and an EGFR Tyrosine Kinase Domain of the reference EGFR.

78. The cell surface conjugate of any of embodiments 74-77, wherein the modified EGFR comprises an extracellular domain that consists of or consists essentially of subdomain III and subdomain IV of the reference EGFR.

79. The cell surface conjugate of any of embodiments 74-78, wherein the modified EGFR comprises the sequence of amino acids set forth in SEQ ID NOS: 44 or 46 or a sequence of amino acids that exhibits at least at or about 85%, 90%, or 95% sequence identity to SEQ ID NOS: 44 or 46.

80. The cell surface conjugate of any of embodiments 973, wherein the reference cell surface molecule is a reference HER2 and the modified cell surface molecule is a modified HER2.

81. The cell surface conjugate of embodiment 80, wherein the modified HER2 comprises an epitope specifically recognized by trastuzumab or an antigen binding fragment thereof.

82. The cell surface conjugate of embodiment 80 or embodiment 81, wherein the modified HER2 lacks one or more of an HER2 Domain I, an HER2 Domain II, an HER2 Domain III of the reference HER2.

83. The cell surface conjugate of any of embodiments 80-82, wherein the modified HER2 lacks all of the domains HER2 Domain I, HER2 Domain II, and HER2 Domain III of the reference EGFR of the reference HER2.

84. The cell surface conjugate of any of embodiments 80-83, wherein the modified HER2 comprises an extracellular domain that consists of or consists essentially of Domain IV of the reference HER2.

85. The cell surface conjugate of any of embodiments 80-84, wherein the modified HER2 comprises the sequence of amino acids set forth in SEQ ID NO: 92 or a sequence of amino acids that exhibits at least at or about 85%, 90%, or 95% sequence identity to SEQ ID NO: 92.

86. The cell surface conjugate of any of embodiments 9-72, wherein the reference cell surface molecule is a reference PSMA and the modified cell surface molecule is a modified PSMA.

87. The cell surface conjugate of embodiment 86, wherein the reference PSMA is a wild-type PSMA, optionally wild-type human PSMA.

88. The cell surface conjugate of embodiment 87, wherein the reference PSMA is a human PSMA and/or comprises the sequence of amino acids set forth in SEQ ID NO: 94 or a sequence of amino acids encoded by the sequence of nucleotides set forth in SEQ ID NO: 96 or 97.

89. The cell surface conjugate of any of embodiments 86-88, wherein the modified PSMA comprises an extracellular portion and a transmembrane domain of the reference PSMA.

90. The cell surface conjugate of any of embodiments 86-89, wherein the modified PSMA comprises one or more amino acid modifications in the intracellular region compared to the reference PSMA.

91. The cell surface conjugate of any of embodiments 86-90, wherein the one or more amino acid modification comprises one or more amino acid substitutions, deletions and/or insertions.

92. The cell surface conjugates of any of embodiments 86-91, wherein the modified PSMA exhibits altered cellular internalization compared to the reference PSMA.

93. The cell surface conjugate of any of embodiments 86-92, wherein the modified PSMA comprises an amino acid substitution corresponding to W2G or does not comprise W2 or does not comprise any residue at position 2, with reference to positions in the sequence of amino acids set forth in SEQ ID NO:94.

94. The cell surface conjugate of any of embodiments 86-93, wherein the modified PSMA comprises a deletion or truncation of 11 N-terminal amino acids, compared to the reference PSMA.

95. The cell surface conjugate of any of embodiments 86-94, wherein the modified PSMA comprises an epitope capable of being recognized by an antibody or antigen-binding fragment thereof.

96. The cell surface conjugate of embodiment 95, wherein the antibody or antigen-binding fragment thereof is selected from among J591, DFO-J591, CYT-356, J415, 3/A12, 3/F11, 3/E7, D2B, 107-1A4, YPSMA-1, YPSMA-2, 3E6, 2G7, 24.4E6, GCP-02, GCP-04, GCP-05, J533, E99, 1G9, 3C6, 4.40, 026, D7-Fc, D7-CH3, 4D4, A5, and antigen-binding fragments thereof.

97. The cell surface conjugate of any of embodiments 1-96, wherein the cell surface conjugate is not immunogenic and/or does not induce an immune response in a subject in which it is administered.

98. A polynucleotide, comprising a nucleic acid sequence encoding the cell surface conjugate of any of embodiments 1-97.

99. The polynucleotide of embodiment 98, wherein the nucleic acid sequence further comprising a signal sequence.

100. The polynucleotide of embodiment 99, wherein the signal sequence encodes a signal peptide derived from GMCSFR alpha chain.

101. The polynucleotide of any of embodiments 98-100, wherein the nucleic acid sequence is a first nucleic acid sequence and the polynucleotide further comprises a second nucleic acid sequence encoding a recombinant receptor.

102. The polynucleotide of embodiment 101, wherein the recombinant receptor is or comprises a chimeric antigen receptor (CAR).

103. The polynucleotide of embodiment 101 or embodiment 102, wherein the first and second nucleic acid sequences are separated by an internal ribosome entry site (IRES), or a nucleotide sequence encoding a self-cleaving peptide or a peptide that causes ribosome skipping, which optionally is a T2A, a P2A, an E2A or an F2A.

104. The polynucleotide of any of embodiments 101-103, wherein the first nucleic acid sequence is upstream of the second nucleic acid sequence.

105. The polynucleotide of any of embodiments 101-103, wherein the first nucleic acid sequence is downstream of the second nucleic acid sequence.

106. A vector, comprising the polynucleotide of any of embodiments 98-105.

107. The vector of embodiment 106 that is a viral vector.

108. The vector of embodiment 106 or embodiment 107 that is a retroviral vector.

109. The vector of any of embodiments 106-108 that is a lentiviral vector or a gammaretroviral vector.

110. A method of producing an engineered cell, comprising introducing the polynucleotide of any of embodiments 96-105 or the vector of any of embodiments 106-109 into a cell.

111. An engineered cell produced by the method of embodiment 110.

112. An engineered cell, comprising the polynucleotide of any of embodiments 98-105 or the vector of any of embodiments 106-109.

113. An engineered cell, comprising the cell surface conjugate of any of embodiments 1-97.

114. The engineered cell of embodiment 113, further comprising a recombinant receptor.

115. The engineered cell of embodiment 114, wherein the recombinant receptor is capable of binding to a target antigen that is associated with, specific to, and/or expressed on a cell or tissue of a disease or disorder.

116. The engineered cell of embodiment 115, wherein the disease or disorder is an infectious disease or disorder, an autoimmune disease, an inflammatory disease, or a tumor or a cancer.

117. The engineered cell of embodiment 115 or embodiment 116, wherein the target antigen is a tumor antigen.

118. The engineered cell of any of embodiments 115-117, wherein the target antigen is selected from the group consisting of αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD138, CD171, epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), G Protein Coupled Receptor 5D (GPCR5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22Ra), IL-13 receptor alpha 2 (IL-13Ra2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, mesothelin, c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), vascular endothelial growth factor receptor (VEGFR), vascular endothelial growth factor receptor 2 (VEGFR2), Wilms Tumor 1 (WT-1)

119. The engineered cell of any of embodiments 115-118, wherein the target antigen is selected from the group consisting of ROR1, HER2, L1-CAM, CD19, CD20, CD22, mesothelin, CEA, hepatitis B surface antigen, anti-folate receptor, CD23, CD24, CD30, CD33, CD38, CD44, EGFR, EGP-2, EGP-4, EPHa2, ErbB2, ErbB3, ErbB4, FBP, fetal acethycholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, TAG72, VEGF-R2, carcinoembryonic antigen (CEA), prostate specific antigen, PSMA, estrogen receptor, progesterone receptor, ephrinB2, CD123, CS-1, c-Met, GD-2, MAGE A3, CE7, Wilms Tumor 1 (WT-1), and cyclin A1 (CCNA1).

120. The engineered cell of any of embodiments 114-119, wherein the recombinant receptor is a functional non-TCR antigen receptor or a transgenic TCR.

121. The engineered cell of any of embodiments 114-120, wherein the recombinant receptor is a chimeric antigen receptor (CAR).

122. The engineered cell of any of embodiments 114-121, wherein the recombinant receptor comprises an extracellular portion comprising an antigen-binding domain.

123. The engineered cell of embodiment 122, wherein the antigen-binding domain is or comprises an antibody or an antibody fragment.

124. The engineered cell of embodiment 123, wherein the antibody fragment is a single chain fragment.

125. The engineered cell of embodiment 123 or embodiment 124, wherein the fragment comprises antibody variable regions joined by a flexible linker.

126. The engineered cell of any of embodiments 123-125, wherein the fragment comprises an scFv.

127. The engineered cell of any of embodiments 114-126, wherein the recombinant receptor comprises an intracellular signaling region.

128. The engineered cell of embodiment 127, wherein the intracellular signaling region comprises an intracellular signaling domain.

129. The engineered cell of embodiment 128, wherein the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM).

130. The engineered cell of embodiment 128 or embodiment 129, wherein the intracellular signaling domain is or comprises an intracellular signaling domain of a CD3 chain, optionally a CD3-zeta (CD3) chain or a signaling portion thereof.

131. The engineered cell of any of embodiments 127-130, further comprising a transmembrane domain disposed between the extracellular domain and the intracellular signaling region.

132. The engineered cell of any of embodiments 127-131, wherein the intracellular signaling region further comprises a costimulatory signaling domain.

133. The engineered cell of embodiment 132, wherein the costimulatory signaling domain comprises an intracellular signaling domain of a T cell costimulatory molecule or a signaling portion thereof.

134. The engineered cell of embodiment 132 or embodiment 133, wherein the costimulatory signaling domain comprises an intracellular signaling domain of a CD28, a 4-1BB or an ICOS or a signaling portion thereof.

135. The engineered cell of any of embodiments 132-134, wherein the costimulatory signaling domain is between the transmembrane domain and the intracellular signaling domain.

136. The engineered cell of any of embodiments 111-135, wherein the cell is an immune cell.

137. The engineered cell of embodiment 136, wherein the cell is a lymphocyte.

138. The engineered cell of any of embodiments 111-137, wherein the cell is a T cell or an NK cell.

139. The engineered cell of embodiment 138, wherein the cell is a T cell that is a CD8+ T cell or a CD4+ T cell.

140. A composition comprising the engineered cells of any of embodiments 111-139.

141. The composition of embodiment 140, further comprising a pharmaceutically acceptable excipient.

142. A method of treatment comprising administering the engineered cells of any of embodiments 111-139 or the composition of embodiment 140 or embodiment 141 to a subject having a disease or disorder.

143. The method of embodiment 142, wherein the disease or disorder is a cancer, a tumor, an autoimmune disease or disorder, or an infectious disease.

144. The method of embodiment 142 or embodiment 143, further comprising administering to the subject a binding molecule capable of recognizing the agent of the cell surface conjugate expressed on the engineered cell and detecting cells that express the cell surface conjugate.

145. The method of embodiment 144, wherein detection comprises in vivo imaging.

146. A method of identifying a cell expressing a cell surface conjugate, comprising contacting a composition comprising cells that express or are likely to express a cell surface conjugate of any of embodiments 1-97 or the engineered cell of any of embodiments 111-139 or the composition of embodiment 140 or embodiment 141, with a binding molecule capable of recognizing the agent of the cell surface conjugate.

147. The method of embodiment 146 that is performed in vitro, ex vivo or in vivo.

148. The method of any of embodiment 146 or embodiment 147, wherein the cell expressing the cell surface molecule is detected via in vivo imaging.

149. The method of embodiment 145 or embodiment 148, wherein the in vivo imaging method is selected from among magnetic resonance imaging (MRI), single-photon emission computed tomography (SPECT), computed tomography (CT), computed axial tomography (CAT), electron beam computed tomography (EBCT), high resolution computed tomography (HRCT), hypocycloidal tomography, positron emission tomography (PET), scintigraphy, gamma camera, a β+ detector, a γ detector, fluorescence imaging, low-light imaging, X-rays, and bioluminescence imaging.

150. The method of embodiment 145, embodiment 148, or embodiment 149, wherein the binding molecule is conjugated to a moiety that provides a signal or induces a signal that is detectable in vivo.

151. The method of embodiment 150, wherein the moiety is a radioisotope, bioluminescent compound, chemiluminescent compound, fluorescent compound, metal chelate or enzyme.

152. A method of identifying cells transduced with a cell surface conjugate, comprising:
(a) contacting a composition transduced with a polynucleotide of any of embodiments 98-105 or the vector of any of embodiments 106-109 encoding the cell surface conjugate or the engineered cell of any of embodiments 111-139 or the composition of embodiment 140 or embodiment 141 with a binding molecule capable of recognizing the agent of the cell surface conjugate; and
(b) identifying cells bound to the binding molecule.

153. A method of identifying cells transduced with a cell surface conjugate, comprising:
(a) introducing a polynucleotide of any of embodiments 98-105 or the vector of any of embodiments 106-109 encoding the cell surface conjugate into a cell;
(b) contacting a composition comprising the cell of (a) with a binding molecule capable of recognizing the agent of the cell surface conjugate; and
(c) identifying cells of the composition bound to the binding molecule.

154. A method of selecting cells transduced with a cell surface conjugate, comprising:
(a) contacting a composition transduced with a polynucleotide of any of embodiments 98-105 or the vector of any of embodiments 106-109 encoding the cell surface conjugate or the engineered cell of any of embodiments 111-139 or the composition of embodiment 140 or embodiment 141 with a binding molecule capable of recognizing the agent of the cell surface conjugate; and
(b) isolating cells bound to the binding molecule.

155. A method of selecting cells transduced with a cell surface conjugate, comprising:
(a) introducing a polynucleotide of any of embodiments 98-105 or the vector of any of embodiments 106-109 encoding the cell surface conjugate into a cell;
(b) contacting a composition comprising the cell of (a) with a binding molecule capable of recognizing the agent of the cell surface conjugate; and
(c) isolating cells of the composition bound to the binding molecule.

156. The method of embodiment 154 or embodiment 155, wherein the binding molecule is conjugated to a detectable moiety or is capable of producing a detectable signal.

157. The method of embodiment 156, wherein the detectable moiety comprises a fluorescent protein.

158. The method of any of embodiments 144-157, wherein the agent is a streptavidin binding peptide.

159. The method of embodiment 158, wherein the streptavidin binding peptide is or comprises the sequence Trp-Ser-His-Pro-Gln-Phe-Glu-Lys (SEQ ID NO: 8) or Trp-Arg-His-Pro-Gln-Phe-Gly-Gly (SEQ ID NO:7).

160. The method of embodiment 159, wherein the streptavidin binding peptide is or comprises the sequence Trp-Ser-His-Pro-Gln-Phe-Glu-Lys-(GlyGlyGlySer)$_3$-Trp-Ser-His-Pro-Gln-Phe-Glu-Lys (SEQ ID NO: 17), Trp-Ser-His-Pro-Gln-Phe-Glu-Lys-(GlyGlyGlySer)$_2$-Trp-Ser-His-Pro-Gln-Phe-Glu-Lys (SEQ ID NO: 18) and Trp-Ser-His-Pro-Gln-Phe-Glu-Lys-(GlyGlyGlySer)$_2$Gly-Gly-Ser-Ala-Trp-Ser-His-Pro-Gln-Phe-Glu-Lys (SEQ ID NO: 19).

161. The method of any of embodiments 144-160, wherein the binding molecule is a reagent capable of reversibly binding to the agent and/or capable of being competed in the presence of a competition substance.

162. The method of embodiment 161, wherein the reagent is a streptavidin, a streptavidin analog or mutein.

163. The method of embodiment 162, wherein the streptavidin analog or mutein comprises the amino acid sequence Val$^{44}$-Thr$^{45}$-Ala$^{46}$-Arg$^{47}$ or Ile$^{44}$-Gly$^{45}$-Ala$^{46}$-Arg$^{47}$ at sequence positions corresponding to positions 44 to 47 with reference to positions in streptavidin in the sequence of amino acids set forth in SEQ ID NO:1.

164. The method of embodiment 162 or embodiment 163, wherein the streptavidin analog or mutein comprises:
a) the sequence of amino acids set forth in any of SEQ ID NOS: 3-6, 27 and 28;
b) a sequence of amino acids that exhibits at least at or about 85%, 86%, 87%, 88%, 89%, 89%, 90%, 91%, 92%, 93%, 94%, 95%, 96%, 97%, 98%, 99% or more sequence identity to any of SEQ ID NOS: 3-6, 27 and 28 and contains the amino acid sequence corresponding to Val$^{44}$-Thr$^{45}$-Ala$^{46}$-Arg$^{47}$ or Ile$^{44}$-Gly$^{45}$-Ala$^{46}$-Arg$^{47}$ and that reversibly binds to the agent; or
c) a functional fragment of a) or b) that reversibly binds to the agent.

165. The method of embodiment 163 or embodiment 164, wherein the streptavidin analog or mutein further comprises an amino acid replacement or replacements at a position corresponding to 117, 120 and/or 121 with reference to positions in streptavidin in the sequence of amino acids set forth in SEQ ID NO:1.

166. The method of embodiment 165, wherein:
the amino acid replacement or replacements are selected from among Glu$^{117}$, Asp$^{117}$, Arg$^{117}$, Ser$^{120}$, Ala$^{120}$, Gly$^{120}$, Trp$^{121}$, Tyr$^{121}$ or Phe$^{121}$; or the amino acid replacement or replacements are selected from one or more of Glu$^{117}$, Gly$^{120}$ or Tyr$^{121}$; or
the amino acid replacements are selected from Glu$^{117}$, Gly$^{120}$ or Tyr$^{121}$.

167. The method of any of embodiments 162-166, wherein the streptavidin analog or mutein comprises:
a) the sequence of amino acids set forth in SEQ ID NO: 27 or 28;
b) a sequence of amino acids that exhibits at least at or about 85%, 86%, 87%, 88%, 89%, 89%, 90%, 91%, 92%, 93%, 94%, 95%, 96%, 97%, 98%, 99% or more sequence identity to SEQ ID NOS:27 or 28 and contains the amino acid sequence corresponding to Val$^{44}$, Thr$^{45}$, Ala$^{46}$, Arg$^{47}$, Glu$^{117}$, Gly$^{120}$ and Tyr$^{121}$ and reversibly binds to the agent; or
c) a functional fragment of a) or b) that reversibly binds to the agent.

168. The method of any of embodiments 161-167, further comprising disrupting the reversible binding of the binding molecule to the agent.

169. The method of embodiment 168, wherein said disruption comprises contacting the cells with a composition comprising a competition substance capable of reversing the bond between the binding molecule and agent.

170. The method of embodiment 169, wherein the competition substance is a free binding partner and/or is a competition agent.

171. The method of embodiment 169 or embodiment 170, wherein the competition substance is or comprises biotin, a biotin analog or a biologically active fragment thereof.

172. The method of any of embodiments 144-171, wherein the binding molecule is an antibody or antigen binding fragment that specifically binds the agent.

173. The method of embodiment 172, wherein the binding molecule is an anti-StrepTag antibody.

174. A molecule, comprising a streptavidin or a streptavidin analog or mutein conjugated to a cytotoxic agent.

175. The molecule of embodiment 174, comprising a streptavidin analog or mutein.

176. The molecule of embodiment 174 or embodiment 175, wherein the streptavidin or streptavidin analog or mutein binds to a streptavidin binding peptide.

177. The molecule of embodiment 176, wherein the streptavidin binding peptide is or comprises the sequence Trp-Ser-His-Pro-Gln-Phe-Glu-Lys (SEQ ID NO: 8) or Trp-Arg-His-Pro-Gln-Phe-Gly-Gly (SEQ ID NO:7).

178. The molecule of embodiment 176 or embodiment 177, wherein the streptavidin binding peptide is or comprises the sequence Trp-Ser-His-Pro-Gln-Phe-Glu-Lys-(GlyGlyGlySer)$_3$-Trp-Ser-His-Pro-Gln-Phe-Glu-Lys ((SEQ ID NO: 17), Trp-Ser-His-Pro-Gln-Phe-Glu-Lys-(GlyGlyGlySer)$_2$-Trp-Ser-His-Pro-Gln-Phe-Glu-Lys (SEQ ID NO: 18) and Trp-Ser-His-Pro-Gln-Phe-Glu-Lys-(GlyGlyGly Ser)$_2$Gly-Gly-Ser-Ala-Trp-Ser-His-Pro-Gln-Phe-Glu-Lys (SEQ ID NO: 19).

179. The molecule of any of embodiments 176-178, wherein the streptavidin or streptavidin analog or mutein exhibits a binding affinity for the streptavidin binding peptide with an equilibrium dissociation constant ($K_D$) of from or from about $10^{-4}$ M to or to about $10^{-10}$ M.

180. The molecule of any of embodiments 174-179, wherein the streptavidin analog or mutein comprises the amino acid sequence Val$^{44}$-Thr$^{45}$-Ala$^{46}$-Arg$^{47}$ or Ile$^{44}$-Gly$^{45}$-Ala$^{46}$-Arg$^{47}$ at sequence positions corresponding to positions 44 to 47 with reference to positions in streptavidin in the sequence of amino acids set forth in SEQ ID NO:1.

181. The molecule of any of embodiments 174-180, wherein the streptavidin analog or mutein comprises:
a) the sequence of amino acids set forth in any of SEQ ID NOS: 3-6, 27 and 28;
b) a sequence of amino acids that exhibits at least at or about 85%, 86%, 87%, 88%, 89%, 89%, 90%, 91%, 92%, 93%, 94%, 95%, 96%, 97%, 98%, 99% or more sequence identity to any of SEQ ID NOS: 3-6, 27 and 28 and contains the amino acid sequence corresponding to Val$^{44}$-Thr$^{45}$-Ala$^{46}$-Arg$^{47}$ or Ile$^{44}$-Gly$^{45}$-Ala$^{46}$-Arg$^{47}$ and that reversibly binds to the agent; or
c) a functional fragment of a) or b) that binds to the streptavidin binding peptide.

182. The molecule of embodiment 180 or embodiment 181, wherein the streptavidin analog or mutein further comprises an amino acid replacement or replacements at a position corresponding to 117, 120 and/or 121 with reference to positions in streptavidin in the sequence of amino acids set forth in SEQ ID NO:1.

183. The molecule of embodiment 182, wherein:
the amino acid replacement or replacements are selected from among $Glu^{117}$, $Asp^{117}$, $Arg^{117}$, $Ser^{120}$, $Ala^{120}$, $Gly^{120}$, $Trp^{121}$, $Tyr^{121}$ or $Phe^{121}$; or
the amino acid replacement or replacements are selected from one or more of $Glu^{117}$, $Gly^{120}$ or $Tyr^{121}$; or
the amino acid replacements are selected from $Glu^{117}$, $Gly^{120}$ or $Tyr^{121}$.

184. The molecule of any of embodiments 174-183, wherein the streptavidin analog or mutein comprises:
a) the sequence of amino acids set forth in SEQ ID NO: 27 or 28;
b) a sequence of amino acids that exhibits at least at or about 85%, 86%, 87%, 88%, 89%, 89%, 90%, 91%, 92%, 93%, 94%, 95%, 96%, 97%, 98%, 99% or more sequence identity to SEQ ID NOS:27 or 28 and contains the amino acid sequence corresponding to $Val^{44}$, $Thr^{45}$, $Ala^{46}$, $Arg^{47}$, $Glu^{117}$, $Gly^{120}$ and $Tyr^{121}$ and reversibly binds to the agent; or
c) a functional fragment of a) or b) that reversibly binds to the streptavidin binding peptide.

185. The molecule of any of embodiments 174-184, wherein the cytotoxic agent is a toxin.

186. The molecule of embodiment 185, wherein the toxin is a peptide toxin, ricin A chain toxin, Abrin A chain, Diptheria Toxin (DT) A chain, *Pseudomonas* exotoxin, Shiga Toxin A chain, Gelonin, Momordin, Pokeweed Antiviral Protein, Saporin, Trichosanthin, or Barley Toxin.

187. The molecule of embodiment 185, wherein the toxin is a phototoxin.

188. A method of killing cells, comprising administering the molecule of any of embodiments 174-187 to a subject previously administered the cells of any of embodiments 111-139 or the composition of embodiment 140 or embodiment 141.

189. The method of embodiment 188, wherein the molecule is administered at a time at which the subject is exhibiting a toxic outcome associated with the administered cells or at a time at which the subject is exhibiting a detectable and/or cell-mediated immune response to the administered cells.

190. The method of embodiment 189, wherein the toxic outcome is associated with neurotoxicity or cytokine release syndrome (CRS).

The present invention is not to be limited in scope by the embodiments disclosed herein, which are intended as single illustrations of individual aspects of the invention, and any that are functionally equivalent are within the scope of the invention. Various modifications to the compositions and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

SEQUENCES

| SEQ ID | Sequence | Description |
|---|---|---|
| 1 | DPSKDSKAQVSAAEAGITGTWYNQLGSTFIVTAGADGALTGTYESAVGNAES RYVLTGRYDSAPATDGSGTALGWTVAWKNNYRNAHSATTWSGQYVGGAEARI NTQWLLTSGTTEANAWKSTLVGHDTFTKVKPSAASIDAAKKAGVNNGNPLDA VQQ | Streptavidin Species: *Streptomyces avidinii* UniProt No. P22629 |
| 2 | EAGITGTWYNQLGSTFIVTAGADGALTGTYESAVGNAESRYVLTGRYDSAPA TDGSGTALGWTVAWKNNYRNAHSATTWSGQYVGGAEARINTQWLLTSGTTEA NAWKSTLVGHDTFTKVKPSAAS | Minimal streptavidin Species: *Streptomyces avidinii* |
| 3 | DPSKDSKAQVSAAEAGITGTWYNQLGSTFIVTAGADGALTGTYVTARGNAES RYVLTGRYDSAPATDGSGTALGWTVAWKNNYRNAHSATTWSGQYVGGAEARI NTQWLLTSGTTEANAWKSTLVGHDTFTKVKPSAASIDAAKKAGVNNGNPLDA VQQ | Mutein Streptavidin Val44-Thr45-Ala46-Arg47 Species: *Streptomyces avidinii* |
| 4 | EAGITGTWYNQLGSTFIVTAGADGALTGTYVTARGNAESRYVLTGRYDSAPA TDGSGTALGWTVAWKNNYRNAHSATTWSGQYVGGAEARINTQWLLTSGTTEA NAWKSTLVGHDTFTKVKPSAAS | Mutein Streptavidin Val44-Thr45-Ala46-Arg47 Species: *Streptomyces avidinii* |
| 5 | DPSKDSKAQVSAAEAGITGTWYNQLGSTFIVTAGADGALTGTYIGARGNAES RYVLTGRYDSAPATDGSGTALGWTVAWKNNYRNAHSATTWSGQYVGGAEARI NTQWLLTSGTTEANAWKSTLVGHDTFTKVKPSAASIDAAKKAGVNNGNPLDA VQQ | Mutein Streptavidin Ile44-Gly45-Ala-46-Arg47 Species: *Streptomyces avidinii* |
| 6 | EAGITGTWYNQLGSTFIVTAGADGALTGTYIGARGNAESRYVLTGRYDSAPA TDGSGTALGWTVAWKNNYRNAHSATTWSGQYVGGAEARINTQWLLTSGTTEA NAWKSTLVGHDTFTKVKPSAAS | Mutein Streptavidin Ile44-Gly45-Ala-46-Arg47 Species: *Streptomyces avidinii* |
| 7 | Trp-Arg-His-Pro-Gln-Phe-Gly-Gly | Streptavidin binding peptide, Strep-tag ® |
| 8 | WSHPQFEK | Strep-tag ® II |

| SEQ ID | Sequence | Description |
| --- | --- | --- |
| 9 | His-Pro-Baa | Streptavidin Binding peptide<br>Baa is selected from glutamine, asparagine and methionine |
| 10 | His-Pro-Gln-Phe | Streptavidin-binding peptide |
| 11 | Oaa-Xaa-His-Pro-Gln-Phe-Yaa-Zaa | Streptavidin-binding peptide<br>Oaa is Trp, Lys or Arg;<br>Xaa is any amino acid;<br>Yaa is Gly or Glu<br>Zaa is Gly, Lys or Arg |
| 12 | -Trp-Xaa-His-Pro-Gln-Phe-Yaa-Zaa- | Streptavidin-binding peptide<br>Xaa is any amino acid;<br>Yaa is Gly or Glu<br>Zaa is Gly, Lys or Arg |
| 13 | Trp-Ser-His-Pro-Gln-Phe-Glu-Lys-(Xaa)n-Trp-Ser-His-Pro-Gln-Phe-Glu-Lys- | Sequential modules of streptavidin-binding peptide<br>Xaa is any amino acid;<br>n is either 8 or 12 |
| 14 | Trp-Ser-His-Pro-Gln-Phe-Glu-Lys-(GlyGlyGlySer)n-Trp-Ser-His-Pro-Gln-Phe-Glu-Lys | Sequential modules of streptavidin-binding peptide<br>n is 2 or 3 |
| 15 | SAWSHPQFEKGGGSGGGSGGGSWSHPQFEK | Twin-Strep-tag |
| 16 | SAWSHPQFEKGGGSGGGSGGSAWSHPQFEK | Twin-Strep-tag |
| 17 | WSHPQFEKGGGSGGGSGGGSWSHPQFEK | Twin-Strep-tag |
| 18 | WSHPQFEKGGGSGGGSWSHPQFEK | Twin-Strep-tag |
| 19 | WSHPQFEKGGGSGGGSGGSAWSHPQFEK | Twin-Strep-tag |
| 20 | Tyr-Pro-Tyr-Asp-Val-Pro-Asp-Tyr-Ala | HA-tag |
| 21 | Tyr-Thr-Asp-Ile-Glu-Met-Asn-Arg-Leu-Gly-Lys | VSV-G-tag |
| 22 | Gln-Pro-Glu-Leu-Ala-Pro-Glu-Asp-Pro-Glu-Asp | HSV-tag |
| 23 | Ala-Ser-Met-Thr-Gly-Gly-Gln-Gln-Met-Gly | T7 epitope |
| 24 | Glu-Gln-Lys-Leu-Ile-Ser-Glu-Glu-Asp-Leu | HSV epitope |
| 25 | Glu-Gln-Lys-Leu-Ile-Ser-Glu-Glu-Asp-Leu | Myc epitope |
| 26 | Gly-Lys-Pro-Ile-Pro-Asn-Pro-Leu-Leu-Gly-Leu-Asp-Ser-Thr | V5-tag |
| 27 | EAGITGTWYNQLGSTFIVTAGADGALTGTYVTARGNAESRYVLTGRYDSAPATDGSGTALGWTVAWKNNYRNAHSATTWSGQYVGGAEARINTQWLLTSGTTEENAGYSTINGHDTFTKVKPSAAS | Mutein Streptavidin Val44-Thr45-Ala46-Arg47 and Glu117, Gly120, Try121 (mutein m1-9)<br>Species: *Streptomyces avidinii* |
| 28 | DPSKDSKAQVSAAEAGITGTWYNQLGSTFIVTAGADGALTGTYVTARGNAESRYVLTGRYDSAPATDGSGTALGWTVAWKNNYRNAHSATTWSGQYVGGAEARINTQWLLTSGTTEENAGYSTLVGHDTFTKVKPSAAS | Mutein Streptavidin Val44-Thr45-Ala46-Arg47 and Glu117, Gly120, Try121 (mutein m1-9)<br>Species: *Streptomyces avidinii* |

-continued

| SEQ ID | Sequence | Description |
|---|---|---|
| 29 | AMQVQLKQSGPGLVQPSQSLSITCTVSGFSLTTFGVHWVRQSPGKGLEWLGV IWASGITDYNVPFMSRLSITKDNSKSQVFFKLNSLQPDDTAIYYCAKNDPGT GFAYWGQGTLVTVSAGSTKGPSVFPLAPSSKSTSGGTAALGCLVKDYFPEPV TVSWNSGALTSGVHTFPAVLQSSGLYSLSSVVTVPSSSLGTQTYICNVNHKP SNTKVDKKVEPKSCGSAWSHPQFEKGGGSGGGSGGSAWSHPQFEK | Variable Heavy chain of Fab fragment m13B8.2 |
| 30 | AMDIQMTQSPASLSASVGETVTFTCRASEMIYSYLAWYQQKQGKSPQLLVHD AKTLAEGVPSRFSGGGSGTQFSLKINTLQPEDFGTYYCQAHYGNPPTFGGGT KLEIKRGIAAPSVFIFPPSDEQLKSGTASVVCLLNNFYPREAKVQWKVDNAL QSGNSQESVTEQDSKDSTYSLSSTLTLSKADYEKHKVYACEVTHQGLSSPVT KSFNRGECGS | Variable Light chain of Fab Fragment m13B8.2 |
| 31 | Gln Val Gln Leu Gln Gln Ser Gly Ala Glu Leu Ala Arg Pro Gly Ala Ser Val Lys Met Ser Cys Lys Ala Ser Gly Tyr Thr Phe Thr Arg Tyr Thr Met His Trp Val Lys Gln Arg Pro Gly Gln Gly Leu Glu Trp Ile Gly Tyr Ile Asn Pro Ser Arg Gly Tyr Thr Asn Tyr Asn Gln Lys Phe Lys Asp Lys Ala Thr Leu Thr Thr Asp Lys Ser Ser Ser Thr Ala Tyr Met Gln Leu Ser Ser Leu Thr Ser Glu Asp Ser Ala Val Tyr Tyr Cys Ala Arg Tyr Tyr Asp Asp His Tyr Cys Leu Asp Tyr Trp Gly Gln Gly Thr Thr Leu Thr Val Ser Ser | Variable Heavy chain of anti-CD3 antibody OKT3 |
| 32 | Gln Ile Val Leu Thr Gln Ser Pro Ala Ile Met Ser Ala Ser Pro Gly Glu Lys Val Thr Met Thr Cys Ser Ala Ser Ser Ser Val Ser Tyr Met Asn Trp Tyr Gln Gln Lys Ser Gly Thr Ser Pro Lys Arg Trp Ile Tyr Asp Thr Ser Lys Leu Ala Ser Gly Val Pro Ala His Phe Arg Gly Ser Gly Ser Gly Thr Ser Tyr Ser Leu Thr Ile Ser Gly Met Glu Ala Glu Asp Ala Ala Thr Tyr Tyr Cys Gln Gln Trp Ser Ser Asn Pro Phe Thr Phe Gly Ser Gly Thr Lys Leu Glu Ile Asn | Variable Light chain of anti-CD3 antibody OKT3 |
| 33 | Leu Gln Gln Ser Gly Ala Glu Leu Val Lys Pro Gly Ala Ser Val Arg Leu Ser Cys Lys Ala Ser Gly Tyr Thr Phe Thr Glu Tyr Ile Ile His Trp Ile Lys Leu Arg Ser Gly Gln Gly Leu Glu Trp Ile Gly Trp Phe Tyr Pro Gly Ser Asn Asp Ile Gln Tyr Asn Ala Lys Phe Lys Gly Lys Ala Thr Leu Thr Ala Asp Lys Ser Ser Ser Thr Val Tyr Met Glu Leu Thr Gly Leu Thr Ser Glu Asp Ser Ala Val Tyr Phe Cys Ala Arg Arg Asp Asp Phe Ser Gly Tyr Asp Ala Leu Pro Tyr Trp Gly Gln Gly Thr Met Val Thr Val | Variable Heavy chain of anti-CD28 antibody CD28.3 |
| 34 | Asp Ile Gln Met Thr Gln Ser Pro Ala Ser Leu Ser Val Ser Val Gly Glu Thr Val Thr Ile Thr Cys Arg Thr Asn Glu Asn Ile Tyr Ser Asn Leu Ala Trp Tyr Gln Gln Lys Gln Gly Lys Ser Pro Gln Leu Leu Ile Tyr Ala Ala Thr His Leu Val Glu Gly Val Pro Ser Arg Phe Ser Gly Ser Gly Ser Gly Thr Gln Tyr Ser Leu Lys Ile Thr Ser Leu Gln Ser Glu Asp Phe Gly Asn Tyr Tyr Cys Gln His Phe Trp Gly Thr Pro Cys Thr Phe Gly Gly Gly Thr Lys Leu Glu Ile Lys Arg | Variable Light chain of anti-CD28 antibody CD28.3 |
| 35 | RVKFSRSADAPAYQQGQNQLYNELNLGRREEYDVLDKRRGRDPEMGGKPRRK NPQEGLYNELQKDKMAEAYSEIGMKGERRRGKGHDGLYQGLSTATKDTYDAL HMQALPPR | CD3 zeta *Homo sapiens* |
| 36 | RVKFSRSAEPPAYQQGQNQLYNELNLGRREEYDVLDKRRGRDpEMGGKPRRK NPQEGLYNELQKDKMAEAYSEIGMKGERRRGKGHDGLYQGLSTATKDTYDAL HMQALPPR | CD3 zeta *Homo sapiens* |
| 37 | RVKFSRSADAPAYKQGQNQLYNELNLGRREEYDVLDKRRGRDPEMGGKPRRK NPQEGLYNELQKDKMAEAYSEIGMKGERRRGKGHDGLYQGLSTATKDTYDAL HMQALPPR | CD3 zeta *Homo sapiens* |
| 38 | ESKYGPPCPPCP | spacer (IgG4hinge) (aa) *Homo sapiens* |
| 39 | GAATCTAAGTACGGACCGCCCTGCCCCCCTTGCCCT | spacer (IgG4hinge) (nt) *Homo sapiens* |

| SEQ ID | Sequence | Description |
|---|---|---|
| 40 | ESKYGPPCPPCPGQPREPQVYTLPPSQEEMTKNQVSLTCLVKGFYPSDIAVE WESNGQPENNYKTTPPVLDSDGSFFLYSRLTVDKSRWQEGNVFSCSVMHEAL HNHYTQKSLSLSLGK | Hinge-CH3 spacer<br>*Homo sapiens* |
| 41 | ESKYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYKCK VSNKGLPSSIEKTISKAKGQPREPQVYTLPPSQEEMTKNQVSLTCLVKGFYP SDIAVEWESNGQPENNYKTTPPVLDSDGSFFLYSRLTVDKSRWQEGNVFSCS VMHEALHNHYTQKSLSLSLGK | Hinge-CH2-CH3 spacer<br>*Homo sapiens* |
| 42 | RWPESPKAQASSVPTAQPQAEGSLAKATTApATTRNTGRGGEEKKKEKEKEE QEERETKTPECPSHTQPLGVYLLTPAVQDLWLRDKATFTCFVVGSDLKDAHL TWEVAGKVPTGGVEEGLLERHSNGSQSQHSRLTLPRSLWNAGTSVTCTLNHP SLPPQRLMALREPAAQAPVKLSLNLLASSDPPEAASWLLCEVSGFSPPNILL MWLEDQREVNTSGFAPARPPPQPGSTTFWAWSVLRVPAPPSPQPATYTCVVS HEDSRTLLNASRSLEVSYVTDH | IgD-hinge-Fc<br>*Homo sapiens* |
| 43 | LEGGGEGRGSLLTCGDVEENPGPR | T2A<br>artificial |
| 44 | MLLLVTSLLLCELPHPAFLLIPRKVCNGIGIGEFKDSLSINATNIKHFKNCT SISGDLHILPVAFRGDSFTHTPPLDPQELDILKTVKEITGFLLIQAWPENRT DLHAFENLEIIRGRTKQHGQFSLAVVSLNITSLGLRSLKEISDGDVIISGNK NLCYANTINWKKLFGTSGQKTKIISNRGENSCKATGQVCHALCSPEGCWGPE PRDCVSCRNVSRGRECVDKCNLLEGEPREFVENSECIQCHPECLPQAMNITC TGRGPDNCIQCAHYIDGPHCVKTCPAGVMGENNTLVWKYADAGHVCHLCHPN CTYGCTGPGLEGCPTNGPKIPSIATGMVGALLLLLVVALGIGLFM | tEGFR<br>artificial |
| 45 | atgcttctcctggtgacaagccttctgctctgtgagttaccacacccagcat tcctcctgatcccacgcaaagtgtgtaacggaataggtattggtgaatttaa agactcactctccataaatgctacgaatattaaacacttcaaaaactgcacc tccatcagtggcgatctccacatcctgccggtggcatttagggggtgactcct tcacacatactcctcctctggatccacaggaactggatattctgaaaaccgt aaaggaaatcacaggttttttgctgattcaggcttggcctgaaaacaggacg gacctccatgcctttgagaacctagaaatcatacgcggcaggaccaagcaac atggtcagttttctcttgcagtcgtcagcctgaacataacatccttgggatt acgctccctcaaggagataagtgatggagatgtgataatttcaggaaacaaa aatttgtgctatgcaaatacaataaactggaaaaaactgtttgggacctccg gtcagaaaaccaaaattataagcaacagaggtgaaaacagctgcaaggccac aggccaggtctgccatgccttgtgctccccgagggctgctggggcccggag cccagggactgcgtctcttgccggaatgtcagccgaggcagggaatgcgtgg acaagtgcaaccttctggagggtgagccaagggagtttgtggagaactctga gtgcatacagtgccacccagagtgcctgcctcaggccatgaacatcacctgc acaggacggggaccagacaactgtatccagtgtgcccactacattgacggcc cccactgcgtcaagacctgcccggcaggagtcatgggagaaaacaacaccct ggtctggaagtacgcagacgccggccatgtgtgccacctgtgccatccaaac tgcacctacggatgcactgggcaggtcttgaaggctgtccaacgaatgggc ctaagatcccgtccatcgccactgggatggtggggggcccctcctcttgctgct ggtggtggccctggggatcggcctcttcatg | tEGFR<br>artificial |
| 46 | RKVCNGIGIGEFKDSLSINATNIKHFKNCTSISGDLHILPVAFRGDSFTHTP PLDPQELDILKTVKEITGFLLIQAWPENRTDLHAFENLEIIRGRTKQHGQFS LAVVSLNITSLGLRSLKEISDGDVIISGNKNLCYANTINWKKLFGTSGQKTK IISNRGENSCKATGQVCHALCSPEGCWGPEPRDCVSCRNVSRGRECVDKCNL LEGEPREFVENSECIQCHPECLPQAMNITCTGRGPDNCIQCAHYIDGPHCVK TCPAGVMGENNTLVWKYADAGHVCHLCHPNCTYGCTGPGLEGCPTNGPKIPS IATGMVGALLLLLVVALGIGLFM | tEGFR<br>artificial |
| 47 | atgcttctcctggtgacaagccttctgctctgtgagttaccacacccagcat tcctcctgatccca | GMCSFR alpha chain signal sequence<br>*Homo sapiens* |
| 48 | MLLLVTSLLLCELPHPAFLLIP | GMCSFR alpha chain signal sequence<br>*Homo sapiens*<br>UniProt No. P15509 |
| 49 | LEEKKVCQGTSNKLTQLGTFEDHFLSLQRMFNNCEVVLGNLEITYVQRNYDL SFLKTIQEVAGYVLIALNTVERIPLENLQIIRGNMYYENSYALAVLSNYDAN KTGLKELPMRNLQEILHGAVRFSNNPALCNVESIQWRDIVSSDFLSNMSMDF QNHLGSCQKCDPSCPNGSCWGAGEENCQKLTKIICAQQCSGRCRGKSPSDCC HNQCAAGCTGPRESDCLVCRKFRDEATCKDTCPPLMLYNPTTYQMDVNPEGK YSFGATCVKKCPRNYVVTDHGSCVRACGADSYEMEEDGVRKCKKCEGPCRKV CNGIGIGEFKDSLSINATNIKHFKNCTSISGDLHILPVAFRGDSFTHTPPLD | HER1/ErbB1/EGFR Full Length (mature) Transmembrane domain: amino acids 622-644 Cytoplasmic domain: amino acids 645-1186 |

| SEQ ID | Sequence | Description |
|---|---|---|
| | PQELDILKTVKEITGFLLIQAWPENRTDLHAFENLEIIRGRTKQHGQFSLAV VSLNITSLGLRSLKEISDGDVIISGNKNLCYANTINWKKLFGTSGQKTKIIS NRGENSCKATGQVCHALCSPEGCWGPEPRDCVSCRNVSRGRECVDKCNLLEG EPREFVENSECIQCHPECLPQAMNITCTGRGPDNCIQCAHYIDGPHCVKTCP AGVMGENNTLVWKYADAGHVCHLCHPNCTYGCTGPGLEGCPTNGPKIPSIAT GMVGALLLLLVVALGIGLFMRRRHIVRKRTLRRLLQERELVEPLTPSGEAPN QALLRILKETEFKKIKVLGSGAFGTVYKGLWIPEGEKVKIPVAIKELREATS PKANKEILDEAYVMASVDNPHVCRLLGICLTSTVQLITQLMPFGCLLDYVRE HKDNIGSQYLLNWCVQIAKGMNYLEDRRLVHRDLAARNVLVKTPQHVKITDF GLAKLLGAEEKEYHAEGGKVPIKWMALESILHRIYTHQSDVWSYGVTVWELM TFGSKPYDGIPASEISSILEKGERLPQPPICTIDVYMIMVKCWMIDADSRPK FRELIIEFSKMARDPQRYLVIQGDERMHLPSPTDSNFYRALMDEEDMDDVVD ADEYLIPQQGFFSSPSTSRTPLLSSLSATSNNSTVACIDRNGLQSCPIKEDS FLQRYSSDPTGALTEDSIDDTFLPVPEYINQSVPKRPAGSVQNPVYHNQPLN PAPSRDPHYQDPHSTAVGNPEYLNTVQPTCVNSTFDSPAHWAQKGSHQISLD NPDYQQDFFPKEAKPNGIFKGSTAENAEYLRVAPQSSEFIGA | Homo sapiens UniProt No. P00533 |
| 50 | TQVCTGTDMKLRLPASPETHLDMLRHLYQGCQVVQGNLELTYLPTNASLSFL QDIQEVQGYVLIAHNQVRQVPLQRLRIVRGTQLFEDNYALAVLDNGDPLNNT TPVTGASPGGLRELQLRSLTEILKGGVLIQRNPQLCYQDTILWKDIFHKNNQ LALTLIDTNRSRACHPCSPMCKGSRCWGESSEDCQSLTRTVCAGGCARCKGP LPTDCCHEQCAAGCTGPKHSDCLACLHFNHSGICELHCPALVTYNTDTFESM PNPEGRYTFGASCVTACPYNYLSTDVGSCTLVCPLHNQEVTAEDGTQRCEKC SKPCARVCYGLGMEHLREVRAVTSANIQEFAGCKKIFGSLAFLPESFDGDPA SNTAPLQPEQLQVFETLEEITGYLYISAWPDSLPDLSVFQNLQVIRGRILHN GAYSLTLQGLGISWLGLRSLRELGSGLALIHHNTHLCFVHTVPWDQLFRNPH QALLHTANRPEDECVGEGLACHQLCARGHCWGPGPTQCVNCSQFLRGQECVE ECRVLQGLPREYVNARHCLPCHPECQPQNGSVTCFGPEADQCVACAHYKDPP FCVARCPSGVKPDLSYMPIWKFPDEEGACQPCPINCTHSCVDLDDKGCPAEQ RASPITSIISAVVGILLVVVLGVVFGILIKRRQQKIRKYTMRRLLQETELVE PLTPSGAMPNQAQMRILKETELRKVKVLGSGAFGTVYKGIWIPDGENVKIPV AIKVLRENTSPKANKEILDEAYVMAGVGSPYVSRLLGICLTSTVQLVTQLMP YGCLLDHVRENRGRLGSQDLLNWCMQIAKGMSYLEDVRLVHRDLAARNVLVK SPNHVKITDFGLARLLDIDETEYHADGGKVPIKWMALESILRRRFTHQSDVW SYGVTVWELMTFGAKPYDGIPAREIPDLLEKGERLPQPPICTIDVYMIMVKC WMIDSECRPRFRELVSEFSRMARDPQRFVVIQNEDLGPASPLDSTFYRSLLE DDDMGDLVDAEEYLVPQQGFFCPDPAPGAGGMVHHRHRSSSTRSGGGDLTLG LEPSEEEAPRSPLAPSEGAGSDVFDGDLGMGAAKGLQSLPTHDPSPLQRYSE DPTVPLPSETDGYVAPLTCSPQPEYVNQPDVRPQPPSPREGPLPAARPAGAT LERPKTLSPGKNGVVKDVFAFGGAVENPEYLTPQGGAAPQPHPPPAFSPAFD NLYYWDQPPERGAPPSTFKGTPTAENPEYLGLDVPV | HER2/neu/ErbB2 Full Length (mature) Transmembrane domain: amino acids 631-653 Cytoplasmic domain: amino acids 654-1233 Homo sapiens UniProt No. P04626 |
| 51 | SEVGNSQAVCPGTLNGLSVTGDAENQYQTLYKLYERCEVVMGNLEIVLTGHN ADLSFLQWIREVTGYVLVAMNEFSTLPLPNLRVVRGTQVYDGKFAIFVMLNY NTNSSHALRQLRLTQLTEILSGGVYIEKNDKLCHMDTIDWRDIVRDRDAEIV VKDNGRSCPPCHEVCKGRCWGPGSEDCQTLTKTICAPQCNGHCFGPNQCC HDECAGGCSGPQDTDCFACRHFNDSGACVPRCPQPLVYNKLTFQLEPNPHTK YQYGGVCVASCPHNFVVDQTSCVRACPPDKMEVDKNGLKMCEPCGGLCPKAC EGTGSGSRFQTVDSSNIDGFVNCTKILGNLDFLITGLNGDPWHKIPALDPEK LNVFRTVREITGYLNIQSWPPHMHNFSVFSNLTTIGGRSLYNRGFSLLIMKN LNVTSLGFRSLKEISAGRIYISANRQLCYHHSLNWTKVLRGPTEERLDIKHN RPRRDCVAEGKVCDPLCSSGGCWGPGPGQCLSCRNYSRGGVCVTHCNFLNGE PREFAHEAECFSCHPECQPMEGTATCNGSGSDTCAQCAHFRDGPHCVSSCPH GVLGAKGPIYKYPDVQNECRPCHENCTQGCKGPELQDCLGQTLVLIGKTHLT MALTVIAGLVVIFMMLGGTFLYWRGRRIQNKRAMRRYLERGESIEPLDPSEK ANKVLARIFKETELRKLKVLGSGVFGTVHKGVWIPEGESIKIPVCIKVIEDK SGRQSFQAVTDHMLAIGSLDHAHIVRLLGLCPGSSLQLVTQYLPLGSLLDHV RQHRGALGPQLLLNWGVQIAKGMYYLEEHGMVHRNLAARNVLLKSPSQVQVA DFGVADLLPPDDKQLLYSEAKTPIKWMALESIHFGKYTHQSDVWSYGVTVWE LMTFGAEPYAGLRLAEVPDLLEKGERLAQPQICTIDVYMVMVKCWMIDENIR PTFKELANEFTRMARDPPRYLVIKRESGPGIAPGPEPHGLTNKKLEEVELEP ELDLDLDLEAEEDNLATTTLGSALSLPVGTLNRPRGSQSLLSPSSGYMPMNQ GNLGESCQESAVSGSSERCPRPVSLHPMPRGCLASESSEGHVTGSEAELQEK VSMCRSRSRSRPRPRGDSAYHSQRHSLLTPVTPLSPPGLEEEDVNGYVMPD THLKGTPSSREGTLSSVGLSSVLGTEEEDEDEEYEYMNRRRRHSPPHPPRPS SLEELGYEYMDVGSDLSASLGSTQSCPLHPVPIMPTAGTTPDEDYEYMNRQR DGGGPGGDYAAMGACPASEQGYEEMRAFQGPGHQAPHVHYARLKTLRSLEAT DSAFDNPDYWHSRLFPKANAQRT | HER3/ErbB3 Full Length (mature) Transmembrane domain: amino acids 625-645 Cytoplasmic domain: amino acids 646-1323 Homo sapiens UniProt No. P21860 |
| 52 | QSVCAGTENKLSSLSDLEQQYRALRKYYENCEVVMGNLEITSIEHNRDLSFL RSVREVTGYVLVALNQFRYLPLENLRIIRGTKLYEDRYALAIFLNYRKDGNF GLQELGLKNLTEILNGGVYVDQNKFLCYADTIHWQDIVRNPWPSNLTLVSTN GSSSGCGRCHKSCTGRCWGPTENHCQTLTRTVCAEQCDGRCYGPYVSDCCHRE CAGGCSGPKDTDCFACMNFNDSGACVTQCPQTFVYNPTTFQLEHNFNAKYTY | HER4/ErbB4 Full Length (mature) Transmembrane domain: amino acids 627-650 |

| SEQ ID | Sequence | Description |
|---|---|---|
| | GAFCVKKCPHNFVVDSSSCVRACPSSKMEVEENGIKMCKPCTDICPKACDGI GTGSLMSAQTVDSSNIDKFINCTKINGNLIFLVTGIHGDPYNAIEAIDPEKL NVFRTVREITGFLNIQSWPPNMTDFSVFSNLVTIGGRVLYSGLSLLILKQQG ITSLQFQSLKEISAGNIYITDNSNLCYYHTINWTTLFSTINQRIVIRDNRKA ENCTAEGMVCNHLCSSDGCWGPGPDQCLSCRRFSRGRICIESCNLYDGEFRE FENGSICVECDPQCEKMEDGLLTCHGPGPDNCTKCSHFKDGPNCVEKCPDGL QGANSFIFKYADPDRECHPCHPNCTQGCNGPTSHDCIYYPWTGHSTLPQHAR TPLIAAGVIGGLFILVIVGLTFAVYVRRKSIKKKRALRRFLETELVEPLTPS GTAPNQAQLRILKETELKRVKVLGSGAFGTVYKGIWVPEGETVKIPVAIKIL NETTGPKANVEFMDEALIMASMDHPHLVRLLGVCLSPTIQLVTQLMPHGCLL EYVHEHKDNIGSQLLLNWCVQIAKGMMYLEERRLVHRDLAARNVLVKSPNHV KITDFGLARLLEGDEKEYNADGGKMPIKWMALECIHYRKFTHQSDVWSYGVT IWELMTFGGKPYDGIPTPEIPDIIEKGEPIPQPPICTIDVYNVNVKCWMIDA DSRPKFKELAAEFSRMARDPQRYLVIQGDDRMKLPSPNDSKFFQNLLDEEDL EDMMDAEEYLVPQAFNIPPPIYTSRARIDSNRSEIGHSPPPAYTPMSGNQFV YRDGGFAAEQGVSVPYRAPTSTIPEAPVAQGATAEIFDDSCCNGTLRKPVAP HVQEDSSTQRYSADPTVFAPERSPRGELDEEGYMTPMRDKPKQEYLNPVEEN PFVSRRKNGDLQALDNPEYHNASNGPPKAEDEYVNEPLYLNTFANTLGKAEY LKNNILSMPEKAKKAFDNPDYWNHSLPPRSTLQHPDYLQEYSTKYFYKQNGR IRPIVAENPEYLSEFSLKPGTVLPPPPYRHRNTVV | Cytoplasmic domain: amino acids 651-1283 Homo sapiens UniProt No. Q15303 |
| 53 | ECKEALAKSEMNVNMKYQLPNFTAETPIQNVILHEHHIFLGATNYIYVLNEE DLQKVAEYKTGPVLEHPDCFPCQDCSSKANLSGGVWKDNINMALVVDTYYDD QLISCGSVNRGTCQRHVFPHNHTADIQSEVHCIFSPQIEEPSQCPDCVVSAL GAKVLSSVKDRFINFFVGNTINSSYFPDHPLHSISVRRLKETKDGFMFLTDQ SYIDVLPEFRDSYPIKYVHAFESNNFIYFLTVQRETLDAQTFHTRIIRFCSI NSGLHSYMEMPLECILTEKRKKRSTKKEVFNILQAAYVSKPGAQLARQIGAS LNDDILFGVFAQSKPDSAEPMDRSAMCAFPIKYVNDFFNKIVNKNNVRCLQH FYGPNHEHCFNRTLLRNSSGCEARRDEYRTEFTTALQRVDLFMGQFSEVLLT sISTFIKGDLTIANLGTSEGRFMQVVVSRSGPSTPHVNFLLDSHPVSPEVIV EHTLNQNGYTLVITGKKITKIPLNGLGCRHFQSCSQCLSAPPFVQCGWCHDK CVRSEECLSGTWTQQICLPAIYKVFPNSAPLEGGTRLTICGWDFGFRRNNKF DLKKTRVLLGNESCTLTLSESTMNTLKCTVGPAMNKHFNMSIIISNGHGTTQ YSTFSYVDPVITSISPKYGPMAGGTLLTLTGNYLNSGNSRHISIGGKTCTLK SVSNSILECYTPAQTISTEFAVKLKIDLANRETSIFSYREDPIVYEIHPTKS FISGGSTITGVGKNLNSVSVPRMVINVHEAGRNFTVACQHRSNSEIICCTTP SLQQLNLQLPLKTKAFFMLDGILSKYFDLIYVHNPVFKPFEKPVMISMGNEN VLEIKGNDIDPEAVKGEVLKVGNKSCENIHLHSEAVLCTVPNDLLKLNSELN IEWKQAISSTVLGKVIVQPDQNFTGLIAGVVSISTALLLLLGFFLWLKKRKQ IKDLGSELVRYDARVHTPHLDRLVSARSVSPTTEMVSNESVDYRATFPEDQF PNSSQNGSCRQVQYPLTDMSPILTSGDSDISSPLLQNTVHIDLSALNPELVQ AVQHVVIGPSSLIVHFNEVIGRGHFGCVYHGTLLDNDGKKIHCAVKSLNRIT DIGEVSQFLTEGIIMKDFSHPNVLSLLGICLRSEGSPLVVLPYMKHGDLRNF IRNETHNPTVKDLIGFGLQVAKGMKYLASKKFVHRDLAARNCMLDEKFTVKV ADFGLARDMYDKEYYSVHNKTGAKLPVKWMALESLQTQKFTTKSDVWSFGVL LWELMTRGAPPYPDVNTFDITVYLLQGRRLLQPEYCPDPLYEVMLKCWHPKA EMRPSFSELVSRISAIFSTFIGEHYVHVNATYVNVKCVAPYPSLLSSEDNAD DEVDTRPASFWETS | HGFR/c-Met Full Length (mature) Transmembrane domain: amino acids 909-931 Cytoplasmic domain: amino acids 932-1366 Homo sapiens UniProt No. P08581 |
| 54 | MKSGSGGGSPTSLWGLLFLSAALSLWPTSGEICGPGIDIRNDYQQLKRLENC TVIEGYLHILLISKAEDYRSYRFPKLTVITEYLLLFRVAGLESLGDLFPNLT VIRGWKLFYNYALVIFEMTNLKDIGLYNLRNITRGAIRIEKNADLCYLSTVD WSLILDAVSNNYIVGNKPPKECGDLCPGTMEEKPMCEKTTINNEYNYRCWTT NRCQKMCPSTCGKRACTENNECCHPECLGSCSAPDNDTACVACRHYYYAGVC VPACPPNTYRFEGWRCVDRDFCANILSAESSDSEGFVIHDGECMQECPSGFI RNGSQSMYCIPCEGPCPKVCEEEKKTKTIDSVTSAQMLQGCTIFKGNLLINI RRGNNIASELENFMGLIEVVTGYVKIRHSHALVSISFLKNLRLILGEEQLEG NYSFYVLDNQNLQQLWDWDHRNLTIKAGKMYFAFNPKLCVSEEMEEVTGT KGRQSKGDINTRNNGERASCESDVLHFTSTTTSKNRIIITWHRYRPPDYRDL ISFTVYYKEAPFKNVTEYDGQDACGSNSWNMVDVDLPPNKDVEPGILLHGLK PWTQYAVYVKAVTLTMVENDHIRGAKSEILYIRTNASVPSIPLDVLSASNSS SQLIVKWNPPSLPNGNLSYYIVRWQRQPQDGYLRHNYCSKDKIPIRKYADG TIDIEEVTENPKTEVCGGEKGPCCACPKTEAEKQAEKEEAEYRKVFENPLHN SIFVPRPERKRRDVMQVANTTMSSRSRNTTAADTYNITDPEELETEYPFFES RVDNKERTVISNLRPFTLYRIDIHSCNHEAEKLGCSASNFVFARTMPAEGAD DIPGPVTWEPRPENSIFLKWPEPENPNGLILMYEIKYGSQVEDQRECVSRQE YRKYGGAKLNRLNPGNYTARIQATSISGNGSWTDPVFFYVQAKTGYENFIHL IIALPVAVLLIVGGLVIMLYVFHRKRNNSRLGNGVLYASVNPEYFSAADVYV PDEWEVAREKITMSRELGQGSFGMVYEGVAKGVVKDEPETRVAIKTVNEAAS MRERIEFLNEASVMKEFNCHHVVRLLGVVSQGQPTLVIMELMTRGDLKSYLR SLRPEMENNPVLAPPSLSKMIQMAGEIADGMAYLNANKFVHRDLAARNCMVA EDFTVKIGDFGMTRDIYETDYYRKGGKGLLPVRWMSPESLKDGVFTTYSDVW SFGVVLWEIATLAEQPYQGLSNEQVLRFVMEGGLLDKPDNCPDMLFELMRMC WQYNPKMRPSFLEIISSIKEEMEPGFREVSFYYSEENKLPEPEELDLEPENM | IGF-1 R full length (mature) Transmembrane domain: amino acids 906-929 Cytoplasmic domain: amino acids 930-1337 Homo sapiens UniProt No. P08069 |

| SEQ ID | Sequence | Description |
|---|---|---|
| | ESVPLDPSASSSSLPLPDRHSGHKAENGPGPGVLVLRASFDERQPYAHMNGG<br>RKNERALPLPQSSTC | |
| 55 | GSTSGSGKPGSGEGSTKG | Linker<br>artificial |
| 56 | GGGGSGGGGS | Linker<br>Artificial |
| 57 | cgcaaagtgtgtaacggaataggtattggtgaatttaaagactcactctcca<br>taaatgctacgaatattaaacacttcaaaaactgcacctccatcagtggcga<br>tctccacatcctgccggtggcatttaggggtgactccttcacacatactcct<br>cctctggatccacaggaactggatattctgaaaaccgtaaaggaaatcacag<br>gttttttgctgattcaggcttggcctgaaaacaggacggacctccatgcctt<br>tgagaacctagaaatcatacgcggcaggaccaagcaacatggtcagttttct<br>cttgcagtcgtcagcctgaacataacatccttgggattacgctccctcaagg<br>agataagtgatggagatgtgataatttcaggaaacaaaaatttgtgctatgc<br>aaatacaataaactggaaaaaactgtttgggacctccggtcagaaaaccaaa<br>attataagcaacagaggtgaaaacagctgcaaggcacaggccaggtctgcc<br>atgccttgtgctcccccgagggctgctggggccggagcccagggactgcgt<br>ctccttgccggaatgtcagccgaggcagggaatgcgtggacaagtgcaacctt<br>ctggagggtgagccaagggagtttgtggagaactctgagtgcatacagtgcc<br>acccagagtgcctgcctcaggccatgaacatcacctgcacaggacggggacc<br>agacaactgtatccagtgtgcccactacattgacggccccactgcgtcaag<br>acctgcccggcaggagtcatgggagaaaacaacaccctggtctggaagtacg<br>cagacgccggccatgtgtgccacctgtgccatccaaactgcacctacggatg<br>cactgggccaggtcttgaaggctgtccaacgaatgggcctaagatcccgtcc<br>atcgccactgggatggtgggggcccctcctcttgctgctggtggtggccctgg<br>ggatcggcctcttcatg | tEGFR<br>artificial |
| 58 | SAWSHPQFEK | Streptavidin binding<br>peptide, Strep-tag ® II<br>artificial |
| 59 | GGGSGGGS | Linker<br>artificial |
| 60 | GGGGS | Linker<br>artificial |
| 61 | GGGS | Linker<br>artificial |
| 62 | GGGGSGGGGSGGGGS | Linker<br>artificial |
| 63 | His-Asn-His-Arg-His-Lys-His-Gly-Gly-Gly-Cys | MAT tag<br>artificial |
| 64 | MRPSGTAGAALLALLAALCPASRALEEKKVCQGTSNKLTQLGTFEDHFLSLQ<br>RMFNNCEVVLGNLEITYVQRNYDLSFLKTIQEVAGYVLIALNTVERIPLENL<br>QIIRGNMYYENSYALAVLSNYDANKTGLKELPMRNLQEILHGAVRFSNNPAL<br>CNVESIQWRDIVSSDFLSNMSMDFQNHLGSCQKCDPSCPNGSCWGAGEENCQ<br>KLTKIICAQQCSGRCRGKSPSDCCHNQCAAGCTGPRESDCLVCRKFRDEATC<br>KDTCPPLMLYNPTTYQMDVNPEGKYSFGATCVKKCPRNYVVTDHGSCVRACG<br>ADSYEMEEDGVRKCKKCEGPCRKVCNGIGIGEFKDSLSINATNIKHFKNCTS<br>ISGDLHILPVAFRGDSFTHTPPLDPQELDILKTVKEITGFLLIQAWPENRTD<br>LHAFENLEIIRGRTKQHGQFSLAVVSLNITSLGLRSLKEISDGDVIISGNKN<br>LCYANTINWKKLFGTSGQKTKIISNRGENSCKATGQVCHALCSPEGCWGPEP<br>RDCVSCRNVSRGRECVDKCNLLEGEPREFVENSECIQCHPECLPQAMNITCT<br>GRGPDNCIQCAHYIDGPHCVKTCPAGVMGENNTLVWKYADAGHVCHLCHPNC<br>TYGCTGPGLEGCPTNGPKIPSIATGMVGALLLLLVVALGIGLFMRRRHIVRK<br>RTLRRLLQERELVEPLTPSGEAPNQALLRILKETEFKKIKVLGSGAFGTVYK<br>GLWIPEGEKVKIPVAIKELREATSPKANKEILDEAYVMASVDNPHVCRLLGI<br>CLTSTVQLITQLMPFGCLLDYVREHKDNIGSQYLLNWCVQIAKGMNYLEDRR<br>LVHRDLAARNVLVKTPQHVKITDFGLAKLLGAEEKEYHAEGGKVPIKWMALE<br>SILHRIYTHQSDVWSYGVTVWELMTFGSKPYDGIPASEISSILEKGERLPQP<br>PICTIDVYMIMVKCWMIDADSRPKFRELIIEFSKMARDPQRYLVIQGDERMH<br>LPSPTDSNFYRALMDEEDMDDVVDADEYLIPQQGFFSSPSTSRTPLLSSLSA<br>TSNNSTVACIDRNGLQSCPIKEDSFLQRYSSDPTGALTEDSIDDTFLPVPEY<br>INQSVPKRPAGSVQNPVYHNQPLNPAPSRDPHYQDPHSTAVGNPEYLNTVQP<br>TCVNSTFDSPAHWAQKGSHQISLDNPDYQQDFFPKEAKPNGIFKGSTAENAE<br>YLRVAPQSSEFIGA | HER1/ErbB1/EGFR<br>Full Length<br>(precursor)<br>Signal peptide: amino<br>acids 1-24<br>Extracellular domain:<br>amino acids 25-645<br>Transmembrane<br>domain:<br>amino acids 646-668<br>Cytoplasmic domain:<br>amino acids 669-1210<br>*Homo sapiens*<br>UniProt No.<br>P00533 |

| SEQ ID | Sequence | Description |
|---|---|---|
| 65 | MELAALCRWGLLLALLPPGAASTQVCTGTDMKLRLPASPETHLDMLRHLYQG CQVVQGNLELTYLPTNASLSFLQDIQEVQGYVLIAHNQVRQVPLQRLRIVRG TQLFEDNYALAVLDNGDPLNNTTPVTGASPGGLRELQLRSLTEILKGGVLIQ RNPQLCYQDTILWKDIFHKNNQLALTLIDTNRSRACHPCSPMCKGSRCWGES SEDCQSLTRTVCAGGCARCKGPLPTDCCHEQCAAGCTGPKHSDCLACLHFNH SGICELHCPALVTYNTDTFESMPNPEGRYTFGASCVTACPYNYLSTDVGSCT LVCPLHNQEVTAEDGTQRCEKCSKPCARVCYGLGMEHLREVRAVTSANIQEF AGCKKIFGSLAFLPESFDGDPASNTAPLQPEQLQVFETLEEITGYLYISAWP DSLPDLSVFQNLQVIRGRILHNGAYSLTLQGLGISWLGLRSLRELGSGLALI HHNTHLCFVHTVPWDQLFRNPHQALLHTANRPEDECVGEGLACHQLCARGHC WGPGPTQCVNCSQFLRGQECVEECRVLQGLPREYVNARHCLPCHPECQPQNG SVTCFGPEADQCVACAHYKDPPFCVARCPSGVKPDLSYMPIWKFPDEEGACQ PCPINCTHSCVDLDDKGCPAEQRASPLTSIISAVVGILLVVVLGVVFGILIK RRQQKIRKYTMRRLLQETELVEPLTPSGAMPNQAQMRILKETELRKVKVLGS GAFGTVYKGIWIPDGENVKIPVAIKVLRENTSPKANKEILDEAYVMAGVGSP YVSRLLGICLTSTVQLVTQLMPYGCLLDHVRENRGRLGSQDLLNWCMQIAKG MSYLEDVRLVHRDLAARNVLVKSPNHVKITDFGLARLLDIDETEYHADGGKV PIKWMALESILRRRFTHQSDVWSYGVTVWELMTFGAKPYDGIPAREIPDLLE KGERLPQPPICTIDVYMIMVKCWMIDSECRPRFRELVSEFSRMARDPQRFVV IQNEDLGPASPLDSTFYRSLLEDDDMGDLVDAEEYLVPQQGFFCPDPAPGAG GMVHHRHRSSSTRSGGGDLTLGLEPSEEEAPRSPLAPSEGAGSDVFDGDLGM GAAKGLQSLPTHDPSPLQRYSEDPTVPLPSETDGYVAPLTCSPQPEYVNQPD VRPQPPSPREGPLPAARPAGATLERPKTLSPGKNGVVKDVFAFGGAVENPEY LTPQGGAAPQPHPPPAFSPAFDNLYYWDQDPPERGAPPSTFKGTPTAENPEY LGLDVPV | HER2/neu/ErbB2 Full Length (precursor) Signal peptide: amino acids 1-22 Extracellular domain: amino acids 23-652 Transmembrane domain: amino acids 653-675 Cytoplasmic domain: amino acids 676-1255 *Homo sapiens* UniProt No. P04626 |
| 66 | MRANDALQVLGLLFSLARGSEVGNSQAVCPGTLNGLSVTGDAENQYQTLYKL YERCEVVMGNLEIVLTGHNADLSFLQWIREVTGYVLVAMNEFSTLPLPNLRV VRGTQVYDGKFAIFVMLNYNTNSSHALRQLRLTQLTEIISGGVYIEKNDKLC HMDTIDWRDIVRDRDAEIVVKDNGRSCPPCHEVCKGRCWGPGSEDCQTLTKT ICAPQCNGHCFGPNPNQCCHDECAGGCSGPQDTDCFACRHFNDSGACVRCP QPLVYNKLTFQLEPNPHTKYQYGGVCVASCPHNFVVDQTSCVRACPPDKMEV DKNGLKMCEPCGGLCPKACEGTGSGSRFQTVDSSNIDGFVNCTKILGNLDFL ITGLNGDPWHKIPALDPEKLNVFRTVREITGYLNIQSWPPHMHNFSVFSNLT TIGGRSLYNRGFSLLIMKNLNVTSLGFRSLKEISAGRIYISANRQLCYHHSL NWTKVLRGPTEERLDIKHNRPRRDCVAEGKVCDPLCSSGGCWGPGPGQCLSC RNYSRGGVCVTHCNFLNGEPREFAHEAECFSCHPECQPMEGTATCNGSGSDT CAQCAHFRDGPHCVSSCPHGVLGAKGPIYKYPDVQNECRPCHENCTQGCKGP ELQDCLGQTLVLIGKTHLTMALTVIAGLVVIFMMLGGTFLYWRGRRIQNKRA MRRYLERGESIEPLDPSEKANKVLARIFKETELRKLKVLGSGVFGTVHKGVW IPEGESIKIPVCIKVIEDKSGRQSFQAVTDHMLAIGSLDHAHIVRLLGLCPG sSLQLVTQYLPLGSLLDHVRQHRGALGPQLLLNWGVQIAKGMYYLEEHGMVH RNLAARNVLLKSPSQVQVADFGVADLLPPDDKQLLYSEAKTPIKWMALESIH FGKYTHQSDVWSYGVTVWELMTFGAEPYAGLRLAEVPDLLEKGERLAQPQIC TIDVYMVMVKCWMIDENIRPTFKELANEFTRMARDPPRYLVIKRESGPGIAP GPEPHGLTNKKLEEVELEPELDLDLDLEAEEDNLATTTLGSALSLPVGTLNR PRGSQSLLSPSSGYMPMNQGNLGESCQESAVSGSSERCPRPVSLHPMPRGCL ASESESSEGHVTGSEAELQEKVSMCRSRSRSRSPRPRGDSAYHSQRHSLLTPVT PLSPPGLEEEDVNGYVMPDTHLKGTPSSREGTLSSVGLSSVLGTEEEDEDEE YEYMNRRRRHSPPHPPRPSSLEELGYEYMDVGSDLSASLGSTQSCPLHPVPI MPTAGTTPDEDYEYMNRQRDGGGPGGDYAAMGACPASEQGYEEMRAFQGPGH QAPHVHYARLKTLRSLEATDSAFDNPDYWHSRLFPKANAQRT | HER3/ErbB3 Full Length (precursor) Signal peptide: amino acids 1-19 Extracellular domain: amino acids 20-643 Transmembrane domain: amino acids 644-664 Cytoplasmic domain: amino acids 665-1342 *Homo sapiens* UniProt No. P21860 |
| 67 | MKPATGLWVWVSLLVAAGTVQPSDSQSVCAGTENKLSSLSDLEQQYRALRKY YENCEVVMGNLEITSIEHNRDLSFLRSVREVTGYVLVALNQFRYLPLENLRI IRGTKLYEDRYALAIFLNYRKDGNFGLQELGLKNLTEILNGGVYVDQNKFLC YADTIHWQDIVRNPWPSNLTLVSTNGSSGCGRCHKSCTGRCWGPTENHCQTL TRTVCAEQCDGRCYGPYVSDCCHRECAGGCSGPKDTDCFACMNFNDSGACVT QCPQTFVYNPTTFQLEHNFNAKYTYGAFCVKKCPHNFVVDSSSCVRACPSSK MEVEENGIKMCKPCTDICPKACDGIGTGSLMSAQTVDSSNIDKFINCTKING NLIFLVTGIHGDPYNAIEAIDPEKLNVFRTVREITGFLNIQSWPPNMTDFSV FSNLVTIGGRVLYSGLSLLILKQQGITSLQFQSLKEISAGNIYITDNSNLCY YHTINWTTLFSTINQRIVIRDNRKAENCTAEGMVCNHLCSSDGCWGPGPDKC LSCRRFSRGRICIESCNLYDGEFREFENGSICVECDPQCEKMEDGLLTCHGP GPDNCTKCSHFKDGPNCVEKCPDGLQGANSFIFKYADPDRECHCPHPNCTQG CNGPTSHDCIYYPWTGHSTLPQHARTPLIAAGVIGGLFILVIVGLTFAVYR RKSIKKKRALRRFLETELVEPLTPSGTAPNQAQLRILKETELRKVKVLGSGA FGTVYKGIWVPEGETVKIPVAIKILNETTGPKANVEFMDEALIMASMDHPHL VRLLGVCLSPTIQLVTQLMPHGCLLEYVHEHKDNIGSQLLLNWCVQIAKGMM YLEERRLVHRDLAARNVLVKSPNHVKITDFGLARLLEGDEKEYNADGGKMPI KWMALECIHYRKFTHQSDVWSYGVTIWELMTFGGKPYDGIPTREIPDLLEKG ERLPQPPICTIDVYMVMVKCWMIDADSRPKFKELAAEFSRMARDPQRYLVIQ GDDRMKLPSPNDSKFFQNLLDEEDLEDMMDAEEYLVPQAFNIPPPIYTSRAR IDSNRSEIGHSPPPAYTPMSGNQFVYRDGGFAAEQGVSVPYRAPTSTIPEAP | HER4/ErbB4 Full Length (precursor) Signal peptide: amino acids 1-25 Extracellular domain: amino acids 26-651 Transmembrane domain: amino acids 652-675 Cytoplasmic domain: amino acids 676-1308 *Homo sapiens* UniProt No. Q15303 |

| SEQ ID | Sequence | Description |
|---|---|---|
| | VAQGATAEIFDDSCCNGTLRKPVAPHVQEDSSTQRYSADPTVFAPERSPRGE LDEEGYMTPMRDKPKQEYLNPVEENPFVSRRKNGDLQALDNPEYHNASNGPP KAEDEYVNEPLYLNTFANTLGKAEYLKNNILSMPEKAKKAFDNPDYWNHSLP PRSTLQHPDYLQEYSTKYFYKQNGRIRPIVAENPEYLSEFSLKPGTVLPPPP YRHRNTVV | |
| 68 | MKAPAVLAPGILVLLFTLVQRSNGECKEALAKSEMNVNMKyQLpNFTAETPI QNVILHEHHIFLGATNYIYVLNEEDLQKVAEYKTGPVLEHPDCFPCQDCSSK ANLSGGVWKDNINMALVVDTYYDDQLISCGSVNRGTCQRHVFPHNHTADIQS EVHCIFSPQIEEPSQCPDCVVSALGAKVLSSVKDRFINFFVGNTINSSYFPD HPLHSISVRRLKETKDGFMFLTDQSYIDVLPEFRDSYPIKYVHAFESNNFIY FLTVQRETLDAQTFHTRIIRFCSINSGLHSYMEMPLECILTEKRKKRSTKKE VFNILQAAYVSKPGAQLARQIGASLNDDILFGVFAQSKPDSAEPMDRSAMCA FPIKYVNDFFNKIVNKNNVRCLQHFYGPNHEHCFNRTLLRNSSGCEARRDEY RTEFTTALQRVDLFMGQFSEVLLTSISTFIKGDLTIANLGTSEGRFMQVVVS RSGPSTPHVNFLLDSHPVSPEVIVEHTLNQNGYTLVITGKKITKIPLNGLGC RHFQSCSQCLSAPPFVQCGWCHDKCVRSEECLSGTWTQQICLPAIYKVFPNS APLEGGTRLTICGWDFGFRRNNKFDLKKTRVLLGNESCTLTLSESTMNTLKC TVGPAMNKHFNMSIIISNGHGTTQYSTFSYVDPVITSISPKYGPMAGGTLLT LTGNYLNSGNSRHISIGGKTCTLKSVSNSILECYTPAQTISTEFAVKLKIDL ANRETSIFSYREDPIVYEIHPTKSFISGGSTITGVGKNLNSVSVPRMVINVH EAGRNFTVACQHRSNSEIICCTTPSLQQLNLQLPLKTKAFFMLDGILSKYFD LIYVHNPVFKPFEKPVMISMGNENVLEIKGNDIDPEAVKGEVLKVGNKSCEN IHLHSEAVLCTVPNDLLKLNSELNIEWKQAISSTVLGKVIVQPDQNFTGLIA GVVSISTALLLLLGFFLWLKKRKQIKDLGSELVRYDARVHTPHLDRLVSARS VSPTTEMVSNESVDYRATFPEDQFPNSSQNGSCRQVQYPLTDMSPILTSGDS DISSPLLQNTVHIDLSALNPELVQAVQHVVIGPSSLIVHFNEVIGRGHFGCV YHGTLLDNDGKKIHCAVKSLNRITDIGEVSQFLTEGIIMKDFSHPNVLSLLG ICLRSEGSPLVVLPYMKHGDLRNFIRNETHNPTVKDLIGFGLQVAKGMKYLA SKKFVHRDLAARNCMLDEKFTVKVADFGLARDMYDKEYYSVHNKTGAKLPVK WMALESLQTQKFTTKSDVWSFGVLLWELMTRGAPPYPDVNTFDITVYLLQGR RLLQPEYCPDPLYEVMLKCWHPKAEMRPSFSELVSRISAIFSTFIGEHYVHV NATYVNVKCVAPYPSLLSSEDNADDEVDTRPASFWETS | HGFR/c-Met Full Length (precursor) Signal peptide: amino acids 1-24 Extracellular domain: amino acids 25-932 Transmembrane domain: amino acids 933-955 Cytoplasmic domain: amino acids 956-1390 *Homo sapiens* UniProt No. P08581 |
| 69 | MKSGSGGGSPTSLWGLLFLSAALSLWPTSGEICGPGIDIRNDYQQLKRLENC TVIEGYLHILLISKAEDYRSYRFPKLTVITEYLLLFRVAGLESLGDLFPNLT VIRGWKLFYNYALVIFEMTNLKDIGLYNLRNITRGAIRIEKNADLCYLSTVD WSLILDAVSNNYIVGNKPPKECGDLCPGTMEEKPMCEKTTINNEYNYRCWTT NRCQKMCPSTCGKRACTENNECCHPECLGSCSAPDNDTACVACRHYYYAGVC VPACPPNTYRFEGWRCVDRDFCANILSAESSDSEGFVIHDGECMQECPSGFI RNGSQSMYCIPCEGPCPKVCEEEKKTKTIDSVTSAQMLQGCTIFKGNLLINI RRGNNIASELENFMGLIEVVTGYVKIRHSHALVSLSFLKNLRLILGEEQLEG NYSFYVLDNQNLQQLWDWDHRNLTIKAGKMYFAFNPKLCVSEIYRMEEVTGT KGRQSKGDINTRNNGERASCESDVLHFTSTTTSKNRIIITWHRYRPPDYRDL ISFTVYYKEAPFKNVTEYDGQDACGSNSWNMVDVDLPNKDVEPGILLHGLK PWTQYAVYVKAVTLTMVENDHIRGAKSEILYIRTNASVPSIPLDVLSASNSS SQLIVKWNPPSLPNGNLSYYIVRWQRQPQDGYLRHNYCSKDKIPIRKYADG TIDIEEVTENPKTEVCGEKGPCCACPKTEAEKQAEKEEEAEYRKVFENPLHN SIFVPRPERKRRDVMQVANTTMSSRSRNTTAADTYNITDPEELETEYPFFES RVDNKERTVISNLRPFTLYRIDIHSCNHEAEKLGCSASNFVFARTMPAEGAD DIPGPVTWEPRPENSIFLKWPEPENPNGLILMYEIKYGSQVEDQRECVSRQE YRKYGGAKLNRLNPGNYTARIQATSISGNGSWTDPVFFYVQAKTGYENFIHL IIALPVAVLLIVGGLVIMLYVFHRKRNNSRLGNGVLYASVNPEYFSAADVYV PDEWEVAREKITMSRELGQGSFGMVYEGVAKGVVKDEPETRVAIKTVNEAAS MRERIEFLNEASVMKEFNCHHVVRLLGVVSQGQPTLVIMELMTRGDLKSYLR SLRPEMENNPVLAPPSLSKMIQMAGEIADGMAYLNANKFVHRDLAARNCMVA EDFTVKIGDFGMTRDIYETDYYRKGGKGLLPVRWMSPESLKDGVFTTYSDVW SFGVVLWEIATLAEQPYQGLSNEQVLRFVMEGGLLDKPDNCPDMLFELMRMC WQYNPKMRPSFLEIISSIKEEMEPGFREVSFYYSEENKLPEPEELDLEPENM ESVPLDPSASSSSLPLPDRHSGHKAENGPGPGVLVLRASFDERQPYAHMNGG RKNERALPLPQSSTC | IGF-1 R full length (precursor) Signal peptide: amino acids 1-30 Extracellular domain: amino acids 741-935 Transmembrane domain: amino acids 936-959 Cytoplasmic domain: amino acids 960-1367 *Homo sapiens* UniProtNo. P08069 |
| 70 | ESKYGPPCPPCP | spacer (IgG4hinge) |
| 71 | GAATCTAAGTACGGACCGCCCTGCCCCCCTTGCCCT | spacer (IgG4hinge) |
| 72 | ESKYGPPCPPCPGQPREPQVYTLPPSQEEMTKNQVSLTCLVKGFYPSDIAVE WESNGQPENNYKTTPPVLDSDGSFFLYSRLTVDKSRWQEGNVFSCSVMHEAL HNHYTQKSLSLSLGK | Hinge-CH3 spacer |

-continued

| SEQ ID | Sequence | Description |
|---|---|---|
| 73 | ESKYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYKCK VSNKGLPSSIEKTISKAKGQPREPQVYTLPPSQEEMTKNQVSLTCLVKGFYP SDIAVEWESNGQPENNYKTTPPVLDSDGSFFLYSRLTVDKSRWQEGNVFSCS VMHEALHNHYTQKSLSLSLGK | Hinge-CH2-CH3 spacer |
| 74 | RWPESPKAQASSVPTAQPQAEGSLAKATTApATTRNTGRGGEEKKKEKEKEE QEERETKTPECPSHTQPLGVYLLTPAVQDLWLRDKATFTCFVVGSDLKDAHL TWEVAGKVPTGGVEEGLLERHSNGSQSQHSRLTLPRSLWNAGTSVTCTLNHP SLPPQRLMALREPAAQAPVKLSLNLLASSDPPEAASWLLCEVSGFSPPNILL MWLEDQREVNTSGFAPARPPPQPGSTTFWAWSVLRVPAPPSPQPATYTCVVS HEDSRTLLNASRSLEVSYVTDH | IgD-hinge-Fc |
| 75 | MALPVTALLLPLALLLHA | CD8 alpha signal peptide |
| 76 | EGRGSLLTCGDVEENPGP | T2A |
| 77 | FWVLVVVGGVLACYSLLVTVAFIIFWV | CD28 (amino acids 153-179 of Accession No. P10747) |
| 78 | IEVMYPPPYLDNEKSNGTIIHVKGKHLCPSPLFPGPSKP FWVLVVVGGVLACYSLLVTVAFIIFWV | CD28 (amino acids 114-179 of Accession No. P10747) |
| 79 | RSKRSRLLHSDYMNMTPRRPGPTRKHYQPYAPPRDFAAYRS | CD28 (amino acids 180-220 of P10747) |
| 80 | RSKRSRGGHSDYMNMTPRRPGPTRKHYQPYAPPRDFAAYRS | CD28 (LL to GG) |
| 81 | KRGRKKLLYIFKQPFMRPVQTTQEEDGCSCRFPEEEEGGCEL | 4-1BB (amino acids 214-255 of Q07011.1) |
| 82 | RVKFSRSADAPAYQQGQNQLYNELNLGRREEYDVLDKRRGRDPEMGGKPRRK NPQEGLYN ELQKDKMAEA YSEIGMKGER RRGKGHDGLY QGLSTATKDTYDALHMQALP PR | CD3 zeta |
| 83 | RVKFSRSAEPPAYQQGQNQLYNELNLGRREEYDVLDKRRGRDPEMGGKPRRK NPQEGLYN ELQKDKMAEA YSEIGMKGER RRGKGHDGLY QGLSTATKDTYDALHMQALP PR | CD3 zeta |
| 84 | RVKFSRSADAPAYKQGQNQLYNELNLGRREEYDVLDKRRGRDPEMGGKPRRK NPQEGLYN ELQKDKMAEA YSEIGMKGER RRGKGHDGLY QGLSTATKDTYDALHMQALP PR | CD3 zeta |
| 85 | GSGATNFSLLKQAGDVEENPGP | P2A |
| 86 | ATNFSLLKQAGDVEENPGP | P2A |
| 87 | QCTNYALLKLAGDVESNPGP | E2A |
| 88 | VKQTLNFDLLKLAGDVESNPGP | F2A |
| 89 | PGGG-(SGGGG)5-P- wherein P is proline, G is glycine and S is serine | linker |
| 90 | GSADDAKKDAAKKDGKS | linker |
| 91 | TGCCACCCTGAGTGTCAGCCCCAGAATGGCTCAGTGACCTGTTTTGGACCGG AGGCTGACCAGTGTGTGGCCTGTGCCCACTATAAGGACCCTCCCTTCTGCGT GGCCCGCTGCCCCAGCGGTGTGAAACCTGACCTCTCCTACATGCCCATCTGG AAGTTTCCAGATGAGGAGGGCGCATGCCAGCCTTGCCCCATCAACTGCACCC ACTCCTGTGTGGACCTGGATGACAAGGGCTGCCCCGCCGAGCAGAGAGCCAG CCCTCTGACGGGTGGAGGAAGCGGAGGTGGCAGCTCCATCATCTCTGCGGTG GTTGGCATTCTGCTGGTCGTGGTCTTGGGGGTGGTCTTTGGGATCCTCATC | Modified HER2t (nt) artificial |
| 92 | CHPECQPQNGSVTCFGPEADQCVACAHYKDPPFCVARCPSGVKPDLSYMPIW KFPDEEGACQPCPINCTHSCVDLDDKGCPAEQRASPLTGGGSGGGSSIISAV VGILLVVVLGVVFGILI | Modified HER2t (aa) artificial |
| 93 | ATGCTTCTCCTGGTGACAAGCCTTCTGCTCTGTGAGTTACCACACCCAGCAT TCCTCCTGATCCCATGCCACCCTGAGTGTCAGCCCCAGAATGGCTCAGTGAC CTGTTTTGGACCGGAGGCTGACCAGTGTGTGGCCTGTGCCCACTATAAGGAC | Modified HERt2 with signal sequence (nt) Artificial |

| SEQ ID | Sequence | Description |
|---|---|---|
|  | CCTCCCTTCTGCGTGGCCCGCTGCCCCAGCGGTGTGAAACCTGACCTCTCCT<br>ACATGCCCATCTGGAAGTTTCCAGATGAGGAGGGCGCATGCCAGCCTTGCCC<br>CATCAACTGCACCCACTCCTGTGTGGACCTGGATGACAAGGGCTGCCCCGCC<br>GAGCAGAGAGCCAGCCCTCTGACGGGTGGAGGAAGCGGAGGTGGCAGCTCCA<br>TCATCTCTGCGGTGGTTGGCATTCTGCTGGTCGTGGTCTTGGGGGTGGTCTT<br>TGGGATCCTCATC |  |
| 94 | MWNLLHETDSAVATARRPRWLCAGALVLAGGFFLLGFLFGWFIKSSNEATNI<br>TPKHNMKAFLDELKAENIKKFLYNFTQIPHLAGTEQNFQLAKQIQSQWKEFG<br>LDSVELAHYDVLLSYPNKTHPNYISIINEDGNEIFNTSLFEPPPPGYENVSD<br>IVPPFSAFSPQGMPEGDLVYVNYARTEDFFKLERDMKINCSGKIVIARYGKV<br>FRGNKVKNAQLAGAKGVILYSDPADYFAPGVKSYPDGWNLPGGGVQRGNILN<br>LNGAGDPLTPGYPANEYAYRRGIAEAVGLPSIPVHPIGYYDAQKLLEKMGGS<br>APPDSSWRGSLKVPYNVGPGFTGNFSTQKVKMHIHSTNEVTRIYNVIGTLRG<br>AVEPDRYVILGGHRDSWVFGGIDPQSGAAVVHEIVRSFGTLKKEGWRPRRTI<br>LFASWDAEEFGLLGSTEWAEENSRLLQERGVAYINADSSIEGNYTLRVDCTP<br>LMYSLVHNLTKELKSPDEGFEGKSLYESWTKKSPSPEFSGMPRISKLGSGND<br>FEVFFQRLGIASGRARYTKNWETNKFSGYPLYHSVYETYELVEKFYDPMFKY<br>HLTVAQVRGGMVFELANSIVLPFDCRDYAVVLRKYADKIYSISMKHPQEMKT<br>YSVSFDSLFSAVKNFTEIASKFSERLQDFDKSNPIVLRMMNDQLMFLERAFI<br>DPLGLPDRPFYRHVIYAPSSHNKYAGESFPGIYDALFDIESKVDPSKAWGEV<br>KRQIYVAAFTVQAAAETLSEVA | PSMA WT (full length) |
| 95 | MGNLLHETDSAVATARRPRWLCAGALVLAGGFFLLGFLFGWFIKSSNEATNI<br>TPKHNMKAFLDELKAENIKKFLYNFTQIPHLAGTEQNFQLAKQIQSQWKEFG<br>LDSVELAHYDVLLSYPNKTHPNYISIINEDGNEIFNTSLFEPPPPGYENVSD<br>IVPPFSAFSPQGMPEGDLVYVNYARTEDFFKLERDMKINCSGKIVIARYGKV<br>FRGNKVKNAQLAGAKGVILYSDPADYFAPGVKSYPDGWNLPGGGVQRGNILN<br>LNGAGDPLTPGYPANEYAYRRGIAEAVGLPSIPVHPIGYYDAQKLLEKMGGS<br>APPDSSWRGSLKVPYNVGPGFTGNFSTQKVKMHIHSTNEVTRIYNVIGTLRG<br>AVEPDRYVILGGHRDSWVFGGIDPQSGAAVVHEIVRSFGTLKKEGWRPRRTI<br>LFASWDAEEFGLLGSTEWAEENSRLLQERGVAYINADSSIEGNYTLRVDCTP<br>LMYSLVHNLTKELKSPDEGFEGKSLYESWTKKSPSPEFSGMPRISKLGSGND<br>FEVFFQRLGIASGRARYTKNWETNKFSGYPLYHSVYETYELVEKFYDPMFKY<br>HLTVAQVRGGMVFELANSIVLPFDCRDYAVVLRKYADKIYSISMKHPQEMKT<br>YSVSFDSLFSAVKNFTEIASKFSERLQDFDKSNPIVLRMMNDQLMFLERAFI<br>DPLGLPDRPFYRHVIYAPSSHNKYAGESFPGIYDALFDIESKVDPSKAWGEV<br>KRQIYVAAFTVQAAAETLSEVA | PSMA W2G (full length) |
| 96 | atgtggaatctccttcacgaaaccgactcggctgtggccaccgcgcgccgcc<br>cgcgctggctgtgcgctggggcgctggtgctggcgggtggcttctttctcct<br>cggcttcctcttcgggtggtttataaaatcctccaatgaagctactaacatt<br>actccaaagcataatatgaaagcatttttggatgaattgaaagctgagaaca<br>tcaagaagttcttatataattttacacagataccacatttagcaggaacaga<br>acaaaactttcagcttgcaaagcaaattcaatcccagtggaagaatttggc<br>ctggattctgttgagctagcacattatgatgtcctgttgtcctacccaaata<br>agactcatcccaactacatctcaataattaatgaagatggaaatgagatttt<br>caacacatcattatttgaaccacctcctccaggatatgaaaatgtttcggat<br>attgtaccaccttttcagtgctttctctcctcaaggaatgccagagggcgatc<br>tagtgtatgttaactatgcacgaactgaagacttcttaaattggaacggga<br>catgaaaatcaattgctctgggaaaattgtaattgccagatatgggaaagtt<br>ttcagaggaaataaggttaaaaatgcccagctggcaggggccaaaggagtca<br>ttctctactccgaccctgctgactactttgctcctggggtgaagtcctatcc<br>agatggttggaatcttcctggaggtggtgtccagcgtggaaatatcctaaat<br>ctgaatggtgcaggagaccctctcacaccaggttacccagcaaatgaatatg<br>cttataggcgtggaattgcagaggctgttggtcttccaagtattcctgttca<br>tccaattggatactatgatgcacagaagctcctagaaaaatgggtggctca<br>gcaccaccagatagcagctggagaggaagtctcaaagtgccctacaatgttg<br>gacctggctttactggaaactttctacacaaaaagtcaagatgcacatcca<br>ctctaccaatgaagtgacaagaatttacaatgtgataggtactctcagagga<br>gcagtggaaccagacagatatgtcattctggggtcaccgggactcatggg<br>tgtttggtggtattgaccctcagagtggagcagctgttgttcatgaaattgt<br>gaggagctttggaacactgaaaaaggaagggtggagacctagaagaacaatt<br>tgtttgcaagctgggatgcagaagaattggtcttcttggttctactgagt<br>gggcagaggagaattcaagactccttcaagagcgtggcgtggcttatattaa<br>tgctgactcatctatagaaggaaactacactctgagagttgattgtacaccg<br>ctgatgtacagcttggtacacaacctaacaaaagagctgaaaagccctgatg<br>aaggctttgaaggcaaatctctttatgaaagttggactaaaaaagtccttc<br>cccagagttcagtggcatgcccaggataagcaaattgggatctggaaatgat<br>tttgaggtgttcttccaacgacttggaattgcttcaggcagagcacggtata<br>ctaaaaattgggaaacaaacaaattcagcggctatccactgtatcacagtgt<br>ctatgaaacatatgagttggtggaaaagttttatgatccaatgtttaaatat<br>cacctcactgtggcccaggttcgaggagggatggtgtttgagctagccaatt<br>ccatagtgctccccttttgattgtcgagattatgctgtagtttaagaaagta | PSMA WT (nt) |

| SEQ ID | Sequence | Description |
|---|---|---|
| | tgctgacaaaatctacagtatttctatgaaacatccacaggaaatgaagaca<br>tacagtgtatcatttgattcactttttctgcagtaaagaattttacagaaa<br>ttgcttccaagttcagtgagagactccaggactttgacaaaagcaacccaat<br>agtattaagaatgatgaatgatcaactcatgtttctggaaagagcatttatt<br>gatccattagggttaccagacaggccttttataggcatgtcatctatgctc<br>caagcagccacaacaagtatgcaggggagtcattcccaggaatttatgatgc<br>tctgtttgatattgaaagcaaagtggacccttccaaggcctggggagaagtg<br>aagagacagatttatgttgcagccttcacagtgcaggcagctgcagagactt<br>tgagtgaagtagcc | |
| 97 | ATGTGGAATCTCCTTCATGAAACAGACTCTGCTGTGGCCACAGCCAGAAGAC<br>CCAGATGGCTGTGTGCTGGGGCCCTGGTGCTGGCTGGTGGCTTCTTTCTCCT<br>GGGCTTCCTCTTTGGGTGGTTTATAAAATCCTCCAATGAAGCTACTAACATT<br>ACTCCAAAGCATAATATGAAAGCATTTTTGGATGAATTGAAAGCTGAGAACA<br>TCAAGAAGTTCTTATATAATTTTACACAGATACCACATTTAGCAGGAACAGA<br>ACAAAACTTTCAGCTTGCAAAGCAAATTCAATCCCAGTGGAAAGAATTTGGC<br>CTGGATTCTGTTGAGCTAGCACATTATGATGTCCTGTTGTCCTACCCAAATA<br>AGACTCATCCCAACTACATCTCAATAATTAATGAAGATGGAAATGAGATTTT<br>CAACACATCATTATTTGAACCACCTCCTCCAGGATATGAAATGTTTCTGAT<br>ATTGTACCACCTTTCAGTGCTTTCTCTCCTCAAGGAATGCCAGAGGGAGATC<br>TAGTGTATGTTAACTATGCAAGAACTGAAGACTTCTTTAAATTGGAAAGGGA<br>CATGAAAATCAATTGCTCTGGGAAAATTGTAATTGCCAGATATGGGAAAGTT<br>TTCAGAGGAAATAAGGTTAAAAATGCCCAGCTGGCAGGGGCCAAAGGAGTCA<br>TTCTCTACTCTGACCCTGCTGACTACTTTGCTCCTGGGGTGAAGTCCTATCC<br>AGATGGTTGGAATCTTCCTGGAGGTGGTGTCCAGAGAGGAAATATCCTAAAT<br>CTGAATGGTGCAGGAGACCCTCTCACACCAGGTTACCCAGCAAATGAATATG<br>CTTATAGGAGAGGAATTGCAGAGGCTGTTGGTCTTCCAAGTATTCCTGTTCA<br>TCCAATTGGATACTATGATGCACAGAAGCTCCTAGAAAAAATGGGTGGCTCA<br>GCACCACCAGATAGCAGCTGGAGAGGAAGTCTCAAAGTGCCCTACAATGTTG<br>GACCTGGCTTTACTGGAAACTTTTCTACACAAAAAGTCAAGATGCACATCCA<br>CTCTACCAATGAAGTGACAAGAATTTACAATGTGATAGGTACTCTCAGAGGA<br>GCAGTGGAACCAGACAGATATGTCATTCTGGGAGGTCACAGGGACTCATGGG<br>TGTTTGGTGGTATTGACCCTCAGAGTGGAGCAGCTGTTGTTCATGAAATTGT<br>GAGGAGCTTTGGAACACTGAAAAAGGAAGGGTGGAGACCTAGAAGAACAATT<br>TTGTTTGCAAGCTGGGATGCAGAAGAATTTGGTCTTCTTGGTTCTACTGAGT<br>GGGCAGAGGAGAATTCAAGACTCCTTCAAGAGAGGGGAGTGGCTTATATTAA<br>TGCTGACTCATCTATAGAAGGAAACTACACTCTGAGAGTTGATTGTACACCC<br>CTGATGTACAGCTTGGTACACAACCTAACAAAAGAGCTGAAAAAGCCCTGATG<br>AAGGCTTTGAAGGCAAATCTCTTTATGAAAGTTGGACTAAAAAAGTCCTTC<br>CCCAGAGTTCAGTGGCATGCCCAGGATAAGCAAATTGGGATCTGGAAATGAT<br>TTTGAGGTGTTCTTCCAAAGACTTGGAATTGCTTCAGGCAGAGCAAGGTATA<br>CTAAAAATTGGGAAACAAACAAATTCAGTGGCTATCCACTGTATCACAGTGT<br>CTATGAAACATATGAGTTGGTGGAAAAGTTTTATGATCCAATGTTTAAATAT<br>CACCTCACTGTGGCCCAGGTTAGAGGAGGGATGGTGTTTGAGCTAGCCAATT<br>CCATAGTGCTCCCTTTTGATTGTAGAGATTATGCTGTAGTTTAAGAAAGTA<br>TGCTGACAAAATCTACAGTATTTCTATGAAACATCCACAGGAAATGAAGACA<br>TACAGTGTATCATTTGATTCACTTTTTCTGCAGTAAAGAATTTTACAGAAA<br>TTGCTTCCAAGTTCAGTGAGAGACTCCAGGACTTTGACAAAAGCAACCCAAT<br>AGTATTAAGAATGATGAATGATCAACTCATGTTTCTGGAAAGAGCATTTATT<br>GATCCATTAGGGTTACCAGACAGGCCTTTTTATAGGCATGTCATCTATGCTC<br>CAAGCAGCCACAACAAGTATGCAGGGGAGTCATTCCCAGGAATTTATGATGC<br>TCTGTTTGATATTGAAAGCAAAGTGGACCCTTCCAAGGCCTGGGGAGAAGTG<br>AAGAGACAGATTTATGTTGCAGCCTTCACAGTGCAGGCAGCTGCAGAGACTT<br>TGAGTGAAGTAGCCTAA | CpG-free PSMA |
| 98 | PLGLWA | cleavable linker |
| 99 | GFLG | linker |
| 100 | KLAKLAKKLAKLAK | peptide toxin |

What is claimed:

1. A method of identifying a cell expressing a cell surface conjugate comprising an agent linked to the N-terminus of a cell surface molecule, wherein the method comprises contacting a composition comprising the cell with a binding molecule capable of binding to the agent,
   wherein the cell surface molecule is a modified member of the epidermal growth factor receptor (EGFR) family that lacks a functional intracellular signaling domain or is not capable of mediating intracellular signaling,
   wherein the agent is a streptavidin binding peptide that binds to streptavidin or a streptavidin mutein,
   wherein the cell surface conjugate is encoded by a first nucleic acid encoding the cell surface conjugate,
   wherein the cell comprises a second nucleic acid encoding a recombinant receptor, and wherein the identified cell is a cell that further expresses the recombinant receptor.

2. The method of claim 1, wherein the agent exhibits a binding affinity for the streptavidin or the streptavidin mutein with an equilibrium dissociation constant ($K_D$) of from about $10^{-4}$ M to about $10^{-10}$ M.

3. The method of claim 1, wherein the binding of the agent to the streptavidin or the streptavidin mutein is reversible.

4. The method of claim 1, wherein the binding of the agent to the streptavidin or the streptavidin mutein competes with binding to biotin, a biotin analog, or a biologically active fragment thereof.

5. The method of claim 1, wherein the agent is linked directly to the cell surface molecule.

6. The method of claim 1, wherein the agent is linked indirectly to the cell surface molecule via at least one linker.

7. The method of claim 1, wherein the agent is a peptide of less than 50 amino acids in length.

8. The method of claim 1, wherein the streptavidin analog or streptavidin mutein comprises the amino acid sequence $Val^{44}$-$Thr^{45}$-$Ala^{46}$-$Arg^{47}$ or $Ile^{44}$-$Gly^{45}$-$Ala^{46}$-$Arg^{47}$ at sequence positions corresponding to positions 44 to 47 with reference to positions in streptavidin in the sequence of amino acids set forth in SEQ ID NO:1.

9. The method of claim 1, wherein the streptavidin analog or mutein comprises:
   a) the sequence of amino acids set forth in any of SEQ ID NOS: 3-6, 27 and 28;
   b) a sequence of amino acids that exhibits 85% or more sequence identity to any of SEQ ID NOS:3-6, 27 and 28 and contains the amino acid sequence corresponding to $Val^{44}$-$Thr^{45}$-$Ala^{46}$-$Arg^{47}$ or $Ile^{44}$-$Gly^{45}$-$Ala^{46}$-$Arg^{47}$ and that reversibly binds to the agent; or
   c) a functional fragment of a) or b) that reversibly binds to the agent.

10. The method of claim 8, wherein the streptavidin mutein further comprises an amino acid replacement at a position corresponding to 117, 120 or 121 with reference to positions in streptavidin in the sequence of amino acids set forth in SEQ ID NO:1.

11. The method of claim 10, wherein:
the amino acid replacement is selected from the group consisting of $Glu^{117}$, $Asp^{117}$, $Arg^{117}$, $Ser^{120}$, $Ala^{120}$, $Gly^{120}$, $Trp^{121}$, $Tyr^{121}$ and $Phe^{121}$.

12. The method of claim 1, wherein the streptavidin or the streptavidin mutein comprises:
   a) the sequence of amino acids set forth in SEQ ID NO: 27 or 28;
   b) a sequence of amino acids that exhibits a 85% or more sequence identity to SEQ ID NOS: 27 or 28 and contains the amino acid sequence corresponding to $Val^{44}$, $Thr^{45}$, $Ala^{46}$, $Arg^{47}$, $Glu^{117}$, $Gly^{120}$ and $Tyr^{121}$ and reversibly binds to the agent; or
   c) a functional fragment of a) or b) that reversibly binds to the agent.

13. The method of claim 1, wherein the streptavidin binding peptide comprises the sequence Trp-Ser-His-Pro-Gln-Phe-Glu-Lys (SEQ ID NO: 8) or Trp-Arg-His-Pro-Gln-Phe-Gly-Gly (SEQ ID NO:7).

14. The method of claim 13, wherein the agent comprises the sequence Trp-Ser-His-Pro-Gln-Phe-Glu-Lys-(GlyGlyGlySer)$_3$-Trp-Ser-His-Pro-Gln-Phe-Glu-Lys (SEQ ID NO: 17), Trp-Ser-His-Pro-Gln-Phe-Glu-Lys-(GlyGlyGlySer)$_2$-Trp-Ser-His-Pro-Gln-Phe-Glu-Lys (SEQ ID NO: 18) and Trp-Ser-His-Pro-Gln-Phe-Glu-Lys-(GlyGlyGlySer)$_2$Gly-Gly-Ser-Ala-Trp-Ser-His-Pro-Gln-Phe-Glu-Lys (SEQ ID NO: 19).

15. The method of claim 1, wherein the cell surface molecule comprises at least one extracellular domain, wherein the at least one extracellular domain comprises an epitope recognized by an antibody or antigen-binding fragment thereof that specifically binds to a reference cell surface molecule.

16. The method of claim 1 wherein the modified member of the EGFR family comprises an epitope specifically recognized by cetuximab or an antigen binding fragment thereof.

17. The method of claim 1, wherein:
the modified member of the EGFR family lacks one or more of an EGFR Domain I, an EGFR Domain II, an EGFR Juxtamembrane Domain, and an EGFR Tyrosine Kinase Domain of a reference wild-type EGFR;
the modified member of the EGFR family lacks all of the domains EGFR Domain I, an EGFR Domain II, an EGFR Juxtamembrane Domain, and an EGFR Tyrosine Kinase Domain of the reference wild-type EGFR; or
the modified member of the EGFR family comprises an extracellular domain that consists of subdomain III and subdomain IV of the reference wild-type EGFR.

18. The method of claim 1, wherein the modified member of the EGFR family has at least a 85% sequence identity to SEQ ID NOS: 44 or 46.

19. The method of claim 1, wherein the reference cell surface receptor is a reference wild-type HER2 and the cell surface receptor is a modified HER2 thereof.

20. The method of claim 1, wherein the modified member of the EGFR family comprises a modified HER2 comprising an epitope specifically recognized by trastuzumab or an antigen binding fragment thereof.

21. The method of claim 1, wherein:
the modified member of the EGFR family comprises a modified HER2 that lacks one or more of an HER2 Domain I, an HER2 Domain II, an HER2 Domain III of a reference wild-type HER2;
the modified HER2 lacks all of the domains HER2 Domain I, HER2 Domain II, and HER2 Domain III of the reference EGFR of the reference wild-type HER2; or
the modified HER2 comprises an extracellular domain that consists of or consists essentially of Domain IV of the reference wild-type HER2.

22. The method of claim 1, wherein the modified member of the EGFR family comprises a modified HER2 comprising at least 85% sequence identity to SEQ ID NO: 92.

23. The method of claim 1, further comprising introducing a polynucleotide into a composition comprising the cell prior to contacting the cells with the binding molecule, wherein the polynucleotide comprises the nucleic acid sequence encoding the cell surface conjugate.

24. The method of claim 23, wherein the polynucleotide comprises the nucleic acid sequence encoding the cell surface conjugate is a first nucleic acid sequence encoding the cell surface conjugate and a second nucleic acid sequence encoding the recombinant receptor.

25. The method of claim 24, wherein the recombinant receptor comprises a chimeric antigen receptor (CAR).

26. The method of claim 24, wherein the first and second nucleic acid sequences are separated by an internal ribosome entry site (IRES), or a nucleotide sequence encoding a self-cleaving peptide or a peptide that causes ribosome skipping, which is a T2A, a P2A, an E2A or an F2A.

27. The method of claim 24, wherein the polynucleotide is in a vector.

28. The method of claim 1, further comprising:
   (a) introducing a polynucleotide into a cell, wherein the polynucleotide comprises a nucleic acid sequence encoding the cell surface conjugate;
   (b) contacting a composition comprising the cell of (a) with a binding molecule capable of reversibly binding to the agent; and
   (c) identifying cells of the composition bound to the binding molecule.

29. The method of claim 28, further comprising disrupting the reversible binding of the binding molecule to the agent.

30. The method of claim 29, wherein said disruption comprises contacting the cells with a composition comprising a competition substance capable of reversing the bond between the binding molecule and agent.

31. The method of claim 30, wherein the competition substance is a free binding partner or is a competition agent.

32. The method of claim 31, wherein the competition substance comprises biotin, a biotin analog or a biologically active fragment thereof.

33. The method of claim 28, wherein the binding molecule is an antibody or antigen binding fragment that specifically binds to the agent.

* * * * *

SEQUENCE LISTING

<160> NUMBER OF SEQ ID NOS: 100

<210> SEQ ID NO 1
<211> LENGTH: 159
<212> TYPE: PRT
<213> ORGANISM: Streptomyces avidinii
<220> FEATURE:

<223> OTHER INFORMATION: Streptavidin
<300> PUBLICATION INFORMATION:
<308> DATABASE ACCESSION NUMBER: UniProt No. P22629
<309> DATABASE ENTRY DATE: 1991-08-01

<400> SEQUENCE: 1

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Glu Ser Ala Val Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val Gln Gln
145                 150                 155

<210> SEQ ID NO 2
<211> LENGTH: 126
<212> TYPE: PRT
<213> ORGANISM: Streptomyces avidinii
<220> FEATURE:
<223> OTHER INFORMATION: Minimal streptavidin

<400> SEQUENCE: 2

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Glu Ser
            20                  25                  30

Ala Val Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
            100                 105                 110

Gly His Asp Thr Phe Thr Lys Val Lys Pro Ser Ala Ala Ser
        115                 120                 125

<210> SEQ ID NO 3
<211> LENGTH: 159
<212> TYPE: PRT
<213> ORGANISM: Streptomyces avidinii
<220> FEATURE:
<223> OTHER INFORMATION: Mutein Streptavidin Val44-Thr45-Ala46-Arg47

```
<400> SEQUENCE: 3

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Val Thr Ala Arg Gly
        35                  40                  45

Asn Ala Glu Ser Arg Tyr Val Leu Thr Gly Arg Tyr Asp Ser Ala Pro
50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val Gln Gln
145                 150                 155

<210> SEQ ID NO 4
<211> LENGTH: 126
<212> TYPE: PRT
<213> ORGANISM: Streptomyces avidinii
<220> FEATURE:
<223> OTHER INFORMATION: Mutein Streptavidin Val44-Thr45-Ala46-Arg47

<400> SEQUENCE: 4

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
            100                 105                 110

Gly His Asp Thr Phe Thr Lys Val Lys Pro Ser Ala Ala Ser
        115                 120                 125

<210> SEQ ID NO 5
<211> LENGTH: 159
<212> TYPE: PRT
<213> ORGANISM: Streptomyces avidinii
<220> FEATURE:
<223> OTHER INFORMATION: Mutein Streptavidin Ile44-Gly45-Ala-46-Arg47

<400> SEQUENCE: 5

Asp Pro Ser Lys Asp Ser Lys Ala Gln Val Ser Ala Ala Glu Ala Gly
1               5                   10                  15
```

```
Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Ile Gly Ala Arg Gly
        35                  40                  45

Asn Ala Glu Ser Arg Tyr Val Leu Thr Gly Arg Tyr Asp Ser Ala Pro
50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val Gln Gln
145                 150                 155

<210> SEQ ID NO 6
<211> LENGTH: 126
<212> TYPE: PRT
<213> ORGANISM: Streptomyces avidinii
<220> FEATURE:
<223> OTHER INFORMATION: Mutein Streptavidin Ile44-Gly45-Ala-46-Arg47

<400> SEQUENCE: 6

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Ile Gly
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
            100                 105                 110

Gly His Asp Thr Phe Thr Lys Val Lys Pro Ser Ala Ala Ser
        115                 120                 125

<210> SEQ ID NO 7
<211> LENGTH: 8
<212> TYPE: PRT
<213> ORGANISM: Artificial Sequence
<220> FEATURE:
<223> OTHER INFORMATION: Streptavidin binding peptide, Strep-tag

<400> SEQUENCE: 7

Trp Arg His Pro Gln Phe Gly Gly
1               5

<210> SEQ ID NO 8
<211> LENGTH: 8
<212> TYPE: PRT
<213> ORGANISM: Artificial Sequence
```

-continued

<220> FEATURE:
<223> OTHER INFORMATION: Strep-tag II

<400> SEQUENCE: 8

Trp Ser His Pro Gln Phe Glu Lys
1               5

<210> SEQ ID NO 9
<211> LENGTH: 3
<212> TYPE: PRT
<213> ORGANISM: Artificial Sequence
<220> FEATURE:
<223> OTHER INFORMATION: Streptavidin Binding peptide
<220> FEATURE:
<221> NAME/KEY: VARIANT
<222> LOCATION: (3)...(3)
<223> OTHER INFORMATION: Xaa is Gln, Asp, or Met

<400> SEQUENCE: 9

His Pro Xaa
1

<210> SEQ ID NO 10
<211> LENGTH: 4
<212> TYPE: PRT
<213> ORGANISM: Artificial Sequence
<220> FEATURE:
<223> OTHER INFORMATION: Streptavidin Binding peptide

<400> SEQUENCE: 10

His Pro Gln Phe
1

<210> SEQ ID NO 11
<211> LENGTH: 8
<212> TYPE: PRT
<213> ORGANISM: Artificial Sequence
<220> FEATURE:
<223> OTHER INFORMATION: Streptavidin Binding peptide
<220> FEATURE:
<221> NAME/KEY: VARIANT
<222> LOCATION: (1)...(1)
<223> OTHER INFORMATION: Xaa is Trp, Lys or Arg
<220> FEATURE:
<221> NAME/KEY: VARIANT
<222> LOCATION: (2)...(2)
<223> OTHER INFORMATION: Xaa is any amino acid
<220> FEATURE:
<221> NAME/KEY: VARIANT
<222> LOCATION: (7)...(7)
<223> OTHER INFORMATION: Xaa is Gly or Glu
<220> FEATURE:
<221> NAME/KEY: VARIANT
<222> LOCATION: (8)...(8)
<223> OTHER INFORMATION: Xaa is Gly, Lys or Arg

<400> SEQUENCE: 11

Xaa Xaa His Pro Gln Phe Xaa Xaa
1               5

<210> SEQ ID NO 12
<211> LENGTH: 8
<212> TYPE: PRT
<213> ORGANISM: Artificial Sequence
<220> FEATURE:
<223> OTHER INFORMATION: Streptavidin Binding peptide
<220> FEATURE:
<221> NAME/KEY: VARIANT
<222> LOCATION: (2)...(2)
<223> OTHER INFORMATION: Xaa is any amino acid
<220> FEATURE:

```
<221> NAME/KEY: VARIANT
<222> LOCATION: (7)...(7)
<223> OTHER INFORMATION: Xaa is Gly or Glu
<220> FEATURE:
<221> NAME/KEY: VARIANT
<222> LOCATION: (8)...(8)
<223> OTHER INFORMATION: Xaa is Gly, Lys or Arg

<400> SEQUENCE: 12

Trp Xaa His Pro Gln Phe Xaa Xaa
1               5

<210> SEQ ID NO 13
<211> LENGTH: 17
<212> TYPE: PRT
<213> ORGANISM: Artificial Sequence
<220> FEATURE:
<223> OTHER INFORMATION: Sequential modules of streptavidin-binding
      peptide
<220> FEATURE:
<221> NAME/KEY: VARIANT
<222> LOCATION: (9)...(9)
<223> OTHER INFORMATION: Xaa is any amino acid
<220> FEATURE:
<221> NAME/KEY: REPEAT
<222> LOCATION: (9)...(9)
<223> OTHER INFORMATION: Repeated 8 or 12 times

<400> SEQUENCE: 13

Trp Ser His Pro Gln Phe Glu Lys Xaa Trp Ser His Pro Gln Phe Glu
1               5                   10                  15

Lys

<210> SEQ ID NO 14
<211> LENGTH: 20
<212> TYPE: PRT
<213> ORGANISM: Artificial Sequence
<220> FEATURE:
<223> OTHER INFORMATION: Sequential modules of streptavidin-binding
      peptide
<220> FEATURE:
<221> NAME/KEY: REPEAT
<222> LOCATION: (9)...(12)
<223> OTHER INFORMATION: Repeated 2 or 3 times

<400> SEQUENCE: 14

Trp Ser His Pro Gln Phe Glu Lys Gly Gly Gly Ser Trp Ser His Pro
1               5                   10                  15

Gln Phe Glu Lys
            20

<210> SEQ ID NO 15
<211> LENGTH: 30
<212> TYPE: PRT
<213> ORGANISM: Artificial Sequence
<220> FEATURE:
<223> OTHER INFORMATION: Twin-Strep-tag

<400> SEQUENCE: 15

Ser Ala Trp Ser His Pro Gln Phe Glu Lys Gly Gly Gly Ser Gly Gly
1               5                   10                  15

Gly Ser Gly Gly Gly Ser Trp Ser His Pro Gln Phe Glu Lys
            20                  25                  30

<210> SEQ ID NO 16
<211> LENGTH: 30
<212> TYPE: PRT
<213> ORGANISM: Artificial Sequence
```

```
<220> FEATURE:
<223> OTHER INFORMATION: Twin-Strep-tag

<400> SEQUENCE: 16

Ser Ala Trp Ser His Pro Gln Phe Glu Lys Gly Gly Gly Ser Gly Gly
1               5                   10                  15

Gly Ser Gly Gly Ser Ala Trp Ser His Pro Gln Phe Glu Lys
            20                  25                  30

<210> SEQ ID NO 17
<211> LENGTH: 28
<212> TYPE: PRT
<213> ORGANISM: Artificial Sequence
<220> FEATURE:
<223> OTHER INFORMATION: Twin-Strep-tag

<400> SEQUENCE: 17

Trp Ser His Pro Gln Phe Glu Lys Gly Gly Gly Ser Gly Gly Gly Ser
1               5                   10                  15

Gly Gly Gly Ser Trp Ser His Pro Gln Phe Glu Lys
            20                  25

<210> SEQ ID NO 18
<211> LENGTH: 24
<212> TYPE: PRT
<213> ORGANISM: Artificial Sequence
<220> FEATURE:
<223> OTHER INFORMATION: Twin-Strep-tag

<400> SEQUENCE: 18

Trp Ser His Pro Gln Phe Glu Lys Gly Gly Gly Ser Gly Gly Gly Ser
1               5                   10                  15

Trp Ser His Pro Gln Phe Glu Lys
            20

<210> SEQ ID NO 19
<211> LENGTH: 28
<212> TYPE: PRT
<213> ORGANISM: Artificial Sequence
<220> FEATURE:
<223> OTHER INFORMATION: Twin-Strep-tag

<400> SEQUENCE: 19

Trp Ser His Pro Gln Phe Glu Lys Gly Gly Gly Ser Gly Gly Gly Ser
1               5                   10                  15

Gly Gly Ser Ala Trp Ser His Pro Gln Phe Glu Lys
            20                  25

<210> SEQ ID NO 20
<211> LENGTH: 9
<212> TYPE: PRT
<213> ORGANISM: Artificial Sequence
<220> FEATURE:
<223> OTHER INFORMATION: HA-tag

<400> SEQUENCE: 20

Tyr Pro Tyr Asp Val Pro Asp Tyr Ala
1               5

<210> SEQ ID NO 21
<211> LENGTH: 11
<212> TYPE: PRT
<213> ORGANISM: Artificial Sequence
<220> FEATURE:
<223> OTHER INFORMATION: VSV-G-tag
```

```
<400> SEQUENCE: 21

Tyr Thr Asp Ile Glu Met Asn Arg Leu Gly Lys
1               5                   10

<210> SEQ ID NO 22
<211> LENGTH: 11
<212> TYPE: PRT
<213> ORGANISM: Artificial Sequence
<220> FEATURE:
<223> OTHER INFORMATION: HSV-tag

<400> SEQUENCE: 22

Gln Pro Glu Leu Ala Pro Glu Asp Pro Glu Asp
1               5                   10

<210> SEQ ID NO 23
<211> LENGTH: 10
<212> TYPE: PRT
<213> ORGANISM: Artificial Sequence
<220> FEATURE:
<223> OTHER INFORMATION: T7 epitope

<400> SEQUENCE: 23

Ala Ser Met Thr Gly Gly Gln Gln Met Gly
1               5                   10

<210> SEQ ID NO 24
<211> LENGTH: 10
<212> TYPE: PRT
<213> ORGANISM: Artificial Sequence
<220> FEATURE:
<223> OTHER INFORMATION: HSV epitope

<400> SEQUENCE: 24

Glu Gln Lys Leu Ile Ser Glu Glu Asp Leu
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Myc epitope

<400> SEQUENCE: 25

Glu Gln Lys Leu Ile Ser Glu Glu Asp Leu
1               5                   10

<210> SEQ ID NO 26
<211> LENGTH: 14
<212> TYPE: PRT
<213> ORGANISM: Artificial Sequence
<220> FEATURE:
<223> OTHER INFORMATION: V5-tag

<400> SEQUENCE: 26

Gly Lys Pro Ile Pro Asn Pro Leu Leu Gly Leu Asp Ser Thr
1               5                   10

<210> SEQ ID NO 27
<211> LENGTH: 126
<212> TYPE: PRT
<213> ORGANISM: Streptomyces avidinii
<220> FEATURE:
<223> OTHER INFORMATION: Mutein Streptavidin Val44-Thr45-Ala46-Arg47 and
      Glu117, Gly120, Try121 (mutein m1-9)
```

<400> SEQUENCE: 27

```
Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Glu Asn Ala Gly Tyr Ser Thr Leu Val
            100                 105                 110

Gly His Asp Thr Phe Thr Lys Val Lys Pro Ser Ala Ala Ser
        115                 120                 125
```

<210> SEQ ID NO 28
<211> LENGTH: 139
<212> TYPE: PRT
<213> ORGANISM: Streptomyces avidinii
<220> FEATURE:
<223> OTHER INFORMATION: Mutein Streptavidin Val44-Thr45-Ala46-Arg47 and
      Glu117, Gly120, Try121 (mutein m1-9)

<400> SEQUENCE: 28

```
Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Val Thr Ala Arg Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Glu Asn Ala Gly Tyr Ser Thr Leu Val Gly His Asp
        115                 120                 125

Thr Phe Thr Lys Val Lys Pro Ser Ala Ala Ser
        130                 135
```

<210> SEQ ID NO 29
<211> LENGTH: 253
<212> TYPE: PRT
<213> ORGANISM: Artificial Sequence
<220> FEATURE:
<223> OTHER INFORMATION: Variable Heavy chain of Fab fragment m13B8.2

<400> SEQUENCE: 29

```
Ala Met Gln Val Gln Leu Lys Gln Ser Gly Pro Gly Leu Val Gln Pro
1               5                   10                  15

Ser Gln Ser Leu Ser Ile Thr Cys Thr Val Ser Gly Phe Ser Leu Thr
```

```
            20                  25                  30
Thr Phe Gly Val His Trp Val Arg Gln Ser Pro Gly Lys Gly Leu Glu
        35                  40                  45

Trp Leu Gly Val Ile Trp Ala Ser Gly Ile Thr Asp Tyr Asn Val Pro
 50                  55                  60

Phe Met Ser Arg Leu Ser Ile Thr Lys Asp Asn Ser Lys Ser Gln Val
 65                  70                  75                  80

Phe Phe Lys Leu Asn Ser Leu Gln Pro Asp Asp Thr Ala Ile Tyr Tyr
                85                  90                  95

Cys Ala Lys Asn Asp Pro Gly Thr Gly Phe Ala Tyr Trp Gly Gln Gly
               100                 105                 110

Thr Leu Val Thr Val Ser Ala Gly Ser Thr Lys Gly Pro Ser Val Phe
               115                 120                 125

Pro Leu Ala Pro Ser Ser Lys Ser Thr Ser Gly Gly Thr Ala Ala Leu
               130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Gly Ser
                210                 215                 220

Ala Trp Ser His Pro Gln Phe Glu Lys Gly Gly Gly Ser Gly Gly Gly
225                 230                 235                 240

Ser Gly Gly Ser Ala Trp Ser His Pro Gln Phe Glu Lys
                245                 250

<210> SEQ ID NO 30
<211> LENGTH: 218
<212> TYPE: PRT
<213> ORGANISM: Artificial Sequence
<220> FEATURE:
<223> OTHER INFORMATION: Variable Light chain of Fab Fragment m13B8.2

<400> SEQUENCE: 30

Ala Met Asp Ile Gln Met Thr Gln Ser Pro Ala Ser Leu Ser Ala Ser
 1               5                  10                  15

Val Gly Glu Thr Val Thr Phe Thr Cys Arg Ala Ser Glu Met Ile Tyr
                20                  25                  30

Ser Tyr Leu Ala Trp Tyr Gln Gln Lys Gln Gly Lys Ser Pro Gln Leu
                35                  40                  45

Leu Val His Asp Ala Lys Thr Leu Ala Glu Gly Val Pro Ser Arg Phe
 50                  55                  60

Ser Gly Gly Gly Ser Gly Thr Gln Phe Ser Leu Lys Ile Asn Thr Leu
 65                  70                  75                  80

Gln Pro Glu Asp Phe Gly Thr Tyr Tyr Cys Gln Ala His Tyr Gly Asn
                85                  90                  95

Pro Pro Thr Phe Gly Gly Gly Thr Lys Leu Glu Ile Lys Arg Gly Ile
               100                 105                 110

Ala Ala Pro Ser Val Phe Ile Phe Pro Pro Ser Asp Glu Gln Leu Lys
               115                 120                 125

Ser Gly Thr Ala Ser Val Val Cys Leu Leu Asn Asn Phe Tyr Pro Arg
```

```
                130                 135                 140
Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
                180                 185                 190

Val Tyr Ala Cys Glu Val Thr His Gln Gly Leu Ser Ser Pro Val Thr
                195                 200                 205

Lys Ser Phe Asn Arg Gly Glu Cys Gly Ser
            210                 215

<210> SEQ ID NO 31
<211> LENGTH: 119
<212> TYPE: PRT
<213> ORGANISM: Artificial Sequence
<220> FEATURE:
<223> OTHER INFORMATION: Variable Heavy chain of anti-CD3 antibody OKT3

<400> SEQUENCE: 31

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
                100                 105                 110

Thr Thr Leu Thr Val Ser Ser
        115

<210> SEQ ID NO 32
<211> LENGTH: 106
<212> TYPE: PRT
<213> ORGANISM: Artificial Sequence
<220> FEATURE:
<223> OTHER INFORMATION: Variable Light chain of anti-CD3 antibody OKT3

<400> SEQUENCE: 32

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

Asn Trp Tyr Gln Gln Lys Ser Gly Thr Ser Pro Lys Arg Trp Ile Tyr
            35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95
```

Phe Gly Ser Gly Thr Lys Leu Glu Ile Asn
            100                 105

<210> SEQ ID NO 33
<211> LENGTH: 116
<212> TYPE: PRT
<213> ORGANISM: Artificial Sequence
<220> FEATURE:
<223> OTHER INFORMATION: Variable Heavy chain of anti-CD28 antibody
      CD28.3

<400> SEQUENCE: 33

Leu Gln Gln Ser Gly Ala Glu Leu Val Lys Pro Gly Ala Ser Val Arg
1               5                   10                  15

Leu Ser Cys Lys Ala Ser Gly Tyr Thr Phe Thr Glu Tyr Ile Ile His
            20                  25                  30

Trp Ile Lys Leu Arg Ser Gly Gln Gly Leu Glu Trp Ile Gly Trp Phe
        35                  40                  45

Tyr Pro Gly Ser Asn Asp Ile Gln Tyr Asn Ala Lys Phe Lys Gly Lys
    50                  55                  60

Ala Thr Leu Thr Ala Asp Lys Ser Ser Ser Thr Val Tyr Met Glu Leu
65                  70                  75                  80

Thr Gly Leu Thr Ser Glu Asp Ser Ala Val Tyr Phe Cys Ala Arg Arg
                85                  90                  95

Asp Asp Phe Ser Gly Tyr Asp Ala Leu Pro Tyr Trp Gly Gln Gly Thr
            100                 105                 110

Met Val Thr Val
        115

<210> SEQ ID NO 34
<211> LENGTH: 108
<212> TYPE: PRT
<213> ORGANISM: Artificial Sequence
<220> FEATURE:
<223> OTHER INFORMATION: Variable Light chain of anti-CD28 antibody
      CD28.3

<400> SEQUENCE: 34

Asp Ile Gln Met Thr Gln Ser Pro Ala Ser Leu Ser Val Ser Val Gly
1               5                   10                  15

Glu Thr Val Thr Ile Thr Cys Arg Thr Asn Glu Asn Ile Tyr Ser Asn
            20                  25                  30

Leu Ala Trp Tyr Gln Gln Lys Gln Gly Lys Ser Pro Gln Leu Leu Ile
        35                  40                  45

Tyr Ala Ala Thr His Leu Val Glu Gly Val Pro Ser Arg Phe Ser Gly
    50                  55                  60

Ser Gly Ser Gly Thr Gln Tyr Ser Leu Lys Ile Thr Ser Leu Gln Ser
65                  70                  75                  80

Glu Asp Phe Gly Asn Tyr Tyr Cys Gln His Phe Trp Gly Thr Pro Cys
                85                  90                  95

Thr Phe Gly Gly Gly Thr Lys Leu Glu Ile Lys Arg
            100                 105

<210> SEQ ID NO 35
<211> LENGTH: 112
<212> TYPE: PRT
<213> ORGANISM: Homo sapiens
<220> FEATURE:
<223> OTHER INFORMATION: CD3 zeta

<400> SEQUENCE: 35

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 36
<211> LENGTH: 112
<212> TYPE: PRT
<213> ORGANISM: Homo sapiens
<220> FEATURE:
<223> OTHER INFORMATION: CD3 zeta

<400> SEQUENCE: 36

Arg Val Lys Phe Ser Arg Ser Ala Glu Pro Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 37
<211> LENGTH: 112
<212> TYPE: PRT
<213> ORGANISM: Homo sapiens
<220> FEATURE:
<223> OTHER INFORMATION: CD3 zeta

<400> SEQUENCE: 37

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala

```
                    85                  90                  95

Thr Lys Asp Thr Tyr Asp Ala Leu His Met Gln Ala Leu Pro Pro Arg
                100                 105                 110

<210> SEQ ID NO 38
<211> LENGTH: 12
<212> TYPE: PRT
<213> ORGANISM: Homo sapiens
<220> FEATURE:
<223> OTHER INFORMATION: spacer (IgG4hinge)

<400> SEQUENCE: 38

Glu Ser Lys Tyr Gly Pro Pro Cys Pro Pro Cys Pro
1               5                   10

<210> SEQ ID NO 39
<211> LENGTH: 36
<212> TYPE: DNA
<213> ORGANISM: Homo sapiens
<220> FEATURE:
<223> OTHER INFORMATION: spacer (IgG4hinge)

<400> SEQUENCE: 39
gaatctaagt acggaccgcc ctgccccct tgccct                              36

<210> SEQ ID NO 40
<211> LENGTH: 119
<212> TYPE: PRT
<213> ORGANISM: Homo sapiens
<220> FEATURE:
<223> OTHER INFORMATION: Hinge-CH3 spacer

<400> SEQUENCE: 40

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
                20                  25                  30

Asn Gln Val Ser Leu Thr Cys Leu Val Lys Gly Phe Tyr Pro Ser Asp
                35                  40                  45

Ile Ala Val Glu Trp Glu Ser Asn Gly Gln Pro Glu Asn Asn Tyr Lys
        50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
                100                 105                 110

Leu Ser Leu Ser Leu Gly Lys
        115

<210> SEQ ID NO 41
<211> LENGTH: 229
<212> TYPE: PRT
<213> ORGANISM: Homo sapiens
<220> FEATURE:
<223> OTHER INFORMATION: Hinge-CH2-CH3 spacer

<400> SEQUENCE: 41

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
                20                  25                  30
```

```
Leu Met Ile Ser Arg Thr Pro Glu Val Thr Cys Val Val Asp Val
            35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Gln Gly Asn Val Phe Ser Cys Ser
            195                 200                 205

Val Met His Glu Ala Leu His Asn His Tyr Thr Gln Lys Ser Leu Ser
210                 215                 220

Leu Ser Leu Gly Lys
225

<210> SEQ ID NO 42
<211> LENGTH: 282
<212> TYPE: PRT
<213> ORGANISM: Homo sapiens
<220> FEATURE:
<223> OTHER INFORMATION: IgD-hinge-Fc

<400> SEQUENCE: 42

Arg Trp Pro Glu Ser Pro Lys Ala Gln Ala Ser Ser Val Pro Thr Ala
 1               5                  10                  15

Gln Pro Gln Ala Glu Gly Ser Leu Ala Lys Ala Thr Thr Ala Pro Ala
             20                  25                  30

Thr Thr Arg Asn Thr Gly Arg Gly Gly Glu Glu Lys Lys Lys Glu Lys
             35                  40                  45

Glu Lys Glu Glu Gln Glu Glu Arg Glu Thr Lys Thr Pro Glu Cys Pro
 50                  55                  60

Ser His Thr Gln Pro Leu Gly Val Tyr Leu Leu Thr Pro Ala Val Gln
 65                  70                  75                  80

Asp Leu Trp Leu Arg Asp Lys Ala Thr Phe Thr Cys Phe Val Val Gly
                 85                  90                  95

Ser Asp Leu Lys Asp Ala His Leu Thr Trp Glu Val Ala Gly Lys Val
            100                 105                 110

Pro Thr Gly Gly Val Glu Glu Gly Leu Leu Glu Arg His Ser Asn Gly
            115                 120                 125

Ser Gln Ser Gln His Ser Arg Leu Thr Leu Pro Arg Ser Leu Trp Asn
            130                 135                 140

Ala Gly Thr Ser Val Thr Cys Thr Leu Asn His Pro Ser Leu Pro Pro
145                 150                 155                 160
```

```
Gln Arg Leu Met Ala Leu Arg Glu Pro Ala Gln Ala Pro Val Lys
                165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
            195                 200                 205

Met Trp Leu Glu Asp Gln Arg Glu Val Asn Thr Ser Gly Phe Ala Pro
210                 215                 220

Ala Arg Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
                245                 250                 255

Cys Val Val Ser His Glu Asp Ser Arg Thr Leu Leu Asn Ala Ser Arg
                260                 265                 270

Ser Leu Glu Val Ser Tyr Val Thr Asp His
            275                 280

<210> SEQ ID NO 43
<211> LENGTH: 24
<212> TYPE: PRT
<213> ORGANISM: Artificial Sequence
<220> FEATURE:
<223> OTHER INFORMATION: T2A

<400> SEQUENCE: 43

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 44
<211> LENGTH: 357
<212> TYPE: PRT
<213> ORGANISM: Artificial Sequence
<220> FEATURE:
<223> OTHER INFORMATION: tEGFR

<400> SEQUENCE: 44

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
```

```
                145                 150                 155                 160
        Ala Asn Thr Ile Asn Trp Lys Lys Leu Phe Gly Thr Ser Gly Gln Lys
                        165                 170                 175

Thr Lys Ile Ile Ser Asn Arg Gly Glu Asn Ser Cys Lys Ala Thr Gly
                        180                 185                 190

Gln Val Cys His Ala Leu Cys Ser Pro Glu Gly Cys Trp Gly Pro Glu
                        195                 200                 205

Pro Arg Asp Cys Val Ser Cys Arg Asn Val Ser Arg Gly Arg Glu Cys
                        210                 215                 220

Val Asp Lys Cys Asn Leu Leu Glu Gly Glu Pro Arg Glu Phe Val Glu
        225                 230                 235                 240

Asn Ser Glu Cys Ile Gln Cys His Pro Glu Cys Leu Pro Gln Ala Met
                            245                 250                 255

Asn Ile Thr Cys Thr Gly Arg Gly Pro Asp Asn Cys Ile Gln Cys Ala
                        260                 265                 270

His Tyr Ile Asp Gly Pro His Cys Val Lys Thr Cys Pro Ala Gly Val
                    275                 280                 285

Met Gly Glu Asn Asn Thr Leu Val Trp Lys Tyr Ala Asp Ala Gly His
                290                 295                 300

Val Cys His Leu Cys His Pro Asn Cys Thr Tyr Gly Cys Thr Gly Pro
        305                 310                 315                 320

Gly Leu Glu Gly Cys Pro Thr Asn Gly Pro Lys Ile Pro Ser Ile Ala
                        325                 330                 335

Thr Gly Met Val Gly Ala Leu Leu Leu Leu Leu Val Val Ala Leu Gly
                        340                 345                 350

Ile Gly Leu Phe Met
                    355

<210> SEQ ID NO 45
<211> LENGTH: 1071
<212> TYPE: DNA
<213> ORGANISM: Artificial Sequence
<220> FEATURE:
<223> OTHER INFORMATION: tEGFR

<400> SEQUENCE: 45
atgcttctcc tggtgacaag ccttctgctc tgtgagttac cacacccagc attcctcctg     60
atcccacgca aagtgtgtaa cggaataggt attggtgaat ttaaagactc actctccata    120
aatgctacga atattaaaca cttcaaaaac tgcacctcca tcagtggcga tctccacatc    180
ctgccggtgg catttagggg tgactccttc acacatactc ctcctctgga tccacaggaa    240
ctggatattc tgaaaaccgt aaaggaaatc acagggtttt gctgattca ggcttggcct    300
gaaaacagga cggacctcca tgcctttgag aacctagaaa tcatacgcgg caggaccaag    360
caacatggtc agttttctct tgcagtcgtc agcctgaaca taacatcctt gggattacgc    420
tccctcaagg ataagtga tggagatgtg ataatttcag gaaacaaaaa tttgtgctat    480
gcaaatacaa taaactggaa aaaactgttt gggacctccg gtcagaaaac caaaattata    540
agcaacagag gtgaaaacag ctgcaaggcc acaggccagg tctgccatgc cttgtgctcc    600
cccgagggct gctgggccc ggagcccagg gactgcgtct cttgccggaa tgtcagccga    660
ggcagggaat gcgtggacaa gtgcaacctt ctggagggtg agccaaggga gtttgtggag    720
aactctgagt gcatacagtg ccacccagag tgcctgcctc aggccatgaa catcacctgc    780
acaggacggg gaccagacaa ctgtatccag tgtgcccact acattgacgg cccccactgc    840
```

```
gtcaagacct gcccggcagg agtcatggga gaaaacaaca ccctggtctg gaagtacgca      900
gacgccggcc atgtgtgcca cctgtgccat ccaaactgca cctacggatg cactgggcca      960
ggtcttgaag gctgtccaac gaatgggcct aagatcccgt ccatcgccac tgggatggtg     1020
ggggccctcc tcttgctgct ggtggtggcc ctggggatcg gcctcttcat g             1071
```

<210> SEQ ID NO 46
<211> LENGTH: 335
<212> TYPE: PRT
<213> ORGANISM: Artificial Sequence
<220> FEATURE:
<223> OTHER INFORMATION: tEGFR

<400> SEQUENCE: 46

```
Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
    290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
```

<210> SEQ ID NO 47
<211> LENGTH: 66
<212> TYPE: DNA
<213> ORGANISM: Homo sapiens
<220> FEATURE:
<223> OTHER INFORMATION: GMCSFR alpha chain signal sequence

<400> SEQUENCE: 47
atgcttctcc tggtgacaag ccttctgctc tgtgagttac cacacccagc attcctcctg    60
atccca    66

<210> SEQ ID NO 48
<211> LENGTH: 22
<212> TYPE: PRT
<213> ORGANISM: Homo sapiens
<220> FEATURE:
<223> OTHER INFORMATION: GMCSFR alpha chain signal sequence

<400> SEQUENCE: 48

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 49
<211> LENGTH: 1186
<212> TYPE: PRT
<213> ORGANISM: Homo sapiens
<220> FEATURE:
<223> OTHER INFORMATION: HER1/ErbB1/EGFR Full Length (mature)
<300> PUBLICATION INFORMATION:
<308> DATABASE ACCESSION NUMBER: Uniprot No. P00533
<309> DATABASE ENTRY DATE: 1986-07-21

<400> SEQUENCE: 49

Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
            20                  25                  30

Asn Cys Glu Val Val Leu Gly Asn Leu Glu Ile Thr Tyr Val Gln Arg
        35                  40                  45

Asn Tyr Asp Leu Ser Phe Leu Lys Thr Ile Gln Glu Val Ala Gly Tyr
    50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
    130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala

```
                180                 185                 190
Gln Gln Cys Ser Gly Arg Cys Arg Gly Lys Ser Pro Ser Asp Cys Cys
            195                 200                 205

His Asn Gln Cys Ala Ala Gly Cys Thr Gly Pro Arg Glu Ser Asp Cys
    210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
            260                 265                 270

Arg Asn Tyr Val Val Thr Asp His Gly Ser Cys Val Arg Ala Cys Gly
        275                 280                 285

Ala Asp Ser Tyr Glu Met Glu Glu Asp Gly Val Arg Lys Cys Lys Lys
    290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
                325                 330                 335

Asn Cys Thr Ser Ile Ser Gly Asp Leu His Ile Leu Pro Val Ala Phe
            340                 345                 350

Arg Gly Asp Ser Phe Thr His Thr Pro Pro Leu Asp Pro Gln Glu Leu
        355                 360                 365

Asp Ile Leu Lys Thr Val Lys Glu Ile Thr Gly Phe Leu Leu Ile Gln
    370                 375                 380

Ala Trp Pro Glu Asn Arg Thr Asp Leu His Ala Phe Glu Asn Leu Glu
385                 390                 395                 400

Ile Ile Arg Gly Arg Thr Lys Gln His Gly Gln Phe Ser Leu Ala Val
                405                 410                 415

Val Ser Leu Asn Ile Thr Ser Leu Gly Leu Arg Ser Leu Lys Glu Ile
            420                 425                 430

Ser Asp Gly Asp Val Ile Ile Ser Gly Asn Lys Asn Leu Cys Tyr Ala
        435                 440                 445

Asn Thr Ile Asn Trp Lys Lys Leu Phe Gly Thr Ser Gly Gln Lys Thr
    450                 455                 460

Lys Ile Ile Ser Asn Arg Gly Glu Asn Ser Cys Lys Ala Thr Gly Gln
465                 470                 475                 480

Val Cys His Ala Leu Cys Ser Pro Glu Gly Cys Trp Gly Pro Glu Pro
                485                 490                 495

Arg Asp Cys Val Ser Cys Arg Asn Val Ser Arg Gly Arg Glu Cys Val
            500                 505                 510

Asp Lys Cys Asn Leu Leu Glu Gly Glu Pro Arg Glu Phe Val Glu Asn
        515                 520                 525

Ser Glu Cys Ile Gln Cys His Pro Glu Cys Leu Pro Gln Ala Met Asn
    530                 535                 540

Ile Thr Cys Thr Gly Arg Gly Pro Asp Asn Cys Ile Gln Cys Ala His
545                 550                 555                 560

Tyr Ile Asp Gly Pro His Cys Val Lys Thr Cys Pro Ala Gly Val Met
                565                 570                 575

Gly Glu Asn Asn Thr Leu Val Trp Lys Tyr Ala Asp Ala Gly His Val
            580                 585                 590

Cys His Leu Cys His Pro Asn Cys Thr Tyr Gly Cys Thr Gly Pro Gly
        595                 600                 605
```

```
Leu Glu Gly Cys Pro Thr Asn Gly Pro Lys Ile Pro Ser Ile Ala Thr
610                 615                 620

Gly Met Val Gly Ala Leu Leu Leu Leu Val Val Ala Leu Gly Ile
625                 630                 635                 640

Gly Leu Phe Met Arg Arg His Ile Val Arg Lys Arg Thr Leu Arg
            645                 650                 655

Arg Leu Leu Gln Glu Arg Glu Leu Val Glu Pro Leu Thr Pro Ser Gly
                660                 665                 670

Glu Ala Pro Asn Gln Ala Leu Leu Arg Ile Leu Lys Glu Thr Glu Phe
            675                 680                 685

Lys Lys Ile Lys Val Leu Gly Ser Gly Ala Phe Gly Thr Val Tyr Lys
690                 695                 700

Gly Leu Trp Ile Pro Glu Gly Glu Lys Val Lys Ile Pro Val Ala Ile
705                 710                 715                 720

Lys Glu Leu Arg Glu Ala Thr Ser Pro Lys Ala Asn Lys Glu Ile Leu
                725                 730                 735

Asp Glu Ala Tyr Val Met Ala Ser Val Asp Asn Pro His Val Cys Arg
                740                 745                 750

Leu Leu Gly Ile Cys Leu Thr Ser Thr Val Gln Leu Ile Thr Gln Leu
            755                 760                 765

Met Pro Phe Gly Cys Leu Leu Asp Tyr Val Arg Glu His Lys Asp Asn
770                 775                 780

Ile Gly Ser Gln Tyr Leu Leu Asn Trp Cys Val Gln Ile Ala Lys Gly
785                 790                 795                 800

Met Asn Tyr Leu Glu Asp Arg Arg Leu Val His Arg Asp Leu Ala Ala
                805                 810                 815

Arg Asn Val Leu Val Lys Thr Pro Gln His Val Lys Ile Thr Asp Phe
                820                 825                 830

Gly Leu Ala Lys Leu Leu Gly Ala Glu Glu Lys Glu Tyr His Ala Glu
            835                 840                 845

Gly Gly Lys Val Pro Ile Lys Trp Met Ala Leu Glu Ser Ile Leu His
850                 855                 860

Arg Ile Tyr Thr His Gln Ser Asp Val Trp Ser Tyr Gly Val Thr Val
865                 870                 875                 880

Trp Glu Leu Met Thr Phe Gly Ser Lys Pro Tyr Asp Gly Ile Pro Ala
                885                 890                 895

Ser Glu Ile Ser Ser Ile Leu Glu Lys Gly Glu Arg Leu Pro Gln Pro
            900                 905                 910

Pro Ile Cys Thr Ile Asp Val Tyr Met Ile Met Val Lys Cys Trp Met
            915                 920                 925

Ile Asp Ala Asp Ser Arg Pro Lys Phe Arg Glu Leu Ile Ile Glu Phe
930                 935                 940

Ser Lys Met Ala Arg Asp Pro Gln Arg Tyr Leu Val Ile Gln Gly Asp
945                 950                 955                 960

Glu Arg Met His Leu Pro Ser Pro Thr Asp Ser Asn Phe Tyr Arg Ala
                965                 970                 975

Leu Met Asp Glu Glu Asp Met Asp Asp Val Val Asp Ala Asp Glu Tyr
            980                 985                 990

Leu Ile Pro Gln Gln Gly Phe Phe Ser Ser Pro Ser Thr Ser Arg Thr
            995                 1000                1005

Pro Leu Leu Ser Ser Leu Ser Ala Thr Ser Asn Asn Ser Thr Val Ala
    1010                1015                1020
```

-continued

```
Cys Ile Asp Arg Asn Gly Leu Gln Ser Cys Pro Ile Lys Glu Asp Ser
1025                1030                1035                1040

Phe Leu Gln Arg Tyr Ser Ser Asp Pro Thr Gly Ala Leu Thr Glu Asp
                1045                1050                1055

Ser Ile Asp Asp Thr Phe Leu Pro Val Pro Glu Tyr Ile Asn Gln Ser
            1060                1065                1070

Val Pro Lys Arg Pro Ala Gly Ser Val Gln Asn Pro Val Tyr His Asn
        1075                1080                1085

Gln Pro Leu Asn Pro Ala Pro Ser Arg Asp Pro His Tyr Gln Asp Pro
    1090                1095                1100

His Ser Thr Ala Val Gly Asn Pro Glu Tyr Leu Asn Thr Val Gln Pro
1105                1110                1115                1120

Thr Cys Val Asn Ser Thr Phe Asp Ser Pro Ala His Trp Ala Gln Lys
                1125                1130                1135

Gly Ser His Gln Ile Ser Leu Asp Asn Pro Asp Tyr Gln Gln Asp Phe
            1140                1145                1150

Phe Pro Lys Glu Ala Lys Pro Asn Gly Ile Phe Lys Gly Ser Thr Ala
        1155                1160                1165

Glu Asn Ala Glu Tyr Leu Arg Val Ala Pro Gln Ser Ser Glu Phe Ile
    1170                1175                1180

Gly Ala
1185

<210> SEQ ID NO 50
<211> LENGTH: 1233
<212> TYPE: PRT
<213> ORGANISM: Homo sapiens
<220> FEATURE:
<223> OTHER INFORMATION: HER2/neu/ErbB2 Full Length (mature)
<300> PUBLICATION INFORMATION:
<308> DATABASE ACCESSION NUMBER: UniProt No. P04626
<309> DATABASE ENTRY DATE: 1987-08-13

<400> SEQUENCE: 50

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
                20                  25                  30

Val Val Gln Gly Asn Leu Glu Leu Thr Tyr Leu Pro Thr Asn Ala Ser
            35                  40                  45

Leu Ser Phe Leu Gln Asp Ile Gln Glu Val Gln Gly Tyr Val Leu Ile
        50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175
```

```
Cys Lys Gly Ser Arg Cys Trp Gly Glu Ser Ser Glu Asp Cys Gln Ser
                180                 185                 190
Leu Thr Arg Thr Val Cys Ala Gly Gly Cys Ala Arg Cys Lys Gly Pro
            195                 200                 205
Leu Pro Thr Asp Cys Cys His Glu Gln Cys Ala Ala Gly Cys Thr Gly
        210                 215                 220
Pro Lys His Ser Asp Cys Leu Ala Cys Leu His Phe Asn His Ser Gly
225                 230                 235                 240
Ile Cys Glu Leu His Cys Pro Ala Leu Val Thr Tyr Asn Thr Asp Thr
                245                 250                 255
Phe Glu Ser Met Pro Asn Pro Glu Gly Arg Tyr Thr Phe Gly Ala Ser
            260                 265                 270
Cys Val Thr Ala Cys Pro Tyr Asn Tyr Leu Ser Thr Asp Val Gly Ser
        275                 280                 285
Cys Thr Leu Val Cys Pro Leu His Asn Gln Glu Val Thr Ala Glu Asp
    290                 295                 300
Gly Thr Gln Arg Cys Glu Lys Cys Ser Lys Pro Cys Ala Arg Val Cys
305                 310                 315                 320
Tyr Gly Leu Gly Met Glu His Leu Arg Glu Val Arg Ala Val Thr Ser
                325                 330                 335
Ala Asn Ile Gln Glu Phe Ala Gly Cys Lys Lys Ile Phe Gly Ser Leu
            340                 345                 350
Ala Phe Leu Pro Glu Ser Phe Asp Gly Asp Pro Ala Ser Asn Thr Ala
        355                 360                 365
Pro Leu Gln Pro Glu Gln Leu Gln Val Phe Glu Thr Leu Glu Glu Ile
    370                 375                 380
Thr Gly Tyr Leu Tyr Ile Ser Ala Trp Pro Asp Ser Leu Pro Asp Leu
385                 390                 395                 400
Ser Val Phe Gln Asn Leu Gln Val Ile Arg Gly Arg Ile Leu His Asn
                405                 410                 415
Gly Ala Tyr Ser Leu Thr Leu Gln Gly Leu Gly Ile Ser Trp Leu Gly
            420                 425                 430
Leu Arg Ser Leu Arg Glu Leu Gly Ser Gly Leu Ala Leu Ile His His
        435                 440                 445
Asn Thr His Leu Cys Phe Val His Thr Val Pro Trp Asp Gln Leu Phe
    450                 455                 460
Arg Asn Pro His Gln Ala Leu Leu His Thr Ala Asn Arg Pro Glu Asp
465                 470                 475                 480
Glu Cys Val Gly Glu Gly Leu Ala Cys His Gln Leu Cys Ala Arg Gly
                485                 490                 495
His Cys Trp Gly Pro Gly Pro Thr Gln Cys Val Asn Cys Ser Gln Phe
            500                 505                 510
Leu Arg Gly Gln Glu Cys Val Glu Glu Cys Arg Val Leu Gln Gly Leu
        515                 520                 525
Pro Arg Glu Tyr Val Asn Ala Arg His Cys Leu Pro Cys His Pro Glu
    530                 535                 540
Cys Gln Pro Gln Asn Gly Ser Val Thr Cys Phe Gly Pro Glu Ala Asp
545                 550                 555                 560
Gln Cys Val Ala Cys Ala His Tyr Lys Asp Pro Pro Phe Cys Val Ala
                565                 570                 575
Arg Cys Pro Ser Gly Val Lys Pro Asp Leu Ser Tyr Met Pro Ile Trp
            580                 585                 590
Lys Phe Pro Asp Glu Glu Gly Ala Cys Gln Pro Cys Pro Ile Asn Cys
```

-continued

```
                595                 600                 605
Thr His Ser Cys Val Asp Leu Asp Asp Lys Gly Cys Pro Ala Glu Gln
610                 615                 620

Arg Ala Ser Pro Leu Thr Ser Ile Ile Ser Ala Val Val Gly Ile Leu
625                 630                 635                 640

Leu Val Val Val Leu Gly Val Val Phe Gly Ile Leu Ile Lys Arg Arg
                645                 650                 655

Gln Gln Lys Ile Arg Lys Tyr Thr Met Arg Arg Leu Leu Gln Glu Thr
            660                 665                 670

Glu Leu Val Glu Pro Leu Thr Pro Ser Gly Ala Met Pro Asn Gln Ala
        675                 680                 685

Gln Met Arg Ile Leu Lys Glu Thr Glu Leu Arg Lys Val Lys Val Leu
690                 695                 700

Gly Ser Gly Ala Phe Gly Thr Val Tyr Lys Gly Ile Trp Ile Pro Asp
705                 710                 715                 720

Gly Glu Asn Val Lys Ile Pro Val Ala Ile Lys Val Leu Arg Glu Asn
                725                 730                 735

Thr Ser Pro Lys Ala Asn Lys Glu Ile Leu Asp Glu Ala Tyr Val Met
            740                 745                 750

Ala Gly Val Gly Ser Pro Tyr Val Ser Arg Leu Leu Gly Ile Cys Leu
        755                 760                 765

Thr Ser Thr Val Gln Leu Val Thr Gln Leu Met Pro Tyr Gly Cys Leu
770                 775                 780

Leu Asp His Val Arg Glu Asn Arg Gly Arg Leu Gly Ser Gln Asp Leu
785                 790                 795                 800

Leu Asn Trp Cys Met Gln Ile Ala Lys Gly Met Ser Tyr Leu Glu Asp
                805                 810                 815

Val Arg Leu Val His Arg Asp Leu Ala Ala Arg Asn Val Leu Val Lys
            820                 825                 830

Ser Pro Asn His Val Lys Ile Thr Asp Phe Gly Leu Ala Arg Leu Leu
        835                 840                 845

Asp Ile Asp Glu Thr Glu Tyr His Ala Asp Gly Gly Lys Val Pro Ile
850                 855                 860

Lys Trp Met Ala Leu Glu Ser Ile Leu Arg Arg Arg Phe Thr His Gln
865                 870                 875                 880

Ser Asp Val Trp Ser Tyr Gly Val Thr Val Trp Glu Leu Met Thr Phe
                885                 890                 895

Gly Ala Lys Pro Tyr Asp Gly Ile Pro Ala Arg Glu Ile Pro Asp Leu
            900                 905                 910

Leu Glu Lys Gly Glu Arg Leu Pro Gln Pro Ile Cys Thr Ile Asp
        915                 920                 925

Val Tyr Met Ile Met Val Lys Cys Trp Met Ile Asp Ser Glu Cys Arg
930                 935                 940

Pro Arg Phe Arg Glu Leu Val Ser Glu Phe Ser Arg Met Ala Arg Asp
945                 950                 955                 960

Pro Gln Arg Phe Val Val Ile Gln Asn Glu Asp Leu Gly Pro Ala Ser
                965                 970                 975

Pro Leu Asp Ser Thr Phe Tyr Arg Ser Leu Leu Glu Asp Asp Asp Met
            980                 985                 990

Gly Asp Leu Val Asp Ala Glu Glu Tyr Leu Val Pro Gln Gln Gly Phe
        995                 1000                1005

Phe Cys Pro Asp Pro Ala Pro Gly Ala Gly Gly Met Val His His Arg
1010                1015                1020
```

-continued

```
His Arg Ser Ser Ser Thr Arg Ser Gly Gly Gly Asp Leu Thr Leu Gly
1025                1030                1035                1040

Leu Glu Pro Ser Glu Glu Ala Pro Arg Ser Pro Leu Ala Pro Ser
            1045                1050                1055

Glu Gly Ala Gly Ser Asp Val Phe Asp Gly Asp Leu Gly Met Gly Ala
        1060                1065                1070

Ala Lys Gly Leu Gln Ser Leu Pro Thr His Asp Pro Ser Pro Leu Gln
    1075                1080                1085

Arg Tyr Ser Glu Asp Pro Thr Val Pro Leu Pro Ser Glu Thr Asp Gly
        1090                1095                1100

Tyr Val Ala Pro Leu Thr Cys Ser Pro Gln Pro Glu Tyr Val Asn Gln
1105                1110                1115                1120

Pro Asp Val Arg Pro Gln Pro Pro Ser Pro Arg Glu Gly Pro Leu Pro
                1125                1130                1135

Ala Ala Arg Pro Ala Gly Ala Thr Leu Glu Arg Pro Lys Thr Leu Ser
            1140                1145                1150

Pro Gly Lys Asn Gly Val Val Lys Asp Val Phe Ala Phe Gly Gly Ala
        1155                1160                1165

Val Glu Asn Pro Glu Tyr Leu Thr Pro Gln Gly Gly Ala Ala Pro Gln
    1170                1175                1180

Pro His Pro Pro Pro Ala Phe Ser Pro Ala Phe Asp Asn Leu Tyr Tyr
1185                1190                1195                1200

Trp Asp Gln Asp Pro Pro Glu Arg Gly Ala Pro Pro Ser Thr Phe Lys
                1205                1210                1215

Gly Thr Pro Thr Ala Glu Asn Pro Glu Tyr Leu Gly Leu Asp Val Pro
            1220                1225                1230

Val

<210> SEQ ID NO 51
<211> LENGTH: 1323
<212> TYPE: PRT
<213> ORGANISM: Homo sapiens
<220> FEATURE:
<223> OTHER INFORMATION: HER3/ErbB3 Full Length (mature)
<300> PUBLICATION INFORMATION:
<308> DATABASE ACCESSION NUMBER: UniProt No. P21860
<309> DATABASE ENTRY DATE: 1991-05-01

<400> SEQUENCE: 51

Ser Glu Val Gly Asn Ser Gln Ala Val Cys Pro Gly Thr Leu Asn Gly
1               5                   10                  15

Leu Ser Val Thr Gly Asp Ala Glu Asn Gln Tyr Gln Thr Leu Tyr Lys
            20                  25                  30

Leu Tyr Glu Arg Cys Glu Val Val Met Gly Asn Leu Glu Ile Val Leu
        35                  40                  45

Thr Gly His Asn Ala Asp Leu Ser Phe Leu Gln Trp Ile Arg Glu Val
    50                  55                  60

Thr Gly Tyr Val Leu Val Ala Met Asn Glu Phe Ser Thr Leu Pro Leu
65                  70                  75                  80

Pro Asn Leu Arg Val Val Arg Gly Thr Gln Val Tyr Asp Gly Lys Phe
                85                  90                  95

Ala Ile Phe Val Met Leu Asn Tyr Asn Thr Asn Ser Ser His Ala Leu
            100                 105                 110

Arg Gln Leu Arg Leu Thr Gln Leu Thr Glu Ile Leu Ser Gly Gly Val
        115                 120                 125
```

```
Tyr Ile Glu Lys Asn Asp Lys Leu Cys His Met Asp Thr Ile Asp Trp
    130                 135                 140
Arg Asp Ile Val Arg Asp Arg Asp Ala Glu Ile Val Lys Asp Asn
145                 150                 155                 160
Gly Arg Ser Cys Pro Pro Cys His Glu Val Cys Lys Gly Arg Cys Trp
                165                 170                 175
Gly Pro Gly Ser Glu Asp Cys Gln Thr Leu Thr Lys Thr Ile Cys Ala
                180                 185                 190
Pro Gln Cys Asn Gly His Cys Phe Gly Pro Asn Pro Asn Gln Cys Cys
            195                 200                 205
His Asp Glu Cys Ala Gly Gly Cys Ser Gly Pro Gln Asp Thr Asp Cys
    210                 215                 220
Phe Ala Cys Arg His Phe Asn Asp Ser Gly Ala Cys Val Pro Arg Cys
225                 230                 235                 240
Pro Gln Pro Leu Val Tyr Asn Lys Leu Thr Phe Gln Leu Glu Pro Asn
                245                 250                 255
Pro His Thr Lys Tyr Gln Tyr Gly Gly Val Cys Val Ala Ser Cys Pro
            260                 265                 270
His Asn Phe Val Val Asp Gln Thr Ser Cys Val Arg Ala Cys Pro Pro
    275                 280                 285
Asp Lys Met Glu Val Asp Lys Asn Gly Leu Lys Met Cys Glu Pro Cys
290                 295                 300
Gly Gly Leu Cys Pro Lys Ala Cys Glu Gly Thr Gly Ser Gly Ser Arg
305                 310                 315                 320
Phe Gln Thr Val Asp Ser Ser Asn Ile Asp Gly Phe Val Asn Cys Thr
                325                 330                 335
Lys Ile Leu Gly Asn Leu Asp Phe Leu Ile Thr Gly Leu Asn Gly Asp
                340                 345                 350
Pro Trp His Lys Ile Pro Ala Leu Asp Pro Glu Lys Leu Asn Val Phe
            355                 360                 365
Arg Thr Val Arg Glu Ile Thr Gly Tyr Leu Asn Ile Gln Ser Trp Pro
    370                 375                 380
Pro His Met His Asn Phe Ser Val Phe Ser Asn Leu Thr Thr Ile Gly
385                 390                 395                 400
Gly Arg Ser Leu Tyr Asn Arg Gly Phe Ser Leu Leu Ile Met Lys Asn
                405                 410                 415
Leu Asn Val Thr Ser Leu Gly Phe Arg Ser Leu Lys Glu Ile Ser Ala
                420                 425                 430
Gly Arg Ile Tyr Ile Ser Ala Asn Arg Gln Leu Cys Tyr His His Ser
            435                 440                 445
Leu Asn Trp Thr Lys Val Leu Arg Gly Pro Thr Glu Glu Arg Leu Asp
    450                 455                 460
Ile Lys His Asn Arg Pro Arg Arg Asp Cys Val Ala Glu Gly Lys Val
465                 470                 475                 480
Cys Asp Pro Leu Cys Ser Ser Gly Gly Cys Trp Gly Pro Gly Pro Gly
                485                 490                 495
Gln Cys Leu Ser Cys Arg Asn Tyr Ser Arg Gly Gly Val Cys Val Thr
                500                 505                 510
His Cys Asn Phe Leu Asn Gly Glu Pro Arg Glu Phe Ala His Glu Ala
            515                 520                 525
Glu Cys Phe Ser Cys His Pro Glu Cys Gln Pro Met Glu Gly Thr Ala
    530                 535                 540
Thr Cys Asn Gly Ser Gly Ser Asp Thr Cys Ala Gln Cys Ala His Phe
```

```
            545                 550                 555                 560
        Arg Asp Gly Pro His Cys Val Ser Ser Cys Pro His Gly Val Leu Gly
                        565                 570                 575
        Ala Lys Gly Pro Ile Tyr Lys Tyr Pro Asp Val Gln Asn Glu Cys Arg
                        580                 585                 590
        Pro Cys His Glu Asn Cys Thr Gln Gly Cys Lys Gly Pro Glu Leu Gln
                        595                 600                 605
        Asp Cys Leu Gly Gln Thr Leu Val Leu Ile Gly Lys Thr His Leu Thr
                        610                 615                 620
        Met Ala Leu Thr Val Ile Ala Gly Leu Val Val Ile Phe Met Met Leu
        625                 630                 635                 640
        Gly Gly Thr Phe Leu Tyr Trp Arg Gly Arg Arg Ile Gln Asn Lys Arg
                        645                 650                 655
        Ala Met Arg Arg Tyr Leu Glu Arg Gly Glu Ser Ile Glu Pro Leu Asp
                        660                 665                 670
        Pro Ser Glu Lys Ala Asn Lys Val Leu Ala Arg Ile Phe Lys Glu Thr
                        675                 680                 685
        Glu Leu Arg Lys Leu Lys Val Leu Gly Ser Gly Val Phe Gly Thr Val
                        690                 695                 700
        His Lys Gly Val Trp Ile Pro Glu Gly Glu Ser Ile Lys Ile Pro Val
        705                 710                 715                 720
        Cys Ile Lys Val Ile Glu Asp Lys Ser Gly Arg Gln Ser Phe Gln Ala
                        725                 730                 735
        Val Thr Asp His Met Leu Ala Ile Gly Ser Leu Asp His Ala His Ile
                        740                 745                 750
        Val Arg Leu Leu Gly Leu Cys Pro Gly Ser Ser Leu Gln Leu Val Thr
                        755                 760                 765
        Gln Tyr Leu Pro Leu Gly Ser Leu Leu Asp His Val Arg Gln His Arg
                        770                 775                 780
        Gly Ala Leu Gly Pro Gln Leu Leu Leu Asn Trp Gly Val Gln Ile Ala
        785                 790                 795                 800
        Lys Gly Met Tyr Tyr Leu Glu Glu His Gly Met Val His Arg Asn Leu
                        805                 810                 815
        Ala Ala Arg Asn Val Leu Leu Lys Ser Pro Ser Gln Val Gln Val Ala
                        820                 825                 830
        Asp Phe Gly Val Ala Asp Leu Leu Pro Pro Asp Lys Gln Leu Leu
                        835                 840                 845
        Tyr Ser Glu Ala Lys Thr Pro Ile Lys Trp Met Ala Leu Glu Ser Ile
        850                 855                 860
        His Phe Gly Lys Tyr Thr His Gln Ser Asp Val Trp Ser Tyr Gly Val
        865                 870                 875                 880
        Thr Val Trp Glu Leu Met Thr Phe Gly Ala Glu Pro Tyr Ala Gly Leu
                        885                 890                 895
        Arg Leu Ala Glu Val Pro Asp Leu Leu Glu Lys Gly Glu Arg Leu Ala
                        900                 905                 910
        Gln Pro Gln Ile Cys Thr Ile Asp Val Tyr Met Val Met Val Lys Cys
                        915                 920                 925
        Trp Met Ile Asp Glu Asn Ile Arg Pro Thr Phe Lys Glu Leu Ala Asn
                        930                 935                 940
        Glu Phe Thr Arg Met Ala Arg Asp Pro Arg Tyr Leu Val Ile Lys
        945                 950                 955                 960
        Arg Glu Ser Gly Pro Gly Ile Ala Pro Gly Pro Glu Pro His Gly Leu
                        965                 970                 975
```

-continued

Thr Asn Lys Lys Leu Glu Val Glu Leu Glu Pro Glu Leu Asp Leu
            980             985              990

Asp Leu Asp Leu Glu Ala Glu Asp Asn Leu Ala Thr Thr Thr Leu
        995              1000             1005

Gly Ser Ala Leu Ser Leu Pro Val Gly Thr Leu Asn Arg Pro Arg Gly
        1010             1015             1020

Ser Gln Ser Leu Leu Ser Pro Ser Ser Gly Tyr Met Pro Met Asn Gln
1025             1030             1035             1040

Gly Asn Leu Gly Glu Ser Cys Gln Glu Ser Ala Val Ser Gly Ser Ser
             1045             1050             1055

Glu Arg Cys Pro Arg Pro Val Ser Leu His Pro Met Pro Arg Gly Cys
        1060             1065             1070

Leu Ala Ser Glu Ser Ser Glu Gly His Val Thr Gly Ser Glu Ala Glu
        1075             1080             1085

Leu Gln Glu Lys Val Ser Met Cys Arg Ser Arg Ser Arg Ser Arg Ser
    1090             1095             1100

Pro Arg Pro Arg Gly Asp Ser Ala Tyr His Ser Gln Arg His Ser Leu
1105             1110             1115             1120

Leu Thr Pro Val Thr Pro Leu Ser Pro Pro Gly Leu Glu Glu Glu Asp
             1125             1130             1135

Val Asn Gly Tyr Val Met Pro Asp Thr His Leu Lys Gly Thr Pro Ser
        1140             1145             1150

Ser Arg Glu Gly Thr Leu Ser Ser Val Gly Leu Ser Ser Val Leu Gly
            1155             1160             1165

Thr Glu Glu Glu Asp Glu Asp Glu Glu Tyr Glu Tyr Met Asn Arg Arg
        1170             1175             1180

Arg Arg His Ser Pro Pro His Pro Pro Arg Pro Ser Ser Leu Glu Glu
1185             1190             1195             1200

Leu Gly Tyr Glu Tyr Met Asp Val Gly Ser Asp Leu Ser Ala Ser Leu
             1205             1210             1215

Gly Ser Thr Gln Ser Cys Pro Leu His Pro Val Pro Ile Met Pro Thr
        1220             1225             1230

Ala Gly Thr Thr Pro Asp Glu Asp Tyr Glu Tyr Met Asn Arg Gln Arg
        1235             1240             1245

Asp Gly Gly Gly Pro Gly Gly Asp Tyr Ala Ala Met Gly Ala Cys Pro
1250             1255             1260

Ala Ser Glu Gln Gly Tyr Glu Glu Met Arg Ala Phe Gln Gly Pro Gly
1265             1270             1275             1280

His Gln Ala Pro His Val His Tyr Ala Arg Leu Lys Thr Leu Arg Ser
             1285             1290             1295

Leu Glu Ala Thr Asp Ser Ala Phe Asp Asn Pro Asp Tyr Trp His Ser
        1300             1305             1310

Arg Leu Phe Pro Lys Ala Asn Ala Gln Arg Thr
        1315             1320

<210> SEQ ID NO 52
<211> LENGTH: 1283
<212> TYPE: PRT
<213> ORGANISM: Homo sapiens
<220> FEATURE:
<223> OTHER INFORMATION: HER4/ErbB4 Full Length (mature)
<300> PUBLICATION INFORMATION:
<308> DATABASE ACCESSION NUMBER: UniProt No. Q15303
<309> DATABASE ENTRY DATE: 1998-12-15

<400> SEQUENCE: 52

```
Gln Ser Val Cys Ala Gly Thr Glu Asn Lys Leu Ser Ser Leu Ser Asp
1               5                   10                  15

Leu Glu Gln Gln Tyr Arg Ala Leu Arg Lys Tyr Tyr Glu Asn Cys Glu
            20                  25                  30

Val Val Met Gly Asn Leu Glu Ile Thr Ser Ile Glu His Asn Arg Asp
            35                  40                  45

Leu Ser Phe Leu Arg Ser Val Arg Glu Val Thr Gly Tyr Val Leu Val
    50                  55                  60

Ala Leu Asn Gln Phe Arg Tyr Leu Pro Leu Glu Asn Leu Arg Ile Ile
65                  70                  75                  80

Arg Gly Thr Lys Leu Tyr Glu Asp Arg Tyr Ala Leu Ala Ile Phe Leu
                85                  90                  95

Asn Tyr Arg Lys Asp Gly Asn Phe Gly Leu Gln Glu Leu Gly Leu Lys
            100                 105                 110

Asn Leu Thr Glu Ile Leu Asn Gly Gly Val Tyr Val Asp Gln Asn Lys
            115                 120                 125

Phe Leu Cys Tyr Ala Asp Thr Ile His Trp Gln Asp Ile Val Arg Asn
    130                 135                 140

Pro Trp Pro Ser Asn Leu Thr Leu Val Ser Thr Asn Gly Ser Ser Gly
145                 150                 155                 160

Cys Gly Arg Cys His Lys Ser Cys Thr Gly Arg Cys Trp Gly Pro Thr
                165                 170                 175

Glu Asn His Cys Gln Thr Leu Thr Arg Thr Val Cys Ala Glu Gln Cys
            180                 185                 190

Asp Gly Arg Cys Tyr Gly Pro Tyr Val Ser Asp Cys Cys His Arg Glu
            195                 200                 205

Cys Ala Gly Gly Cys Ser Gly Pro Lys Asp Thr Asp Cys Phe Ala Cys
    210                 215                 220

Met Asn Phe Asn Asp Ser Gly Ala Cys Val Thr Gln Cys Pro Gln Thr
225                 230                 235                 240

Phe Val Tyr Asn Pro Thr Thr Phe Gln Leu Glu His Asn Phe Asn Ala
                245                 250                 255

Lys Tyr Thr Tyr Gly Ala Phe Cys Val Lys Cys Pro His Asn Phe
            260                 265                 270

Val Val Asp Ser Ser Ser Cys Val Arg Ala Cys Pro Ser Ser Lys Met
            275                 280                 285

Glu Val Glu Glu Asn Gly Ile Lys Met Cys Lys Pro Cys Thr Asp Ile
    290                 295                 300

Cys Pro Lys Ala Cys Asp Gly Ile Gly Thr Gly Ser Leu Met Ser Ala
305                 310                 315                 320

Gln Thr Val Asp Ser Ser Asn Ile Asp Lys Phe Ile Asn Cys Thr Lys
                325                 330                 335

Ile Asn Gly Asn Leu Ile Phe Leu Val Thr Gly Ile His Gly Asp Pro
            340                 345                 350

Tyr Asn Ala Ile Glu Ala Ile Asp Pro Glu Lys Leu Asn Val Phe Arg
            355                 360                 365

Thr Val Arg Glu Ile Thr Gly Phe Leu Asn Ile Gln Ser Trp Pro Pro
    370                 375                 380

Asn Met Thr Asp Phe Ser Val Phe Ser Asn Leu Val Thr Ile Gly Gly
385                 390                 395                 400

Arg Val Leu Tyr Ser Gly Leu Ser Leu Leu Ile Leu Lys Gln Gln Gly
                405                 410                 415
```

```
Ile Thr Ser Leu Gln Phe Gln Ser Leu Lys Glu Ile Ser Ala Gly Asn
            420                 425                 430
Ile Tyr Ile Thr Asp Asn Ser Asn Leu Cys Tyr Tyr His Thr Ile Asn
            435                 440                 445
Trp Thr Thr Leu Phe Ser Thr Ile Asn Gln Arg Ile Val Ile Arg Asp
450                 455                 460
Asn Arg Lys Ala Glu Asn Cys Thr Ala Glu Gly Met Val Cys Asn His
465                 470                 475                 480
Leu Cys Ser Ser Asp Gly Cys Trp Gly Pro Gly Pro Asp Gln Cys Leu
            485                 490                 495
Ser Cys Arg Arg Phe Ser Arg Gly Arg Ile Cys Ile Glu Ser Cys Asn
            500                 505                 510
Leu Tyr Asp Gly Glu Phe Arg Glu Phe Glu Asn Gly Ser Ile Cys Val
            515                 520                 525
Glu Cys Asp Pro Gln Cys Glu Lys Met Glu Asp Gly Leu Leu Thr Cys
            530                 535                 540
His Gly Pro Gly Pro Asp Asn Cys Thr Lys Cys Ser His Phe Lys Asp
545                 550                 555                 560
Gly Pro Asn Cys Val Glu Lys Cys Pro Asp Gly Leu Gln Gly Ala Asn
            565                 570                 575
Ser Phe Ile Phe Lys Tyr Ala Asp Pro Asp Arg Glu Cys His Pro Cys
            580                 585                 590
His Pro Asn Cys Thr Gln Gly Cys Asn Gly Pro Thr Ser His Asp Cys
            595                 600                 605
Ile Tyr Tyr Pro Trp Thr Gly His Ser Thr Leu Pro Gln His Ala Arg
            610                 615                 620
Thr Pro Leu Ile Ala Ala Gly Val Ile Gly Gly Leu Phe Ile Leu Val
625                 630                 635                 640
Ile Val Gly Leu Thr Phe Ala Val Tyr Val Arg Arg Lys Ser Ile Lys
            645                 650                 655
Lys Lys Arg Ala Leu Arg Arg Phe Leu Glu Thr Glu Leu Val Glu Pro
            660                 665                 670
Leu Thr Pro Ser Gly Thr Ala Pro Asn Gln Ala Gln Leu Arg Ile Leu
            675                 680                 685
Lys Glu Thr Glu Leu Lys Arg Val Lys Val Leu Gly Ser Gly Ala Phe
            690                 695                 700
Gly Thr Val Tyr Lys Gly Ile Trp Val Pro Glu Gly Thr Val Lys
705                 710                 715                 720
Ile Pro Val Ala Ile Lys Ile Leu Asn Glu Thr Thr Gly Pro Lys Ala
            725                 730                 735
Asn Val Glu Phe Met Asp Glu Ala Leu Ile Met Ala Ser Met Asp His
            740                 745                 750
Pro His Leu Val Arg Leu Leu Gly Val Cys Leu Ser Pro Thr Ile Gln
            755                 760                 765
Leu Val Thr Gln Leu Met Pro His Gly Cys Leu Leu Glu Tyr Val His
            770                 775                 780
Glu His Lys Asp Asn Ile Gly Ser Gln Leu Leu Leu Asn Trp Cys Val
785                 790                 795                 800
Gln Ile Ala Lys Gly Met Met Tyr Leu Glu Glu Arg Arg Leu Val His
            805                 810                 815
Arg Asp Leu Ala Ala Arg Asn Val Leu Val Lys Ser Pro Asn His Val
            820                 825                 830
Lys Ile Thr Asp Phe Gly Leu Ala Arg Leu Leu Glu Gly Asp Glu Lys
```

-continued

```
            835                 840                 845
Glu Tyr Asn Ala Asp Gly Gly Lys Met Pro Ile Lys Trp Met Ala Leu
850                 855                 860
Glu Cys Ile His Tyr Arg Lys Phe Thr His Gln Ser Asp Val Trp Ser
865                 870                 875                 880
Tyr Gly Val Thr Ile Trp Glu Leu Met Thr Phe Gly Gly Lys Pro Tyr
                885                 890                 895
Asp Gly Ile Pro Thr Arg Glu Ile Pro Asp Leu Leu Glu Lys Gly Glu
            900                 905                 910
Arg Leu Pro Gln Pro Pro Ile Cys Thr Ile Asp Val Tyr Met Val Met
            915                 920                 925
Val Lys Cys Trp Met Ile Asp Ala Asp Ser Arg Pro Lys Phe Lys Glu
            930                 935                 940
Leu Ala Ala Glu Phe Ser Arg Met Ala Arg Asp Pro Gln Arg Tyr Leu
945                 950                 955                 960
Val Ile Gln Gly Asp Asp Arg Met Lys Leu Pro Ser Pro Asn Asp Ser
                965                 970                 975
Lys Phe Phe Gln Asn Leu Leu Asp Glu Glu Asp Leu Glu Asp Met Met
                980                 985                 990
Asp Ala Glu Glu Tyr Leu Val Pro Gln Ala Phe Asn Ile Pro Pro Pro
            995                 1000                1005
Ile Tyr Thr Ser Arg Ala Arg Ile Asp Ser Asn Arg Ser Glu Ile Gly
            1010                1015                1020
His Ser Pro Pro Pro Ala Tyr Thr Pro Met Ser Gly Asn Gln Phe Val
1025                1030                1035                1040
Tyr Arg Asp Gly Gly Phe Ala Ala Glu Gln Gly Val Ser Val Pro Tyr
                1045                1050                1055
Arg Ala Pro Thr Ser Thr Ile Pro Glu Ala Pro Val Ala Gln Gly Ala
            1060                1065                1070
Thr Ala Glu Ile Phe Asp Asp Ser Cys Cys Asn Gly Thr Leu Arg Lys
            1075                1080                1085
Pro Val Ala Pro His Val Gln Glu Asp Ser Ser Thr Gln Arg Tyr Ser
1090                1095                1100
Ala Asp Pro Thr Val Phe Ala Pro Glu Arg Ser Pro Arg Gly Glu Leu
1105                1110                1115                1120
Asp Glu Glu Gly Tyr Met Thr Pro Met Arg Asp Lys Pro Lys Gln Glu
                1125                1130                1135
Tyr Leu Asn Pro Val Glu Glu Asn Pro Phe Val Ser Arg Arg Lys Asn
                1140                1145                1150
Gly Asp Leu Gln Ala Leu Asp Asn Pro Glu Tyr His Asn Ala Ser Asn
            1155                1160                1165
Gly Pro Pro Lys Ala Glu Asp Glu Tyr Val Asn Glu Pro Leu Tyr Leu
            1170                1175                1180
Asn Thr Phe Ala Asn Thr Leu Gly Lys Ala Glu Tyr Leu Lys Asn Asn
1185                1190                1195                1200
Ile Leu Ser Met Pro Glu Lys Ala Lys Lys Ala Phe Asp Asn Pro Asp
                1205                1210                1215
Tyr Trp Asn His Ser Leu Pro Pro Arg Ser Thr Leu Gln His Pro Asp
                1220                1225                1230
Tyr Leu Gln Glu Tyr Ser Thr Lys Tyr Phe Tyr Lys Gln Asn Gly Arg
            1235                1240                1245
Ile Arg Pro Ile Val Ala Glu Asn Pro Glu Tyr Leu Ser Glu Phe Ser
            1250                1255                1260
```

```
Leu Lys Pro Gly Thr Val Leu Pro Pro Pro Tyr Arg His Arg Asn
1265                1270                1275                1280

Thr Val Val

<210> SEQ ID NO 53
<211> LENGTH: 1366
<212> TYPE: PRT
<213> ORGANISM: Homo sapiens
<220> FEATURE:
<223> OTHER INFORMATION: HGFR/c-Met Full Length (mature)
<300> PUBLICATION INFORMATION:
<308> DATABASE ACCESSION NUMBER: UniProt No. P08581
<309> DATABASE ENTRY DATE: 1988-08-01

<400> SEQUENCE: 53

Glu Cys Lys Glu Ala Leu Ala Lys Ser Glu Met Asn Val Asn Met Lys
1               5                   10                  15

Tyr Gln Leu Pro Asn Phe Thr Ala Glu Thr Pro Ile Gln Asn Val Ile
            20                  25                  30

Leu His Glu His His Ile Phe Leu Gly Ala Thr Asn Tyr Ile Tyr Val
        35                  40                  45

Leu Asn Glu Glu Asp Leu Gln Lys Val Ala Glu Tyr Lys Thr Gly Pro
    50                  55                  60

Val Leu Glu His Pro Asp Cys Phe Pro Cys Gln Asp Cys Ser Ser Lys
65                  70                  75                  80

Ala Asn Leu Ser Gly Gly Val Trp Lys Asp Asn Ile Asn Met Ala Leu
                85                  90                  95

Val Val Asp Thr Tyr Tyr Asp Asp Gln Leu Ile Ser Cys Gly Ser Val
            100                 105                 110

Asn Arg Gly Thr Cys Gln Arg His Val Phe Pro His Asn His Thr Ala
        115                 120                 125

Asp Ile Gln Ser Glu Val His Cys Ile Phe Ser Pro Gln Ile Glu Glu
    130                 135                 140

Pro Ser Gln Cys Pro Asp Cys Val Val Ser Ala Leu Gly Ala Lys Val
145                 150                 155                 160

Leu Ser Ser Val Lys Asp Arg Phe Ile Asn Phe Phe Val Gly Asn Thr
                165                 170                 175

Ile Asn Ser Ser Tyr Phe Pro Asp His Pro Leu His Ser Ile Ser Val
            180                 185                 190

Arg Arg Leu Lys Glu Thr Lys Asp Gly Phe Met Phe Leu Thr Asp Gln
        195                 200                 205

Ser Tyr Ile Asp Val Leu Pro Glu Phe Arg Asp Ser Tyr Pro Ile Lys
    210                 215                 220

Tyr Val His Ala Phe Glu Ser Asn Asn Phe Ile Tyr Phe Leu Thr Val
225                 230                 235                 240

Gln Arg Glu Thr Leu Asp Ala Gln Thr Phe His Thr Arg Ile Ile Arg
                245                 250                 255

Phe Cys Ser Ile Asn Ser Gly Leu His Ser Tyr Met Glu Met Pro Leu
            260                 265                 270

Glu Cys Ile Leu Thr Glu Lys Arg Lys Lys Arg Ser Thr Lys Lys Glu
        275                 280                 285

Val Phe Asn Ile Leu Gln Ala Ala Tyr Val Ser Lys Pro Gly Ala Gln
    290                 295                 300

Leu Ala Arg Gln Ile Gly Ala Ser Leu Asn Asp Asp Ile Leu Phe Gly
305                 310                 315                 320
```

```
Val Phe Ala Gln Ser Lys Pro Asp Ser Ala Glu Pro Met Asp Arg Ser
                325                 330                 335

Ala Met Cys Ala Phe Pro Ile Lys Tyr Val Asn Asp Phe Phe Asn Lys
            340                 345                 350

Ile Val Asn Lys Asn Asn Val Arg Cys Leu Gln His Phe Tyr Gly Pro
        355                 360                 365

Asn His Glu His Cys Phe Asn Arg Thr Leu Leu Arg Asn Ser Ser Gly
    370                 375                 380

Cys Glu Ala Arg Arg Asp Glu Tyr Arg Thr Glu Phe Thr Thr Ala Leu
385                 390                 395                 400

Gln Arg Val Asp Leu Phe Met Gly Gln Phe Ser Glu Val Leu Leu Thr
                405                 410                 415

Ser Ile Ser Thr Phe Ile Lys Gly Asp Leu Thr Ile Ala Asn Leu Gly
            420                 425                 430

Thr Ser Glu Gly Arg Phe Met Gln Val Val Ser Arg Ser Gly Pro
        435                 440                 445

Ser Thr Pro His Val Asn Phe Leu Leu Asp Ser His Pro Val Ser Pro
    450                 455                 460

Glu Val Ile Val Glu His Thr Leu Asn Gln Asn Gly Tyr Thr Leu Val
465                 470                 475                 480

Ile Thr Gly Lys Lys Ile Thr Lys Ile Pro Leu Asn Gly Leu Gly Cys
                485                 490                 495

Arg His Phe Gln Ser Cys Ser Gln Cys Leu Ser Ala Pro Pro Phe Val
            500                 505                 510

Gln Cys Gly Trp Cys His Asp Lys Cys Val Arg Ser Glu Glu Cys Leu
        515                 520                 525

Ser Gly Thr Trp Thr Gln Gln Ile Cys Leu Pro Ala Ile Tyr Lys Val
    530                 535                 540

Phe Pro Asn Ser Ala Pro Leu Glu Gly Gly Thr Arg Leu Thr Ile Cys
545                 550                 555                 560

Gly Trp Asp Phe Gly Phe Arg Arg Asn Asn Lys Phe Asp Leu Lys Lys
                565                 570                 575

Thr Arg Val Leu Leu Gly Asn Glu Ser Cys Thr Leu Thr Leu Ser Glu
            580                 585                 590

Ser Thr Met Asn Thr Leu Lys Cys Thr Val Gly Pro Ala Met Asn Lys
        595                 600                 605

His Phe Asn Met Ser Ile Ile Ile Ser Asn Gly His Gly Thr Thr Gln
    610                 615                 620

Tyr Ser Thr Phe Ser Tyr Val Asp Pro Val Ile Thr Ser Ile Ser Pro
625                 630                 635                 640

Lys Tyr Gly Pro Met Ala Gly Gly Thr Leu Leu Thr Leu Thr Gly Asn
                645                 650                 655

Tyr Leu Asn Ser Gly Asn Ser Arg His Ile Ser Ile Gly Gly Lys Thr
            660                 665                 670

Cys Thr Leu Lys Ser Val Ser Asn Ser Ile Leu Glu Cys Tyr Thr Pro
        675                 680                 685

Ala Gln Thr Ile Ser Thr Glu Phe Ala Val Lys Leu Lys Ile Asp Leu
    690                 695                 700

Ala Asn Arg Glu Thr Ser Ile Phe Ser Tyr Arg Glu Asp Pro Ile Val
705                 710                 715                 720

Tyr Glu Ile His Pro Thr Lys Ser Phe Ile Ser Gly Gly Ser Thr Ile
                725                 730                 735

Thr Gly Val Gly Lys Asn Leu Asn Ser Val Ser Val Pro Arg Met Val
```

```
            740                 745                 750
Ile Asn Val His Glu Ala Gly Arg Asn Phe Thr Val Ala Cys Gln His
            755                 760                 765
Arg Ser Asn Ser Glu Ile Ile Cys Cys Thr Thr Pro Ser Leu Gln Gln
            770                 775                 780
Leu Asn Leu Gln Leu Pro Leu Lys Thr Lys Ala Phe Phe Met Leu Asp
785                 790                 795                 800
Gly Ile Leu Ser Lys Tyr Phe Asp Leu Ile Tyr Val His Asn Pro Val
                805                 810                 815
Phe Lys Pro Phe Glu Lys Pro Val Met Ile Ser Met Gly Asn Glu Asn
                820                 825                 830
Val Leu Glu Ile Lys Gly Asn Asp Ile Asp Pro Glu Ala Val Lys Gly
            835                 840                 845
Glu Val Leu Lys Val Gly Asn Lys Ser Cys Glu Asn Ile His Leu His
            850                 855                 860
Ser Glu Ala Val Leu Cys Thr Val Pro Asn Asp Leu Leu Lys Leu Asn
865                 870                 875                 880
Ser Glu Leu Asn Ile Glu Trp Lys Gln Ala Ile Ser Ser Thr Val Leu
                885                 890                 895
Gly Lys Val Ile Val Gln Pro Asp Gln Asn Phe Thr Gly Leu Ile Ala
                900                 905                 910
Gly Val Val Ser Ile Ser Thr Ala Leu Leu Leu Leu Leu Gly Phe Phe
            915                 920                 925
Leu Trp Leu Lys Lys Arg Lys Gln Ile Lys Asp Leu Gly Ser Glu Leu
            930                 935                 940
Val Arg Tyr Asp Ala Arg Val His Thr Pro His Leu Asp Arg Leu Val
945                 950                 955                 960
Ser Ala Arg Ser Val Ser Pro Thr Thr Glu Met Val Ser Asn Glu Ser
                965                 970                 975
Val Asp Tyr Arg Ala Thr Phe Pro Glu Asp Gln Phe Pro Asn Ser Ser
                980                 985                 990
Gln Asn Gly Ser Cys Arg Gln Val Gln Tyr Pro Leu Thr Asp Met Ser
            995                 1000                1005
Pro Ile Leu Thr Ser Gly Asp Ser Asp Ile Ser Ser Pro Leu Leu Gln
            1010                1015                1020
Asn Thr Val His Ile Asp Leu Ser Ala Leu Asn Pro Glu Leu Val Gln
1025                1030                1035                1040
Ala Val Gln His Val Val Ile Gly Pro Ser Ser Leu Ile Val His Phe
                1045                1050                1055
Asn Glu Val Ile Gly Arg Gly His Phe Gly Cys Val Tyr His Gly Thr
                1060                1065                1070
Leu Leu Asp Asn Asp Gly Lys Lys Ile His Cys Ala Val Lys Ser Leu
            1075                1080                1085
Asn Arg Ile Thr Asp Ile Gly Glu Val Ser Gln Phe Leu Thr Glu Gly
            1090                1095                1100
Ile Ile Met Lys Asp Phe Ser His Pro Asn Val Leu Ser Leu Leu Gly
1105                1110                1115                1120
Ile Cys Leu Arg Ser Glu Gly Ser Pro Leu Val Val Leu Pro Tyr Met
                1125                1130                1135
Lys His Gly Asp Leu Arg Asn Phe Ile Arg Asn Glu Thr His Asn Pro
                1140                1145                1150
Thr Val Lys Asp Leu Ile Gly Phe Gly Leu Gln Val Ala Lys Gly Met
            1155                1160                1165
```

```
Lys Tyr Leu Ala Ser Lys Lys Phe Val His Arg Asp Leu Ala Ala Arg
            1170            1175                1180

Asn Cys Met Leu Asp Glu Lys Phe Thr Val Lys Val Ala Asp Phe Gly
1185                1190                1195                1200

Leu Ala Arg Asp Met Tyr Asp Lys Glu Tyr Tyr Ser Val His Asn Lys
                1205                1210                1215

Thr Gly Ala Lys Leu Pro Val Lys Trp Met Ala Leu Glu Ser Leu Gln
            1220                1225                1230

Thr Gln Lys Phe Thr Thr Lys Ser Asp Val Trp Ser Phe Gly Val Leu
                1235                1240                1245

Leu Trp Glu Leu Met Thr Arg Gly Ala Pro Pro Tyr Pro Asp Val Asn
            1250                1255                1260

Thr Phe Asp Ile Thr Val Tyr Leu Leu Gln Gly Arg Arg Leu Leu Gln
1265                1270                1275                1280

Pro Glu Tyr Cys Pro Asp Pro Leu Tyr Glu Val Met Leu Lys Cys Trp
                1285                1290                1295

His Pro Lys Ala Glu Met Arg Pro Ser Phe Ser Glu Leu Val Ser Arg
            1300                1305                1310

Ile Ser Ala Ile Phe Ser Thr Phe Ile Gly Glu His Tyr Val His Val
            1315                1320                1325

Asn Ala Thr Tyr Val Asn Val Lys Cys Val Ala Pro Tyr Pro Ser Leu
            1330                1335                1340

Leu Ser Ser Glu Asp Asn Ala Asp Asp Glu Val Asp Thr Arg Pro Ala
1345                1350                1355                1360

Ser Phe Trp Glu Thr Ser
            1365

<210> SEQ ID NO 54
<211> LENGTH: 1367
<212> TYPE: PRT
<213> ORGANISM: Homo sapiens
<220> FEATURE:
<223> OTHER INFORMATION: IGF-1 R full length  (mature)
<300> PUBLICATION INFORMATION:
<308> DATABASE ACCESSION NUMBER: UniProt No. P08069
<309> DATABASE ENTRY DATE: 1988-08-01

<400> SEQUENCE: 54

Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
    50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140
```

```
Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
    210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
        275                 280                 285

Glu Ser Ser Asp Ser Glu Gly Phe Val Ile His Asp Gly Glu Cys Met
290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
                325                 330                 335

Lys Thr Lys Thr Ile Asp Ser Val Thr Ser Ala Gln Met Leu Gln Gly
            340                 345                 350

Cys Thr Ile Phe Lys Gly Asn Leu Leu Ile Asn Ile Arg Arg Gly Asn
        355                 360                 365

Asn Ile Ala Ser Glu Leu Glu Asn Phe Met Gly Leu Ile Glu Val Val
    370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
                405                 410                 415

Asn Tyr Ser Phe Tyr Val Leu Asp Asn Gln Asn Leu Gln Gln Leu Trp
            420                 425                 430

Asp Trp Asp His Arg Asn Leu Thr Ile Lys Ala Gly Lys Met Tyr Phe
        435                 440                 445

Ala Phe Asn Pro Lys Leu Cys Val Ser Glu Ile Tyr Arg Met Glu Glu
    450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
                485                 490                 495

Ser Thr Thr Thr Ser Lys Asn Arg Ile Ile Ile Thr Trp His Arg Tyr
            500                 505                 510

Arg Pro Pro Asp Tyr Arg Asp Leu Ile Ser Phe Thr Val Tyr Tyr Lys
        515                 520                 525

Glu Ala Pro Phe Lys Asn Val Thr Glu Tyr Asp Gly Gln Asp Ala Cys
    530                 535                 540

Gly Ser Asn Ser Trp Asn Met Val Asp Val Asp Leu Pro Pro Asn Lys
545                 550                 555                 560
```

Asp Val Glu Pro Gly Ile Leu Leu His Gly Leu Lys Pro Trp Thr Gln
            565                 570                 575

Tyr Ala Val Tyr Val Lys Ala Val Thr Leu Thr Met Val Glu Asn Asp
            580                 585                 590

His Ile Arg Gly Ala Lys Ser Glu Ile Leu Tyr Ile Arg Thr Asn Ala
            595                 600                 605

Ser Val Pro Ser Ile Pro Leu Asp Val Leu Ser Ala Ser Asn Ser Ser
            610                 615                 620

Ser Gln Leu Ile Val Lys Trp Asn Pro Pro Ser Leu Pro Asn Gly Asn
625                 630                 635                 640

Leu Ser Tyr Tyr Ile Val Arg Trp Gln Arg Gln Pro Gln Asp Gly Tyr
                645                 650                 655

Leu Tyr Arg His Asn Tyr Cys Ser Lys Asp Lys Ile Pro Ile Arg Lys
            660                 665                 670

Tyr Ala Asp Gly Thr Ile Asp Ile Glu Glu Val Thr Glu Asn Pro Lys
            675                 680                 685

Thr Glu Val Cys Gly Gly Glu Lys Gly Pro Cys Cys Ala Cys Pro Lys
            690                 695                 700

Thr Glu Ala Glu Lys Gln Ala Glu Lys Glu Glu Ala Glu Tyr Arg Lys
705                 710                 715                 720

Val Phe Glu Asn Phe Leu His Asn Ser Ile Phe Val Pro Arg Pro Glu
                725                 730                 735

Arg Lys Arg Arg Asp Val Met Gln Val Ala Asn Thr Thr Met Ser Ser
            740                 745                 750

Arg Ser Arg Asn Thr Thr Ala Ala Asp Thr Tyr Asn Ile Thr Asp Pro
            755                 760                 765

Glu Glu Leu Glu Thr Glu Tyr Pro Phe Phe Glu Ser Arg Val Asp Asn
            770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                805                 810                 815

Ala Ser Asn Phe Val Phe Ala Arg Thr Met Pro Ala Glu Gly Ala Asp
            820                 825                 830

Asp Ile Pro Gly Pro Val Thr Trp Glu Pro Arg Pro Glu Asn Ser Ile
            835                 840                 845

Phe Leu Lys Trp Pro Glu Pro Glu Asn Pro Asn Gly Leu Ile Leu Met
850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                885                 890                 895

Asn Pro Gly Asn Tyr Thr Ala Arg Ile Gln Ala Thr Ser Leu Ser Gly
            900                 905                 910

Asn Gly Ser Trp Thr Asp Pro Val Phe Phe Tyr Val Gln Ala Lys Thr
            915                 920                 925

Gly Tyr Glu Asn Phe Ile His Leu Ile Ile Ala Leu Pro Val Ala Val
            930                 935                 940

Leu Leu Ile Val Gly Gly Leu Val Ile Met Leu Tyr Val Phe His Arg
945                 950                 955                 960

Lys Arg Asn Asn Ser Arg Leu Gly Asn Gly Val Leu Tyr Ala Ser Val
                965                 970                 975

Asn Pro Glu Tyr Phe Ser Ala Ala Asp Val Tyr Val Pro Asp Glu Trp

```
                        980             985             990
Glu Val Ala Arg Glu Lys Ile Thr Met Ser Arg Glu Leu Gly Gln Gly
            995                 1000                1005

Ser Phe Gly Met Val Tyr Glu Gly Val Ala Lys Gly Val Val Lys Asp
    1010                1015                1020

Glu Pro Glu Thr Arg Val Ala Ile Lys Thr Val Asn Glu Ala Ala Ser
1025                1030                1035                1040

Met Arg Glu Arg Ile Glu Phe Leu Asn Glu Ala Ser Val Met Lys Glu
                1045                1050                1055

Phe Asn Cys His His Val Val Arg Leu Leu Gly Val Val Ser Gln Gly
                1060                1065                1070

Gln Pro Thr Leu Val Ile Met Glu Leu Met Thr Arg Gly Asp Leu Lys
            1075                1080                1085

Ser Tyr Leu Arg Ser Leu Arg Pro Glu Met Glu Asn Asn Pro Val Leu
            1090                1095                1100

Ala Pro Pro Ser Leu Ser Lys Met Ile Gln Met Ala Gly Glu Ile Ala
1105                1110                1115                1120

Asp Gly Met Ala Tyr Leu Asn Ala Asn Lys Phe Val His Arg Asp Leu
                1125                1130                1135

Ala Ala Arg Asn Cys Met Val Ala Glu Asp Phe Thr Val Lys Ile Gly
                1140                1145                1150

Asp Phe Gly Met Thr Arg Asp Ile Tyr Glu Thr Asp Tyr Tyr Arg Lys
            1155                1160                1165

Gly Gly Lys Gly Leu Leu Pro Val Arg Trp Met Ser Pro Glu Ser Leu
            1170                1175                1180

Lys Asp Gly Val Phe Thr Thr Tyr Ser Asp Val Trp Ser Phe Gly Val
1185                1190                1195                1200

Val Leu Trp Glu Ile Ala Thr Leu Ala Glu Gln Pro Tyr Gln Gly Leu
                1205                1210                1215

Ser Asn Glu Gln Val Leu Arg Phe Val Met Glu Gly Gly Leu Leu Asp
                1220                1225                1230

Lys Pro Asp Asn Cys Pro Asp Met Leu Phe Glu Leu Met Arg Met Cys
            1235                1240                1245

Trp Gln Tyr Asn Pro Lys Met Arg Pro Ser Phe Leu Glu Ile Ile Ser
    1250                1255                1260

Ser Ile Lys Glu Glu Met Glu Pro Gly Phe Arg Glu Val Ser Phe Tyr
1265                1270                1275                1280

Tyr Ser Glu Glu Asn Lys Leu Pro Glu Pro Glu Glu Leu Asp Leu Glu
                1285                1290                1295

Pro Glu Asn Met Glu Ser Val Pro Leu Asp Pro Ser Ala Ser Ser Ser
            1300                1305                1310

Ser Leu Pro Leu Pro Asp Arg His Ser Gly His Lys Ala Glu Asn Gly
            1315                1320                1325

Pro Gly Pro Gly Val Leu Val Leu Arg Ala Ser Phe Asp Glu Arg Gln
            1330                1335                1340

Pro Tyr Ala His Met Asn Gly Gly Arg Lys Asn Glu Arg Ala Leu Pro
1345                1350                1355                1360

Leu Pro Gln Ser Ser Thr Cys
            1365

<210> SEQ ID NO 55
<211> LENGTH: 18
<212> TYPE: PRT
<213> ORGANISM: Artificial Sequence
```

```
<220> FEATURE:
<223> OTHER INFORMATION: Linker

<400> SEQUENCE: 55

Gly Ser Thr Ser Gly Ser Gly Lys Pro Gly Ser Gly Glu Gly Ser Thr
1               5                   10                  15

Lys Gly

<210> SEQ ID NO 56
<211> LENGTH: 10
<212> TYPE: PRT
<213> ORGANISM: Artificial Sequence
<220> FEATURE:
<223> OTHER INFORMATION: Linker

<400> SEQUENCE: 56

Gly Gly Gly Gly Ser Gly Gly Gly Gly Ser
1               5                   10

<210> SEQ ID NO 57
<211> LENGTH: 1005
<212> TYPE: DNA
<213> ORGANISM: Artificial Sequence
<220> FEATURE:
<223> OTHER INFORMATION: tEGFR

<400> SEQUENCE: 57
cgcaaagtgt gtaacggaat aggtattggt gaatttaaag actcactctc cataaatgct      60
acgaatatta aacacttcaa aaactgcacc tccatcagtg gcgatctcca catcctgccg     120
gtggcattta ggggtgactc cttcacacat actcctcctc tggatccaca ggaactggat     180
attctgaaaa ccgtaaagga atcacagggt ttttgctga ttcaggcttg gcctgaaaac     240
aggacggacc tccatgcctt tgagaaccta gaaatcatac gcggcaggac caagcaacat     300
ggtcagtttt ctcttgcagt cgtcagcctg aacataacat ccttgggatt acgctccctc     360
aaggagataa gtgatggaga tgtgataatt tcaggaaaca aaaatttgtg ctatgcaaat     420
acaataaact ggaaaaaact gtttgggacc tccggtcaga aaaccaaaat tataagcaac     480
agaggtgaaa acagctgcaa ggccacaggc caggtctgcc atgccttgtg ctcccccgag     540
ggctgctggg gcccggagcc cagggactgc gtctcttgcc ggaatgtcag ccgaggcagg     600
gaatgcgtgg acaagtgcaa ccttctggag ggtgagccaa gggagtttgt ggagaactct     660
gagtgcatac agtgccaccc agagtgcctg cctcaggcca tgaacatcac ctgcacagga     720
cggggaccag acaactgtat ccagtgtgcc cactacattg acggccccca ctgcgtcaag     780
acctgcccgg caggagtcat gggagaaaac aacacccctgg tctggaagta cgcagacgcc     840
ggccatgtgt gccacctgtg ccatccaaac tgcacctacg gatgcactgg gccaggtctt     900
gaaggctgtc caacgaatgg gcctaagatc ccgtccatcg ccactgggat ggtgggggcc     960
ctcctcttgc tgctggtggt ggccctgggg atcggcctct tcatg                   1005

<210> SEQ ID NO 58
<211> LENGTH: 10
<212> TYPE: PRT
<213> ORGANISM: Artificial Sequence
<220> FEATURE:
<223> OTHER INFORMATION: Streptavidin binding peptide, Strep-tag II

<400> SEQUENCE: 58

Ser Ala Trp Ser His Pro Gln Phe Glu Lys
1               5                   10
```

<210> SEQ ID NO 59
<211> LENGTH: 8
<212> TYPE: PRT
<213> ORGANISM: Artificial Sequence
<220> FEATURE:
<223> OTHER INFORMATION: Linker

<400> SEQUENCE: 59

Gly Gly Gly Ser Gly Gly Gly Ser
1               5

<210> SEQ ID NO 60
<211> LENGTH: 5
<212> TYPE: PRT
<213> ORGANISM: Artificial Sequence
<220> FEATURE:
<223> OTHER INFORMATION: Linker

<400> SEQUENCE: 60

Gly Gly Gly Gly Ser
1               5

<210> SEQ ID NO 61
<211> LENGTH: 4
<212> TYPE: PRT
<213> ORGANISM: Artificial Sequence
<220> FEATURE:
<223> OTHER INFORMATION: Linker

<400> SEQUENCE: 61

Gly Gly Gly Ser
1

<210> SEQ ID NO 62
<211> LENGTH: 15
<212> TYPE: PRT
<213> ORGANISM: Artificial Sequence
<220> FEATURE:
<223> OTHER INFORMATION: Linker

<400> SEQUENCE: 62

Gly Gly Gly Gly Ser Gly Gly Gly Ser Gly Gly Gly Gly Ser
1               5                   10                  15

<210> SEQ ID NO 63
<211> LENGTH: 11
<212> TYPE: PRT
<213> ORGANISM: Artificial Sequence
<220> FEATURE:
<223> OTHER INFORMATION: MAT tag

<400> SEQUENCE: 63

His Asn His Arg His Lys His Gly Gly Gly Cys
1               5                   10

<210> SEQ ID NO 64
<211> LENGTH: 1210
<212> TYPE: PRT
<213> ORGANISM: Homo sapiens
<220> FEATURE:
<223> OTHER INFORMATION: HER1/ErbB1/EGFR Full Length (precursor)
<300> PUBLICATION INFORMATION:
<308> DATABASE ACCESSION NUMBER: UniProt No. P00533
<309> DATABASE ENTRY DATE: 1986-07-21

<400> SEQUENCE: 64

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
            130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
            195                 200                 205

Lys Leu Thr Lys Ile Ile Cys Ala Gln Gln Cys Ser Gly Arg Cys Arg
            210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
            275                 280                 285

Ala Thr Cys Val Lys Lys Cys Pro Arg Asn Tyr Val Val Thr Asp His
            290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
            370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
```

```
            420                 425                 430
His Gly Gln Phe Ser Leu Ala Val Val Ser Leu Asn Ile Thr Ser Leu
            435                 440                 445
Gly Leu Arg Ser Leu Lys Glu Ile Ser Asp Gly Asp Val Ile Ile Ser
            450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                    485                 490                 495
Asn Ser Cys Lys Ala Thr Gly Gln Val Cys His Ala Leu Cys Ser Pro
                500                 505                 510
Glu Gly Cys Trp Gly Pro Glu Pro Arg Asp Cys Val Ser Cys Arg Asn
            515                 520                 525
Val Ser Arg Gly Arg Glu Cys Val Asp Lys Cys Asn Leu Leu Glu Gly
            530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                    565                 570                 575
Asp Asn Cys Ile Gln Cys Ala His Tyr Ile Asp Gly Pro His Cys Val
                580                 585                 590
Lys Thr Cys Pro Ala Gly Val Met Gly Glu Asn Asn Thr Leu Val Trp
            595                 600                 605
Lys Tyr Ala Asp Ala Gly His Val Cys His Leu Cys His Pro Asn Cys
            610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                    645                 650                 655
Leu Leu Val Val Ala Leu Gly Ile Gly Leu Phe Met Arg Arg Arg His
                660                 665                 670
Ile Val Arg Lys Arg Thr Leu Arg Arg Leu Leu Gln Glu Arg Glu Leu
            675                 680                 685
Val Glu Pro Leu Thr Pro Ser Gly Glu Ala Pro Asn Gln Ala Leu Leu
            690                 695                 700
Arg Ile Leu Lys Glu Thr Glu Phe Lys Lys Ile Lys Val Leu Gly Ser
705                 710                 715                 720
Gly Ala Phe Gly Thr Val Tyr Lys Gly Leu Trp Ile Pro Glu Gly Glu
                    725                 730                 735
Lys Val Lys Ile Pro Val Ala Ile Lys Glu Leu Arg Glu Ala Thr Ser
                740                 745                 750
Pro Lys Ala Asn Lys Glu Ile Leu Asp Glu Ala Tyr Val Met Ala Ser
            755                 760                 765
Val Asp Asn Pro His Val Cys Arg Leu Leu Gly Ile Cys Leu Thr Ser
            770                 775                 780
Thr Val Gln Leu Ile Thr Gln Leu Met Pro Phe Gly Cys Leu Leu Asp
785                 790                 795                 800
Tyr Val Arg Glu His Lys Asp Asn Ile Gly Ser Gln Tyr Leu Leu Asn
                    805                 810                 815
Trp Cys Val Gln Ile Ala Lys Gly Met Asn Tyr Leu Glu Asp Arg Arg
                820                 825                 830
Leu Val His Arg Asp Leu Ala Ala Arg Asn Val Leu Val Lys Thr Pro
            835                 840                 845
```

```
Gln His Val Lys Ile Thr Asp Phe Gly Leu Ala Lys Leu Leu Gly Ala
    850                 855                 860
Glu Lys Glu Tyr His Ala Glu Gly Gly Lys Val Pro Ile Lys Trp
865                 870                 875                 880
Met Ala Leu Glu Ser Ile Leu His Arg Ile Tyr Thr His Gln Ser Asp
                885                 890                 895
Val Trp Ser Tyr Gly Val Thr Val Trp Glu Leu Met Thr Phe Gly Ser
                900                 905                 910
Lys Pro Tyr Asp Gly Ile Pro Ala Ser Glu Ile Ser Ser Ile Leu Glu
                915                 920                 925
Lys Gly Glu Arg Leu Pro Gln Pro Pro Ile Cys Thr Ile Asp Val Tyr
            930                 935                 940
Met Ile Met Val Lys Cys Trp Met Ile Asp Ala Asp Ser Arg Pro Lys
945                 950                 955                 960
Phe Arg Glu Leu Ile Ile Glu Phe Ser Lys Met Ala Arg Asp Pro Gln
                965                 970                 975
Arg Tyr Leu Val Ile Gln Gly Asp Glu Arg Met His Leu Pro Ser Pro
                980                 985                 990
Thr Asp Ser Asn Phe Tyr Arg Ala Leu Met Asp Glu Glu Asp Met Asp
            995                 1000                1005
Asp Val Val Asp Ala Asp Glu Tyr Leu Ile Pro Gln Gln Gly Phe Phe
    1010                1015                1020
Ser Ser Pro Ser Thr Ser Arg Thr Pro Leu Leu Ser Ser Leu Ser Ala
1025                1030                1035                1040
Thr Ser Asn Asn Ser Thr Val Ala Cys Ile Asp Arg Asn Gly Leu Gln
                1045                1050                1055
Ser Cys Pro Ile Lys Glu Asp Ser Phe Leu Gln Arg Tyr Ser Ser Asp
                1060                1065                1070
Pro Thr Gly Ala Leu Thr Glu Asp Ser Ile Asp Asp Thr Phe Leu Pro
                1075                1080                1085
Val Pro Glu Tyr Ile Asn Gln Ser Val Pro Lys Arg Pro Ala Gly Ser
    1090                1095                1100
Val Gln Asn Pro Val Tyr His Asn Gln Pro Leu Asn Pro Ala Pro Ser
1105                1110                1115                1120
Arg Asp Pro His Tyr Gln Asp Pro His Ser Thr Ala Val Gly Asn Pro
                1125                1130                1135
Glu Tyr Leu Asn Thr Val Gln Pro Thr Cys Val Asn Ser Thr Phe Asp
                1140                1145                1150
Ser Pro Ala His Trp Ala Gln Lys Gly Ser His Gln Ile Ser Leu Asp
                1155                1160                1165
Asn Pro Asp Tyr Gln Gln Asp Phe Phe Pro Lys Glu Ala Lys Pro Asn
    1170                1175                1180
Gly Ile Phe Lys Gly Ser Thr Ala Glu Asn Ala Glu Tyr Leu Arg Val
1185                1190                1195                1200
Ala Pro Gln Ser Ser Glu Phe Ile Gly Ala
                1205                1210

<210> SEQ ID NO 65
<211> LENGTH: 1255
<212> TYPE: PRT
<213> ORGANISM: Homo sapiens
<220> FEATURE:
<223> OTHER INFORMATION: HER2/neu/ErbB2 Full Length (precursor)
<300> PUBLICATION INFORMATION:
<308> DATABASE ACCESSION NUMBER: Uniprot No. P04626
```

<309> DATABASE ENTRY DATE: 1987-08-13

<400> SEQUENCE: 65

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400
```

```
Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
```

```
                820                 825                 830
Met Ser Tyr Leu Glu Asp Val Arg Leu Val His Arg Asp Leu Ala Ala
            835                 840                 845

Arg Asn Val Leu Val Lys Ser Pro Asn His Val Lys Ile Thr Asp Phe
            850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
            915                 920                 925

Arg Glu Ile Pro Asp Leu Leu Glu Lys Gly Glu Arg Leu Pro Gln Pro
            930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
            995                 1000                1005

Leu Glu Asp Asp Asp Met Gly Asp Leu Val Asp Ala Glu Glu Tyr Leu
            1010                1015                1020

Val Pro Gln Gln Gly Phe Phe Cys Pro Asp Pro Ala Pro Gly Ala Gly
1025                1030                1035                1040

Gly Met Val His His Arg His Arg Ser Ser Ser Thr Arg Ser Gly Gly
                1045                1050                1055

Gly Asp Leu Thr Leu Gly Leu Glu Pro Ser Glu Glu Glu Ala Pro Arg
            1060                1065                1070

Ser Pro Leu Ala Pro Ser Glu Gly Ala Gly Ser Asp Val Phe Asp Gly
            1075                1080                1085

Asp Leu Gly Met Gly Ala Ala Lys Gly Leu Gln Ser Leu Pro Thr His
            1090                1095                1100

Asp Pro Ser Pro Leu Gln Arg Tyr Ser Glu Asp Pro Thr Val Pro Leu
1105                1110                1115                1120

Pro Ser Glu Thr Asp Gly Tyr Val Ala Pro Leu Thr Cys Ser Pro Gln
            1125                1130                1135

Pro Glu Tyr Val Asn Gln Pro Asp Val Arg Pro Gln Pro Pro Ser Pro
            1140                1145                1150

Arg Glu Gly Pro Leu Pro Ala Ala Arg Pro Ala Gly Ala Thr Leu Glu
            1155                1160                1165

Arg Pro Lys Thr Leu Ser Pro Gly Lys Asn Gly Val Val Lys Asp Val
            1170                1175                1180

Phe Ala Phe Gly Gly Ala Val Glu Asn Pro Glu Tyr Leu Thr Pro Gln
1185                1190                1195                1200

Gly Gly Ala Ala Pro Gln Pro His Pro Pro Ala Phe Ser Pro Ala
                1205                1210                1215

Phe Asp Asn Leu Tyr Tyr Trp Asp Gln Asp Pro Pro Glu Arg Gly Ala
            1220                1225                1230

Pro Pro Ser Thr Phe Lys Gly Thr Pro Thr Ala Glu Asn Pro Glu Tyr
            1235                1240                1245
```

```
Leu Gly Leu Asp Val Pro Val
        1250                1255

<210> SEQ ID NO 66
<211> LENGTH: 1342
<212> TYPE: PRT
<213> ORGANISM: Homo sapiens
<220> FEATURE:
<223> OTHER INFORMATION: HER3/ErbB3 Full Length (precursor)
<300> PUBLICATION INFORMATION:
<308> DATABASE ACCESSION NUMBER: UniProt No. P21860
<309> DATABASE ENTRY DATE: 1991-05-01

<400> SEQUENCE: 66

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
    290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
                325                 330                 335
```

```
Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
            355                 360                 365

Asn Gly Asp Pro Trp His Lys Ile Pro Ala Leu Asp Pro Glu Lys Leu
370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
                405                 410                 415

Thr Ile Gly Gly Arg Ser Leu Tyr Asn Arg Gly Phe Ser Leu Leu Ile
            420                 425                 430

Met Lys Asn Leu Asn Val Thr Ser Leu Gly Phe Arg Ser Leu Lys Glu
            435                 440                 445

Ile Ser Ala Gly Arg Ile Tyr Ile Ser Ala Asn Arg Gln Leu Cys Tyr
            450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Arg Asp Cys Val Ala Glu
                485                 490                 495

Gly Lys Val Cys Asp Pro Leu Cys Ser Ser Gly Gly Cys Trp Gly Pro
            500                 505                 510

Gly Pro Gly Gln Cys Leu Ser Cys Arg Asn Tyr Ser Arg Gly Gly Val
            515                 520                 525

Cys Val Thr His Cys Asn Phe Leu Asn Gly Glu Pro Arg Glu Phe Ala
            530                 535                 540

His Glu Ala Glu Cys Phe Ser Cys His Pro Glu Cys Gln Pro Met Glu
545                 550                 555                 560

Gly Thr Ala Thr Cys Asn Gly Ser Gly Ser Asp Thr Cys Ala Gln Cys
                565                 570                 575

Ala His Phe Arg Asp Gly Pro His Cys Val Ser Ser Cys Pro His Gly
                580                 585                 590

Val Leu Gly Ala Lys Gly Pro Ile Tyr Lys Tyr Pro Asp Val Gln Asn
            595                 600                 605

Glu Cys Arg Pro Cys His Glu Asn Cys Thr Gln Gly Cys Lys Gly Pro
610                 615                 620

Glu Leu Gln Asp Cys Leu Gly Gln Thr Leu Val Leu Ile Gly Lys Thr
625                 630                 635                 640

His Leu Thr Met Ala Leu Thr Val Ile Ala Gly Leu Val Val Ile Phe
                645                 650                 655

Met Met Leu Gly Gly Thr Phe Leu Tyr Trp Arg Gly Arg Arg Ile Gln
            660                 665                 670

Asn Lys Arg Ala Met Arg Arg Tyr Leu Glu Arg Gly Glu Ser Ile Glu
            675                 680                 685

Pro Leu Asp Pro Ser Glu Lys Ala Asn Lys Val Leu Ala Arg Ile Phe
            690                 695                 700

Lys Glu Thr Glu Leu Arg Lys Leu Lys Val Leu Gly Ser Gly Val Phe
705                 710                 715                 720

Gly Thr Val His Lys Gly Val Trp Ile Pro Glu Gly Glu Ser Ile Lys
                725                 730                 735

Ile Pro Val Cys Ile Lys Val Ile Glu Asp Lys Ser Gly Arg Gln Ser
            740                 745                 750
```

```
Phe Gln Ala Val Thr Asp His Met Leu Ala Ile Gly Ser Leu Asp His
            755                 760                 765

Ala His Ile Val Arg Leu Leu Gly Leu Cys Pro Gly Ser Ser Leu Gln
    770                 775                 780

Leu Val Thr Gln Tyr Leu Pro Leu Gly Ser Leu Leu Asp His Val Arg
785                 790                 795                 800

Gln His Arg Gly Ala Leu Gly Pro Gln Leu Leu Leu Asn Trp Gly Val
                805                 810                 815

Gln Ile Ala Lys Gly Met Tyr Tyr Leu Glu Glu His Gly Met Val His
            820                 825                 830

Arg Asn Leu Ala Ala Arg Asn Val Leu Leu Lys Ser Pro Ser Gln Val
        835                 840                 845

Gln Val Ala Asp Phe Gly Val Ala Asp Leu Leu Pro Pro Asp Asp Lys
    850                 855                 860

Gln Leu Leu Tyr Ser Glu Ala Lys Thr Pro Ile Lys Trp Met Ala Leu
865                 870                 875                 880

Glu Ser Ile His Phe Gly Lys Tyr Thr His Gln Ser Asp Val Trp Ser
                885                 890                 895

Tyr Gly Val Thr Val Trp Glu Leu Met Thr Phe Gly Ala Glu Pro Tyr
            900                 905                 910

Ala Gly Leu Arg Leu Ala Glu Val Pro Asp Leu Leu Glu Lys Gly Glu
        915                 920                 925

Arg Leu Ala Gln Pro Gln Ile Cys Thr Ile Asp Val Tyr Met Val Met
    930                 935                 940

Val Lys Cys Trp Met Ile Asp Glu Asn Ile Arg Pro Thr Phe Lys Glu
945                 950                 955                 960

Leu Ala Asn Glu Phe Thr Arg Met Ala Arg Asp Pro Pro Arg Tyr Leu
                965                 970                 975

Val Ile Lys Arg Glu Ser Gly Pro Gly Ile Ala Pro Gly Pro Glu Pro
            980                 985                 990

His Gly Leu Thr Asn Lys Lys Leu Glu Glu Val Glu Leu Glu Pro Glu
        995                1000                1005

Leu Asp Leu Asp Leu Asp Leu Glu Ala Glu Glu Asp Asn Leu Ala Thr
    1010                1015                1020

Thr Thr Leu Gly Ser Ala Leu Ser Leu Pro Val Gly Thr Leu Asn Arg
1025                1030                1035                1040

Pro Arg Gly Ser Gln Ser Leu Leu Ser Pro Ser Ser Gly Tyr Met Pro
                1045                1050                1055

Met Asn Gln Gly Asn Leu Gly Glu Ser Cys Gln Glu Ser Ala Val Ser
            1060                1065                1070

Gly Ser Ser Glu Arg Cys Pro Arg Pro Val Ser Leu His Pro Met Pro
        1075                1080                1085

Arg Gly Cys Leu Ala Ser Glu Ser Ser Glu Gly His Val Thr Gly Ser
    1090                1095                1100

Glu Ala Glu Leu Gln Glu Lys Val Ser Met Cys Arg Ser Arg Ser Arg
1105                1110                1115                1120

Ser Arg Ser Pro Arg Pro Arg Gly Asp Ser Ala Tyr His Ser Gln Arg
                1125                1130                1135

His Ser Leu Leu Thr Pro Val Thr Pro Leu Ser Pro Pro Gly Leu Glu
            1140                1145                1150

Glu Glu Asp Val Asn Gly Tyr Val Met Pro Asp Thr His Leu Lys Gly
        1155                1160                1165

Thr Pro Ser Ser Arg Glu Gly Thr Leu Ser Ser Val Gly Leu Ser Ser
```

```
                    1170              1175              1180

Val Leu Gly Thr Glu Glu Asp Glu Glu Tyr Glu Tyr Met
1185              1190              1195              1200

Asn Arg Arg Arg Arg His Ser Pro Pro His Pro Arg Pro Ser Ser
                    1205              1210              1215

Leu Glu Glu Leu Gly Tyr Glu Tyr Met Asp Val Gly Ser Asp Leu Ser
                1220              1225              1230

Ala Ser Leu Gly Ser Thr Gln Ser Cys Pro Leu His Pro Val Pro Ile
            1235              1240              1245

Met Pro Thr Ala Gly Thr Thr Pro Asp Glu Asp Tyr Glu Tyr Met Asn
            1250              1255              1260

Arg Gln Arg Asp Gly Gly Pro Gly Gly Asp Tyr Ala Ala Met Gly
1265              1270              1275              1280

Ala Cys Pro Ala Ser Glu Gln Gly Tyr Glu Glu Met Arg Ala Phe Gln
                    1285              1290              1295

Gly Pro Gly His Gln Ala Pro His Val His Tyr Ala Arg Leu Lys Thr
                1300              1305              1310

Leu Arg Ser Leu Glu Ala Thr Asp Ser Ala Phe Asp Asn Pro Asp Tyr
            1315              1320              1325

Trp His Ser Arg Leu Phe Pro Lys Ala Asn Ala Gln Arg Thr
            1330              1335              1340

<210> SEQ ID NO 67
<211> LENGTH: 1308
<212> TYPE: PRT
<213> ORGANISM: Homo sapiens
<220> FEATURE:
<223> OTHER INFORMATION: HER4/ErbB4 Full Length (precursor)
<300> PUBLICATION INFORMATION:
<308> DATABASE ACCESSION NUMBER: UniProt No. Q15303
<309> DATABASE ENTRY DATE: 1998-12-15

<400> SEQUENCE: 67

Met Lys Pro Ala Thr Gly Leu Trp Val Trp Val Ser Leu Leu Val Ala
1               5                   10                  15

Ala Gly Thr Val Gln Pro Ser Asp Ser Gln Ser Val Cys Ala Gly Thr
            20                  25                  30

Glu Asn Lys Leu Ser Ser Leu Ser Asp Leu Glu Gln Gln Tyr Arg Ala
        35                  40                  45

Leu Arg Lys Tyr Tyr Glu Asn Cys Glu Val Val Met Gly Asn Leu Glu
    50                  55                  60

Ile Thr Ser Ile Glu His Asn Arg Asp Leu Ser Phe Leu Arg Ser Val
65                  70                  75                  80

Arg Glu Val Thr Gly Tyr Val Leu Val Ala Leu Asn Gln Phe Arg Tyr
                85                  90                  95

Leu Pro Leu Glu Asn Leu Arg Ile Ile Arg Gly Thr Lys Leu Tyr Glu
            100                 105                 110

Asp Arg Tyr Ala Leu Ala Ile Phe Leu Asn Tyr Arg Lys Asp Gly Asn
        115                 120                 125

Phe Gly Leu Gln Glu Leu Gly Leu Lys Asn Leu Thr Glu Ile Leu Asn
    130                 135                 140

Gly Gly Val Tyr Val Asp Gln Asn Lys Phe Leu Cys Tyr Ala Asp Thr
145                 150                 155                 160

Ile His Trp Gln Asp Ile Val Arg Asn Pro Trp Pro Ser Asn Leu Thr
                165                 170                 175

Leu Val Ser Thr Asn Gly Ser Ser Gly Cys Gly Arg Cys His Lys Ser
```

```
            180                 185                 190
Cys Thr Gly Arg Cys Trp Gly Pro Thr Glu Asn His Cys Gln Thr Leu
            195                 200                 205
Thr Arg Thr Val Cys Ala Glu Gln Cys Asp Gly Arg Cys Tyr Gly Pro
            210                 215                 220
Tyr Val Ser Asp Cys Cys His Arg Glu Cys Ala Gly Gly Cys Ser Gly
225                 230                 235                 240
Pro Lys Asp Thr Asp Cys Phe Ala Cys Met Asn Phe Asn Asp Ser Gly
                245                 250                 255
Ala Cys Val Thr Gln Cys Pro Gln Thr Phe Val Tyr Asn Pro Thr Thr
            260                 265                 270
Phe Gln Leu Glu His Asn Phe Asn Ala Lys Tyr Thr Tyr Gly Ala Phe
            275                 280                 285
Cys Val Lys Lys Cys Pro His Asn Phe Val Val Asp Ser Ser Ser Cys
            290                 295                 300
Val Arg Ala Cys Pro Ser Ser Lys Met Glu Val Glu Glu Asn Gly Ile
305                 310                 315                 320
Lys Met Cys Lys Pro Cys Thr Asp Ile Cys Pro Lys Ala Cys Asp Gly
                325                 330                 335
Ile Gly Thr Gly Ser Leu Met Ser Ala Gln Thr Val Asp Ser Ser Asn
            340                 345                 350
Ile Asp Lys Phe Ile Asn Cys Thr Lys Ile Asn Gly Asn Leu Ile Phe
            355                 360                 365
Leu Val Thr Gly Ile His Gly Asp Pro Tyr Asn Ala Ile Glu Ala Ile
            370                 375                 380
Asp Pro Glu Lys Leu Asn Val Phe Arg Thr Val Arg Glu Ile Thr Gly
385                 390                 395                 400
Phe Leu Asn Ile Gln Ser Trp Pro Pro Asn Met Thr Asp Phe Ser Val
                405                 410                 415
Phe Ser Asn Leu Val Thr Ile Gly Gly Arg Val Leu Tyr Ser Gly Leu
            420                 425                 430
Ser Leu Leu Ile Leu Lys Gln Gln Gly Ile Thr Ser Leu Gln Phe Gln
            435                 440                 445
Ser Leu Lys Glu Ile Ser Ala Gly Asn Ile Tyr Ile Thr Asp Asn Ser
450                 455                 460
Asn Leu Cys Tyr Tyr His Thr Ile Asn Trp Thr Thr Leu Phe Ser Thr
465                 470                 475                 480
Ile Asn Gln Arg Ile Val Ile Arg Asp Asn Arg Lys Ala Glu Asn Cys
                485                 490                 495
Thr Ala Glu Gly Met Val Cys Asn His Leu Cys Ser Ser Asp Gly Cys
            500                 505                 510
Trp Gly Pro Gly Pro Asp Gln Cys Leu Ser Cys Arg Arg Phe Ser Arg
            515                 520                 525
Gly Arg Ile Cys Ile Glu Ser Cys Asn Leu Tyr Asp Gly Glu Phe Arg
            530                 535                 540
Glu Phe Glu Asn Gly Ser Ile Cys Val Glu Cys Asp Pro Gln Cys Glu
545                 550                 555                 560
Lys Met Glu Asp Gly Leu Leu Thr Cys His Gly Pro Gly Pro Asp Asn
                565                 570                 575
Cys Thr Lys Cys Ser His Phe Lys Asp Gly Pro Asn Cys Val Glu Lys
            580                 585                 590
Cys Pro Asp Gly Leu Gln Gly Ala Asn Ser Phe Ile Phe Lys Tyr Ala
            595                 600                 605
```

```
Asp Pro Asp Arg Glu Cys His Pro Cys His Pro Asn Cys Thr Gln Gly
    610                 615                 620

Cys Asn Gly Pro Thr Ser His Asp Cys Ile Tyr Tyr Pro Trp Thr Gly
625                 630                 635                 640

His Ser Thr Leu Pro Gln His Ala Arg Thr Pro Leu Ile Ala Ala Gly
                645                 650                 655

Val Ile Gly Gly Leu Phe Ile Leu Val Ile Gly Leu Thr Phe Ala
            660                 665                 670

Val Tyr Val Arg Arg Lys Ser Ile Lys Lys Arg Ala Leu Arg Arg
        675                 680                 685

Phe Leu Glu Thr Glu Leu Val Glu Pro Leu Thr Pro Ser Gly Thr Ala
    690                 695                 700

Pro Asn Gln Ala Gln Leu Arg Ile Leu Lys Glu Thr Glu Leu Lys Arg
705                 710                 715                 720

Val Lys Val Leu Gly Ser Gly Ala Phe Gly Thr Val Tyr Lys Gly Ile
                725                 730                 735

Trp Val Pro Glu Gly Glu Thr Val Lys Ile Pro Val Ala Ile Lys Ile
            740                 745                 750

Leu Asn Glu Thr Thr Gly Pro Lys Ala Asn Val Glu Phe Met Asp Glu
    755                 760                 765

Ala Leu Ile Met Ala Ser Met Asp His Pro His Leu Val Arg Leu Leu
770                 775                 780

Gly Val Cys Leu Ser Pro Thr Ile Gln Leu Val Thr Gln Leu Met Pro
785                 790                 795                 800

His Gly Cys Leu Leu Glu Tyr Val His Glu His Lys Asp Asn Ile Gly
                805                 810                 815

Ser Gln Leu Leu Leu Asn Trp Cys Val Gln Ile Ala Lys Gly Met Met
            820                 825                 830

Tyr Leu Glu Glu Arg Arg Leu Val His Arg Asp Leu Ala Ala Arg Asn
        835                 840                 845

Val Leu Val Lys Ser Pro Asn His Val Lys Ile Thr Asp Phe Gly Leu
    850                 855                 860

Ala Arg Leu Leu Glu Gly Asp Glu Lys Glu Tyr Asn Ala Asp Gly Gly
865                 870                 875                 880

Lys Met Pro Ile Lys Trp Met Ala Leu Glu Cys Ile His Tyr Arg Lys
                885                 890                 895

Phe Thr His Gln Ser Asp Val Trp Ser Tyr Gly Val Thr Ile Trp Glu
            900                 905                 910

Leu Met Thr Phe Gly Gly Lys Pro Tyr Asp Gly Ile Pro Thr Arg Glu
        915                 920                 925

Ile Pro Asp Leu Leu Glu Lys Gly Glu Arg Leu Pro Gln Pro Pro Ile
    930                 935                 940

Cys Thr Ile Asp Val Tyr Met Val Met Val Lys Cys Trp Met Ile Asp
945                 950                 955                 960

Ala Asp Ser Arg Pro Lys Phe Lys Glu Leu Ala Ala Glu Phe Ser Arg
                965                 970                 975

Met Ala Arg Asp Pro Gln Arg Tyr Leu Val Ile Gln Gly Asp Asp Arg
            980                 985                 990

Met Lys Leu Pro Ser Pro Asn Asp Ser Lys Phe Phe Gln Asn Leu Leu
        995                 1000                1005

Asp Glu Glu Asp Leu Glu Asp Met Met Asp Ala Glu Glu Tyr Leu Val
    1010                1015                1020
```

```
Pro Gln Ala Phe Asn Ile Pro Pro Ile Tyr Thr Ser Arg Ala Arg
1025                1030                1035                1040

Ile Asp Ser Asn Arg Ser Glu Ile Gly His Ser Pro Pro Ala Tyr
            1045                1050                1055

Thr Pro Met Ser Gly Asn Gln Phe Val Tyr Arg Asp Gly Phe Ala
        1060                1065                1070

Ala Glu Gln Gly Val Ser Val Pro Tyr Arg Ala Pro Thr Ser Thr
    1075                1080                1085

Pro Glu Ala Pro Val Ala Gln Gly Ala Thr Ala Glu Ile Phe Asp Asp
1090                1095                1100

Ser Cys Cys Asn Gly Thr Leu Arg Lys Pro Val Ala Pro His Val Gln
1105                1110                1115                1120

Glu Asp Ser Ser Thr Gln Arg Tyr Ser Ala Asp Pro Thr Val Phe Ala
                1125                1130                1135

Pro Glu Arg Ser Pro Arg Gly Glu Leu Asp Glu Gly Tyr Met Thr
                1140                1145                1150

Pro Met Arg Asp Lys Pro Lys Gln Glu Tyr Leu Asn Pro Val Glu Glu
        1155                1160                1165

Asn Pro Phe Val Ser Arg Arg Lys Asn Gly Asp Leu Gln Ala Leu Asp
    1170                1175                1180

Asn Pro Glu Tyr His Asn Ala Ser Asn Gly Pro Pro Lys Ala Glu Asp
1185                1190                1195                1200

Glu Tyr Val Asn Glu Pro Leu Tyr Leu Asn Thr Phe Ala Asn Thr Leu
                1205                1210                1215

Gly Lys Ala Glu Tyr Leu Lys Asn Asn Ile Leu Ser Met Pro Glu Lys
        1220                1225                1230

Ala Lys Lys Ala Phe Asp Asn Pro Asp Tyr Trp Asn His Ser Leu Pro
    1235                1240                1245

Pro Arg Ser Thr Leu Gln His Pro Asp Tyr Leu Gln Glu Tyr Ser Thr
1250                1255                1260

Lys Tyr Phe Tyr Lys Gln Asn Gly Arg Ile Arg Pro Ile Val Ala Glu
1265                1270                1275                1280

Asn Pro Glu Tyr Leu Ser Glu Phe Ser Leu Lys Pro Gly Thr Val Leu
                1285                1290                1295

Pro Pro Pro Pro Tyr Arg His Arg Asn Thr Val Val
                1300                1305

<210> SEQ ID NO 68
<211> LENGTH: 1390
<212> TYPE: PRT
<213> ORGANISM: Homo sapiens
<220> FEATURE:
<223> OTHER INFORMATION: HGFR/c-Met Full Length (precursor)
<300> PUBLICATION INFORMATION:
<308> DATABASE ACCESSION NUMBER: UniProt No. P08581
<309> DATABASE ENTRY DATE: 1988-08-01

<400> SEQUENCE: 68

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60
```

```
Gly Ala Thr Asn Tyr Ile Tyr Val Leu Asn Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
            115                 120                 125

Gln Leu Ile Ser Cys Gly Ser Val Asn Arg Gly Thr Cys Gln Arg His
            130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
            195                 200                 205

His Pro Leu His Ser Ile Ser Val Arg Arg Leu Lys Glu Thr Lys Asp
            210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
            275                 280                 285

His Ser Tyr Met Glu Met Pro Leu Glu Cys Ile Leu Thr Glu Lys Arg
            290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
            355                 360                 365

Tyr Val Asn Asp Phe Phe Asn Lys Ile Val Asn Lys Asn Asn Val Arg
370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
            435                 440                 445

Asp Leu Thr Ile Ala Asn Leu Gly Thr Ser Glu Gly Arg Phe Met Gln
            450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
```

```
                485                 490                 495
Asn Gln Asn Gly Tyr Thr Leu Val Ile Thr Gly Lys Lys Ile Thr Lys
                500                 505                 510

Ile Pro Leu Asn Gly Leu Gly Cys Arg His Phe Gln Ser Cys Ser Gln
                515                 520                 525

Cys Leu Ser Ala Pro Pro Phe Val Gln Cys Gly Trp Cys His Asp Lys
                530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
                580                 585                 590

Asn Asn Lys Phe Asp Leu Lys Lys Thr Arg Val Leu Leu Gly Asn Glu
                595                 600                 605

Ser Cys Thr Leu Thr Leu Ser Glu Ser Thr Met Asn Thr Leu Lys Cys
                610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                        645                 650                 655

Pro Val Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
                675                 680                 685

His Ile Ser Ile Gly Gly Lys Thr Cys Thr Leu Lys Ser Val Ser Asn
                690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
                740                 745                 750

Phe Ile Ser Gly Gly Ser Thr Ile Thr Gly Val Gly Lys Asn Leu Asn
                755                 760                 765

Ser Val Ser Val Pro Arg Met Val Ile Asn Val His Glu Ala Gly Arg
                770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
                820                 825                 830

Leu Ile Tyr Val His Asn Pro Val Phe Lys Pro Phe Glu Lys Pro Val
                835                 840                 845

Met Ile Ser Met Gly Asn Glu Asn Val Leu Glu Ile Lys Gly Asn Asp
                850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                        885                 890                 895

Pro Asn Asp Leu Leu Lys Leu Asn Ser Glu Leu Asn Ile Glu Trp Lys
                900                 905                 910
```

```
Gln Ala Ile Ser Ser Thr Val Leu Gly Lys Val Ile Val Gln Pro Asp
        915                 920                 925

Gln Asn Phe Thr Gly Leu Ile Ala Gly Val Val Ser Ile Ser Thr Ala
        930                 935                 940

Leu Leu Leu Leu Leu Gly Phe Phe Leu Trp Leu Lys Lys Arg Lys Gln
945                 950                 955                 960

Ile Lys Asp Leu Gly Ser Glu Leu Val Arg Tyr Asp Ala Arg Val His
                965                 970                 975

Thr Pro His Leu Asp Arg Leu Val Ser Ala Arg Ser Val Ser Pro Thr
            980                 985                 990

Thr Glu Met Val Ser Asn Glu Ser Val Asp Tyr Arg Ala Thr Phe Pro
        995                 1000                1005

Glu Asp Gln Phe Pro Asn Ser Ser Gln Asn Gly Ser Cys Arg Gln Val
        1010                1015                1020

Gln Tyr Pro Leu Thr Asp Met Ser Pro Ile Leu Thr Ser Gly Asp Ser
1025                1030                1035                1040

Asp Ile Ser Ser Pro Leu Leu Gln Asn Thr Val His Ile Asp Leu Ser
                1045                1050                1055

Ala Leu Asn Pro Glu Leu Val Gln Ala Val Gln His Val Val Ile Gly
            1060                1065                1070

Pro Ser Ser Leu Ile Val His Phe Asn Glu Val Ile Gly Arg Gly His
        1075                1080                1085

Phe Gly Cys Val Tyr His Gly Thr Leu Leu Asp Asn Asp Gly Lys Lys
    1090                1095                1100

Ile His Cys Ala Val Lys Ser Leu Asn Arg Ile Thr Asp Ile Gly Glu
1105                1110                1115                1120

Val Ser Gln Phe Leu Thr Glu Gly Ile Ile Met Lys Asp Phe Ser His
                1125                1130                1135

Pro Asn Val Leu Ser Leu Leu Gly Ile Cys Leu Arg Ser Glu Gly Ser
            1140                1145                1150

Pro Leu Val Val Leu Pro Tyr Met Lys His Gly Asp Leu Arg Asn Phe
        1155                1160                1165

Ile Arg Asn Glu Thr His Asn Pro Thr Val Lys Asp Leu Ile Gly Phe
    1170                1175                1180

Gly Leu Gln Val Ala Lys Gly Met Lys Tyr Leu Ala Ser Lys Lys Phe
1185                1190                1195                1200

Val His Arg Asp Leu Ala Ala Arg Asn Cys Met Leu Asp Glu Lys Phe
                1205                1210                1215

Thr Val Lys Val Ala Asp Phe Gly Leu Ala Arg Asp Met Tyr Asp Lys
            1220                1225                1230

Glu Tyr Tyr Ser Val His Asn Lys Thr Gly Ala Lys Leu Pro Val Lys
        1235                1240                1245

Trp Met Ala Leu Glu Ser Leu Gln Thr Gln Lys Phe Thr Thr Lys Ser
    1250                1255                1260

Asp Val Trp Ser Phe Gly Val Leu Leu Trp Glu Leu Met Thr Arg Gly
1265                1270                1275                1280

Ala Pro Pro Tyr Pro Asp Val Asn Thr Phe Asp Ile Thr Val Tyr Leu
                1285                1290                1295

Leu Gln Gly Arg Arg Leu Leu Gln Pro Glu Tyr Cys Pro Asp Pro Leu
            1300                1305                1310

Tyr Glu Val Met Leu Lys Cys Trp His Pro Lys Ala Glu Met Arg Pro
        1315                1320                1325
```

```
Ser Phe Ser Glu Leu Val Ser Arg Ile Ser Ala Ile Phe Ser Thr Phe
        1330                1335                1340

Ile Gly Glu His Tyr Val His Val Asn Ala Thr Tyr Val Asn Val Lys
1345                1350                1355                1360

Cys Val Ala Pro Tyr Pro Ser Leu Leu Ser Ser Glu Asp Asn Ala Asp
                1365                1370                1375

Asp Glu Val Asp Thr Arg Pro Ala Ser Phe Trp Glu Thr Ser
                1380                1385                1390
```

<210> SEQ ID NO 69
<211> LENGTH: 1367
<212> TYPE: PRT
<213> ORGANISM: Homo sapiens
<220> FEATURE:
<223> OTHER INFORMATION: IGF-1 R full length (precursor)
<300> PUBLICATION INFORMATION:
<308> DATABASE ACCESSION NUMBER: UniProt No. P08069
<309> DATABASE ENTRY DATE: 1988-08-01

<400> SEQUENCE: 69

```
Met Lys Ser Gly Ser Gly Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
        50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
    210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
        275                 280                 285
```

```
Glu Ser Ser Asp Ser Glu Gly Phe Val Ile His Asp Gly Glu Cys Met
    290             295                 300
Gln Glu Cys Pro Ser Gly Phe Ile Arg Asn Gly Ser Gln Ser Met Tyr
305             310                 315                 320
Cys Ile Pro Cys Glu Gly Pro Cys Pro Lys Val Cys Glu Glu Glu Lys
                325                 330                 335
Lys Thr Lys Thr Ile Asp Ser Val Thr Ser Ala Gln Met Leu Gln Gly
            340                 345                 350
Cys Thr Ile Phe Lys Gly Asn Leu Leu Ile Asn Ile Arg Arg Gly Asn
        355                 360                 365
Asn Ile Ala Ser Glu Leu Glu Asn Phe Met Gly Leu Ile Glu Val Val
370                 375                 380
Thr Gly Tyr Val Lys Ile Arg His Ser His Ala Leu Val Ser Leu Ser
385                 390                 395                 400
Phe Leu Lys Asn Leu Arg Leu Ile Leu Gly Glu Glu Gln Leu Glu Gly
                405                 410                 415
Asn Tyr Ser Phe Tyr Val Leu Asp Asn Gln Asn Leu Gln Gln Leu Trp
            420                 425                 430
Asp Trp Asp His Arg Asn Leu Thr Ile Lys Ala Gly Lys Met Tyr Phe
        435                 440                 445
Ala Phe Asn Pro Lys Leu Cys Val Ser Glu Ile Tyr Arg Met Glu Glu
450                 455                 460
Val Thr Gly Thr Lys Gly Arg Gln Ser Lys Gly Asp Ile Asn Thr Arg
465                 470                 475                 480
Asn Asn Gly Glu Arg Ala Ser Cys Glu Ser Asp Val Leu His Phe Thr
                485                 490                 495
Ser Thr Thr Thr Ser Lys Asn Arg Ile Ile Ile Thr Trp His Arg Tyr
            500                 505                 510
Arg Pro Pro Asp Tyr Arg Asp Leu Ile Ser Phe Thr Val Tyr Tyr Lys
        515                 520                 525
Glu Ala Pro Phe Lys Asn Val Thr Glu Tyr Asp Gly Gln Asp Ala Cys
530                 535                 540
Gly Ser Asn Ser Trp Asn Met Val Asp Val Asp Leu Pro Pro Asn Lys
545                 550                 555                 560
Asp Val Glu Pro Gly Ile Leu Leu His Gly Leu Lys Pro Trp Thr Gln
                565                 570                 575
Tyr Ala Val Tyr Val Lys Ala Val Thr Leu Thr Met Val Glu Asn Asp
            580                 585                 590
His Ile Arg Gly Ala Lys Ser Glu Ile Leu Tyr Ile Arg Thr Asn Ala
        595                 600                 605
Ser Val Pro Ser Ile Pro Leu Asp Val Leu Ser Ala Ser Asn Ser Ser
610                 615                 620
Ser Gln Leu Ile Val Lys Trp Asn Pro Pro Ser Leu Pro Asn Gly Asn
625                 630                 635                 640
Leu Ser Tyr Tyr Ile Val Arg Trp Gln Arg Gln Pro Gln Asp Gly Tyr
                645                 650                 655
Leu Tyr Arg His Asn Tyr Cys Ser Lys Asp Lys Ile Pro Ile Arg Lys
            660                 665                 670
Tyr Ala Asp Gly Thr Ile Asp Ile Glu Glu Val Thr Glu Asn Pro Lys
        675                 680                 685
Thr Glu Val Cys Gly Gly Glu Lys Gly Pro Cys Cys Ala Cys Pro Lys
690                 695                 700
Thr Glu Ala Glu Lys Gln Ala Glu Lys Glu Glu Ala Glu Tyr Arg Lys
```

```
            705                 710                 715                 720
Val Phe Glu Asn Phe Leu His Asn Ser Ile Phe Val Pro Arg Pro Glu
                725                 730                 735

Arg Lys Arg Arg Asp Val Met Gln Val Ala Asn Thr Thr Met Ser Ser
                740                 745                 750

Arg Ser Arg Asn Thr Thr Ala Ala Asp Thr Tyr Asn Ile Thr Asp Pro
                755                 760                 765

Glu Glu Leu Glu Thr Glu Tyr Pro Phe Phe Glu Ser Arg Val Asp Asn
                770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                805                 810                 815

Ala Ser Asn Phe Val Phe Ala Arg Thr Met Pro Ala Glu Gly Ala Asp
                820                 825                 830

Asp Ile Pro Gly Pro Val Thr Trp Glu Pro Arg Pro Glu Asn Ser Ile
                835                 840                 845

Phe Leu Lys Trp Pro Glu Pro Glu Asn Pro Asn Gly Leu Ile Leu Met
                850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                885                 890                 895

Asn Pro Gly Asn Tyr Thr Ala Arg Ile Gln Ala Thr Ser Leu Ser Gly
                900                 905                 910

Asn Gly Ser Trp Thr Asp Pro Val Phe Phe Tyr Val Gln Ala Lys Thr
                915                 920                 925

Gly Tyr Glu Asn Phe Ile His Leu Ile Ile Ala Leu Pro Val Ala Val
                930                 935                 940

Leu Leu Ile Val Gly Gly Leu Val Ile Met Leu Tyr Val Phe His Arg
945                 950                 955                 960

Lys Arg Asn Asn Ser Arg Leu Gly Asn Gly Val Leu Tyr Ala Ser Val
                965                 970                 975

Asn Pro Glu Tyr Phe Ser Ala Ala Asp Val Tyr Val Pro Asp Glu Trp
                980                 985                 990

Glu Val Ala Arg Glu Lys Ile Thr Met Ser Arg Glu Leu Gly Gln Gly
                995                 1000                1005

Ser Phe Gly Met Val Tyr Glu Gly Val Ala Lys Gly Val Val Lys Asp
                1010                1015                1020

Glu Pro Glu Thr Arg Val Ala Ile Lys Thr Val Asn Glu Ala Ala Ser
1025                1030                1035                1040

Met Arg Glu Arg Ile Glu Phe Leu Asn Glu Ala Ser Val Met Lys Glu
                1045                1050                1055

Phe Asn Cys His His Val Val Arg Leu Leu Gly Val Val Ser Gln Gly
                1060                1065                1070

Gln Pro Thr Leu Val Ile Met Glu Leu Met Thr Arg Gly Asp Leu Lys
                1075                1080                1085

Ser Tyr Leu Arg Ser Leu Arg Pro Glu Met Glu Asn Asn Pro Val Leu
                1090                1095                1100

Ala Pro Pro Ser Leu Ser Lys Met Ile Gln Met Ala Gly Glu Ile Ala
1105                1110                1115                1120

Asp Gly Met Ala Tyr Leu Asn Ala Asn Lys Phe Val His Arg Asp Leu
                1125                1130                1135
```

```
Ala Ala Arg Asn Cys Met Val Ala Glu Asp Phe Thr Val Lys Ile Gly
        1140                1145                1150

Asp Phe Gly Met Thr Arg Asp Ile Tyr Glu Thr Asp Tyr Tyr Arg Lys
        1155                1160                1165

Gly Gly Lys Gly Leu Leu Pro Val Arg Trp Met Ser Pro Glu Ser Leu
        1170                1175                1180

Lys Asp Gly Val Phe Thr Thr Tyr Ser Asp Val Trp Ser Phe Gly Val
1185                1190                1195                1200

Val Leu Trp Glu Ile Ala Thr Leu Ala Glu Gln Pro Tyr Gln Gly Leu
            1205                1210                1215

Ser Asn Glu Gln Val Leu Arg Phe Val Met Glu Gly Gly Leu Leu Asp
        1220                1225                1230

Lys Pro Asp Asn Cys Pro Asp Met Leu Phe Glu Leu Met Arg Met Cys
        1235                1240                1245

Trp Gln Tyr Asn Pro Lys Met Arg Pro Ser Phe Leu Glu Ile Ile Ser
        1250                1255                1260

Ser Ile Lys Glu Glu Met Glu Pro Gly Phe Arg Glu Val Ser Phe Tyr
1265                1270                1275                1280

Tyr Ser Glu Glu Asn Lys Leu Pro Glu Pro Glu Glu Leu Asp Leu Glu
            1285                1290                1295

Pro Glu Asn Met Glu Ser Val Pro Leu Asp Pro Ser Ala Ser Ser Ser
        1300                1305                1310

Ser Leu Pro Leu Pro Asp Arg His Ser Gly His Lys Ala Glu Asn Gly
        1315                1320                1325

Pro Gly Pro Gly Val Leu Val Leu Arg Ala Ser Phe Asp Glu Arg Gln
        1330                1335                1340

Pro Tyr Ala His Met Asn Gly Gly Arg Lys Asn Glu Arg Ala Leu Pro
1345                1350                1355                1360

Leu Pro Gln Ser Ser Thr Cys
            1365

<210> SEQ ID NO 70
<211> LENGTH: 12
<212> TYPE: PRT
<213> ORGANISM: Artificial Sequence
<220> FEATURE:
<223> OTHER INFORMATION: spacer (IgG4hinge)

<400> SEQUENCE: 70

Glu Ser Lys Tyr Gly Pro Pro Cys Pro Pro Cys Pro
1               5                   10

<210> SEQ ID NO 71
<211> LENGTH: 36
<212> TYPE: DNA
<213> ORGANISM: Artificial Sequence
<220> FEATURE:
<223> OTHER INFORMATION: spacer (IgG4hinge)

<400> SEQUENCE: 71
gaatctaagt acggaccgcc ctgcccccct tgccct                              36

<210> SEQ ID NO 72
<211> LENGTH: 119
<212> TYPE: PRT
<213> ORGANISM: Artificial Sequence
<220> FEATURE:
<223> OTHER INFORMATION: Hinge-CH3 spacer
```

```
<400> SEQUENCE: 72

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Met Thr Lys
            20                  25                  30

Asn Gln Val Ser Leu Thr Cys Leu Val Lys Gly Phe Tyr Pro Ser Asp
            35                  40                  45

Ile Ala Val Glu Trp Glu Ser Asn Gly Gln Pro Glu Asn Asn Tyr Lys
50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
            115

<210> SEQ ID NO 73
<211> LENGTH: 229
<212> TYPE: PRT
<213> ORGANISM: Artificial Sequence
<220> FEATURE:
<223> OTHER INFORMATION: Hinge-CH2-CH3 spacer

<400> SEQUENCE: 73

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
            50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
            130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
210                 215                 220

Leu Ser Leu Gly Lys
```

<210> SEQ ID NO 74
<211> LENGTH: 282
<212> TYPE: PRT
<213> ORGANISM: Artificial Sequence
<220> FEATURE:
<223> OTHER INFORMATION: IgD-hinge-Fc

<400> SEQUENCE: 74

Arg Trp Pro Glu Ser Pro Lys Ala Gln Ala Ser Val Pro Thr Ala
1               5                   10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Glu Lys Lys Lys Glu Lys
        35                  40                  45

Glu Lys Glu Glu Gln Glu Glu Arg Glu Thr Lys Thr Pro Glu Cys Pro
    50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
                85                  90                  95

Ser Asp Leu Lys Asp Ala His Leu Thr Trp Glu Val Ala Gly Lys Val
            100                 105                 110

Pro Thr Gly Gly Val Glu Glu Gly Leu Leu Glu Arg His Ser Asn Gly
        115                 120                 125

Ser Gln Ser Gln His Ser Arg Leu Thr Leu Pro Arg Ser Leu Trp Asn
    130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
        195                 200                 205

Met Trp Leu Glu Asp Gln Arg Glu Val Asn Thr Ser Gly Phe Ala Pro
    210                 215                 220

Ala Arg Pro Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
                245                 250                 255

Cys Val Val Ser His Glu Asp Ser Arg Thr Leu Leu Asn Ala Ser Arg
            260                 265                 270

Ser Leu Glu Val Ser Tyr Val Thr Asp His
        275                 280

<210> SEQ ID NO 75
<211> LENGTH: 18
<212> TYPE: PRT
<213> ORGANISM: Artificial Sequence
<220> FEATURE:
<223> OTHER INFORMATION: CD8 alpha signal peptide

<400> SEQUENCE: 75

Met Ala Leu Pro Val Thr Ala Leu Leu Leu Pro Leu Ala Leu Leu Leu
1               5                   10                  15

His Ala

<210> SEQ ID NO 76
<211> LENGTH: 18
<212> TYPE: PRT
<213> ORGANISM: Artificial Sequence
<220> FEATURE:
<223> OTHER INFORMATION: T2A

<400> SEQUENCE: 76

Glu Gly Arg Gly Ser Leu Leu Thr Cys Gly Asp Val Glu Glu Asn Pro
1               5                   10                  15

Gly Pro

<210> SEQ ID NO 77
<211> LENGTH: 27
<212> TYPE: PRT
<213> ORGANISM: Artificial Sequence
<220> FEATURE:
<223> OTHER INFORMATION: CD28
<300> PUBLICATION INFORMATION:
<308> DATABASE ACCESSION NUMBER: UniProt P10747
<309> DATABASE ENTRY DATE: 1989-07-01

<400> SEQUENCE: 77

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 78
<211> LENGTH: 66
<212> TYPE: PRT
<213> ORGANISM: Artificial Sequence
<220> FEATURE:
<223> OTHER INFORMATION: CD28
<300> PUBLICATION INFORMATION:
<308> DATABASE ACCESSION NUMBER: UniProt P10747
<309> DATABASE ENTRY DATE: 1989-07-01

<400> SEQUENCE: 78

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val
65

<210> SEQ ID NO 79
<211> LENGTH: 41
<212> TYPE: PRT
<213> ORGANISM: Artificial Sequence
<220> FEATURE:
<223> OTHER INFORMATION: CD28
<300> PUBLICATION INFORMATION:
<308> DATABASE ACCESSION NUMBER: UniProt P10747
<309> DATABASE ENTRY DATE: 1989-07-01

<400> SEQUENCE: 79

Arg Ser Lys Arg Ser Arg Leu Leu His Ser Asp Tyr Met Asn Met Thr
1               5                   10                  15

```
Pro Arg Arg Pro Gly Pro Thr Arg Lys His Tyr Gln Pro Tyr Ala Pro
            20                  25                  30

Pro Arg Asp Phe Ala Ala Tyr Arg Ser
            35                  40

<210> SEQ ID NO 80
<211> LENGTH: 41
<212> TYPE: PRT
<213> ORGANISM: Artificial Sequence
<220> FEATURE:
<223> OTHER INFORMATION: CD28

<400> SEQUENCE: 80

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
            35                  40

<210> SEQ ID NO 81
<211> LENGTH: 42
<212> TYPE: PRT
<213> ORGANISM: Artificial Sequence
<220> FEATURE:
<223> OTHER INFORMATION: 4-1BB
<300> PUBLICATION INFORMATION:
<308> DATABASE ACCESSION NUMBER: UniProt Q07011.1
<309> DATABASE ENTRY DATE: 1995-02-01

<400> SEQUENCE: 81

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 82
<211> LENGTH: 112
<212> TYPE: PRT
<213> ORGANISM: Artificial Sequence
<220> FEATURE:
<223> OTHER INFORMATION: CD3 zeta

<400> SEQUENCE: 82

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 83
<211> LENGTH: 112
<212> TYPE: PRT
<213> ORGANISM: Artificial Sequence
<220> FEATURE:
<223> OTHER INFORMATION: CD3 zeta

<400> SEQUENCE: 83

Arg Val Lys Phe Ser Arg Ser Ala Glu Pro Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 84
<211> LENGTH: 112
<212> TYPE: PRT
<213> ORGANISM: Artificial Sequence
<220> FEATURE:
<223> OTHER INFORMATION: CD3 zeta

<400> SEQUENCE: 84

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 85
<211> LENGTH: 22
<212> TYPE: PRT
<213> ORGANISM: Artificial Sequence
<220> FEATURE:
<223> OTHER INFORMATION: P2A

<400> SEQUENCE: 85

Gly Ser Gly Ala Thr Asn Phe Ser Leu Leu Lys Gln Ala Gly Asp Val
1               5                   10                  15

Glu Glu Asn Pro Gly Pro
            20

-continued

```
<210> SEQ ID NO 86
<211> LENGTH: 19
<212> TYPE: PRT
<213> ORGANISM: Artificial Sequence
<220> FEATURE:
<223> OTHER INFORMATION: P2A

<400> SEQUENCE: 86

Ala Thr Asn Phe Ser Leu Leu Lys Gln Ala Gly Asp Val Glu Glu Asn
1               5                   10                  15

Pro Gly Pro

<210> SEQ ID NO 87
<211> LENGTH: 20
<212> TYPE: PRT
<213> ORGANISM: Artificial Sequence
<220> FEATURE:
<223> OTHER INFORMATION: E2A

<400> SEQUENCE: 87

Gln Cys Thr Asn Tyr Ala Leu Leu Lys Leu Ala Gly Asp Val Glu Ser
1               5                   10                  15

Asn Pro Gly Pro
            20

<210> SEQ ID NO 88
<211> LENGTH: 22
<212> TYPE: PRT
<213> ORGANISM: Artificial Sequence
<220> FEATURE:
<223> OTHER INFORMATION: F2A

<400> SEQUENCE: 88

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 89
<211> LENGTH: 10
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (5)...(9)
<223> OTHER INFORMATION: SGGGG is repeated 5 times

<400> SEQUENCE: 89

Pro Gly Gly Gly Ser Gly Gly Gly Gly Pro
1               5                   10

<210> SEQ ID NO 90
<211> LENGTH: 17
<212> TYPE: PRT
<213> ORGANISM: Artificial Sequence
<220> FEATURE:
<223> OTHER INFORMATION: Linker

<400> SEQUENCE: 90

Gly Ser Ala Asp Asp Ala Lys Lys Asp Ala Ala Lys Lys Asp Gly Lys
1               5                   10                  15

Ser
```

<210> SEQ ID NO 91
<211> LENGTH: 363
<212> TYPE: DNA
<213> ORGANISM: Artificial Sequence
<220> FEATURE:
<223> OTHER INFORMATION: Modified HER2t

<400> SEQUENCE: 91

```
tgccaccctg agtgtcagcc ccagaatggc tcagtgacct gttttggacc ggaggctgac      60
cagtgtgtgg cctgtgccca ctataaggac cctcccttct gcgtggcccg ctgccccagc     120
ggtgtgaaac ctgacctctc ctacatgccc atctggaagt ttccagatga ggagggcgca     180
tgccagcctt gccccatcaa ctgcacccac tcctgtgtgg acctggatga caagggctgc     240
cccgccgagc agagagccag ccctctgacg ggtggaggaa gcggaggtgg cagctccatc     300
atctctgcgg tggttggcat tctgctggtc gtggtcttgg ggtggtctt tgggatcctc      360 atc                                                                   363
```

<210> SEQ ID NO 92
<211> LENGTH: 121
<212> TYPE: PRT
<213> ORGANISM: Artificial Sequence
<220> FEATURE:
<223> OTHER INFORMATION: Modified HER2t

<400> SEQUENCE: 92

```
Cys His Pro Glu Cys Gln Pro Gln Asn Gly Ser Val Thr Cys Phe Gly
1               5                  10                  15

Pro Glu Ala Asp Gln Cys Val Ala Cys Ala His Tyr Lys Asp Pro Pro
            20                  25                  30

Phe Cys Val Ala Arg Cys Pro Ser Gly Val Lys Pro Asp Leu Ser Tyr
        35                  40                  45

Met Pro Ile Trp Lys Phe Pro Asp Glu Glu Gly Ala Cys Gln Pro Cys
    50                  55                  60

Pro Ile Asn Cys Thr His Ser Cys Val Asp Leu Asp Asp Lys Gly Cys
65                  70                  75                  80

Pro Ala Glu Gln Arg Ala Ser Pro Leu Thr Gly Gly Gly Ser Gly Gly
                85                  90                  95

Gly Ser Ser Ile Ile Ser Ala Val Val Gly Ile Leu Leu Val Val Val
            100                 105                 110

Leu Gly Val Val Phe Gly Ile Leu Ile
        115                 120
```

<210> SEQ ID NO 93
<211> LENGTH: 429
<212> TYPE: DNA
<213> ORGANISM: Artificial Sequence
<220> FEATURE:
<223> OTHER INFORMATION: Modified HER2t with signal sequence

<400> SEQUENCE: 93

```
atgcttctcc tggtgacaag ccttctgctc tgtgagttac cacacccagc attcctcctg      60
atcccatgcc accctgagtg tcagccccag aatggctcag tgacctgttt tggaccggag     120
gctgaccagt gtgtggcctg tgcccactat aaggaccctc ccttctgcgt ggcccgctgc     180 ccagcggtg tgaaacctga cctctcctac atgcccatct ggaagtttcc agatgaggag     240
ggcgcatgcc agccttgccc catcaactgc acccactcct gtgtggacct ggatgacaag     300
ggctgccccg ccgagcagag agccagccct ctgacgggtg gaggaagcgg aggtggcagc     360
```

```
tccatcatct ctgcggtggt tggcattctg ctggtcgtgg tcttgggggt ggtctttggg    420
atcctcatc                                                            429
```

<210> SEQ ID NO 94
<211> LENGTH: 750
<212> TYPE: PRT
<213> ORGANISM: Artificial Sequence
<220> FEATURE:
<223> OTHER INFORMATION: PSMA WT

<400> SEQUENCE: 94

```
Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
    290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350
```

```
Thr Arg Ile Tyr Asn Val Ile Gly Thr Leu Arg Gly Ala Val Glu Pro
        355                 360                 365

Asp Arg Tyr Val Ile Leu Gly Gly His Arg Asp Ser Trp Val Phe Gly
        370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
                420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
        450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
                500                 505                 510

Ser Lys Leu Gly Ser Gly Asn Asp Phe Glu Val Phe Phe Gln Arg Leu
        515                 520                 525

Gly Ile Ala Ser Gly Arg Ala Arg Tyr Thr Lys Asn Trp Glu Thr Asn
        530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
                580                 585                 590

Leu Pro Phe Asp Cys Arg Asp Tyr Ala Val Val Leu Arg Lys Tyr Ala
        595                 600                 605

Asp Lys Ile Tyr Ser Ile Ser Met Lys His Pro Gln Glu Met Lys Thr
        610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
                660                 665                 670

Arg Ala Phe Ile Asp Pro Leu Gly Leu Pro Asp Arg Pro Phe Tyr Arg
        675                 680                 685

His Val Ile Tyr Ala Pro Ser Ser His Asn Lys Tyr Ala Gly Glu Ser
        690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
                740                 745                 750

<210> SEQ ID NO 95
<211> LENGTH: 750
```

```
<212> TYPE: PRT
<213> ORGANISM: Artificial Sequence
<220> FEATURE:
<223> OTHER INFORMATION: PSMA W2G

<400> SEQUENCE: 95

Met Gly Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
    290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
        355                 360                 365

Asp Arg Tyr Val Ile Leu Gly Gly His Arg Asp Ser Trp Val Phe Gly
    370                 375                 380
```

```
Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
            405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
            435                 440                 445

Tyr Ile Asn Ala Asp Ser Ser Ile Glu Gly Asn Tyr Thr Leu Arg Val
        450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
        515                 520                 525

Gly Ile Ala Ser Gly Arg Ala Arg Tyr Thr Lys Asn Trp Glu Thr Asn
530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
        595                 600                 605

Asp Lys Ile Tyr Ser Ile Ser Met Lys His Pro Gln Glu Met Lys Thr
610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
        675                 680                 685

His Val Ile Tyr Ala Pro Ser Ser His Asn Lys Tyr Ala Gly Glu Ser
690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
            740                 745                 750
```

<210> SEQ ID NO 96
<211> LENGTH: 2250
<212> TYPE: DNA
<213> ORGANISM: Artificial Sequence
<220> FEATURE:
<223> OTHER INFORMATION: PSMA WT

<400> SEQUENCE: 96

```
atgtggaatc tccttcacga aaccgactcg gctgtggcca ccgcgcgccg cccgcgctgg      60
ctgtgcgctg gggcgctggt gctggcgggt ggcttctttc tcctcggctt cctcttcggg     120
tggtttataa atcctccaa tgaagctact aacattactc caaagcataa tatgaaagca     180
tttttggatg aattgaaagc tgagaacatc aagaagttct tatataattt tacacagata     240
ccacatttag caggaacaga acaaaacttt cagcttgcaa agcaaattca atcccagtgg     300
aaagaatttg gcctggattc tgttgagcta gcacattatg atgtcctgtt gtcctaccca     360
aataagactc atcccaacta catctcaata attaatgaag atggaaatga gattttcaac     420
acatcattat ttgaaccacc tcctccagga tatgaaaatg tttcggatat tgtaccacct     480
ttcagtgctt tctctcctca aggaatgcca gagggcgatc tagtgtatgt taactatgca     540
cgaactgaag acttctttaa attggaacgg gacatgaaaa tcaattgctc tgggaaaatt     600
gtaattgcca gatatgggaa agttttcaga ggaaataagg ttaaaaatgc ccagctggca     660
ggggccaaag gagtcattct ctactccgac cctgctgact actttgctcc tggggtgaag     720
tcctatccag atggttggaa tcttcctgga ggtggtgtcc agcgtggaaa tatcctaaat     780
ctgaatggtg caggagaccc tctcacacca ggttacccag caaatgaata tgcttatagg     840
cgtggaattg cagaggctgt tggtcttcca agtattcctg ttcatccaat tggatactat     900
gatgcacaga agctcctaga aaaaatgggt ggctcagcac caccagatag cagctggaga     960
ggaagtctca agtgcccta caatgttgga cctggcttta ctgaaaactt ttctacacaa    1020
aaagtcaaga tgcacatcca ctctaccaat gaagtgacaa gaatttacaa tgtgataggt    1080
actctcagag gagcagtgga accagacaga tatgtcattc tgggaggtca ccgggactca    1140
tgggtgtttg gtggtattga ccctcagagt ggagcagctg ttgttcatga aattgtgagg    1200
agctttggaa cactgaaaaa ggaagggtgg agacctagaa gaacaatttt gtttgcaagc    1260
tgggatgcag aagaatttgg tcttcttggt tctactgagt gggcagagga gaattcaaga    1320
ctccttcaag agcgtggcgt ggcttatatt aatgctgact catctataga aggaaactac    1380
actctgagag ttgattgtac accgctgatg tacagcttgg tacacaacct aacaaaagag    1440
ctgaaaagcc ctgatgaagg ctttgaaggc aaatctcttt atgaaagttg gactaaaaaa    1500
agtccttccc cagagttcag tggcatgccc aggataagca aattgggatc tggaaatgat    1560
tttgaggtgt tcttccaacg acttggaatt gcttcaggca gagcacggta tactaaaaat    1620
tgggaaacaa acaaattcag cggctatcca ctgtatcaca gtgtctatga acatatgag     1680
ttggtggaaa agttttatga tccaatgttt aaatatcacc tcactgtggc ccaggttcga    1740
ggagggatgg tgtttgagct agccaattcc atagtgctcc cttttgattg tcgagattat    1800
gctgtagttt taagaaagta tgctgacaaa atctacagta tttctatgaa acatccacag    1860
gaaatgaaga catacagtgt atcatttgat tcacttttt ctgcagtaaa gaattttaca    1920
gaaattgctt ccaagttcag tgagagactc caggactttg acaaaagcaa cccaatagta    1980
ttaagaatga tgaatgatca actcatgttt ctggaaagag catttattga tccattaggg    2040
ttaccagaca ggccttttta taggcatgtc atctatgctc caagcagcca caacaagtat    2100
gcaggggagt cattcccagg aatttatgat gctctgtttg atattgaaag caaagtggac    2160
ccttccaagg cctggggaga agtgaagaga cagatttatg ttgcagcctt cacagtgcag    2220
gcagctgcag agactttgag tgaagtagcc                                     2250
```

<210> SEQ ID NO 97
<211> LENGTH: 2253

<212> TYPE: DNA
<213> ORGANISM: Artificial Sequence
<220> FEATURE:
<223> OTHER INFORMATION: CpG-free PSMA

<400> SEQUENCE: 97

```
atgtggaatc tccttcatga aacagactct gctgtggcca cagccagaag acccagatgg      60
ctgtgtgctg gggccctggt gctggctggt ggcttctttc tcctgggctt cctctttggg     120
tggtttataa atcctccaa tgaagctact aacattactc caaagcataa tatgaaagca     180
tttttggatg aattgaaagc tgagaacatc aagaagttct tatataattt tacacagata     240
ccacatttag caggaacaga acaaaacttt cagcttgcaa agcaaattca atcccagtgg     300
aaagaatttg gcctggattc tgttgagcta gcacattatg atgtcctgtt gtcctaccca     360
aataagactc atcccaacta catctcaata attaatgaag atggaaatga gattttcaac     420
acatcattat ttgaaccacc tcctccagga tatgaaaatg tttctgatat tgtaccacct     480
ttcagtgctt ctctcctca aggaatgcca gaggagatc tagtgtatgt taactatgca     540
agaactgaag acttctttaa attggaaagg acatgaaaaa tcaattgctc tgggaaaatt     600
gtaattgcca gatatgggaa agttttcaga ggaaataagg ttaaaaatgc ccagctggca     660
ggggccaaag gagtcattct ctactctgac cctgctgact actttgctcc tgggggtgaag     720
tcctatccag atggttggaa tcttcctgga ggtggtgtcc agagaggaaa tatcctaaat     780
ctgaatggtg caggagaccc tctcacacca ggttacccag caaatgaata tgcttatagg     840
agaggaattg cagaggctgt tggtcttcca agtattcctg ttcatccaat tggatactat     900
gatgcacaga agctcctaga aaaatgggt ggctcagcac accagatag cagctggaga     960
ggaagtctca aagtgcccta caatgttgga cctggcttta ctggaaactt ttctacacaa    1020
aaagtcaaga tgcacatcca ctctaccaat gaagtgacaa gaatttacaa tgtgataggt    1080
actctcagag gagcagtgga accagacaga tatgtcattc tgggaggtca cagggactca    1140
tgggtgtttg gtggtattga ccctcagagt ggagcagctg ttgttcatga aattgtgagg    1200
agctttggaa cactgaaaaa ggaagggtgg agacctagaa gaacaatttt gtttgcaagc    1260
tgggatgcag aagaatttgg tcttcttggt tctactgagt gggcagagga gaattcaaga    1320
ctccttcaag agaggggagt ggcttatatt aatgctgact catctataga aggaaactac    1380
actctgagag ttgattgtac accctgatg tacagcttgg tacacaacct aacaaaagag    1440
ctgaaaagcc ctgatgaagg ctttgaaggc aaatctcttt atgaaagttg gactaaaaaa    1500
agtccttccc cagagttcag tggcatgccc aggataagca aattgggatc tggaaatgat    1560
tttgaggtgt tcttccaaag acttggaatt gcttcaggca gagcaaggta tactaaaaat    1620
tgggaaacaa acaaattcag tggctatcca ctgtatcaca gtgtctatga acatatgag    1680
ttggtggaaa agttttatga tccaatgttt aaatatcacc tcactgtggc ccaggttaga    1740
ggagggatgg tgtttgagct agccaattcc tagtgctcc cttttgattg tagagattat    1800
gctgtagttt taagaaagta tgctgacaaa atctacagta tttctatgaa acatccacag    1860
gaaatgaaga catacagtgt atcatttgat tcacttttttt ctgcagtaaa gaattttaca    1920
gaaattgctt ccagttcag tgagagactc caggactttac acaaaagcaa cccaatagta    1980
ttaagaatga tgaatgatca actcatgttt ctggaaagag catttattga tccattaggg    2040
ttaccagaca ggccttttta taggcatgtc atctatgctc caagcagcca caacaagtat    2100
gcaggggagt cattcccagg aatttatgat gctctgtttg atattgaaag caaagtggac    2160
```

```
cccttccaagg cctggggaga agtgaagaga cagatttatg ttgcagcctt cacagtgcag    2220
gcagctgcag agactttgag tgaagtagcc taa                                  2253

<210> SEQ ID NO 98
<211> LENGTH: 6
<212> TYPE: PRT
<213> ORGANISM: Artificial Sequence
<220> FEATURE:
<223> OTHER INFORMATION: Cleavable linker

<400> SEQUENCE: 98

Pro Leu Gly Leu Trp Ala
1               5

<210> SEQ ID NO 99
<211> LENGTH: 4
<212> TYPE: PRT
<213> ORGANISM: Artificial Sequence
<220> FEATURE:
<223> OTHER INFORMATION: Linker

<400> SEQUENCE: 99

Gly Phe Leu Gly
1

<210> SEQ ID NO 100
<211> LENGTH: 14
<212> TYPE: PRT
<213> ORGANISM: Artificial Sequence
<220> FEATURE:
<223> OTHER INFORMATION: Peptide toxin

<400> SEQUENCE: 100

Lys Leu Ala Lys Leu Ala Lys Lys Leu Ala Lys Leu Ala Lys
1               5                   10
```